US009580754B2

(12) United States Patent
Markowitz et al.

(10) Patent No.: US 9,580,754 B2
(45) **Date of Patent: *Feb. 28, 2017**

(54) METHODS AND COMPOSITIONS FOR DETECTING GASTROINTESTINAL AND OTHER CANCERS

(71) Applicant: Case Western Reserve University, Cleveland, OH (US)

(72) Inventors: Sanford D. Markowitz, Pepper Pike, OH (US); Joseph Willis, Shaker Heights, OH (US); Amitabh Chak, University Heights, OH (US); Rom Leidner, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 198 days.

This patent is subject to a terminal disclaimer.

(21) Appl. No.: 13/670,155

(22) Filed: Nov. 6, 2012

(65) Prior Publication Data

US 2013/0131329 A1 May 23, 2013

Related U.S. Application Data

(63) Continuation of application No. 13/167,670, filed on Jun. 23, 2011, now Pat. No. 8,415,100, which is a continuation-in-part of application No. 13/105,588, filed on May 11, 2011, now Pat. No. 8,221,977, which is a continuation of application No. 12/322,202, filed on Jan. 30, 2009, now Pat. No. 7,964,353, which is a continuation of application No. 10/920,119, filed on Aug. 16, 2004, now Pat. No. 7,485,420.

(60) Provisional application No. 60/495,064, filed on Aug. 14, 2003.

(51) Int. Cl.
*C12Q 1/68* (2006.01)
*C07H 21/04* (2006.01)

(52) U.S. Cl.
CPC ........... *C12Q 1/6886* (2013.01); *C07H 21/04* (2013.01); *C12Q 2600/106* (2013.01); *C12Q 2600/112* (2013.01); *C12Q 2600/136* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,786,146 A | 7/1998 | Herman et al. | |
| 6,017,704 A | 1/2000 | Herman et al. | |
| 6,057,109 A | 5/2000 | Tartaglia | |
| 6,200,756 B1 | 3/2001 | Herman et al. | |
| 6,265,171 B1 | 7/2001 | Herman et al. | |
| 6,812,339 B1 * | 11/2004 | Venter | C12Q 1/6883 435/6.11 |
| 7,217,805 B2 | 5/2007 | Imanishi et al. | |
| 7,485,420 B2 | 2/2009 | Markowitz | |
| 7,964,353 B2 | 6/2011 | Markowitz | |
| 8,221,977 B2 | 7/2012 | Markowitz | |
| 8,415,100 B2 | 4/2013 | Markowitz et al. | |
| 2003/0148327 A1 | 8/2003 | Olek et al. | |
| 2004/0048279 A1 | 3/2004 | Olek et al. | |
| 2010/0144836 A1 | 6/2010 | Van Engeland et al. | |
| 2010/0297658 A1 | 11/2010 | Ahlquist et al. | |

FOREIGN PATENT DOCUMENTS

| | | |
|---|---|---|
| WO | WO 97/46705 A1 | 12/1997 |
| WO | WO 01/77373 A2 | 10/2001 |
| WO | WO 01/77376 A2 | 10/2001 |
| WO | WO 02/18632 A2 | 3/2002 |
| WO | WO 02/38801 A1 | 5/2002 |

OTHER PUBLICATIONS

Jubb et al. Methylation and colorectal cancer. J Pathology 2001;195:111-34.*
USPTO. SEQ ID No. 181 of WO 01/77376 A2 demonstrating alignment with SEQ ID Nos. 41 and 44.*
Stover et al. (A Negative Regulatory Factor Is Missing in a Human Metastatic Breast Cancer Cell Line, Cancer Res Jun. 15, 1994 (54) (12) 3092-3095).*
Attwood, J.T. et al. DNA methylation and the regulation of gene transcription. Cell Mol. Life Sci. 59, 241-257 (2002).
Baylin, S., et al., “Altered methylation patterns in cancer cell genomes: Cause or consequence?,” Cancer Cell, 1:299-305 (2002).
Baylin, S.B. et al. Alterations in DNA Methylation: A Fundamental Aspect of Neoplasia. Adv. Cancer Res., 72, 141-96 (1998).
Breivik and Gaudernack, “Genomic instability, DNA methylation, and natural selection in colorectal carcinogenesis,” Cancer Biology, vol. 9, pp. 245-254 (1999).
Buck et al, “Design Strategies and Performance of Custom DNA Sequencing Primers,” Biotechniques, vol. 27(3), pp. 528-536 (1999).
Chen, et al., Natl. Cancer Inst., 97(15):1124-32 (2005).
Costello, J.F. et al. Aberrant CpG-island methylation has non-random and tumour-type-specific patterns. Nat. Genet. 24, 132-8 (2000).
Domagala, W., et al., “Vimentin Is Preferentially Expressed in Human Breast Carcinomas With Low Estrogen Receptor and High Ki-67 Growth Fraction,” American Journal of Pathology, 136(1):219-227 (1990).

(Continued)

*Primary Examiner* — Aaron Priest
(74) *Attorney, Agent, or Firm* — Ropes & Gray LLP

(57) ABSTRACT

This application describes methods and compositions for detecting and treating vimentin-associated neoplasia. Differential methylation of the vimentin nucleotide sequences has been observed in vimentin-associated neoplasia such as neoplasia of the upper or lower gastrointestinal tract, pancreas, and/or bladder. Nucleic acid sequences for regions of vimentin that are found to be differentially methylated are described. The present disclosure further describes bisulfite-converted vimentin template DNA sequences. Oligonucleotide primer sequences for use in assays (e.g., methylation-sensitive PCR assays or HpaII assays) designed to detect the methylation status of the vimentin gene are also described.

12 Claims, 67 Drawing Sheets

(56) References Cited

OTHER PUBLICATIONS

Eden, S., et al., "Role of DNA methylation in the regulation of tanscription," Current Opinion in Genetics and Development, 4(2):255-259 (1994).
Evans, R.M., et al., "Vimentin: the conundrum of the intermediate filament gene family," BioEssays, 20:79-86 (1998).
Fraga and Esteller, "DNA Methylation: A Profile of Methods and Applications," BioTechniques, vol. 33, pp. 632, 634, 636-640 (2002).
Fraga and Esteller, "DNA Methylation: A Profile of Methods and Applications," BioTechniques, vol. 33, pp. 632, 634, 636-649 (2002).
Galipeau et al., "Barrett's Esophagus and Esophageal Adenocarcinoma Epigenetic Biomarker Discovery Using Infinium Methylation," Illumina iCommunity Newsletter; http://www.illumina.com/documents/icommunity/article_2008_02_barrett.pdf>(retrieved Oct. 1, 2012). Especially p. 1 col. 2 para 2 (2008).
Gonzalez-Zulueta, M. et al. Methylation of the 5' CpG Island of the p16/CDKN2 Tumor Suppressor Gene in Normal and Transformed Human Tissues Correlates with Gene Silencing. Cancer Res. 55, 4531-4535 (Oct. 15, 1995).
Gonzalgo, M.L. and Jones, P.A. Rapid quantitation of methylation differences at specific sites using methylation-sensitive single nucleotide primer extension (Ms-SNuPE). Nucleic Acids Res. 25, 2529-31 (1997).
Grady, W.M. et al. Detection of Aberrantly Methylated hMLH1 Promoter DNA in the Serum of Patients with Microsatellite Unstable Colon Cancer. Cancer Res. 61, 900-2 (2001).
Herman, J.G. et al. Inactivation of the CDKN2/p16/MTS1 Gene is Frequently Associated with Aberrant DNA Methylation in all Common Human Cancers. Cancer Res. 55, 4525-4530 (1995).
Herman, J.G., et al., "Methylation-specific PCR: A novel PCR assay for methylation status of CpG islands," PNAS 93:9821-9826 (1996).
Hibi, K. et al. Molecular Detection of Genetic Alterations in the Serum of Colorectal Cancer Patients. Cancer Res. 58, 1405-7 (1998).
Issa, Jean-Pierre, "The Epigenetics of Colorectal Cancer," Ann. N.Y. Acad. Sci., vol. 910, pp. 140-155 (2000).
Itzkowitz et al., "Improved Fecal DNA Test for Colorectal Cancer Screening," Clinical Gastroenterology and Hepatology, vol. 5(1), pp. 1-7 (2007).
Izmailova, E. S. et al., "A GC-box is required for expression of the human vimentin gene," Gene, 235(1-2) p. 69-75 (1999).
Jeronimo, C. et al. Quantitation of GSTP1 Methylation in Non-neoplastic Prostatic Tissue and Organ-Confined Prostate Adenocarcinoma. J. Natl. Cancer Inst. 93, 1747-1752 (2001).
Jones, P.A. et al. The DNA methylation paradox. Trends Genet. 15, 34-7 (1999).
Kane, M.F. et al. Methylation of the hMLH1 Promoter Correlates with Lack of Expression of hMLH1 in Sporadic Colon Tumors and Mismatch Repair-defective Human Tumor Cell Lines. Cancer Res. 57, 808-11 (1997).
Kusinska et al., "Does vimentin help to delineate the so-called 'basal type breast cancer'?," Journal of Experimental & Clinical Cancer Research, 28:118 (2009).
Lagendijk, et al., Clin. Pathol., 52(4):283-290 (1999).
Lange, F., et al., "Teratocarcinomas induced by embryonic stem (ES) cells lacking vimentin: An approach to study the role of vimentin in tumorigenesis," Journal of Cell Science, 113(19):3463-3472 (2000).
Li, H. et al. SLC5A8, a sodium transporter, is a tumor suppressor gene silenced by methylation in human colon aberrant crypt foci and cancers. PNAS 100(14), 8412-7 (2003).
Lowe et al, "A computer program for selection of oligonucleotide primers for polymerase chain reactions," Nucleic Acids Research, vol. 18(7); pp. 757-1761 (1990).
Lucentini, et al., The Scientist, vol. 18 (2004).
Markowitz, S. et al. Inactivation of the Type II TGF-$\beta$ Receptor in Colon Cancer Cells with Microsatellite Instability. Science 268, 1336-1338 (1995).
McClelland and Nelson, "The effect of site-specific DNA methylation on restriction endonucleases and DNA modification methyltransferases—a review," Gene. vol. 74, pp. 291-304 (1988).
Moinova, H.R. et al. HLTF gene silencing in human colon cancer. PNAS 99, 4562-7 (2002).
NCB I GENBANK Accession No. AX281517 (Nov. 2, 2001).
NCB I GENBANK Accession No. BD011730 (Aug. 2, 2002).
Paramio, J.M., et al., "Beyond structure: do intermediate filaments modulate cell signalling?," BioEssays, 24:836-844 (2001).
Petko, Zsolt, et al., "Aberrantly methylated CDKN2A, MGMT and hMLH1 are biomarkers for colon adenomas and colon adenocarcinomas", Proceedings of the American Association for Cancer Research Annual Meeting, 44, pp. 698 (2003).
Prudkin et al., "Epithelial-to-Mesenchymal Transition in the Development and Progression of Adenocarcinoma and Squamous Cell Carcinoma of the Lung," Mod Pathol., vol. 22(5): 668-678 (2009).
Ricciardiello et al., "Frequent loss of hMLH1 by promoter hypermethylation leads to microsatellite instability in adenomatous polyps of patients with a single first-degree member affected by colon cancer," Cancer Research, vol. 63(4), pp. 787-792 (2003).
Sakai et al., "Allele-specific Hypermethylation of the Retinoblastoma Tumor-suppressor Gene," Am. J. Hum. Genet., vol. 48, pp. 880-888 (1991).
"Short Technical Reports: Quantification of 5-Methylcytosine in DNA by the Chloroacetalde-hyde Reaction," Biotechniques, vol. 27, pp. 744-752 (1999).
Usadel, H. et al. Quantitative Adenomatous Polyposis Coli Promoter Methylation Analysis in Tumor Tissue, Serum, and Plasma DNA of Patients with Lung Cancer. Cancer Res. 62, 371-5 (2002).
USPTO SEQ ID No. 2 search Result 11.
Veigl, M.L. et al. Biallelic inactivation of hMLH1 by epigenetic gene silencing, a novel mechanism causing human MSI cancers. PNAS 95, 8698-702 (1998).
Wacholder, et al., J. Natl. Cancer Institute, 96(6):434-442 (2004).
Willson, J.K.V. et al. Cell Culture of Human Colon Adenomas and Carcinomas. Cancer Res. 47, 2704-2713 (1987).
WIPO http://www.wipo.int/pctdb/en/search-adv.jsp.
Xiong, Z. and Laird, P.W. Cobra: a sensitive and quantitative DNA methylation assay. Nucleic Acids Res. 25, 2532-4 (1997).
Yoo et al., "Delivery of 5-Aza-2'-Deoxycytidine to Cells Using Oligodeoxynucleotides," Cancer Research, vol. 67(13), pp. 6400-6408 (2007).
Putz et al., "Phenotypic Characteristics of Cell Lines Derived from Disseminated Cancer Cells in Bone Marrow of Patients with Solid Epithelial Tumors," Cancer Research, vol. 59(1):241-248 (1999).

* cited by examiner

Human Vimentin Genomic DNA Sequence (sense strand): (SEQ ID NO: 51) FIG. 1B

5'-
CTGCAGTTAATCCTTTTCAGTACACCATAAATCTAAATACTCTCAAAAAAACCTGTGCCTTTTCAATTGCTACTAAATCACGAGAAGACTGATTTACATAGTCTCCTTTTATCTCCCTTGGCGGGTAAGTACTC
AGCTCTGCTCGTTACTAATATTGAAACAACAGCCCTTGAATTGAGTGATTTCCCTAGAAAGGTTAAGGTGACCGAATCTGAACACTCCCTCCATGTCTTGGACACGAAGTTTTTTTTCTGCGTAGACAGTTTTA
TCCCCTCATCCCAAGGTCAATTGCACGAATTCTTTTGGAAAACAGAACCTATGGCATTTCCCAGACAAATCACCGTGAACCCTGTACTGTGCATTGCTGTCCTAAAATTAACACATAAATCTATTGCCGCCAAA
GATTCTGTCATTTGTGTTACATAATTGCCTTTCATTTGAACTCATTAATCAAATTGGGGTTTTTAAGCAACACCTAATTAATTCTTTAACTGGCTCATATTAACCTTTAATGACTTCCACCAGGGTAAAAACCA
CTGATCACTGAGTTCTATTTTGAAACTACGGACGTCGAGTTTCCTCTTTCACCCAGAATTTTCAGATCTTGTTTAAAAAGTTGGGTGTGGTTTCATGGGGGGAGGGGGAAGAGCGAGAGGAGACCAGAGGGACG
GGGGCGGGGACTCTGCAAGAAAAACCTTCCCGGTGCAATCGTGATCTGGGAGGCCCACGTATGGCGCCTCTCCAAAGGCTGCAGAAGTTTCTTGCTAACAAAAAGTCCGCACATTCGAGCAAAGACAGGCTTTA
GCGAGTTATTAAAAACTTAGGGGCGCTCTTGTCCCCCACAGGGCCCGACCGCACACAGCAAGGCGATGGGCCCAGCTGTAAGTTGGTAGCACTGAGAACTAGCAGCGCGCGCGGAGCCCGCTGAGACTTGAATC
AATCTGGTCTAACGGTTTCCCCTAAACCGCTAGGAGCCCTCAATCGGCGGGACAGCAGGGCGCGGTGAGTCACCGCCGGTGACTAAGCGACCCCACCCCTCTCCCTCGGGCTTTCCTCTGCCACCGCCGTCTCG
CAACTCCCGCCGTCCGAAGCTGGACTGAGCCCGTTAGGTCCCTCGACAGAACCTCCCCTCCCCCCAACATCTCCCCCCAAGGCAAGTCGATGGACAGAGGCGCGGGCCGGAGCAGCCCCCCTTTCCAAGCGGGC
GGCGCGCGAGGCTGCGGCGAGGCCTGAGCCCTGCGTTCCTGCGCTGTGCGCGCCCCCACCCCGCGTTCCAATCTCAGGCGCTCTTTGTTTCTTTCTCCGCGACTTCAGATCTGAGGGATTCCTTACTCTTTCC
TCTTCCCGCTCCTTTGCCCGCGGGTCTCCCCGCCTGACCGCAGCCCCGAGGCCGCCGCGCACCTCCTCCCACGCCCCTTTGGCGTGGTGCCACCGGACCCCTCTGGTTCAGTCCCAGGCGGACCCCCCCCTCAC
CGCGCGACCCCGCCTTTTTCAGCACCCCAGGGTGAGCCCAGCTCAGACTATCATCCGGAAAGCCCCCAAAAGTCCCAGCCCAGCGCTGAAGTAACGGGACCATGCCCAGTCCCACGCCCCGGAGCAGGAAGGCT
CGAGGCGCCCCCACCCCACCCGCCCACCCTCCCCGCTTCTCGCTAGGTCCCTATTGGCTGGGGCGCTCCGCGGCTGGGATGGCAGTGGGAGGGGACCCTCTTTCCTAACGGGGTTATAAAAACAGCGCCCTCGG
CGGGGTCCAGTCCTCTGCCACTCTCGCTCCGAGGTCCCCGCGCCAGAGACGCAGCCGCGCTCCCACCACCCACACCCACCGCGCCCTCGTTCGCCTCTTCTCCGGGAGCCAGTCCGCGCCACCGCCGCCGCCCA
GGCCATCGCCACCCTCCGCAGCCATGTCCACCAGGTCCGTGTCCTCGTCCTCCTACCGCAGGATGTTCGGCGGCCCGGGCACCGCGAGCCGGCCGAGCTCCAGCCGGAGCTACGTGACTACGTCCACCCGCACC
TACAGCCTGGGCAGCGCGCTGCGCCCCAGCACCAGCCGCAGCCTCTACGCCTCGTCCCCGGGCGGCGTGTATGCCACGCGCTCCTCTGCCGTGCGCCTGCGGAGCAGCGTGCCCGGGGTGCGGCTCCTGCAGGA
CTCGGTGGACTTCTCGCTGGCCGACGCCATCAACACCGAGTTCAAGAACACCCGCACCAACGAGAAGGTGGAGCTGCAGGAGCTGAATGACCGCTTCGCCAACTACATCGACAAGGTGCGCTTCCTGGAGCAGC
AGAATAAGATCCTGCTGGCCGAGCTCGAGCAGCTCAAGGGCCAAGGCAAGTCGCGCCTAGGGGACCTCTACGAGGAGGAGATGCGGGAGCTGCGCCGGCAGGTGGACCAGCTAACCAACGACAAAGCCCGCGTC
GAGGTGGAGCGCGACAACCTGGCCGAGGACATCATGCGCCTCCGGGAGAAGTAAGGCTGCGCCCATGCAAGTAGCTGGGCCTCGGGAGGGGGCTGGAGGGAGAGGGGAACGCCCCCCCGGCCCCCGCGAGAGCT
GCCACGCCCTTGGGGATGTGGCCGGGGGGAGGCCTGCCAGGGAGACAGCGGAGAGCGGGGCTGTGGCTGTGGTGGCGCAGCCCCGCCCAGAACCCAGACCTTGCAGTTCGCATTTCCTCCTCTGTCCCCACACA
TTGCCCAAGGACGCTCCGTTTCAAGTTACAGATTTCTTAAAACTACCACTTTGTGTGCAGTTGAAGGCCCTTGGGCACAATGAGAGCCAGTCCTCCAAACTTTCAGAAAGTTTCCTGCCCCTTCTGGCAGGCTG
CCAATCACCGGGCGGGAGAAGGAAGGAGGGGAAGGCGGTGGAGGGAGCGAGACAAAGGGATGGTCCCTCGGGGGCGGGGATGGCGGGGCTGTCCTGTAGGTCTGTGCGGCCACCGTGATTGCCCCTCTGCGCGG
TGCCCGAAGTCCCGCTGAAACCTGCCGAGGGCAGCAGGTCTGAAAGCTGCAGGCGCTAGTTGCGCGGAGGTGGCGCAGCTGCTCTGGAGGCGCAGAGCGAATACGTGGTGTTTGGGTGTGGCCGCCCCGCCCCT
GGCGGTTTCCTCGTTCCCCTTTGGTTAATGCGCAACTGTTTCAGATTGCAGGAGGAGATGCTTCAGAGAGAGGAAGCCGAAAACACCCTGCAATCTTTCAGACAGGTTTGTAGACTCTCTTCCCACTCGCAGCC
GCCTGACCCCACCCAACACAACCCACGAGCAATTCTAAAAGTTGCTTAACTCACGTCTAAAAAGTGCAAAACTTCAGGGCTGCGCGTAAAGCCCTCTAGTGGCGGGAAGACCACAGGTTGGAGCTTCTCATGAT
TAGAAAAATATTAATAAAACCCCTTGAGCGATTTTTTTTTTTTTTTTGAGACGGAGTCTTACTCTGTCGCCCAGGCTGGAGTGCAGTGGCGAGATCTTGGCTCACTGCATCCTCCGCCTCCCGGGTTCAAGCGA
TCCTTGAATGATTTCTAAGCAGTTCCTTGGGACATAAAGAAAAATCTTTTAACTTTTTACTTTGTTTCCCAAATGTTGCACAGTTTTGCAACACATTGACCTTCTGGTTTCGAACGGTTACAATTTTAGATTGT
GGTTTGCCAAAGTCAAGTTGCTTAATTTTTACAAGGCCACAAAAAGCGCAATTATGCCCTGCAGTTTAAAATGGAAAACGTGTTGGAAGATAAGAAAACTTAGTTTCCAACTGGAATGGAGCCAGCAAGTTTCT
TTTCTTCTTTGCAAATTCTATTGTGTCATTAAAGTTCGATGGAAGTATCACTATGCACAACTATTTTGTGATCTAATAAGGGTGAAAAGGAGCCATCTGTCCCCTTGGCTAAGGGGTATTAATGGTTTCTATGG
GCTTCACTATGGAATGTAGATACAGACATTCTGGCAAATGTGGTGGCTCTGGACAGAAATAATAGGAGTCTTTGTATTCCCAGGGAAGCTTTGCAACAGGCTACATTCTTACTGAATATGTAATGATGTAAGCA
CGGTTCTAATTGGACACAAGTATTTGCTAACATCCGTTATCTAATATCTGGCCCAGACTTGAGAAGTAGGTAATGTGAAAAGTTTTTAAAGCTACAAGCATACCTCACATTTTAAAAGTCCTTTCTTGATTGGG
TTCTTGTGTTCTTTAGCACTCTTGCCATAAAAAATAATAACAGTAATAAACCCAAGGCTGAAAAACTGAATTTTAACTAAAGGGTTTTTGTGCGTGTTTTTTTTTTTTTTTCACCAAAATTAGATGGACTTACAG
AATTTTTAACTTAAAATTGGAATCCAAAAGCCAGAAGATCCCCATTATAGTTTATAGTTGTATTCCCTGGAATATTTACTGGGATTAACTGCAAAGCACTCTCAGATGAATAGTGTAGTATAACATTTTGAAAC
TGAAATACATTTACCAAATTAATTTAACCACAGCAATGTGTGTGGTTCATTTTAGTCCTTGAGCATTTTTGATTATCATACCTGTCATGTTTTCTGCAGTGTAGTGAGTTAACATAAAACAACATCAATACAAA
AGATCCTCTGTTTCGAGATTAAGCAAAATTCCTCATTCTCTTCAATGTGATAGAATACCACATTGATCTTTCTTTGGAGGTTAGTAAAATATCTTTTATGTATTTTTCAGGGCTTAACAAGTAAAAATCAATGT
TTTCATCAAGTCTGATCTTTTTGTCACCCACTCTTCATTCATTTTTCCACTAAGGTGATAGAAAAGTCTCAACAGTTTAAGACCGTAAGGCTATGAACTCCAAATATAATTGCTGACAAGATAAGCAATCCTCA
CGCATCCTTTTGAGAGGAAATAAAATCTTAGTTGCAAGATTACATATTCTGATTTGGAATGCTGAGCTTTTTAAATGGAAATATAGAAGGACGGCTGAATCAGCAAAAATCCTTTATGTAGTTTCATTCTTTGC
AAGCTTGACCAGTCATTCTGAAACAGGCTAACTGAACTGATACAGTGGCAAGTGAAAAAGACATGCCTTTACAGGATGAGTCAAAGGAGTTTTAGAAGAAAAATCCACCAGAGAAAGCCAAGCAAATACAGTTC
AGAGTTACATTTCTTTTCCATTTTTTCCTGAACTGAATCTTTGGCATGCATATCCTGAATTGGGTTATTGAATATAAATCTAGCCTTGTACAATGGATGCCAGATGACTACATATTTGCTTTGGAGCCTAAGGA
TAAGTTTCAAAAGATTTGAGTGGAGAAGAAAAGCTAAAACTCTTGAAGCACAAGTTTCTGTTCTCCATGTACTCAAGTGTACATGAAGTTGTGAAAATTTGTCCACCTCTATCATCATGTTATTCCATGAAATT
ACAAAACAAATCTTAAAAATGTTGTGGCATAGATTTTCTAGATTTAAAAAGTAATTAAATTAAATGAATTACTTTATTTTTTGAGACAGAGTGTCACTCTGTTGCCCAGGCTGGAGTGCAGTGGCACTATGTTG
GCTCACTGCAACCTCTGCCTCCTGGGTTGAAGAAATTCTCCTGCCTCAACCTCCCAAGTAGCTGGGACTACAGGCATGTGCCACCACACCCAGCTAATTTTTGTATTTTTGGTAGAGACGGGGTTTCGCCATGT
TGGCTAGGCTGGTCTCGAACTCCTGACCTCAAGTGATCCACCCGTCTCAGCCTCCCAAAGTGCTGGGATTACAGGCATAAGCCACCATGACCAGCCTTAAAAAGTAATTTTAAAATATCACTGGTAAAATGTGG
ATTCAGTCATGATTGAGTGCAGTTTACCATGTGTGTGGACATTTATTTATTTTAAAATTGTCTGATCACCACCTTGAGTAAAACACAAGCAGTCACAATTAAAATATATTAGTGAGCAGGAGAAAGCACAGCAT
ATTATAGCACTGAATGATTTATAAACCTATTCCAGGGTCATAAAATGTGTCAACGGCTTTTCTATAGTAAGGAGACTAGGTTCAGATGGTTAATCTAAGACAAATAAATGAGATAAGCCATACACTTTTACATC
CTCCATGTCCTGTCTTTTCTCTGTTCAAAATAGGATGTTGACAATGCGTCTCTGGCACGTCTTGACCTTGAACGCAAAGTGGAATCTTTGCAAGAAGAGATTGCCTTTTTGAAGAAACTCCACGAAGAGGTTAG
TGGAGTGACTTTCGGGGAATGAATGAGGGTAAGGCAGCCCCCACGGTTGGCAGAGC-3'

5 aza turned on/increase: V400, V429, V503, RCA, V5, RKO, V432, V703, V457
5 aza no change lines: V364, SW480, V6

PCR: 30X

Vimentin HpaII assay---C region, cell lines

Vimentin HpaII assay— C region, 40X

N/T--N(-)/T(+)--1,5,8,9
N/T--N(-)/T(-)--3,4,10
N/T--N(+)/T(+)--6,7
N/T--N(+)/T(-)--2

HpaII assays: 1826U/2195D, 40X

N/T--N(-)/T(+)--11,13,14,17,18,20,22,23,25,26,29,31
N/T--N(-)/T(-)--21,24,32
N/T--N(+)/T(+)--12,15,19,27,28
N/T--N(+)/T(-)--30
N/T--uninformative--16 x51907-from 5UTR to exon3-MS pr

MS-PCR using primer covering part of B, C region, 40 CYCLES.

MS-PCR of Vimentin using MSP3 primer

MS-PCR of Vimentin using MSP3 primer

MS-PCR of Vimentin using MSP3 primer, 40X

MS-PCR of Vimentin using MSP3 primer, 40X

MSP3 PCR of vimentin in cell lines, 40X

Figure 13

Primer Sets for HpaII Assays for Vimentin Methylation

| | | Primer Name | Primer Sequence |
|---|---|---|---|
| A. | A Region | VM-HpaII-679U: | GACTCTGCAAGAAAAACCTTCC (SEQ ID NO: 8) |
| | | VM-HpaII-1266D: | TGAGATTGGAACGCGGGG (SEQ ID NO: 9) |
| B. | C Region | VM-HpaII-1826U: | CCCTCGTTCGCCTCTTCTCC (SEQ ID NO: 10) |
| | | VM-HpaII-2195D: | GTGTTCTTGAACTCGGTGTTGATG (SEQ ID NO: 11) |
| C. | D Region | VM-HpaII-2264U: | GCTTCCTGGAGCAGCAGAATAA (SEQ ID NO: 12) |
| | | VM-HpaII-2695D: | AGCGTCCTTGGGCAATGTGT (SEQ ID NO: 13) |

Figure 14

MS-PCR Primer Sets for Vimentin Methylation

| | Primer Name | (SEQ ID NO:) | Primer Sequence | DNA Length | Tm (°C) |
|---|---|---|---|---|---|
| VIM-MSP1 | VIM1374MF: | (14) | TTGATCGTAGTTTCGAGGTCGTCGC | 130bp | 76 |
| | VIM1504MR: | (15) | CTAAAATACTAAAAAAAACGAAATCGCGCG | | 73 |
| | VIM1368UF: | (18) | TTTTGTTTGATTGTAGTTTTGAGGTTGTTGT | 138bp | 72 |
| | VIM1506UR: | (17) | CCCTAAAATACTAAAAAAAACAAAATCACACA | | 71 |
| VIM-MSP1-2 | **VIM1374MF:** | (14) | **TTGATCGTAGTTTCGAGGTCGTCGC** | **132bp** | 76 |
| | **VIM1506MR:** | (18) | **CCCTAAAATACTAAAAAAAACGAAATCGCG** | | 73 |
| | **VIM1368UF:** | (16) | **TTTTGTTTGATTGTAGTTTTGAGGTTGTTGT** | **138bp** | 72 |
| | **VIM1506UR:** | (17) | **CCCTAAAATACTAAAAAAAACAAAATCACACA** | | 71 |
| VIMMSP2 | VIM1655MF(ASS): | (19) | ATCCCGATTAACTAAAACGCTCCGCG | 142bp | 76 |
| | VIM1797MR(ASS): | (20) | GTTGCGTTTTTGGCGCGGGGATTTC | | 77 |
| | VIM1651UF(ASS): | (21) | CTAAATCCCAATTAACTAAAACACTCCACA | 148bp | 73 |
| | VIM1799UR(ASS): | (22) | TGGTTGTGTTTTTGGTGTGGGGATTTT | | 73 |
| VIM-MSP3 | **VIM1776MF:** | (23) | **GTTTTCGCGTTAGAGACGTAGTCGC** | **206bp** | 76 |
| | **VIM1982MR:** | (24) | **CGACTAAAACTCGACCGACTCGCGA** | | 77 |
| | **VIM1771UF:** | (25) | **TTGAGGTTTTTGTGTTAGAGATGTAGTTGT** | **215bp** | 73 |
| | **VIM1986UR:** | (26) | **ACTCCAACTAAAACTCAACCAACTCACA** | | 74 |
| VIM-MSP5 | VIM1935MF(ASS): | (27) | CAAAATATTCGACGACCCGAACACCG | 159bp | 76 |
| | VIM2094MR(ASS): | (28) | GGAGCGCGTGGTATATACGTCGTTC | | 77 |
| | VIM1934UF(ASS): | (29) | ACAAAATATTCAACAACCCAAACACCACA | 155bp | 72 |
| | VIM2089UR(ASS): | (30) | TAGAGGAGTGTGTGGTATATATGTTGTTT | | 72 |

Figure 15

MS-PCR Primer Sets for Vimentin Methylation

| | Primer Name | (SEQ ID NO:) | Primer Sequence | DNA Length | Tm (°C) |
|---|---|---|---|---|---|
| VIM-MSP6 | VIM1655MF: | (31) | GTTTCGATTGGTTGGGGCGTTTCGC | 137bp | 77 |
| | VIM1792MR: | (32) | GTCTCTAACGCGAAAACCTCGAAACG | | 76 |
| | VIM1651UF: | (33) | TTAGGTTTCGATTGGTTGGGGTGTTTTGT | 149bp | 75 |
| | VIM1800UR: | (34) | ACAACTACATCTCTAACACAAAAACCTCA | | 72 |
| VIM-MSP7 | VIM1655MF: | (31) | GTTTCGATTGGTTGGGGCGTTTCGC | 141bp | 77 |
| | VIM1796MR: | (35) | CTACGTCTCTAACGCGAAAACCTCGA | | 76 |
| | VIM1651UF: | (33) | TTAGGTTTCGATTGGTTGGGGTGTTTTGT | 149bp | 75 |
| | VIM1800UR: | (34) | ACAACTACATCTCTAACACAAAAACCTCA | | 72 |
| VIM-MSP8 | VIM1655MF: | (31) | GTTTCGATTGGTTGGGGCGTTTCGC | 149bp | 77 |
| | VIM1804MR: | (36) | AAACGCGACTACGTCTCTAACGCGA | | 76 |
| | VIM1651UF: | (33) | TTAGGTTTCGATTGGTTGGGGTGTTTTGT | 149bp | 75 |
| | VIM1800UR: | (34) | ACAACTACATCTCTAACACAAAAACCTCA | | 72 |
| VIM-MSP9 | VIM1843MF: | (37) | TTCGGGAGTTAGTTCGCGTTATCGTC | 139bp | 76 |
| | VIM1982MR: | (24) | CGACTAAAACTCGACCGACTCGCGA | | 77 |
| | VIM1843UR: | (38) | TTTGGGAGTTAGTTTGTGTTATTGTTGTTGT | 143bp | 73 |
| | VIM1986UR: | (26) | ACTCCAACTAAAACTCAACCAACTCACA | | 74 |
| VIM-MSP10 | VIM1929MF(ASS): | (39) | CTACCGCAAAATATTCGACGACCCGA | 165bp | 76 |
| | VIM2094MR(ASS): | (28) | GGAGCGCGTGGTATATACGTCGTTC | | 77 |
| | VIM1934UF(ASS): | (29) | ACAAAATATTCAACAACCCAAACACCACA | 155bp | 72 |
| | VIM2089UR(ASS): | (30) | TAGAGGAGTGTGTGGTATATATGTTGTTT | | 72 |

MS-PCR Assay for Vimentin Methylation
Non-Cancer Normal
2129 2137 2267 2268 2269 2399 2565 2581 2848 2914 3051 3055 V241 V576 V9M V206 V364 V394 V425 V10M V441 V5 HCT116 ddH2O
M
M
U
VIM-MSP1 (130bp)
VIM-MSP1-2 (132cp)
VIM-MSP1
Non-Cancer Normal
2129 2137 2267 2268 2269 2399 2565 2581 2848 2914 3051 3055 V241 V576 V9M V206 V364 V394 V425 V10M V441 V5 HCT116 ddH2O
VIM-MSP3 (206bp)
Methyl: 67 degree C x 45 cycles; Unmethyl: 63 degree C x 38 cycles.

MS-PCR Assay for Vimentin Methylation

MS-PCR assay for ACF samples

Figure 20

Human Vimentin Protein Sequence (SEQ ID NO: 1)

MSTRSVSSSSYRRMFGGPGTASRPSSSRSYVTTSTRTYSLGSALRPSTSRSLYASSPGGVYATRSSAVRLRSSVPGV
RLLQDSVDFSLADAINTEFKNTRTNEKVELQELNDRFANYIDKVRFLEQQNKILLAELEQLKGQGKSRLGDLYEEEM
RELRRQVDQLTNDKARVEVERDNLAEDIMRLREKLQEEMLQREEAENTLQSFRQDVDNASLARLDLERKVESLQEEI
AFLKKLHEEEIQELQAQIQEQHVQIDVDVSKPDLTAALRDVRQQYESVAAKNLQEAEEWYKSKFADLSEAANRNNDA
LRQAKQESTEYRRQVQSLTCEVDALKGTNESLERQMREMEENFAVEAANYQDTIGRLQDEIQNMKEEMARHLREYQD
LLNVKMALDIEIATYRKLLEGEESRISLPLPNFSSLNLRETNLDSLPLVDTHSKRTFLIKTVETRDGQVINETSQHH
DDLE

Figure 21

Vimentin Genetic-Sense Strand (SEQ ID NO: 2)

Numbering-base pair "NCBI (AL133415): 56,822-58,822".
Bolded region: Differentially Methylated Region (DMR): "NCBI(AL133415)-57,427-58,326". (SEQ ID NO: 45)
Underline region: "Best" MS-PCR primer sets covered regions.

5'-
GGTGCAATCGTGATCTGGGAGGCCCACGTATGGCGCCTCTCCAAAGGCTGCAGAAGTTTCTTGCTAACAAAAAGTCCGCACATTCGAGCAA
AGACAGGCTTTAGCGAGTTATTAAAAACTTAGGGGCGCTCTTGTCCCCCACAGGGCCCGACCGCACACAGCAAGGCGATGGCCCAGCTGTA
AGTTGGTAGCACTGAGAACTAGCAGCGCGCGCGGAGCCCGCTGAGACTTGAATCAATCTGGTCTAACGGTTTCCCCTAAACCGCTAGGAGC
CCTCAATCGGCGGGACAGCAGGGCGCGGTGAGTCACCGCCGGTGACTAAGCGACCCCACCCCTCTCCCTCGGGCTTTCCTCTGCCACCGCC
GTCTCGCAACTCCCGCCGTCCGAAGCTGGACTGAGCCCGTTAGGTCCCTCGACAGAACCTCCCCTCCCCCCAACATCTCTCCGCCAAGGCA
AGTCGATGGACAGAGGCGCGGGCCGGAGCAGCCCCCCTTTCCAAGCGGGCGGCGCGCGAGGCTGCGGCGAGGCCTGAGCCCTGCGTTCCTG
CGCTGTGCGCGCCCCCACCCCGCGTTCCAATCTCAGGCGCTCTTTGTTTCTTTCTCCGCGACTTCAGATCTGAGGGATTCCTTACTCTTTC
CTCTTCCCGCTCCTTTGCCCGCGGGTCTCCCCGCCTGACCGCAGCCCCGAGACCGCCGCGCACCTCCTCCCACGCCCCTTTGGCGTGGTGC
CACCGGACCCCTCTGGTTCAGTCCCAGGCGGACCCCCCCCTCACCGCGCGACCCCGCCTTTTTCAGCACCCCAGGGTGAGCCCAGCTCAGA
CTATCATCCGGAAAGCCCCCAAAAGTCCCAGCCCAGCGCTGAAGTAACGGGACCATGCCCAGTCCCAGGCCCCGGAGCAGGAAGGCTCGAG
GGCGCCCCCACCCCACCCGCCCACCCTCCCCGCTTCTCGCTAGGTCCCTATTGGCTGGCGCGCTCCGCGGCTGGGATGGCAGTGGGAGGGG
ACCCTCTTTCCTAACGGGGTTATAAAAACAGCGCCCTCGGCGGGGTCCAGTCCTCTGCCACTCTCGCTCCGAGGTCCCCGCGCCAGAGACG
CAGCCGCGCTCCCACCACCCACACCCACCGCGCCCTCGTTCGCCTCTTCTCCGGGAGCCAGTCCGCGCCACCGCCGCCGCCCAGGCCATCG
CCACCCTCCGCAGCCATGTCCACCAGGTCCGTGTCCTCGTCCTCCTACCGCAGGATGTTCGGCGGCCCGGGCACCGCGAGCCGGCCGAGCT
CCAGCCGGAGCTACGTGACTACGTCCACCCGCACCTACAGCCTGGGCAGCGCGCTGCGCCCCAGCACCAGCCGCAGCCTCTACGCCTCGTC
CCCGGGCGGCGTGTATGCCACGCGCTCCTCTGCCGTGCGCCTGCGGAGCAGCGTGCCCGGGGTGCGGCTCCTGCAGGACTCGGTGGACTTC
TCGCTGGCCGACGCCATCAACACCGAGTTCAAGAACACCCGCACCAACGAGAAGGTGGAGCTGCAGGAGCTGAATGACCGCTTCGCCAACT
ACATCGACAAGGTGCGCTTCCTGGAGCAGCAGAATAAGATCCTGCTGGCCGAGCTCGAGCAGCTCAAGGGCCAAGGCAAGTCGCGCCTGGG
GGACCTCTACGAGGAGGAGATGCGGGAGCTGCGCCGGCAGGTGGACCAGCTAACCAACGACAAAGCCCGCGTCGAGGTGGAGCGCGACAAC
CTGGCCGAGGACATCATGCGCCTCCGGGAGAAGTAAGGCTGCGCCCATGCAAGTAGCTGGGCCTCGGGAGGGGGCTGGAGGGAGAGGGGAA
CGCCCCCCCGGCCCCCGCGAGAGCTGCCACGCCCTTGGGGATGTGGCCGGGGGGAGGCCTGCCAGGGAGACAGCGGAGAGCGGGGCTGTGG
CTGTGGTGGCGCAGCCCCGCCCAGAACCCAGACCTTGCAGTTCGCATTTCCTCCTCTGTCCCCACACATTGCCCAAGGACGCTCCGTTTC
-3'

Figure 22

Vimentin Genetic-Sense Strand (Bisulfite Converted/Methylated) (SEQ ID NO: 3)

Numbering-base pair "NCBI (AL133415): 56,822-58,822".
Bolded region: Differentially Methylated Region (DMR): "NCBI(AL133415)-57,427-58,326". (SEQ ID NO: 46)
Underline region: "Best" MS-PCR primer sets covered regions.

5'-
GGTGTAATCGTGATTTGGGAGGTTTACGTATGGCGTTTTTTTAAAGGTTGTAGAAGTTTTTTGTTAATAAAAAGTTCGTATATTCGAGTAA
AGATAGGTTTTAGCGAGTTATTAAAAATTTAGGGGCGTTTTTGTTTTTTATAGGGTTCGATCGTATATAGTAAGGCGATGGTTTAGTTGTA
AGTTGGTAGTATTGAGAATTAGTAGCGCGCGCGGAGTTCGTTGAGATTTGAATTAATTTGGTTTAACGGTTTTTTTTAAATCGTTAGGAGT
TTTTAATCGGCGGGATAGTAGGGCGCGGTGAGTTATCGTCGGTGATTAAGCGATTTTATTTTTTTTTTTTCGGGTTTTTTTTTGTTATCGTC
GTTTCGTAATTTTCGTCGTTCGAAGTTGGATTGAGTTCGTTAGGTTTTTCGATAGAATTTTTTTTTTTTTTAATATTTTTTCGTTAAGGTA
AGTCGATGGATAGAGGCGCGGGTCGGAGTAGTTTTTTTTTTTAAGCGGGCGGCGCGCGAGGTTGCGGCGAGGTTTGAGTTTTGCGTTTTTG
CGTTGTGCGCGTTTTTATTTCGCGTTTTAATTTTAGGCGTTTTTTGTTTTTTTTTTTCGCGATTTTAGATTTGAGGGATTTTTTATTTTTTT
TTTTTTTCGTTTTTTTGTTCGCGGGTTTTTTCGTTTGATCGTAGTTTCGAGATCGTCGCGTATTTTTTTTTACGTTTTTTTGGCGTGGTGT
TATCGGATTTTTTTGGTTTAGTTTTAGGCGGATTTTTTTTTTATCGCGCGATTTCGTTTTTTTTAGTATTTTAGGGTGAGTTTAGTTTAGA
TTATTATTCGGAAAGTTTTTAAAAGTTTTAGTTTAGCGTTGAAGTAACGGGATTATGTTTAGTTTTAGGTTTCGGAGTAGGAAGGTTCGAG
GGCGTTTTTATTTTATTCGTTTATTTTTTTCGTTTTTCGTTAGGTTTTTATTGGTTGGCGCGTTTCGCGGTTGGGATGGTAGTGGGAGGGG
ATTTTTTTTTTTAACGGGGTTATAAAAATAGCGTTTTCGGCGGGGTTTAGTTTTTTGTTATTTTCGTTTCGAGGTTTTCGCGTTAGAGACG
TAGTCGCGTTTTTATTATTTATATTTATCGCGTTTTCGTTCGTTTTTTTTTCGGGAGTTAGTTCGCGTTATCGTCGTCGTTTAGGTTATCG
TTATTTTTCGTAGTTATGTTTATTAGGTTCGTGTTTTCGTTTTTTTATCGTAGGATGTTCGGCGGTTCGGGTATCGCGAGTCGGTCGAGTT
TTAGTCGGAGTTACGTGATTACGTTTATTCGTATTTATAGTTTGGGTAGCGCGTTGCGTTTTAGTATTAGTCGTAGTTTTTACGTTTCGTT
TTCGGGCGGCGTGTATGTTACGCGTTTTTTTGTCGTGCGTTTGCGGAGTAGCGTGTTCGGGGTGCGGTTTTTGTAGGATTCGGTGGATTTT
TCGTTGGTCGACGTTATTAATATCGAGTTTAAGAATATTCGTATTAACGAGAAGGTGGAGTTGTAGGAGTTGAATGATCGTTTCGTTAATT
ATATCGATAAGGTGCGTTTTTTGGAGTAGTAGAATAAGATTTTGTTGGTCGAGTTCGAGTAGTTTAAGGGTTAAGGTAAGTCGCGTTTGGG
GGATTTTTACGAGGAGGAGATGCGGGAGTTGCGTCGGTAGGTGGATTAGTTAATTAACGATAAAGTTCGCGTCGAGGTGGAGCGCGATAAT
TTGGTCGAGGATATTATGCGTTTTCGGGAGAAGTAAGGTTGCGTTTATGTAAGTAGTTGGGTTTCGGGAGGGGGTTGGAGGGAGAGGGGAA
CGTTTTTTCGGTTTTCGCGAGAGTTGTTACGTTTTTGGGGATGTGGTCGGGGGGAGGTTTGTTAGGGAGATAGCGGAGAGCGGGGTTGTGG
TTGTGGTGGCGTAGTTTCGTTTAGAATTTAGATTTTGTAGTTCGTATTTTTTTTTTTTGTTTTTATATATTGTTAAGGACGTTTCGTTTT
-3'

Figure 23

Vimentin Genetic-Sense Strand (Bisulfite Converted/Unmethylated) (SEQ ID NO: 4)

Numbering-base pair "NCBI (AL133415): 56,822-58,822".
Bolded region: Differentially Methylated Region (DMR): "NCBI(AL133415)-57,427-58,326". (SEQ ID NO: 47)
Underline region: "Best" MS-PCR primer sets covered regions.

5'-
GGTGTAATTGTGATTTGGGAGGTTTATGTATGGTGTTTTTTTAAAGGTTGTAGAAGTTTTTTGTTAATAAAAAGTTTGTATATTTGAGTAA
AGATAGGTTTTAGTGAGTTATTAAAAATTTAGGGGTGTTTTTGTTTTTTATAGGGTTTGATTGTATATAGTAAGGTGATGGTTTAGTTGTA
AGTTGGTAGTATTGAGAATTAGTAGTGTGTGTGGAGTTTGTTGAGATTTGAATTAATTTGGTTTAATGGTTTTTTTTAAATTGTTAGGAGT
TTTTAATTGGTGGGATAGTAGGGTGTGGTGAGTTATTGTTGGTGATTAAGTGATTTTATTTTTTTTTTTTTGGGTTTTTTTTTGTTATTGTT
GTTTTGTAATTTTTGTTGTTTGAAGTTGGATTGAGTTTGTTAGGTTTTTTGATAGAATTTTTTTTTTTTTTAATATTTTTTTGTTAAGGTA
AGTTGATGGATAGAGGTGTGGGTTGGAGTAGTTTTTTTTTTTAAGTGGGTGGTGTGTGAGGTTGTGGTGAGGTTTGAGTTTTGTGTTTTTG
TGTTGTGTGTGTTTTTATTTTGTGTTTTAATTTTAGGTGTTTTTTGTTTTTTTTTTTTGTGATTTTAGATTTGAGGGATTTTTTATTTTTTT
TTTTTTTTGTTTTTTTGTTTGTGGGTTTTTTTGTTTGATTGTAGTTTTGAGATTGTTGTGTATTTTTTTTTATGTTTTTTTGGTGTGGTGT
TATTGGATTTTTTTGGTTTAGTTTTAGGTGGATTTTTTTTTTATTGTGTGATTTTGTTTTTTTTAGTATTTTAGGGTGAGTTTAGTTTAGA
TTATTATTTGGAAAGTTTTTAAAAGTTTTAGTTTAGTGTTGAAGTAATGGGATTATGTTTAGTTTTAGGTTTTGGAGTAGGAAGGTTTGAG
GGTGTTTTTATTTTATTTGTTTATTTTTTTTGTTTTTTGTTAGGTTTTTATTGGTTGGTGTGTTTTGTGGTTGGGATGGTAGTGGGAGGGG
ATTTTTTTTTTTAATGGGGTTATAAAAATAGTGTTTTTGGTGGGGTTTAGTTTTTTGTTATTTTTGTTTTGAGGTTTTTGTGTTAGAGATG
TAGTTGTGTTTTTATTATTTATATTTATTGTGTTTTTGTTTGTTTTTTTTTTTGGGAGTTAGTTTGTGTTATTGTTGTTGTTTAGGTTATTG
TTATTTTTTGTAGTTATGTTTATTAGGTTTGTGTTTTTGTTTTTTTATTGTAGGATGTTTGGTGGTTTGGGTATTGTGAGTTGGTTGAGTT
TTAGTTGGAGTTATGTGATTATGTTTATTTGTATTTATAGTTTGGGTAGTGTGTTGTGTTTTAGTATTAGTTGTAGTTTTTATGTTTTGTT
TTTGGGTGGTGTGTATGTTATGTGTTTTTTTGTTGTGTGTTTGTGGAGTAGTGTGTTTGGGGTGTGGTTTTTGTAGGATTTGGTGGATTTT
TTGTTGGTTGATGTTATTAATATTGAGTTTAAGAATATTTGTATTAATGAGAAGGTGGAGTTGTAGGAGTTGAATGATTGTTTTGTTAATT
ATATTGATAAGGTGTGTTTTTTTGGAGTAGTAGAATAAGATTTTGTTGGTTGAGTTTGAGTAGTTTAAGGGTTAAGGTAAGTTGTGTTTGGG
GGATTTTTATGAGGAGGAGATGTGGGAGTTGTGTTGGTAGGTGGATTAGTTAATTAATGATAAAGTTTGTGTTGAGGTGGAGTGTGATAAT
TTGGTTGAGGATATTATGTGTTTTTGGGAGAAGTAAGGTTGTGTTTATGTAAGTAGTTGGGTTTTGGGAGGGGGTTGGAGGGAGAGGGGAA
TGTTTTTTTGGTTTTTGTGAGAGTTGTTATGTTTTTGGGGATGTGGTTGGGGGGAGGTTTGTTAGGGAGATAGTGGAGAGTGGGGTTGTGG
TTGTGGTGGTGTAGTTTTGTTTAGAATTTAGATTTTGTAGTTTGTATTTTTTTTTTTTGTTTTTATATATTGTTTAAGGATGTTTTGTTTT
-3'

Figure 24

Vimentin Genetic-Antisense Strand (SEQ ID NO: 5)

Numbering-base pair "NCBI (AL133415): 56,822-58,822".
Bolded region: Differentially Methylated Region (DMR): "NCBI(AL133415)-57,427-58,326". (SEQ ID NO: 48)
Underline region: "Best" MS-PCR primer sets covered regions.

3'-
CCACGTTAGCACTAGACCCTCCGGGTGCATACCGCGGAGAGGTTTCCGACGTCTTCAAAGAACGATTGTTTTTCAGGCGTGTAAGCTCGTT
TCTGTCCGAAATCGCTCAATAATTTTTGAATCCCCGCGAGAACAGGGGGTGTCCCGGGCTGGCGTGTGTCGTTCCGCTACCGGGTCGACAT
TCAACCATCGTGACTCTTGATCGTCGCGCGCGCCTCGGGCGACTCTGAACTTAGTTAGACCAGATTGCCAAAGGGGATTTGGCGATCCTCG
GGAGTTAGCCGCCCTGTCGTCCCGCGCCACTCAGTGGCGGCCACTGATTCGCTGGGGTGGGGAGAGGGAGCCCGAAAGGAGACGGTGGCGG
CAGAGCGTTGAGGGCGGCAGGCTTCGACCTGACTCGGGCAATCCAGGGAGCTGTCTTGGAGGGGAGGGGGGTTGTAGAGAGGCGGTTCCGT
TCAGCTACCTGTCTCCGCGCCCGGCCTCGTCGGGGGGAAAGGTTCGCCCGCCGCGCGCTCCGACGCCGCTCCGGACTCGGGACGCAAGGAC
GCGACACGCGCGGGGGTGGGGCGCAAGGTTAGAGTCCGCGAGAAACAAAGAAAGAGGCGCTGAAGTCTAGACTCCCTAAGGAATGAGAAAG
GAGAAGGGCGAGGAAACGGGCGCCCAGAGGGGCGGACTGGCGTCGGGGCTCTGGCGGCGCGTGGAGGAGGGTGCGGGGAAACCGCACCACG
GTGGCCTGGGGAGACCAAGTCAGGGTCCGCCTGGGGGGGGAGTGGCGCGCTGGGGCGGAAAAAGTCGTGGGGTCCCACTCGGGTCGAGTCT
GATAGTAGGCCTTTCGGGGGTTTTCAGGGTCGGGTCGCGACTTCATTGCCCTGGTACGGGTCAGGGTCCGGGGCCTCGTCCTTCCGAGCTC
CCGCGGGGGTGGGGTGGGCGGGTGGGAGGGGCGAAGAGCGATCCAGGGATAACCGACCGCGCGAGGCGCCGACCCTACCGTCACCCTCCCC
TGGGAGAAAGGATTGCCCCAATATTTTTGTCGCGGGAGCCGCCCCAGGTCAGGAGACGGTGAGAGCGAGGCTCCAGGGGCGCGGTCTCTGC
GTCGGCGCGAGGGTGGTGGGTGTGGGTGGCGCGGGAGCAAGCGGAGAAGAGGCCCTCGGTCAGGCGCGGTGGCGGCGGCGGGTCCGGTAGC
GGTGGGAGGCGTCGGTACAGGTGGTCCAGGCACAGGAGCAGGAGGATGGCGTCCTACAAGCCGCCGGGCCCGTGGCGCTCGGCCGGCTCGA
GGTCGGCCTCGATGCACTGATGCAGGTGGGCGTGGATGTCGGACCCGTCGCGCGACGCGGGGTCGTGGTCGGCGTCGGAGATGCGGAGCAG
GGGCCCGCCGCACATACGGTGCGCGAGGAGACGGCACGCGGACGCCTCGTCGCACGGGCCCCACGCCGAGGACGTCCTGAGCCACCTGAAG
AGCGACCGGCTGCGGTAGTTGTGGCTCAAGTTCTTGTGGGCGTGGTTGCTCTTCCACCTCGACGTCCTCGACTTACTGGCGAAGCGGTTGA
TGTAGCTGTTCCACGCGAAGGACCTCGTCGTCTTATTCTAGGACGACCGGCTCGAGCTCGTCGAGTTCCCGGTTCCGTTCAGCGCGGACCC
CCTGGAGATGCTCCTCCTCTACGCCCTCGACGCGGCCGTCCACCTGGTCGATTGGTTGCTGTTTCGGGCGCAGCTCCACCTCGCGCTGTTG
GACCGGCTCCTGTAGTACGCGGAGGCCCTCTTCATTCCGACGCGGGTACGTTCATCGACCCGGAGCCCTCCCCCGACCTCCCTCTCCCCTT
GCGGGGGGGCCGGGGGCGCTCTCGACGGTGCGGGAACCCCTACACCGGCCCCCCTCCGGACGGTCCCTCTGTCGCCTCTCGCCCCGACACC
GACACCACCGCGTCGGGGCGGGTCTTGGGTCTGGAACGTCAAGCGTAAAGGAGGAGACAGGGGTGTGTAACGGGTTCCTGCGAGGCAAAG
-5'

Figure 25

Vimentin Genetic-Antisense Strand (Bisulfite Converted/Methylated) (SEQ ID NO: 6)

Numbering-base pair "NCBI (AL133415): 56,822-58,822".
Bolded region: Differentially Methylated Region (DMR): "NCBI(AL133415)-57,427-58,326". (SEQ ID: 49)
Underline region: "Best" MS-PCR primer sets covered regions.

3'-

TTATGTTAGCATTAGATTTTTTGGGTGCATATTGCGGAGAGGTTTTTGATGTTTTTAAAGAATGATTGTTTTTTAGGCGTGTAAGCTTGTT
TTTGTTTGAAATTGCTTAATAATTTTTGAATTTTTGCGAGAATAGGGGGTGTTTTGGGCTGGCGTGTGTTGTTTTGCTATTGGGTTGATAT
TTAATTATTGTGATTTTTGATTGTTGCGCGCGCTTTGGGCGATTTTGAATTTAGTTAGATTAGATTGCTAAAGGGGATTTGGCGATTTTTG
GGAGTTAGCTGCTTTGTTGTTTTGCGCTATTTAGTGGCGGCTATTGATTTGCTGGGGTGGGAGAGGGAGCTTGAAAGGAGATGGTGGCGG
CAGAGCGTTGAGGGCGGCAGGCTTTGATTTGATTTGGGCAATTTAGGGAGCTGTTTTGGAGGGGAGGGGGGTTGTAGAGAGGCGGTTTTGT
TTAGCTATTTGTTTTTGCGCTTGGCTTTGTTGGGGGGAAAGGTTTGCTTGCTGCGCGCTTTGATGCTGCTTTGGATTTGGGATGCAAGGAT
GCGATATGCGCGGGGGTGGGGCGCAAGGTTAGAGTTTGCGAGAAATAAAGAAAGAGGCGCTGAAGTTTAGATTTTTTAAGGAATGAGAAAG
GAGAAGGGCGAGGAAATGGGCGCTTAGAGGGGCGGATTGGCGTTGGGGCTTTGGCGGCGCGTGGAGGAGGGTGCGGGGAAATTGCATTATG
GTGGCTTGGGGAGATTAAGTTAGGGTTTGCTTGGGGGGGGAGTGGCGCGCTGGGGCGGAAAAAGTTGTGGGGTTTTATTTGGGTTGAGTTT
GATAGTAGGCTTTTTGGGGGTTTTTAGGGTTGGGTTGCGATTTTATTGCTTTGGTATGGGTTAGGGTTTGGGGCTTTGTTTTTTTGAGCTT
TTGCGGGGGTGGGGTGGGCGGGTGGAGGGGCGAAGAGCGATTTAGGGATAATTGATTGCGCGAGGCGCTGATTTTATTGTTATTTTTTTT
TGGGAGAAAGGATTGCTTTAATATTTTTGTTGCGGGAGCTGCTTTAGGTTAGGAGATGGTGAGAGCGAGGCTTTAGGGGCGCGGTTTTTGC
GTTGGCGCGAGGGTGGTGGGTGTGGGTGGCGCGGGAGCAAGCGGAGAAGAGGCTTTTGGTTAGGCGCGGTGGCGGCGGCGGGTTTGGTAGC
GGTGGGAGGCGTTGGTATAGGTGGTTTAGGCATAGGAGCAGGAGGATGGCGTTTTATAAGCTGCTGGGCTTGTGGCGCTTGGCTGGCTTGA
GGTTGGCTTTGATGCATTGATGCAGGTGGGCGTGGATGTTGGATTTGTTGCGCGATGCGGGGTTGTGGTTGGCGTTGGAGATGCGGAGCAG
GGGCTTGCTGCATATATGGTGCGCGAGGAGATGGCATGCGGATGCTTTGTTGCATGGGCTTTATGCTGAGGATGTTTTGAGCTATTTGAAG
AGCGATTGGCTGCGGTAGTTGTGGCTTAAGTTTTGTGGGCGTGGTTGCTTTTTTATTTTGATGTTTTTGATTTATTGGCGAAGCGGTTGA
TGTAGCTGTTTTATGCGAAGGATTTTGTTGTTTTATTTTAGGATGATTGGCTTGAGCTTGTTGAGTTTTTGGTTTTGTTTAGCGCGGATTT
TTTGGAGATGCTTTTTTTTTATGCTTTTGATGCGGCTGTTTATTTGGTTGATTGGTTGCTGTTTTGGGCGCAGCTTTATTTTGCGCTGTTG
GATTGGCTTTTGTAGTATGCGGAGGCTTTTTTTATTTTGATGCGGGTATGTTTATTGATTTGGAGCTTTTTTTTGATTTTTTTTTTTTTTT
GCGGGGGGGCTGGGGGCGCTTTTGATGGTGCGGGAATTTTTATATTGGCTTTTTTTTGGATGGTTTTTTTGTTGCTTTTTGCTTTGATATT
GATATTATTGCGTTGGGGCGGGTTTTGGGTTTGGAATGTTAAGCGTAAAGGAGGAGATAGGGGTGTGTAATGGGTTTTTGCGAGGCAAAG

Vimentin Genetic-Antisense Strand (Bisulfite Converted/Unmethylated) (SEQ ID NO: 7)

Numbering-base pair "NCBI (AL133415): 56,822-58,822".
Bolded region: Differentially Methylated Region (DMR): "NCBI(AL133415)-57,427-58,326". (SEQ ID NO: 50)
Underline region: "Best" MS-PCR primer sets covered regions.

3′-
TTATGTTAGTATTAGATTTTTTGGGTGTATATTGTGGAGAGGTTTTTGATGTTTTTAAAGAATGATTGTTTTTTAGGTGTGTAAGTTTGTT
TTTGTTTGAAATTGTTTAATAATTTTTGAATTTTTGTGAGAATAGGGGGTGTTTTGGGTTGGTGTGTGTTGTTTTGTTATTGGGTTGATAT
TTAATTATTGTGATTTTTGATTGTTGTGTGTGTTTTGGGTGATTTTGAATTTAGTTAGATTAGATTGTTAAAGGGGATTTGGTGATTTTTG
GGAGTTAGTTGTTTTGTTGTTTTGTGTTATTTAGTGGTGGTTATTGATTTGTTGGGGTGGGGAGAGGGAGTTTGAAAGGAGATGGTGGTGG
TAGAGTGTTGAGGGTGGTAGGTTTTGATTTGATTTGGGTAATTTAGGGAGTTGTTTTGGAGGGGAGGGGGGTTGTAGAGAGGTGGTTTTGT
TTAGTTATTTGTTTTTGTGTTTGGTTTTGTTGGGGGGAAAGGTTTGTTTGTTGTGTGTTTTGATGTTGTTTTGGATTTGGGATGTAAGGAT
GTGATATGTGTGGGGGTGGGGTGTAAGGTTAGAGTTTGTGAGAAATAAAGAAAGAGGTGTTGAAGTTTAGATTTTTTAAGGAATGAGAAAG
GAGAAGGGTGAGGAAATGGGTGTTTAGAGGGGTGGATTGGTGTTGGGGTTTTGGTGGTGTGTGGAGGAGGGTGTGGGGAAATTGTATTATG
GTGGTTTGGGGAGATTAAGTTAGGGTTTGTTTGGGGGGGGAGTGGTGTGTTGGGGTGGAAAAAGTTGTGGGGTTTTATTTGGGTTGAGTTT
GATAGTAGGTTTTTTGGGGGTTTTTAGGGTTGGGTTGTGATTTTATTGTTTTGGTATGGGTTAGGGTTTGGGGTTTTGTTTTTTTGAGTTT
TTGTGGGGGTGGGGTGGGTGGGTGGGAGGGGTGAAGAGTGATTTAGGGATAATTGATTGTGTGAGGTGTTGATTTTATTGTTATTTTTTTT
TGGGAGAAAGGATTGTTTTAATATTTTTGTTGTGGGAGTTGTTTTAGGTTAGGAGATGGTGAGAGTGAGGTTTTAGGGGTGTGGTTTTTGT
GTTGGTGTGAGGGTGGTGGGTGTGGGTGGTGTGGGAGTAAGTGGAGAAGAGGTTTTTGGTTAGGTGTGGTGGTGGTGGTGGGTTTGGTAGT
GGTGGGAGGTGTTGGTATAGGTGGTTTAGGTATAGGAGTAGGAGGATGGTGTTTTATAAGTTGTTGGGTTTGTGGTGTTTGGTTGGTTTGA
GGTTGGTTTTGATGTATTGATGTAGGTGGGTGTGGATGTTGGATTTGTTGTGTGATGTGGGGTTGTGGTTGGTGTTGGAGATGTGGAGTAG
GGGTTTGTTGTATATATGGTGTGTGAGGAGATGGTATGTGGATGTTTTGTTGTATGGGTTTTATGTTGAGGATGTTTTGAGTTATTTGAAG
AGTGATTGGTTGTGGTAGTTGTGGTTTAAGTTTTTGTGGGTGTGGTTGTTTTTTTATTTTGATGTTTTTGATTTATTGGTGAAGTGGTTGA
TGTAGTTGTTTTATGTGAAGGATTTTGTTGTTTTATTTTAGGATGATTGGTTTGAGTTTGTTGAGTTTTTGGTTTTGTTTAGTGTGGATTT
TTTGGAGATGTTTTTTTTTTATGTTTTTGATGTGGTTGTTTATTTGGTTGATTGGTTGTTGTTTTGGGTGTAGTTTTATTTTGTGTTGTTG
GATTGGTTTTTGTAGTATGTGGAGGTTTTTTTTATTTTGATGTGGGTATGTTTATTGATTTGGAGTTTTTTTTTGATTTTTTTTTTTTTTT
GTGGGGGGGTTGGGGGTGTTTTTGATGGTGTGGGAATTTTTATATTGGTTTTTTTTTGGATGGTTTTTTTGTTGTTTTTTGTTTTGATATT
GATATTATTGTGTTGGGGTGGGTTTTGGGTTTGGAATGTTAAGTGTAAAGGAGGAGATAGGGGTGTGTAATGGGTTTTTGTGAGGTAAAG
-5′

Figure 27

"A region" sequence (SEQ ID NO: 40)

5'-
GACTCTGCAAGAAAAACCTTCCCGGTGCAATCGTGATCTGGGAGGCCCACGTATGGCGCCTCTCCAAAGGCTGCAGAA
GTTTCTTGCTAACAAAAAGTCCGCACATTCGAGCAAAGACAGGCTTTAGCGAGTTATTAAAAACTTAGGGGCGCTCTT
GTCCCCCACAGGGCCCGACCGCACACAGCAAGGCGATGGGCCCAGCTGTAAGTTGGTAGCACTGAGAACTAGCAGCGC
GCGCGGAGCCCGCTGAGACTTGAATCAATCTGGTCTAACGGTTTCCCCTAAACCGCTAGGAGCCCTCAATCGGCGGGA
CAGCAGGGCGCGGTGAGTCACCGCCGGTGACTAAGCGACCCCACCCCTCTCCCTCGGGCTTTCCTCTGCCACCGCCGT
CTCGCAACTCCCGCCGTCCGAAGCTGGACTGAGCCCGTTAGGTCCCTCGACAGAACCTCCCCTCCCCCCAACATCTCC
CCCCAAGGCAAGTCGATGGACAGAGGCGCGGGCCGGAGCAGCCCCCCTTTCCAAGCGGGCGGCGCGCGAGGCTGCGGC
GAGGCCTGAGCCCTGCGTTCCTGCGCTGTGCGCGCCCCCCAC-3'

"B region" sequence (SEQ ID NO: 41)

5′-
TCTGAGGGATTCCTTACTCTTTCCTCTTCCCGCTCCTTTGCCCGCGGGTCTCCCCGCCTGACCGCAGCCCCGAGGCCG
CCGCGCACCTCCTCCCACGCCCCTTTGGCGTGGTGCCACCGGACCCCTCTGGTTCAGTCCCAGGCGGACCCCCCCCTC
ACCGCGCGACCCCGCCTTTTTCAGCACCCCAGGGTGAGCCCAGCTCAGACTATCATCCGGAAAGCCCCCAAAAGTCCC
AGCCCAGCGCTGAAGTAACGGGACCATGCCCAGTCCCACGCCCCGGAGCAGGAAGGCTCGAGGCGCCCCCACCCCACC
CGCCCACCCTCCCCGCTTCTCGCTAGGTCCCTA-3′

"C region" sequence (SEQ ID NO: 42)

5'-
CCCTCGTTCGCCTCTTCTCCGGGAGCCAGTCCGCGCCACCGCCGCCGCCCAGGCCATCGCCACCCTCCGCAGCCATGT
CCACCAGGTCCGTGTCCTCGTCCTCCTACCGCAGGATGTTCGGCGGCCCGGGCACCGCGAGCCGGCCGAGCTCCAGCC
GGAGCTACGTGACTACGTCCACCCGCACCTACAGCCTGGGCAGCGCGCTGCGCCCCAGCACCAGCCGCAGCCTCTACG
CCTCGTCCCCGGGCGGCGTGTATGCCACGCGCTCCTCTGCCGTGCGCCTGCGGAGCAGCGTGCCCGGGGTGCGGCTCC
TGCAGGACTCGGTGGACTTCTCGCTGGCCGACGCCATCAACACCGAGTTCAAGAACAC-3'

Figure 30

"D region" sequence (SEQ ID NO: 43)

5'-
GCTTCCTGGAGCAGCAGAATAAGATCCTGCTGGCCGAGCTCGAGCAGCTCAAGGGCCAAGGCAAGTCGCGCCTAGGGG
ACCTCTACGAGGAGGAGATGCGGGAGCTGCGCCGGCAGGTGGACCAGCTAACCAACGACAAAGCCCGCGTCGAGGTGG
AGCGCGACAACCTGGCCGAGGACATCATGCGCCTCCGGGAGAAGTAAGGCTGCGCCCATGCAAGTAGCTGGGCCTCGG
GAGGGGGCTGGAGGGAGAGGGGAACGCCCCCCCGGCCCCCGCGAGAGCTGCCACGCCCTTGGGGATGTGGCCGGGGGG
AGGCCTGCCAGGGAGACAGCGGAGAGCGGGGCTGTGGCTGTGGTGGCGCAGCCCCGCCCAGAACCCAGACCTTGCAGT
TCGCATTTCCTCCTCTGTCCCCACACATTGCCCAAGGACGCT-3'

“B’ region” sequence (SEQ ID NO: 44)

5′-
TCTGAGGGATTCCTTACTCTTTCCTCTTCCCGCTCCTTTGCCCGCGGGTCTCCCCGCCTGACCGCAGCCCCGAGGCCG
CCGCGCACCTCCTCCCACGCCCCTTTGGCGTGGTGCCACCGGACCCCTCTGGTTCAGTCCCAGGCGGACCCCCCCCTC
ACCGCGCGACCCCGCCTTTTTCAGCACCCCAGGGTGAGCCCAGCTCAGACTATCATCCGGAAAGCCCCCAAAAGTCCC
AGCCCAGCGCTGAAGTAACGGGACCATGCCCAGTCCCACGCCCCGGAGCAGGAAGGCTCGAGGCGCCCCCACCCCACC
CGCCCACCCTCCCCGCTTCTCGCTAGGTCCCTATTGGCTGGGGCGCTCCGCGGCTGGGATGGCAGTGGGAGGGGACCC
TCTTTCCTAACGGGGTTATAAAAACAGCGCCCTCGGCGGGGTCCAGTCCTCTGCCACTCTCGCTCCGAGGTCCCCGCG
CCAGAGACGCAGCCGCGCTCCCACCACCCACACCCACCGCG-3′

All MS-PCR primer sets of Vimentin (Tested)

| Primer set # | Primer Name | Primer Sequence | SEQ ID NO | Locations (AL133415) | DNA length (bp) |
|---|---|---|---|---|---|
| **MSP1** | 1VIM1374MF | TTGATCGTAGTTTCGAGATCGTCGC | 14 | 57,493-57,517 | 130 |
| | 2VIM1504MR | CTAAAATACTAAAAAAAACGAAATCGCGCG | 15 | 57,594-57,623 | |
| **MSP1-2** | 1VIM1374MF | TTGATCGTAGTTTCGAGATCGTCGC | 14 | 57,493-57,517 | 132 |
| | 17VIM1506MR | CCCTAAAATACTAAAAAAAACGAAATCGCG | 18 | 57,596-57,525 | |
| **MSP2** | 5VIM1655MF(ASS) | ATCCCTATTAACTAACGCGCTCCGCG | 19 | 57,775-57,800 | 142 |
| | 6VIM1797MR(ASS) | GTTGCGTTTTTGGCGCGGGGATTTC | 20 | 57,893-57,917 | |
| **MSP3** | 9VIM1776MF | GTTTTCGCGTTAGAGACGTAGTCGC | 23 | 57,895-57,920 | 207 |
| | 10VIM1982MR | CGACTAAAACTCGACCGACTCGCGA | 24 | 58,078-58,102 | |
| **MSP5** | 13VIM1935MF(ASS) | CAAAATATTCGACGACCCGAACACCG | 27 | 58,055-58,080 | 159 |
| | 14VIM2094MR(ASS) | GGAGCGCGTGGTATATACGTCGTTC | 28 | 58,190-58214 | |
| **MSP6** | 19VIM1654MF | GGTTTTTATTGGTTGGCGCGTTTCGC | 52 | 57,774-57,799 | 138 |
| | 22VIM1792MR | GTCTCTAACGCGAAAACCTCGAAACG | 32 | 57,887-57,912 | |
| **MSP7** | 19VIM1655MF | GGTTTTTATTGGTTGGCGCGTTTCGC | 31 | 57,774-57,799 | 142 |
| | 23VIM1796MR | CTACGTCTCTAACGCGAAAACCTCGA | 33 | 57,891-57,916 | |
| **MSP8** | 19VIM1654MF | GGTTTTTATTGGTTGGCGCGTTTCGC | 52 | 57,774-57,799 | 150 |
| | 21VIM1804MR | AAACGCGACTACGTCTCTAACGCGA | 36 | 57,900-57,924 | |
| **MSP9** | 25VIM1843MF | TTCGGGAGTTAGTTCGCGTTATCGTC | 37 | 57,963-57,988 | 139 |
| | 10VIM1982MR | CGACTAAAACTCGACCGACTCGCGA | 24 | 58,078-58,102 | |
| **MSP10** | 27VIM1929MF(ASS) | CTACCGCAAAATATTCGACGACCCGA | 39 | 58,049-58,074 | 165 |
| | 14VIM2094MR(ASS) | GGAGCGCGTGGTATATACGTCGTTC | 28 | 58,190-58,214 | |
| **MSP14** | 34VIM1351MF | TTTTTGTTCGCGGGTTTTTTCGTTTGATCG | 54 | 57,470-57,498 | 153 |
| | 2VIM1504MR | CTAAAATACTAAAAAAAACGAAATCGCGCG | 15 | 57,594-57,623 | |
| **MSP15** | 34VIM1351MF | TTTTTGTTCGCGGGTTTTTTCGTTTGATCG | 54 | 57,470-57,498 | 155 |
| | 17VIM1506MR | CCCTAAAATACTAAAAAAAACGAAATCGCG | 18 | 57,596-57,625 | |
| **MSP16** | 34VIM1351MF | TTTTTGTTCGCGGGTTTTTTCGTTTCATCG | 54 | 57,470-57,498 | 153 |
| | 18VIM1504(A)MR | CTAAAATACTAAAAAAAACGAAATCGCGCGA | 55 | 57,593-57,623 | |
| **MSP17** | 35VIM1365MF | TTTTTTCGTTTCATCGTAGTTTCGAGATC | 56 | 57,484-57,512 | 139 |
| | 2VIM1504MR | CTAAAATACTAAAAAAAACGAAATCGCGCG | 15 | 57,594-57,623 | |
| **MSP18** | 35VIM1365MF | TTTTTTCGTTTGATCGTAGTTTCGAGATC | 56 | 57,484-57,512 | 141 |
| | 17VIM1506MR | CCCTAAAATACTAAAAAAAACGAAATCGCG | 18 | 57,596-57,625 | |
| **MSP19** | 35VIM1365MF | TTTTTTCGTTTGATCGTAGTTTCGAGGTC | 56 | 57,484-57,512 | 139 |
| | 18VIM1504(A)MR | CTAAAATACTAAAAAAAACGAAATCGCGCGA | 55 | 57,593-57,623 | |
| **MSP20** | 36VIM1754MF | TTTTTGTTATTTTCGTTTCGAGGTTTTCGC | 57 | 57,874-57,903 | 95 |
| | 38VIM1849AMR | TCCCGAAAAAAAAACGAACGAAAACGCGA | 58 | 57,941-57,969 | |
| **MSP21** | 36VIM1754MF | TTTTTGTTATTTTCGTTTCGAGGTTTTCGC | 57 | 57,874-57,903 | 95 |
| | 39VIM1849MR | TCCCGAAAAAAAAACGAACGAAAACGCG | 59 | 57,942-57,969 | |
| **MSP22** | 36VIM1754MF | TTTTTGTTATTTTCGTTTCGAGGTTTTCGC | 57 | 57,874-57,903 | 128 |
| | 40VIM1882AMR | ATAACCTAAACGACGACGATAACGCGA | 60 | 57,976-58,002 | |
| **MSP23** | 36VIM1754MF | TTTTTGTTATTTTCGTTTCGAGGTTTTCGC | 57 | 57,874-57,903 | 128 |
| | 41VIM1882MR | ATAACCTAAACGACGACGATAACGCG | 61 | 57,977-58,002 | |
| **MSP24** | 36VIM1754MF | TTTTTGTTATTTTCGTTTCGAGGTTTTCGC | 57 | 57,874-57,903 | 228 |
| | 10VIM1982MR | CGACTAAAACTCGACCGACTCGCGA | 24 | 58,078-58,102 | |
| **MSP25** | 37VIM1766MF | TCGTTTCGAGGTTTTCGCGTTAGAGAC | 62 | 57,886-57,912 | 83 |
| | 38VIM1849AMR | TCCCGAAAAAAAAACGAACGAAAACGCGA | 58 | 57,941-57,969 | |
| **MSP26** | 37VIM1766MF | TCGTTTCGAGGTTTTCGCGTTAGAGAC | 62 | 57,886-57,912 | 83 |
| | 39VIM1849MR | TCCCGAAAAAAAAACGAACGAAAACGCG | 59 | 57,942-57,969 | |
| **MSP27** | 37VIM1766MF | TCGTTTCGAGGTTTTCGCGTTAGAGAC | 62 | 57,886-57,912 | 116 |

FIG. 35B

| Primer set # | Primer Name | Primer Sequence | Sequence # | Locations (AL133415) | DNA length (bp) |
|---|---|---|---|---|---|
| | 40VIM1882AMR | ATAACCTAAACGACGACGATAACGCGA | 60 | 57,976-58,002 | |
| MSP28 | 37VIM1766MF | TCGTTTCGAGGTTTTCGCGTTAGAGAC | 62 | 57,887-57,912 | 116 |
| | 41VIM1882MR | ATAACCTAAACGACGACGATAACGCG | 61 | 57,977-58,002 | |
| MSP29 | 37VIM1766MF | TCGTTTCGAGGTTTTCGCGTTAGAGAC | 62 | 57,886-57,912 | 216 |
| | 10VIM1982MR | CGACTAAAACTCGACCGACTCGCGA | 63 | 58,078-58,102 | |
| MSP30 | 9VIM1776MF | GTTTTCGCGTTAGAGACGTAGTCGC | 23 | 57,895-57,920 | 73 |
| | 38VIM1849AMR | TCCCGAAAAAAAAACGAACGAAAACGCGA | 58 | 57,941-57,969 | |
| MSP31 | 9VIM1776MF | GTTTTCGCGTTAGAGACGTAGTCGC | 23 | 57,895-57,920 | 73 |
| | 39VIM1849MR | TCCCGAAAAAAAAACGAACGAAAACGCG | 59 | 57,942-57,969 | |
| MSP32 | 9VIM1776MF | GTTTTCGCGTTAGAGACGTAGTCGC | 23 | 57,895-57,920 | 106 |
| | 40VIM1882AMR | ATAACCTAAACGACGACGATAACGCGA | 60 | 57,976-58,002 | |
| MSP33 | 9VIM1776MF | GTTTTCGCGTTAGAGACGTAGTCGC | 23 | 57,895-57,920 | 106 |
| | 41VIM1882MR | ATAACCTAAACGACGACGATAACGCG | 61 | 57,977-58,002 | |
| MSP34 | 9VIM1776MF | GTTTTCGCGTTAGAGACGTAGTCGC | 23 | 57,895-57,920 | 207 |
| | 10VIM1982MR | CGACTAAAACTCGACCGACTCGCGA | 63 | 58,078-58,102 | |
| MSP35 | 13VIM1935MF(ASS) | CAAAATATTCGACGACCCGAACACCG | 27 | 58,055-58,080 | 164 |
| | 44VIM58219MR(ASS) | GTAGAGGAGCGCGTGGTATATACGTC | 64 | 58,194-58,219 | |
| MSP36 | 13VIM1935MF(ASS) | CAAAATATTCGACGACCCGAACACCG | 27 | 58,055-58,080 | 191 |
| | 45VIM58246MR(ASS) | TCGGGTACGTTGTTTCGTAGGCGTAC | 65 | 58,221-58246 | |
| MSP37 | 27VIM1929MF(ASS) | CTACCGCAAAATATTCGACGACCCGA | 39 | 58,049-58,074 | 170 |
| | 44VIM58219MR(ASS) | GTAGAGGAGCGCGTGGTATATACGTC | 64 | 58,194-58,219 | |
| MSP38 | 27VIM1929MF(ASS) | CTACCGCAAAATATTCGACGACCCGA | 39 | 58,049-58,074 | 197 |
| | 45VIM58246MR(ASS) | TCGGGTACGTTGTTTCGTAGGCGTAC | 65 | 58,221-58,246 | |
| MSP39 | 42VIM58066MF(ASS) | ACGACCCGAACACCGCGAACCGA | 66 | 58,066-58,088 | 153 |
| | 44VIM58219MR(ASS) | GTAGAGGAGCGCGTGGTATATACGTC | 64 | 58,194-58,219 | |
| MSP40 | 42VIM58066MF(ASS) | ACGACCCGAACACCGCGAACCGA | 66 | 58,066-58,088 | 180 |
| | 45VIM58246MR(ASS) | TCGGGTACGTTGTTTCGTAGGCGTAC | 65 | 58,221-58,246 | |
| MSP41 | 42VIM58066MF(ASS) | ACGACCCGAACACCGCGAACCGA | 66 | 58,066-58,088 | 148 |
| | 14VIM2094MR(ASS) | GGAGCGCGTGGTATATACGTCGTTC | 28 | 58,190-58,214 | |
| MSP42 | 43VIM58069MF(ASS) | ACCCGAACACCGCGAACCGACCG | 67 | 58,069-58,091 | 150 |
| | 44VIM58219MR(ASS) | GTAGAGGAGCGCGTGGTATATACGTC | 64 | 58,194-58,219 | |
| MSP43 | 43VIM58069MF(ASS) | ACCCGAACACCGCGAACCGACCG | 67 | 58,069-58,091 | 177 |
| | 45VIM58246MR(ASS) | TCGGGTACGTTGTTTCGTAGGCGTAC | 65 | 58,221-58,246 | |
| MSP44 | 43VIM58069MF(ASS) | ACCCGAACACCGCGAACCGACCG | 67 | 58,069-58,091 | 145 |
| | 14VIM2094MR(ASS) | GGAGCGCGTGGTATATACGTCGTTC | 28 | 58,190-58,214 | |
| MSP45 | 46VIM58068MF | GGTTCGGGTATCGCGAGTCGGTC | 68 | 58,068-58,090 | 134 |
| | 48VIM58202MR | ATACACGCCGCCCGAAAACGAAACG | 69 | 58,178-58,202 | |
| MSP46 | 46VIM58068MF | GGTTCGGGTATCGCGAGTCGGTC | 68 | 58,068-58,090 | 164 |
| | 49VIM58232MR | CCGCAAACGCACGACAAAAAAACGCG | 70 | 58,207-58,232 | |
| MSP47 | 46VIM58068MF | GGTTCGGGTATCGCGAGTCGGTC | 68 | 58,068-58,090 | 175 |
| | 50VIM58243MR | AACACGCTACTCCGCAAACGCACGA | 71 | 58,219-58,243 | |
| MSP48 | 47VIM58076MF | TATCGCGAGTCGGTCGAGTTTTAGTC | 72 | 58,076-58,101 | 126 |
| | 48VIM58202MR | ATACACGCCGCCCGAAAACGAAACG | 69 | 58,178-58,202 | |
| MSP49 | 47VIM58076MF | TATCGCGAGTCGGTCGAGTTTTAGTC | 72 | 58,076-58,101 | 156 |
| | 49VIM58232MR | CCGCAAACGCACGACAAAAAAACGCG | 70 | 58,207-58,232 | 167 |
| MSP50 | 47VIM58076MF | TATCGCGAGTCGGTCGAGTTTTAGTC | 72 | 58,076-58,101 | 167 |
| | 50VIM58243MR | AACACGCTACTCCGCAAACGCACGA | 71 | 58,219-58,243 | |

"SPECIFICITY TEST (SpT-45, 90)" & Phase II "SENSITIVIT TEST (SeTII-45)" for Vimentin SpT-38 and SeT I studies of Vimentin on "testing set" samples (Normal/Tumor pairs, Adenomas and all cell lines)

SpT-38 and SeT I studies of Vimentin on "testing set" samples (Colon cancer cell lines, N.C.N, et al.)

Technical sensitivity studies of Vimentin

Sensitivity studies of Vimentin on "testing set" samples (Normal/Tumor pairs only)

CELL LINES

| NO. | Cell Lines | H-MSP5 | FF1-Sol. No. | V-MSP29 | V-MSP47 | V-MSP50 |
|---|---|---|---|---|---|---|
| 4 | RCA | M | 6001A | M | M | M |
| 5 | V8 | M | 1179B | M | M | M |
| 6 | V457 | M | 5553 | | | |
| 7 | SW48 | M | 4913 | M | M | M |
| 8 | V5-NT | M | 5878 | M | M | M |
| 10 | V6-NT | M | 1178B | M | M | M |
| 12 | V432-NT | M | 5505 | M | M | M |
| 14 | AN3CA-NT | M&U | 6279A | | | |
| 16 | RKO-NT | M | 7708A | M | M | M |
| 18 | SW480-NT | M | 926B | | | |
| 20 | V241 | U | 6003A | M | M | M |
| 21 | V400 | U | 7976 | M | M | M |
| 22 | V576 | M&U | 7538 | M | M | M |
| 23 | V503 | U | 8000 | M | M | M |
| 24 | V429 | U | 8016 | M | M | M |
| 25 | V410 | U | 7234 | M | M | M |
| 26 | 9P | U | 1180A | | M | M |
| 27 | 9M | U | 4064 | M | | |
| 28 | V206 | U | 7351? | | M | M |
| 29 | V364 | U | 3302 | | | |
| 30 | V394 | U | 6073A | M | | |
| 31 | V425 | M&U | 7236 | M | M | M |
| 32 | V451 | U | 5509 | M | M | M |
| 33 | 10M | U | 1181B | M | M | M |
| 34 | V441 | U | 2302 | M | M | M |
| 35 | V389 | U | 5600 | M | M | M |
| 36 | V456 | U | 6075 | M | M | M |

FIG. 44A

N/T PAIRS

| NO. | Name | H-Sol. No. | FF1-Sol. No. | V-MSP29 | V-MSP47 | V-MSP50 | H-MSP5 |
|---|---|---|---|---|---|---|---|
| 2 | 15-18T | 1188A | 1188A | M | M | M | U |
| 4 | 16-14T | 1949 | 1949 | | | | U |
| 6 | 19-11T | 1203 | 1203 | | | | U |
| 8 | 22-19T | 1921 | 1921 | | | | M & U |
| 10 | 529T | 2290 | 2290 | M | M | M | M & U |
| 12 | 23-21T | 1947 | 1947 | M | M | M | U |
| 14 | 25-14T | 1923 | 1923 | M | M | M | U |
| 16 | 37-10T | 1814 | 1814 | | | | M & U |
| 18 | 406T | 1776 | 1776 | M | M | M | U |
| 20 | 421T | 1860 | 1860 | M | M | M | U |
| 22 | 587T | 2438 | 2438 | | | | U |
| 25 | 24-17T | 1919 | 1919 | M | M | M | M & U |
| 27 | 578T | 2411 | 2411 | M | M | M | M & U |
| 29 | 610T | 2529 | 2529 | M | M | M | U |
| 31 | 621T | 2577 | 2577 | M | M | M | M & U |
| 33 | 635T | 2797 | 2797 | M | M | M | M & U |
| 35 | 2447E(T) | 4054 | 4054 | M | M | M | M & U |
| 37 | 3003D(T) | 4555A | 4555A | M | M | M | U |
| 39 | 2632D(T) | 4124 | 4124 | M | M | M | M & U |
| 41 | 2546E(T) | 4039 | 4039 | M | M | M | U |
| 43 | 3265D(T) | 4892 | 4892 | M | M | M | M & U |
| 45 | 16-25T | 1193 | 1193 | M | M | M | U |
| 47 | 17-19T | 1196 | 1197 | M | M | M | U |
| 49 | 17-29T | 1199 | 1199 | M | M | M | U |
| 51 | 17-39T | 1201 | 1201 | M | M | M | M & U |
| 53 | 21-21T | 1951 | 1951 | M | M | M | M & U |

FIG. 44B

COLON ADENOMA SAMPLES

| NO. | Samples | H-Sol.# | H-MSP5 | V-MSP29 | V-MSP47 | V-MSP50 |
|---|---|---|---|---|---|---|
| 1 | 14-16P | 7626 | U | M | M | M |
| 2 | 14-25P | 1186a | U | M | M | M |
| 3 | 23-6P | 7627 | M & U | M | M | M |
| 4 | 24-23P | 7497 | U | | | M |
| 5 | 28-3P | 6917 | U | M | M | M |
| 6 | 453P | 2026 | U | | M | M |
| 7 | 461P | 2356 | U | M | | |
| 8 | 431P | 1902 | U | M | M | M |
| 9 | 493P | 2178 | U | M | M | M |
| 10 | 418P | 1835 | U | M | M | M |
| 11 | 400 4696P | 7266 | U | | | |
| 12 | 400 4828P | 7268 | U | | | |
| 13 | 400 5426P | 7270 | U | | | |
| | | | | 8/13(62%) | 8/13(62%) | 9/13(69%) |

FIG. 44C

Figure 44D:
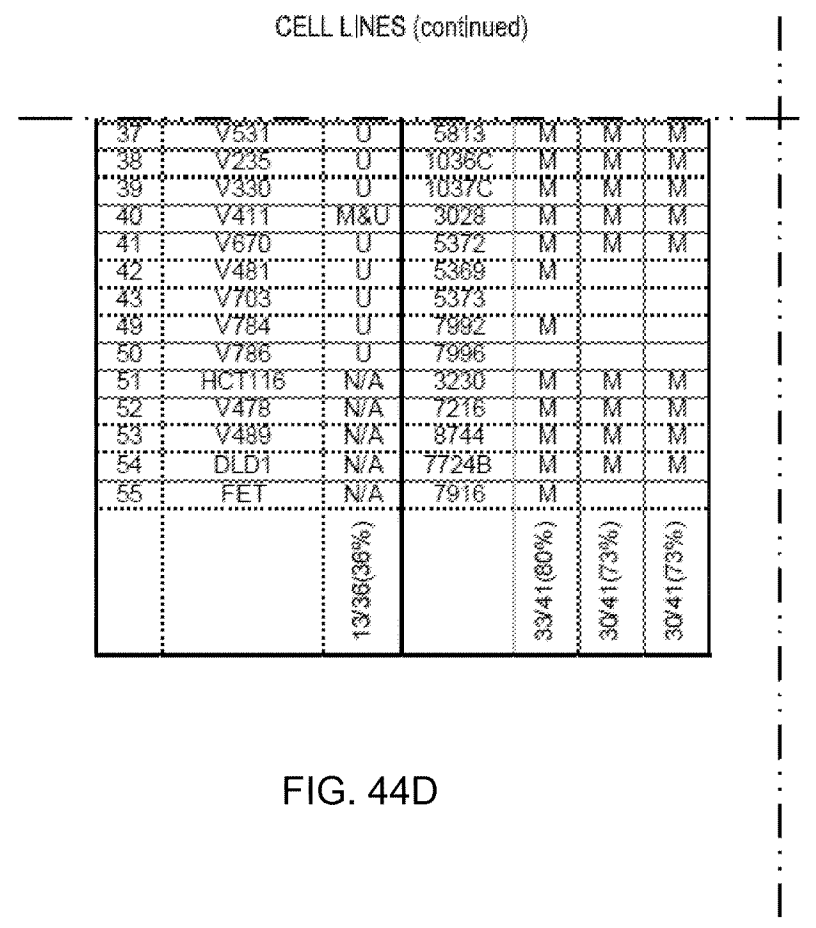

CELL LINES (continued)

| | | | | | | |
|---|---|---|---|---|---|---|
| 37 | V531 | U | 5813 | M | M | M |
| 38 | V235 | U | 1036C | M | M | M |
| 39 | V330 | U | 1037C | M | M | M |
| 40 | V411 | M&U | 3028 | M | M | M |
| 41 | V670 | U | 5372 | M | M | M |
| 42 | V481 | U | 5369 | M | | |
| 43 | V703 | U | 5373 | | | |
| 49 | V784 | U | 7992 | M | | |
| 50 | V786 | U | 7996 | | | |
| 51 | HCT116 | N/A | 3230 | M | M | M |
| 52 | V478 | N/A | 7216 | M | M | M |
| 53 | V489 | N/A | 8744 | M | M | M |
| 54 | DLD1 | N/A | 7724B | M | M | M |
| 55 | FET | N/A | 7916 | M | | |
| | | 13/36(36%) | | 33/41(80%) | 30/41(73%) | 30/41(73%) |

Vimentin Genetic-Sense Strand:
A Differentially Methylated Region (DMR)

"NCBI (AL133415)-57,427-58,326". (SEQ ID NO: 45)

5'-
GACTTCAGATCTGAGGGATTCCTTACTCTTTCCTCTTCCCGCTCCTTTGCCCGCGGGTCTCCCCGCCTGACCGCAGCCCCGAGACCGCCGC
GCACCTCCTCCCACGCCCCTTTGGCGTGGTGCCACCGGACCCCTCTGGTTCAGTCCCAGGCGGACCCCCCCCTCACCGCGCGACCCCGCCT
TTTTCAGCACCCCAGGGTGAGCCCAGCTCAGACTATCATCCGGAAAGCCCCCAAAAGTCCCAGCCCAGCGCTGAAGTAACGGGACCATGCC
CAGTCCCAGGCCCCGGAGCAGGAAGGCTCGAGGGCGCCCCCACCCCACCCGCCCACCCTCCCCGCTTCTCGCTAGGTCCCTATTGGCTGGC
GCGCTCCGCGGCTGGGATGGCAGTGGGAGGGGACCCTCTTTCCTAACGGGGTTATAAAAACAGCGCCCTCGGCGGGGTCCAGTCCTCTGCC
ACTCTCGCTCCGAGGTCCCCGCGCCAGAGACGCAGCCGCGCTCCCACCACCCACACCCACCGCGCCCTCGTTCGCCTCTTCTCCGGGAGCC
AGTCCGCGCCACCGCCGCCGCCCAGGCCATCGCCACCCTCCGCAGCCATGTCCACCAGGTCCGTGTCCTCGTCCTCCTACCGCAGGATGTT
CGGCGGCCCGGGCACCGCGAGCCGGCCGAGCTCCAGCCGGAGCTACGTGACTACGTCCACCCGCACCTACAGCCTGGGCAGCGCGCTGCGC
CCCAGCACCAGCCGCAGCCTCTACGCCTCGTCCCCGGGCGGCGTGTATGCCACGCGCTCCTCTGCCGTGCGCCTGCGGAGCAGCGTGCCCG
GGGTGCGGCTCCTGCAGGACTCGGTGGACTTCTCGCTGGCCGACGCCATCAACACCGAGTTCAAGAACACCCGCACCAACG
-3'

Figure 46

Vimentin Genetic-Sense Strand (Bisulfite Converted/Methylated)
A Differentially Methylated Region (DMR)

"NCBI (AL133415)-57,427-58,326". (SEQ ID NO: 46)

5′-
ATTTTAGATTTGAGGGATTTTTTATTTTTTTTTTTTTCGTTTTTTTGTTCGCGGGTTTTTTCGTTTGATCGTAGTTTCGAGATCGTCGCG
TATTTTTTTTTACGTTTTTTTGGCGTGGTGTTATCGGATTTTTTTGGTTTAGTTTTAGGCGGATTTTTTTTTATCGCGCGATTTCGTTTT
TTTTAGTATTTTAGGGTGAGTTTAGTTTAGATTATTATTCGGAAAGTTTTTAAAAGTTTTAGTTTAGCGTTGAAGTAACGGGATTATGTTT
AGTTTTAGGTTTCGGAGTAGGAAGGTTCGAGGGCGTTTTTATTTTATTCGTTTATTTTTTTCGTTTTTCGTTAGGTTTTTATTGGTTGGCG
CGTTTCGCGGTTGGGATGGTAGTGGGAGGGGATTTTTTTTTTAACGGGGTTATAAAAATAGCGTTTTCGGCGGGGTTTAGTTTTTGTTA
TTTTCGTTTCGAGGTTTTCGCGTTAGAGACGTAGTCGCGTTTTTATTATTTATATTTATCGCGTTTTCGTTCGTTTTTTTTTCGGGAGTTA
GTTCGCGTTATCGTCGTCGTTTAGGTTATCGTTATTTTTCGTAGTTATGTTTATTAGGTTCGTGTTTTCGTTTTTTTATCGTAGGATGTTC
GGCGGTTCGGGTATCGCGAGTCGGTCGAGTTTTAGTCGGAGTTACGTGATTACGTTTATTCGTATTTATAGTTTGGGTAGCGCGTTGCGTT
TTAGTATTAGTCGTAGTTTTTACGTTTCGTTTTCGGGCGGCGTGTATGTTACGCGTTTTTTTGTCGTGCGTTTGCGGAGTAGCGTGTTCGG
GGTGCGGTTTTTGTAGGATTCGGTGGATTTTTCGTTGGTCGACGTTATTAATATCGAGTTTAAGAATATTCGTATTAACG
-3′

Figure 47

Vimentin Genetic-Sense Strand (Bisulfite Converted/Unmethylated)
A Differentially Methylated Region (DMR)

"NCBI (AL133415)-57,427-58,326". (SEQ ID NO: 47)

5'-
ATTTTAGATTTGAGGGATTTTTTATTTTTTTTTTTTTTGTTTTTTTGTTTGTGGGTTTTTTTGTTTGATTGTAGTTTTGAGATTGTTGTG
TATTTTTTTTTATGTTTTTTTGGTGTGGTGTTATTGGATTTTTTTGGTTTAGTTTTAGGTGGATTTTTTTTTTATTGTGTGATTTTGTTTT
TTTTAGTATTTTAGGGTGAGTTTAGTTTAGATTATTATTTGGAAAGTTTTTAAAAGTTTTAGTTTAGTGTTGAAGTAATGGGATTATGTTT
AGTTTTAGGTTTTGGAGTAGGAAGGTTTGAGGGTGTTTTTATTTTATTTGTTTATTTTTTTTGTTTTTTGTTAGGTTTTTATTGGTTGGTG
TGTTTTGTGGTTGGGATGGTAGTGGGAGGGGATTTTTTTTTTAATGGGGTTATAAAAATAGTGTTTTTGGTGGGGTTTAGTTTTTTGTTA
TTTTTGTTTTGAGGTTTTTGTGTTAGAGATGTAGTTGTGTTTTTATTATTTATATTTATTGTGTTTTTGTTTGTTTTTTTTTTGGGAGTTA
GTTTGTGTTATTGTTGTTGTTTAGGTTATTGTTATTTTTTGTAGTTATGTTTATTAGGTTTGTGTTTTTGTTTTTTTATTGTAGGATGTTT
GGTGGTTTGGGTATTGTGAGTTGGTTGAGTTTTAGTTGGAGTTATGTGATTATGTTTATTTGTATTTATAGTTTGGGTAGTGTGTTGTGTT
TTAGTATTAGTTGTAGTTTTTATGTTTTGTTTTTGGGTGGTGTGTATGTTATGTGTTTTTTTGTTGTGTGTTTGTGGAGTAGTGTGTTTGG
GGTGTGGTTTTTGTAGGATTTGGTGGATTTTTTGTTGGTTGATGTTATTAATATTGAGTTTAAGAATATTTGTATTAATG
-3'

Figure 48

Vimentin Genetic-Antisense Strand
A Differentially Methylated Region (DMR)

"NCBI (AL133415)-57,427-58,326". (SEQ ID NO: 48)

3′-
CTGAAGTCTAGACTCCCTAAGGAATGAGAAAGGAGAAGGGCGAGGAAACGGGCGCCCAGAGGGGCGGACTGGCGTCGGGGCTCTGGCGGCG
CGTGGAGGAGGGTGCGGGGAAACCGCACCACGGTGGCCTGGGGAGACCAAGTCAGGGTCCGCCTGGGGGGGGAGTGGCGCGCTGGGGCGGA
AAAAGTCGTGGGGTCCCACTCGGGTCGAGTCTGATAGTAGGCCTTTCGGGGGTTTTCAGGGTCGGGTCGCGACTTCATTGCCCTGGTACGG
GTCAGGGTCCGGGGCCTCGTCCTTCCGAGCTCCCGCGGGGGTGGGGTGGGCGGGTGGGAGGGGCGAAGAGCGATCCAGGGATAACCGACCG
CGCGAGGCGCCGACCCTACCGTCACCCTCCCCTGGGAGAAAGGATTGCCCCAATATTTTTGTCGCGGGAGCCGCCCCAGGTCAGGAGACGG
TGAGAGCGAGGCTCCAGGGGCGCGGTCTCTGCGTCGGCGCGAGGGTGGTGGGTGTGGGTGGCGCGGGAGCAAGCGGAGAAGAGGCCCTCGG
TCAGGCGCGGTGGCGGCGGCGGGTCCGGTAGCGGTGGGAGGCGTCGGTACAGGTGGTCCAGGCACAGGAGCAGGAGGATGGCGTCCTACAA
GCCGCCGGGCCCGTGGCGCTCGGCCGGCTCGAGGTCGGCCTCGATGCACTGATGCAGGTGGGCGTGGATGTCGGACCCGTCGCGCGACGCG
GGGTCGTGGTCGGCGTCGGAGATGCGGAGCAGGGGCCCGCCGCACATACGGTGCGCGAGGAGACGGCACGCGGACGCCTCGTCGCACGGGC
CCCACGCCGAGGACGTCCTGAGCCACCTGAAGAGCGACCGGCTGCGGTAGTTGTGGCTCAAGTTCTTGTGGGCGTGGTTGC
-5′

Figure 49

Vimentin Genetic-Antisense Strand (Bisulfite Converted/Methylated)
A Differentially Methylated Region (DMR)

"NCBI (AL133415)-57,427-58,326". (SEQ ID NO: 49)

3'-
TGAAGTTTAGATTTTTTAAGGAATGAGAAAGGAGAAGGGCGAGGAAATGGGCGCTTAGAGGGGCGGATTGGCGTTGGGGCTTTGGCGGCGC
GTGGAGGAGGGTGCGGGGAAATTGCATTATGGTGGCTTGGGGAGATTAAGTTAGGGTTTGCTTGGGGGGGAGTGGCGCGCTGGGGCGGAA
AAAGTTGTGGGGTTTTATTTGGGTTGAGTTTGATAGTAGGCTTTTTGGGGGTTTTTAGGGTTGGGTTGCGATTTTATTGCTTTGGTATGGG
TTAGGGTTTGGGGCTTTGTTTTTTTGAGCTTTTGCGGGGGTGGGGTGGGCGGGTGGGAGGGGCGAAGAGCGATTTAGGGATAATTGATTGC
GCGAGGCGCTGATTTTATTGTTATTTTTTTTTGGGAGAAAGGATTGCTTTAATATTTTTGTTGCGGGAGCTGCTTTAGGTTAGGAGATGGT
GAGAGCGAGGCTTTAGGGGCGCGGTTTTTGCGTTGGCGCGAGGGTGGTGGGTGTGGGTGGCGCGGGAGCAAGCGGAGAAGAGGCTTTTGGT
TAGGCGCGGTGGCGGCGGCGGGTTTGGTAGCGGTGGGAGGCGTTGGTATAGGTGGTTTAGGCATAGGAGCAGGAGGATGGCGTTTTATAAG
CTGCTGGGCTTGTGGCGCTTGGCTGGCTTGAGGTTGGCTTTGATGCATTGATGCAGGTGGGCGTGGATGTTGGATTTGTTGCGCGATGCGG
GGTTGTGGTTGGCGTTGGAGATGCGGAGCAGGGGCTTGCTGCATATATGGTGCGCGAGGAGATGGCATGCGGATGCTTTGTTGCATGGGCT
TTATGCTGAGGATGTTTTGAGCTATTTGAAGAGCGATTGGCTGCGGTAGTTGTGGCTTAAGTTTTTGTGGGCGTGGTTGC
-5'

Figure 50

Vimentin Genetic-Antisense Strand (Bisulfite Converted/Unmethylated)
A Differentially Methylated Region (DMR)

"NCBI (AL133415)-57,427-58,326". (SEQ ID NO: 50)

3'-
TGAAGTTTAGATTTTTTAAGGAATGAGAAAGGAGAAGGGTGAGGAAATGGGTGTTTAGAGGGGTGGATTGGTGTTGGGGTTTTGGTGGTGT
GTGGAGGAGGGTGTGGGGAAATTGTATTATGGTGGTTTGGGGAGATTAAGTTAGGGTTTGTTTGGGGGGGAGTGGTGTGTTGGGGTGGAA
AAAGTTGTGGGGTTTTATTTGGGTTGAGTTTGATAGTAGGTTTTTTGGGGGTTTTTAGGGTTGGGTTGTGATTTTATTGTTTTGGTATGGG
TTAGGGTTTGGGGTTTTGTTTTTTTGAGTTTTGTGGGGGTGGGGTGGGTGGGTGGGAGGGGTGAAGAGTGATTTAGGGATAATTGATTGT
GTGAGGTGTTGATTTTATTGTTATTTTTTTTTGGGAGAAÀGGATTGTTTTAATATTTTTGTTGTGGGAGTTGTTTTAGGTTAGGAGATGGT
GAGAGTGAGGTTTTAGGGGTGTGGTTTTTGTGTTGGTGTGAGGGTGGTGGGTGTGGGTGGTGTGGGAGTAAGTGGAGAAGAGGTTTTTGGT
TAGGTGTGGTGGTGGTGGTGGGTTTGGTAGTGGTGGGAGGTGTTGGTATAGGTGGTTTAGGTATAGGAGTAGGAGGATGGTGTTTTATAAG
TTGTTGGGTTTGTGGTGTTTGGTTGGTTTGAGGTTGGTTTTGATGTATTGATGTAGGTGGGTGTGGATGTTGGATTTGTTGTGTGATGTGG
GGTTGTGGTTGGTGTTGGAGATGTGGAGTAGGGGTTTGTTGTATATATGGTGTGTGAGGAGATGGTATGTGGATGTTTTGTTGTATGGGTT
TTATGTTGAGGATGTTTTGAGTTATTTGAAGAGTGATTGGTTGTGGTAGTTGTGGTTTAAGTTTTTGTGGGTGTGGTTGT
-5'

METHODS AND COMPOSITIONS FOR DETECTING GASTROINTESTINAL AND OTHER CANCERS

CROSS-REFERENCE TO RELATED APPLICATIONS

This application is a continuation of U.S. application Ser. No. 13/167,670, filed Jun. 23, 2011, now U.S. Pat. No. 8,415,100, which is a continuation-in-part of U.S. application Ser. No. 13/105,588, filed May 11, 2011, now U.S. Pat. No. 8,221,977, which is a continuation of U.S. application Ser. No. 12/322,202, filed Jan. 30, 2009, now U.S. Pat. No. 7,964,353, which is a continuation of U.S. application Ser. No. 10/920,119, filed on Aug. 16, 2004, now U.S. Pat. No. 7,485,420, which claims the benefit of priority of U.S. Provisional Application No. 60/495,064, filed on Aug. 14, 2003. The specifications of each of the foregoing applications are incorporated herein by reference in their entirety.

FUNDING

Work described herein was supported by National Institutes of Health Grant R01CA 67409, and U01CA88130 and U01CA15275. The United States Government has certain rights in the invention.

SEQUENCE LISTING

The instant application contains a Sequence Listing which has been submitted via EFS-Web and is hereby incorporated by reference in its entirety. Said ASCII copy, created on Nov. 6, 2012, is named CWRUP06020_Seq.txt, and is 52,996 bytes in size.

BACKGROUND

In 2001, over 1.2 million new cases of human cancer will be diagnosed and over 0.5 million people will die from cancer (American Cancer Society estimate). Despite this, more people than ever are living with and surviving cancer. In 1997, for example, approximately 8.9 million living Americans had a history of cancer (National Cancer Institute estimate). People are more likely to survive cancer if the disease is diagnosed at an early stage of development, since treatment at that time is more likely to be successful. Early detection depends upon availability of high-quality methods. Such methods are also useful for determining patient prognosis, selecting therapy, monitoring response to therapy and selecting patients for additional therapy. Consequently, there is a need for cancer diagnostic methods that are specific, accurate, minimally invasive, technically simple and inexpensive.

Gastrointestinal cancers affect millions of patients per year. For example, over 15,000 new cases of esophageal cancer were diagnosed in 2010, and there were nearly as many deaths from this cancer alone. Similarly, about 21,000 new cases of stomach cancer were diagnosed in 2010, and over 10,000 deaths resulted from stomach cancer. The occurrence of colorectal cancer (i.e., cancer of the colon or rectum) is even higher. Approximately 40% of individuals with colorectal cancer die. In 2011, it is estimated that there will be over 141,000 new cases of colorectal cancer (101,700 cases of colon and 39,510 cases of rectal cancer) and about 50,000 deaths (all statistics: American Cancer Society). As with other cancers, these rates can be decreased by improved methods for diagnosis. Although methods for detecting each type of cancer exist, the methods are not ideal. Generally, a combination of endoscopy, isolation of cells (for example, via collection of cells/tissues from a fluid sample or from a tissue sample), and/or imaging technologies are used to identify cancerous cells and tumors. There are also a variety of tests conducted for each specific cancer, but these have limitations. For example, colon cancer may be detected with digital rectal exams (i.e., manual probing of rectum by a physician), which are relatively inexpensive, but are unpleasant and can be inaccurate. Fecal occult blood testing (i.e., detection of blood in stool) is nonspecific because blood in the stool has multiple causes. Colonoscopy and sigmoidoscopy (i.e., direct examination of the colon with a flexible viewing instrument) are both uncomfortable for the patient and expensive. Double-contrast barium enema (i.e., taking X-rays of barium-filled colon) is also an expensive procedure, usually performed by a radiologist. Upper endoscopy, an examination of the esophagus, stomach and duodenum, usually performed by a gastroenterologist, can detect neoplasias of these organs, but is also an uncomfortable and expensive procedure.

Because of the disadvantages of existing methods for detecting or treating cancers, new methods are needed for cancer diagnosis and therapy.

SUMMARY OF THE INVENTION

In certain aspects, the present invention is based in part on Applicants' discovery of a particular human genomic DNA region in which the cytosines within CpG dinucleotides are differentially methylated in tissues from human cancers (e.g., upper gastrointestinal cancer, lower gastrointestinal cancer, pancreatic cancer, bladder cancer, and/or cancers associated with the digestive system or other organs) and unmethylated in normal human tissues. The region is referred to hereinafter as the "vimentin-methylation target regions" (e.g., SEQ ID NO: 45 in FIG. 45). The present methods are also based in part on Applicants' discovery that the levels of vimentin transcript in tissues from human cancers are lower than the levels of vimentin transcript in normal tissues.

In one embodiment, the method comprises assaying for the presence of differentially methylated vimentin nucleotide sequences (e.g., in the vimentin methylation target region) in a tissue sample or a bodily fluid sample from a subject. Tissue sample may be obtained from biopsies of the gastrointestinal tract, including but not limited to the esophagus, stomach, duodenum, rectum, colon, and terminal ileum. Tissue samples may also be obtained from biopsies of the bladder and/or pancreas. Tissue samples may be obtained as a biopsy, or as a swab or brushing of the gastrointestinal tract (e.g., colon, stomach or esophagus), bladder, pancreas, or other organs believed to contain cancerous cells or tissues). Preferred bodily fluids include blood, serum, plasma, a blood-derived fraction, stool, colonic effluent, or urine. In one embodiment, the method involves restriction enzyme/methylation-sensitive PCR. In another embodiment, the method comprises reacting DNA from the sample with a chemical compound that converts non-methylated cytosine bases (also called "conversion-sensitive" cytosines), but not methylated cytosine bases, to a different nucleotide base. In a preferred embodiment, the chemical compound is sodium bisulfite, which converts unmethylated cytosine bases to uracil. The compound-converted DNA is then amplified using a methylation-sensitive polymerase chain reaction (MSP) employing primers that amplify the compound-converted DNA template if cytosine bases within CpG dinucleotides of the DNA from the sample are methylated. Production of a PCR product indicates that the subject has cancer or precancerous adenomas. Other methods for assaying for the presence of methylated DNA are known in the art.

In another embodiment, the method comprises assaying for decreased levels of a vimentin transcript in the sample. Examples of such assays include RT-PCR assays which employ primers that derived from the coding sequence of vimentin. The vimentin cDNA sequence can be found, for example, in NCBI Accession No. NM_003380.

In another embodiment, the present invention provides a detection method for prognosis of a cancer (e.g., upper or lower gastrointestinal cancer) in a subject known to have or suspected of having cancer. Such method comprises assaying for the presence of methylated vimentin DNA (e.g., in the vimentin methylation target region) in a tissue sample or bodily fluid from the subject. In certain cases, it is expected that detection of methylated vimentin DNA in a blood fraction is indicative of an advanced state of cancer (e.g., gastrointestinal cancer such as colon cancer, esophagus cancer, gastric cancer, pancreatic cancer, or bladder cancer). In other cases, detection of methylated vimentin DNA in a tissue or stool derived sample or sample from other bodily fluids may be indicative of a cancer that will respond to therapeutic agents that demethylate DNA or reactivate expression of the vimentin gene.

In another embodiment, the present invention provides a method for monitoring over time the status of cancer (e.g., gastrointestinal cancer such as colon cancer, esophagus cancer, gastric cancer, pancreatic cancer, or bladder cancer) in a subject. The method comprises assaying for the presence of methylated vimentin DNA (e.g., in the vimentin methylation target region) in a tissue sample or bodily fluid taken from the subject at a first time and in a corresponding tissue sample or bodily fluid taken from the subject at a second time. Absence of methylated vimentin DNA from the tissue sample or bodily fluid taken at the first time and presence of methylated vimentin DNA in the tissue sample or bodily fluid taken at the second time indicates that the cancer is progressing. Presence of methylated vimentin DNA in the tissue sample or bodily fluid taken at the first time and absence of methylated vimentin DNA from the tissue sample or bodily fluid taken at the second time indicates that the cancer is regressing.

In another embodiment, the present invention provides a method for evaluating therapy in a subject having cancer or suspected of having cancer (e.g., gastrointestinal cancer such as colon cancer, pancreatic cancer, or bladder cancer). The method comprises assaying for the presence of methylated vimentin DNA (e.g., in the vimentin methylation target region) in a tissue sample or bodily fluid taken from the subject prior to therapy and a corresponding bodily fluid taken from the subject during or following therapy. Loss of or a decrease in the levels of methylated vimentin DNA in the sample taken after or during therapy as compared to the levels of methylated vimentin DNA in the sample taken before therapy is indicative of a positive effect of the therapy on cancer regression in the treated subject.

The present invention also relates to oligonucleotide primer sequences for use in assays (e.g., methylation-sensitive PCR assays or HpaII assays) designed to detect the methylation status of the vimentin gene.

The present invention also provides a method of inhibiting or reducing growth of cancer cells (e.g., gastrointestinal cancer such as colon cancer, pancreatic cancer, or bladder cancer). The method comprises increasing the levels of the vimentin protein in cancer cells. In one embodiment, the cells are contacted with the vimentin protein or a biologically active equivalent or fragment thereof under conditions permitting uptake of the protein or fragment. In another embodiment, the cells are contacted with a nucleic acid encoding the vimentin protein and comprising a promoter active in the cancer cell, wherein the promoter is operably linked to the region encoding the vimentin protein, under conditions permitting the uptake of the nucleic acid by the cancer cell. In another embodiment, the method comprises demethylating the methylated vimentin DNA, or otherwise reactivating the silenced vimentin promoter.

In another embodiment, the application provides isolated or recombinant vimentin nucleotide sequences that are at least 80%, 85%, 90%, 95%, 98%, 99% or identical to the nucleotide sequence of any one of SEQ ID NOs: 2-7 and 45-50, and fragments of said sequences that are 10, 15, 20, 25, 50, 100, or 150 base pairs in length wherein the vimentin nucleotide sequences are differentially methylated in a vimentin-associated disease cell.

In another embodiment, the application provides a method for detecting cancer, comprising: a) obtaining a sample from a patient; and b) assaying said sample for the presence of methylation of nucleotide sequences within at least two genes selected from the group consisting of: vimentin, SLC5A8, HLTF, p16, and hMLH1; wherein methylation of nucleotide sequences within the two genes is indicative of cancer. In such methods, the sample is a bodily fluid selected from the group consisting of blood, serum, plasma, a blood-derived fraction, stool, urine, and a colonic effluent. For example, the bodily fluid is obtained from a subject suspected of having or is known to have cancer.

In certain aspects, the application provides a method for detecting neoplasia of the upper gastrointestinal tract, comprising: a) obtaining a human sample; and b) assaying said sample for the presence of methylation within a nucleotide sequence as set forth in SEQ ID NO: 2 or fragments thereof; wherein methylation of said nucleotide sequence is indicative of a neoplasia of the upper gastrointestinal tract. In some embodiments, the sample is a bodily fluid selected from the group consisting of blood, serum, plasma, a blood-derived fraction, stool, urine, and a colonic effluent. In certain embodiments, the sample is derived from a tissue. The tissue sample may be obtained from biopsies of the gastrointestinal tract, including but not limited to the esophagus, stomach, duodenum, rectum, colon, and terminal ileum. In certain embodiments, vimentin methylation may be detected in brushings from the esophagus of a subject.

In some embodiments, the bodily fluid or tissue sample is obtained from a subject suspected of having or is known to have a neoplasia of the upper gastrointestinal tract. In exemplary embodiments, neoplasia of the upper gastrointestinal tract include gastric (also known as stomach cancer) and esophageal cancer. Gastric cancers are typically classified according to their cellular or tissue origin, which include glandular cells (adenocarcinoma), immune cells (lymphoma), hormone-producing cells (carcinoid), and nervous system tissues. Types of esophageal cancer include adenocarcinoma, squamous cell carcinoma, choriocarcinoma, lymphoma, sarcoma, and small cell cancer. In some embodiments, upper gastrointestinal neoplasia include Barrett's esophagus, Barrett's esophagus with high grade dysplasia, adenocarcinoma of the esophagus, adenocarcinoma of the gastroesophageal junction, and adenocarcinoma of the stomach.

In certain embodiments, the foregoing assay comprises assaying for the presence of methylation of the vimentin sequence of SEQ ID NO: 45. In other embodiments, the assay comprises assaying for the presence of methylation of a vimentin sequence selected from SEQ ID NOs: 40-44. In some embodiments, the assay is methylation-specific PCR.

In certain embodiments, the assay further comprises a) treating DNA from the sample with a compound that converts non-methylated cytosine bases in the DNA to a different base; b) amplifying a region of the compound converted vimentin nucleotide sequence with a forward primer and a reverse primer; and c) analyzing the methylation patterns of said vimentin nucleotide sequences.

In other embodiments, the assay further comprises a) treating DNA from the sample with a compound that converts non-methylated cytosine bases in the DNA to a different base; b) amplifying a region of the compound converted vimentin nucleotide sequence with a forward primer and a reverse primer; and c) detecting the presence and/or amount of the amplified product.

In any of the foregoing embodiments, the forward primers are selected from SEQ ID NOs: 14, 16, 19, 21, 23, 25, 27, 29, 31, 33, 37, 38, 39, and the forward primers listed in FIG. 35. Additionally, the reverse primers are selected from SEQ ID NOs: 15, 17, 18, 20, 22, 24, 26, 28, 30, 32, 34, 35, 36, and the reverse primers listed in FIG. 35.

In certain embodiments, the primer is selected from MSP29, MSP47, and MSP50.

In some embodiments, the compound used to treat DNA is a bisulfite compound.

In some embodiments, the assay comprises using a methylation-specific restriction enzyme. In certain embodiments, the methylation-specific restriction enzyme is selected from HpaII, SmaI, SacII, EagI, MspI, BstUI, and BssHII. In other embodiments, the assay further comprises a pair of primers selected from SEQ ID NOs: 8-13, and the primers listed in FIG. 35.

In some aspects, the application provides a method for detecting a neoplasia of the upper gastrointestinal tract in a subject, comprising detecting vimentin protein or nucleic acid expression in a sample from the subject. In some embodiments, the sample is a bodily fluid selected from the group consisting of blood, serum, plasma, a blood-derived fraction, stool, urine, and a colonic effluent. In other embodiments, the sample is derived from a tissue. The tissue sample may be obtained from biopsies of the gastrointestinal tract, including but not limited to the esophagus, stomach, duodenum, rectum, colon, and terminal ileum. In some embodiments, vimentin methylation may be detected in brushings from the esophagus of a subject. In certain embodiments, the vimentin protein is detected by immunoassays.

In some embodiments, the bodily fluid or tissue sample is obtained from a subject suspected of having or is known to have a neoplasia of the upper gastrointestinal tract.

In another aspect, the application provides a method for monitoring over time a neoplasia of the upper gastrointestinal tract comprising: a) detecting the methylation status of a vimentin nucleotide sequence in a sample from the subject for a first time; and b) detecting the methylation status of the vimentin nucleotide sequence in a sample from the same subject at a later time; wherein absence of methylation in the vimentin nucleotide sequence taken at a later time and the presence of methylation in the vimentin nucleotide sequence taken at the first time is indicative of cancer regression; and wherein presence of methylation in the vimentin nucleotide sequence taken at a later time and the absence of methylation in the vimentin nucleotide sequence taken at the first time is indicative of cancer progression.

In some embodiments, the sample is a bodily fluid selected from the group consisting of blood, serum, plasma, a blood-derived fraction, stool, urine, and a colonic effluent. In other embodiments, the sample is derived from a tissue. The tissue sample may be obtained from biopsies of the gastrointestinal tract, including but not limited to the esophagus, stomach, duodenum, rectum, colon, and terminal ileum. In certain embodiments, vimentin methylation may be detected in brushings from the esophagus of a subject.

In any of the foregoing aspects and embodiments, neoplasia of the upper gastrointestinal tract include gastric (also known as stomach cancer) and esophageal cancer. Gastric cancers are typically classified according to their cellular/tissue origin, which include glandular cells (adenocarcinoma), immune cells (lymphoma), hormone-producing cells (carcinoid), and nervous system tissues. Types of esophageal cancer include adenocarcinoma, squamous cell carcinoma, choriocarcinoma, lymphoma, sarcoma, and small cell cancer. In some embodiments, upper gastrointestinal neoplasia include Barrett's esophagus, Barrett's esophagus with high grade dysplasia, adenocarcinoma of the esophagus, adenocarcinoma of the gastroesophageal junction, and adenocarcinoma of the stomach.

BRIEF DESCRIPTION OF THE DRAWINGS

FIG. 1B shows the 5' genomic sequence of the vimentin gene, corresponding to basepairs 56,123-62,340 of the AL133415 sequence (SEQ ID NO: 51).

FIG. 13 shows primer sequences in HpaII assays for amplifying vimentin nucleotide sequences in A, C, and D regions. A. Forward PCR primer VM-HpaII-679U (SEQ ID NO: 8) and reverse PCR primer VM-HpaII-1266D (SEQ ID NO: 9) selectively amplify the methylated but not unmethylated vimentin sequence in the A region, after digestion with HpaII. Unmethylated DNAs are cut by HpaII and so cannot be PCR amplified. B. Forward PCR primer VM-HpaII-1826U (SEQ ID NO: 10) and reverse PCR primer VM-HpaII-2195D (SEQ ID NO: 11) selectively amplify the methylated but not unmethylated vimentin sequence in the C region, after digestion with HpaII. C. Forward PCR primer VM-HpaII-2264U (SEQ ID NO: 12) and reverse PCR primer VM-HpaII-2695D (SEQ ID NO: 13) selectively amplify the methylated but not unmethylated vimentin sequence in the D region, after digestion with HpaII.

FIG. 14 shows the sequences of the MSP-PCR primer sets 1-5 for detecting vimentin methylation. MSP1, MSP1-2, and MSP3 are primer sets for amplifying bisulfite-converted sense sequences of the duplex methylated vimentin DNA, including forward primer VIM1374MF (SEQ ID NO: 14) and reverse primer VIM1504MR (SEQ ID NO: 15); forward primer VIM1374MF (SEQ ID NO: 14) and reverse primer VIM1506MR (SEQ ID NO: 18); forward primer VIM1776MF (SEQ ID NO: 23) and reverse primer VIM1982MR (SEQ ID NO: 24). MSP2 and MSP5 are primer sets for amplifying bisulfite-converted antisense sequences of the duplex methylated vimentin DNA, including: forward primer VIM1655MF(ASS) (SEQ ID NO: 19) and reverse primer VIM1797MR(ASS) (SEQ ID NO: 20); forward primer VIM1935MF(ASS) (SEQ ID NO: 27) and reverse primer VIM2094MR(ASS) (SEQ ID NO: 28). Sequences underlined are the control primer sets used to amplify bisulfite-converted sequences (sense or antisense) of the duplex unmethylated vimentin DNA (designated as UF or UR), including: forward primer VIM1368UF (SEQ ID NO: 16) and reverse primer VIM1506UR (SEQ ID NO: 17); forward primer VIM1651UF(ASS) (SEQ ID NO: 21) and reverse primer VIM1799UR(ASS) (SEQ ID NO: 22); forward primer VIM1771UF (SEQ ID NO: 25) and reverse primer VIM1986UR (SEQ ID NO: 26); forward primer VIM1934UF(ASS) (SEQ ID NO: 29) and reverse primer VIM2089UR(ASS) (SEQ ID NO: 30).

FIG. 15 shows the sequences of the MSP-PCR primer sets 6-10 for detecting vimentin methylation. MSP6, MSP7, MSP8, and MSP9 are primer sets for amplifying bisulfite-converted sense sequences of the duplex methylated vimentin DNA, including forward primer VIM1655MF (SEQ ID NO: 31) and reverse primer VIM1792MR (SEQ ID NO: 32); forward primer VIM1655MF (SEQ ID NO: 31) and reverse primer VIM1796MR (SEQ ID NO: 35); forward primer VIM1655MF (SEQ ID NO: 31) and reverse primer VIM1804MR (SEQ ID NO: 36); forward primer VIM1843MF (SEQ ID NO: 37) and reverse primer VIM1982MR (SEQ ID NO: 24). MSP10 are primer sets for amplifying bisulfite-converted antisense sequences of the duplex methylated vimentin DNA, including: forward primer VIM1929MF(ASS) (SEQ ID NO: 39) and reverse primer VIM2094MR(ASS) (SEQ ID NO: 28). Sequences underlined are the control primer sets used to amplify bisulfite-converted sequences (sense or antisense) of the duplex unmethylated vimentin DNA (designated as UF or UR), including: forward primer VIM1651UF (SEQ ID NO: 33) and reverse primer VIM1800UR (SEQ ID NO: 34); forward primer VIM1843UR (SEQ ID NO: 38) and reverse primer VIM1986UR (SEQ ID NO: 26); forward primer VIM1934UF(ASS) (SEQ ID NO: 29) and reverse primer VIM2089UR(ASS) (SEQ ID NO: 30).

FIG. 20 shows the amino acid sequence (SEQ ID NO: 1) of human vimentin protein.

FIGS. 21-26 provide the definitive sequences of the vimentin 5' genomic region. Each figure provides sequences corresponding to basepairs 56,822-58,822 of NCBI human genomic clone AL133415 that spans the 5' region of the vimentin gene encompassing regions A-D. Each figure designates in bold the region from basepairs 57,427-58,326 that is differentially methylated in colon cancer. Moreover, in each figure, specific sequences that are interrogated by MS-PCR primers are underlined.

FIG. 21 shows the vimentin sense strand sequence, 5' to 3', corresponding to basepairs 56,822-58,822 of the AL133415 sequence (SEQ ID NO: 2). The differentially methylated region is in bold, from basepairs 57,427-58,326 (SEQ ID NO: 45) (also see FIG. 45).

FIG. 22 shows the bisulfite converted sequence of a methylated template derived from the vimentin genetic sense strand shown in FIG. 21 (SEQ ID NO: 3). The sequence derived from the differentially methylated region is in bold, from basepairs 57,427-58,326 (SEQ ID NO: 46).

FIG. 23 shows the bisulfite converted sequence of an unmethylated template derived from the vimentin genetic sense strand shown in FIG. 21 (SEQ ID NO: 4). The sequence derived from the differentially methylated region is in bold, from basepairs 57,427-58,326 (SEQ ID NO: 47).

FIG. 24 shows the vimentin antisense strand sequence (3'-5'), corresponding to basepairs 56,822-58,822 of the AL133415 sequence (SEQ ID NO: 5). The differentially methylated region is in bold, from basepairs 57,427-58,326 (SEQ ID NO: 48).

FIG. 25 shows the bisulfite converted sequence of a methylated template derived from the vimentin genetic antisense strand (3'-5') shown in FIG. 24 (SEQ ID NO: 6). The sequence derived from the differentially methylated region is in bold, from basepairs 57,427-58,326 (SEQ ID NO: 49).

FIG. 26 shows the bisulfite converted sequence of an unmethylated template derived from the vimentin genetic antisense strand (3'-5') shown in FIG. 24 (SEQ ID NO: 7). The sequence derived from the differentially methylated region is in bold, from basepairs 57,427-58,326 (SEQ ID NO: 50).

FIG. 27 shows the "A region" sequence (basepairs 56799-57385 of AL133415, SEQ ID NO: 40) as originally defined by having convenient sites for the HpaII assays. The sequence was also referred to nucleotides 679-1266 of SEQ ID NO: 51 shown in FIGS. 1A and 1B.

FIG. 28 shows the "B region" sequence (basepairs 57436-57781 of AL133415, SEQ ID NO: 41) as originally defined by having convenient sites for the HpaII assays. The sequence was also referred to nucleotides 1317-1661 of SEQ ID NO: 51 shown in FIGS. 1A and 1B.

FIG. 29 shows the "C region" sequence (basepairs 57946-58315 of AL133415, SEQ ID NO: 42) as originally defined by having convenient sites for the HpaII assays. The sequence was also referred to nucleotides 1826-2195 of SEQ ID NO: 51 shown in FIGS. 1A and 1B.

FIG. 30 shows the "D region" sequence (basepairs 58384-58815 of AL133415, SEQ ID NO: 43) as originally defined by having convenient sites for the HpaII assays. The sequence was also referred to nucleotides 2264-2695 of SEQ ID NO: 51 shown in FIGS. 1A and 1B.

FIG. 31 shows the "B' region" sequence (basepairs 57436-57945 of AL133415, SEQ ID NO: 44), which covers the B region as well as the gap between B and C regions. The sequence was also referred to nucleotides 1317-1825 of SEQ ID NO: 51 shown in FIGS. 1A and 1B. This B' region also contains a differentially methylated region.

FIG. 32 designates regions A through B, and FIGS. 33-34 designates regions C through D. Bars under the figures indicate regions interrogated by different methylation specific PCR reactions, as numbered by MSP1-MSP50. In these figures, the primary results of the MS-PCR reactions are shown next to the MS-PCR primers. The leftmost set of reactions are the results of MS-PCR in 12 non-cancer normal samples; wherein a negative result is the preferred outcome. The rightmost set of reactions are the results of assay of 11 colon cancer cell lines; wherein the preferred outcome is a positive reaction.

FIGS. 35A-35B provide the primer sequences (MSP1-MSP50) for the MS-PCR reactions summarized in FIGS. 32-34. MF indicates forward primers, while MR indicates reverse primers. Primers are presumed to amplify the bisulfite converted sequences of the sense genomic strand. Primers that amplify the bisulfite converted sequence of the antisense genomic strand are indicated by (ASS). The table also provides the genomic location corresponding to the amplified product, relative to the basepair numbering system of clone AL133415. The table also provides the length of the amplified fragments. Primers shaded in dark provide the best and preferred reaction. FIGS. 35A and 35B include SEQ ID NOs: 14, 15, 18, 19, 20, 23, 24, 27, 28, 31, 32, 36, 37, 39, and 52-72.

FIGS. 44A-44D provide raw data from MS-PCR with primers MSP29, MSP47, and MSP50. The data is shown in three tables for cell lines, N/T pairs, and colon adenoma samples, respectively. Methylated samples are coded red and labeled M, while unmethylated samples are coded green and labeled U. V-MSP29, VMSP-47, and V-MSP50 are vimentin primers. H-MSP5 is a control primer (HLTF-MSP5) for comparison.

FIG. 45 shows a 5' genomic sequence of human vimentin gene which corresponds to basepairs 57,427-58,326 of GenBank Accession No. AL133415: the sense strand (SEQ ID NO: 45).

FIG. 46 shows a 5' genomic sequence of human vimentin gene which corresponds to basepairs 57,427-58,326 of GenBank Accession No. AL133415: the sense strand (bisulfite-converted/methylated) (SEQ ID NO: 46).

FIG. 47 shows a 5' genomic sequence of human vimentin gene which corresponds to basepairs 57,427-58,326 of GenBank Accession No. AL133415: the sense strand (bisulfite-converted/unmethylated) (SEQ ID NO: 47).

FIG. 48 shows a 5' genomic sequence of human vimentin gene which corresponds to basepairs 57,427-58,326 of GenBank Accession No. AL133415: the antisense strand (SEQ ID NO: 48).

FIG. 49 shows a 5' genomic sequence of human vimentin gene which corresponds to basepairs 57,427-58,326 of GenBank Accession No. AL133415: the antisense strand (bisulfite-converted/methylated) (SEQ ID NO: 49).

FIG. 50 shows a 5' genomic sequence of human vimentin gene which corresponds to basepairs 57,427-58,326 of GenBank Accession No. AL133415: the antisense strand (bisulfite-converted/unmethylated) (SEQ ID NO: 50).

DETAILED DESCRIPTION OF THE INVENTION

I. Definitions

Figure 1A:
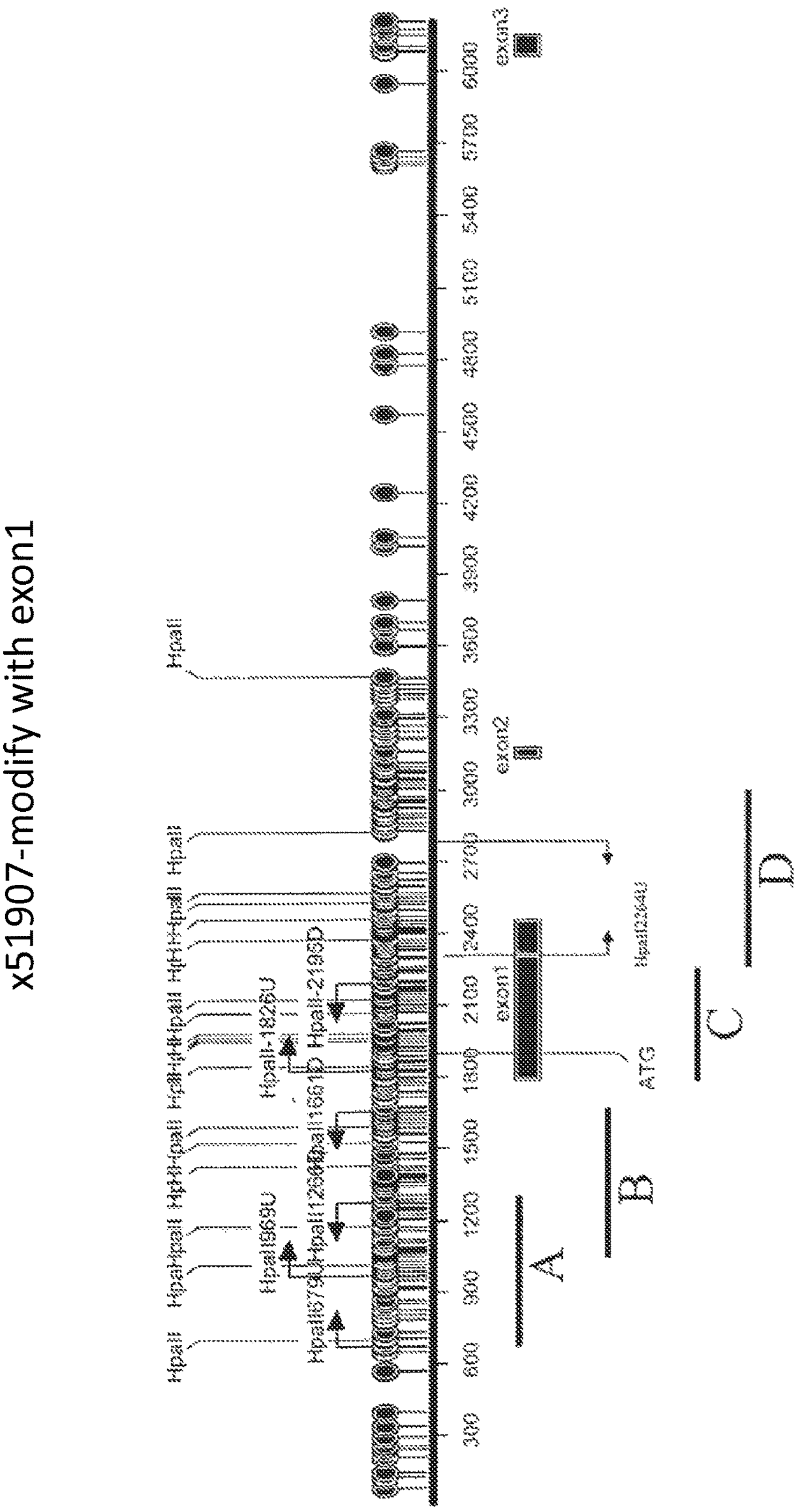
FIG. 1A shows the position of CpG dinucleotides as balloons in the 5' genomic region of the vimentin gene (nucleotides 1-6200). Four subdomains (A-D) of this region are tested for aberrant methylation in cancer.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The terms "adenoma" is used herein to describe any precancerous neoplasia or benign tumor of epithelial tissue, for example, a precancerous neoplasia of the gastrointestinal tract, pancreas, and/or the bladder.

The term "colon adenoma" and "polyp" are used herein to describe any precancerous neoplasia of the colon.

The term "blood-derived fraction" herein refers to a component or components of whole blood. Whole blood comprises a liquid portion (i.e., plasma) and a solid portion (i.e., blood cells). The liquid and solid portions of blood are each comprised of multiple components; e.g., different proteins in plasma or different cell types in the solid portion. One of these components or a mixture of any of these components is a blood-derived fraction as long as such fraction is missing one or more components found in whole blood.

The term "colon" as used herein is intended to encompass the right colon (including the cecum), the transverse colon, the left colon, and the rectum.

The terms "colorectal cancer" and "colon cancer" are used interchangeably herein to refer to any cancerous neoplasia of the colon (including the rectum, as defined above).

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "compound", "test compound," "agent", and "molecule" are used herein interchangeably and are meant to include, but are not limited to, peptides, nucleic acids, carbohydrates, small organic molecules, natural product extract libraries, and any other molecules (including, but not limited to, chemicals, metals, and organometallic compounds).

The term “compound-converted DNA” herein refers to DNA that has been treated or reacted with a chemical compound that converts unmethylated C bases in DNA to a different nucleotide base. For example, one such compound is sodium bisulfite, which converts unmethylated C to U. If DNA that contains conversion-sensitive cytosine is treated with sodium bisulfite, the compound-converted DNA will contain U in place of C. If the DNA which is treated with sodium bisulfite contains only methylcytosine, the compound-converted DNA will not contain uracil in place of the methylcytosine.

The term “de-methylating agent” as used herein refers agents that restore activity and/or gene expression of target genes silenced by methylation upon treatment with the agent. Examples of such agents include without limitation 5-azacytidine and 5-aza-2'-deoxycytidine.

As used herein, the phrase “gene expression” or “protein expression” includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase “gene or protein expression information.” Such information may be given in the form of amounts per cell, amounts relative to a control gene or protein, in unitless measures, etc.; the term “information” is not to be limited to any particular means of representation and is intended to mean any representation that provides relevant information. The term “expression levels” refers to a quantity reflected in or derivable from the gene or protein expression data, whether the data is directed to gene transcript accumulation or protein accumulation or protein synthesis rates, etc.

The term “detection” is used herein to refer to any process of observing a marker, or a change in a marker (such as for example the change in the methylation state of the marker), in a biological sample, whether or not the marker or the change in the marker is actually detected. In other words, the act of probing a sample for a marker or a change in the marker, is a “detection” even if the marker is determined to be not present or below the level of sensitivity. Detection may be a quantitative, semi-quantitative or non-quantitative observation.

The term “differentially methylated vimentin nucleotide sequence” refers to a region of the vimentin nucleotide sequence that is found to be methylated in a vimentin-associated neoplasia such as a region of the vimentin nucleotide sequence that is found to be methylated in cancer tissues or cell lines, but not methylated in the normal tissues or cell lines. For example, FIG. 45 provides a vimentin region that is differentially methylated which corresponds to basepairs 57427-58326 of the NCBI AL133415 sequence (SEQ ID NO: 45). This sequence is mainly within the B and C regions.

“Expression vector” refers to a replicable DNA construct used to express DNA which encodes the desired protein and which includes a transcriptional unit comprising an assembly of (1) genetic element(s) having a regulatory role in gene expression, for example, promoters, operators, or enhancers, operatively linked to (2) a DNA sequence encoding a desired protein (in this case, a vimentin protein) which is transcribed into mRNA and translated into protein, and (3) appropriate transcription and translation initiation and termination sequences. The choice of promoter and other regulatory elements generally varies according to the intended host cell. In general, expression vectors of utility in recombinant DNA techniques are often in the form of “plasmids” which refer to circular double stranded DNA loops which, in their vector form are not bound to the chromosome. In the present specification, “plasmid” and “vector” are used interchangeably as the plasmid is the most commonly used form of vector. However, the invention is intended to include such other forms of expression vectors which serve equivalent functions and which become known in the art subsequently hereto.

In the expression vectors, regulatory elements controlling transcription or translation can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

“Gastrointestinal neoplasia” refers to neoplasia of the upper and lower gastrointestinal tract. As commonly understood in the art, the upper gastrointestinal tract includes the esophagus, stomach, and duodenum; the lower gastrointestinal tract includes the remainder of the small intestine and all of the large intestine.

The terms “healthy”, “normal,” and “non-neoplastic” are used interchangeably herein to refer to a subject or particular cell or tissue that is devoid (at least to the limit of detection) of a disease condition, such as a neoplasia, that is associated with vimentin such as for example neoplasia associated with silencing of vimentin gene expression due to methylation. These terms are often used herein in reference to tissues and cells of the upper and lower gastrointestinal tract, the pancreas, and the bladder. Thus, for the purposes of this application, a patient with severe heart disease but lacking a vimentin silencing-associated disease would be termed “healthy.”

“Homology” or “identity” or “similarity” refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is “unrelated or “non-homologous” shares less than 40% identity, preferably less than 25% identity with a sequence of the present invention. In comparing two sequences, the absence of residues (amino acids or nucleic acids) or presence of extra residues also decreases the identity and homology/similarity.

The term “homology” describes a mathematically based comparison of sequence similarities which is used to identify genes or proteins with similar functions or motifs. The nucleic acid and protein sequences of the present invention may be used as a “query sequence” to perform a search against public databases to, for example, identify other family members, related sequences or homologs. Such searches can be performed using the NBLAST and XBLAST programs (version 2.0) of Altschul, et al. (1990) J Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (*Computational Molecular Biology*, Lesk, A. M., ed., Oxford University Press, New York, 1988*; Biocomputing*: Informatics and Genome Projects, Smith, D. W., ed., Academic Press, New York, 1993*; Computer Analysis of Sequence Data*, Part I, Griffin, A. M., and Griffin, H. G., eds., Humana Press, New Jersey, 1994*; Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. Applied Math., 48: 1073, 1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403-410 (1990) and Altschul et al. *Nuc. Acids Res.* 25: 3389-3402 (1997)). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990)). The well known Smith Waterman algorithm may also be used to determine identity.

The term "including" is used herein to mean, and is used interchangeably with, the phrase "including but not limited to."

The term "isolated" as used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

The term "methylation-sensitive PCR" (i.e., MSP) herein refers to a polymerase chain reaction in which amplification of the compound-converted template sequence is performed. Two sets of primers are designed for use in MSP. Each set of primers comprises a forward primer and a reverse primer. One set of primers, called methylation-specific primers (see below), will amplify the compound-converted template sequence if C bases in CpG dinucleotides within the vimentin DNA are methylated. Another set of primers, called unmethylation-specific primers (see below), will amplify the compound-converted template sequences if C bases in CpG dinucleotides within the vimentin DNA are not methylated.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

"Operably linked" when describing the relationship between two DNA regions simply means that they are functionally related to each other. For example, a promoter or other transcriptional regulatory sequence is operably linked to a coding sequence if it controls the transcription of the coding sequence.

The term "or" is used herein to mean, and is used interchangeably with, the term "and/or", unless context clearly indicates otherwise.

The terms "proteins" and "polypeptides" are used interchangeably herein.

A "sample" includes any material that is obtained or prepared for detection of a molecular marker or a change in a molecular marker such as for example the methylation state, or any material that is contacted with a detection reagent or detection device for the purpose of detecting a molecular marker or a change in the molecular marker.

As used herein, "obtaining a sample" includes directly retrieving a sample from a subject to be assayed, or directly retrieving a sample from a subject to be stored and assayed at a later time. Alternatively, a sample may be obtained via a second party. That is, a sample may be obtained via, e.g., shipment, from another individual who has retrieved the sample, or otherwise obtained the sample.

A "subject" is any organism of interest, generally a mammalian subject, such as a mouse, and preferably a human subject.

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a target sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided below.

As applied to polypeptides, the term "substantial sequence identity" means that two peptide sequences, when optimally aligned such as by the programs GAP or BESTFIT using default gap, share at least 90 percent sequence identity, preferably at least 95 percent sequence identity, more preferably at least 99 percent sequence identity or more. Preferably, residue positions which are not identical differ by conservative amino acid substitutions. For example, the substitution of amino acids having similar chemical properties such as charge or polarity is not likely to effect the properties of a protein. Examples include glutamine for asparagine or glutamic acid for aspartic acid.

As used herein, the term “transgene” means a nucleic acid sequence (encoding, e.g., a vimentin polypeptide), which is partly or entirely heterologous (i.e., foreign) to the transgenic animal or cell into which it is introduced, or, is homologous to an endogenous gene of the transgenic animal or cell into which it is introduced, but which is designed to be inserted, or is inserted, into the animal’s genome in such a way as to alter the genome of the cell into which it is inserted (e.g., it is inserted at a location which differs from that of the natural gene or its insertion results in a knockout). A vimentin transgene can include one or more transcriptional regulatory sequences and any other nucleic acid, such as introns, that may be necessary for optimal expression of a selected nucleic acid. A vimentin transgene can include a vimentin nucleotide sequence (e.g., SEQ ID NO: 2) or fragments thereof.

“Vimentin-associated proliferative disorder” refers to a disease that is associated with either reduced expression or over-expression of the vimentin gene.

“Vimentin-associated neoplasia” refers to neoplasia associated with reduced expression or no expression of the vimentin gene. Examples of vimentin-associated neoplasia include gastro-intestinal neoplasia such as colon neoplasia, esophageal neoplasia, gastric neoplasia, or pancreatic neoplasia, bladder neoplasia, etc. As one of skill in the art would recognize, the term also includes neoplasias in which vimentin is aberrantly expressed, for example, neoplasias showing increased expression of vimentin relative to cells from healthy control tissue, neoplasias showing a reduction of vimentin relative to controls, or neoplasias in which the methylation of vimentin is altered relative to controls.

“Vimentin-methylation target regions” as used herein refer to those regions of vimentin that are found to be differentially methylated. For example, FIG. 45 discloses a vimentin region wherein certain sequences of this region are differentially methylated (e.g., SEQ ID NO: 45).

“Vimentin-nucleotide sequence” or “vimentin-nucleic acid sequence” as used herein refers to the vimentin-genomic sequences as set forth in SEQ ID NOs: 2-7 and fragments thereof.

“Vimentin-silencing associated diseases” as used herein includes vimentin-associated neoplasia.

II. Overview

This application is based at least in part on the recognition that differential methylation of the vimentin nucleotide sequence may be indicative of neoplasia of the upper and lower gastrointestinal tract, neoplasia of the pancreas, and/or neoplasia of the bladder. As demonstrated herein, aberrant vimentin methylation is a highly common epigenetic alteration in neoplasias, for example, neoplasias that arise throughout the gut and other organs. The present findings demonstrate that vimentin methylation may be a useful biomarker of neoplasia in both the upper and lower gastrointestinal tract, pancreas, and/or bladder.

In certain aspects, the invention relates to methods for determining whether a patient is likely or unlikely to suffer from a neoplasia of the upper and/or lower gastrointestinal tract, pancreas, bladder, or other organs. For example, in certain aspects, the invention relates to methods for determining whether a patient is likely or unlikely to have a colon neoplasia. A colon neoplasia is any cancerous or precancerous growth located in, or derived from, the colon. The colon is a portion of the intestinal tract that is roughly three feet in length, stretching from the end of the small intestine to the rectum. Viewed in cross section, the colon consists of four distinguishable layers arranged in concentric rings surrounding an interior space, termed the lumen, through which digested materials pass. In order, moving outward from the lumen, the layers are termed the mucosa, the submucosa, the muscularis propria and the subserosa. The mucosa includes the epithelial layer (cells adjacent to the lumen), the basement membrane, the lamina propria and the muscularis mucosae. In general, the “wall” of the colon is intended to refer to the submucosa and the layers outside of the submucosa. The “lining” is the mucosa.

Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers.

When a colon neoplasia invades into the basement membrane of the colon, it is considered a colon cancer, as the term “colon cancer” is used herein. In describing colon cancers, this specification will generally follow the so-called “Dukes” colon cancer staging system. The characteristics that describe a cancer are generally of greater significance than the particular term used to describe a recognizable stage. The most widely used staging systems generally use at least one of the following characteristics for staging: the extent of tumor penetration into the colon wall, with greater penetration generally correlating with a more dangerous tumor; the extent of invasion of the tumor through the colon wall and into other neighboring tissues, with greater invasion generally correlating with a more dangerous tumor; the extent of invasion of the tumor into the regional lymph nodes, with greater invasion generally correlating with a more dangerous tumor; and the extent of metastatic invasion into more distant tissues, such as the liver, with greater metastatic invasion generally correlating with a more dangerous disease state.

“Dukes A” and “Dukes B” colon cancers are neoplasias that have invaded into the wall of the colon but have not spread into other tissues. Dukes A colon cancers are cancers that have not invaded beyond the submucosa. Dukes B colon cancers are subdivided into two groups: Dukes B1 and Dukes B2. “Dukes B1” colon cancers are neoplasias that have invaded up to but not through the muscularis propria. Dukes B2 colon cancers are cancers that have breached completely through the muscularis propria. Over a five year period, patients with Dukes A cancer who receive surgical treatment (i.e. removal of the affected tissue) have a greater than 90% survival rate. Over the same period, patients with Dukes B1 and Dukes B2 cancer receiving surgical treatment have a survival rate of about 85% and 75%, respectively. Dukes A, B1 and B2 cancers are also referred to as T1, T2 and T3-T4 cancers, respectively.

“Dukes C” colon cancers are cancers that have spread to the regional lymph nodes, such as the lymph nodes of the gut. Patients with Dukes C cancer who receive surgical treatment alone have a 35% survival rate over a five year period, but this survival rate is increased to 60% in patients that receive chemotherapy.

“Dukes D” colon cancers are cancers that have metastasized to other organs. The liver is the most common organ in which metastatic colon cancer is found. Patients with Dukes D colon cancer have a survival rate of less than 5% over a five year period, regardless of the treatment regimen.

In general, neoplasia may develop through one of at least three different pathways, termed chromosomal instability, microsatellite instability, and the CpG island methylator phenotype (CIMP). Although there is some overlap, these pathways tend to present somewhat different biological behavior. By understanding the pathway of tumor development, the target genes involved, and the mechanisms underlying the genetic instability, it is possible to implement strategies to detect and treat the different types of neoplasias.

This application is based at least in part, on the recognition that certain target genes may be silenced or inactivated by the differential methylation of CpG islands in the 5' flanking or promoter regions of the target gene. CpG islands are clusters of cytosine-guanosine residues in a DNA sequence, which are prominently represented in the 5-flanking region or promoter region of about half the genes in our genome. In particular, this application is based at least in part on the recognition that differential methylation of the vimentin nucleotide sequence may be indicative of neoplasia. In one aspect, this application discloses that the vimentin gene can be a common target for methylation and epigenetic gene silencing in cancer cells (e.g., a neoplasia of the upper or lower gastrointestinal tract), and may function as a candidate tumor suppressor gene.

Additionally, this application is based at least in part on the recognition that differential methylation of the vimentin nucleotide sequence may be indicative of neoplasia of the upper gastrointestinal tract including, but not limited to, esophageal adenocarcinoma, as well as other varieties of upper gastrointestinal neoplasias as described herein. As demonstrated herein, aberrant vimentin methylation is a highly common epigenetic alteration in neoplasias that arise throughout the gut. The present findings demonstrate that vimentin methylation may be a useful biomarker of gastrointestinal neoplasia in both the upper and lower gastrointestinal tract.

Esophageal adenocarcinoma (EAC) has steadily increased in incidence over recent decades. With an 85% mortality rate this cancer is the most rapidly increasing cause of cancer mortality from solid tumors in the American population. There has thus been substantial interest in development of screening approaches for early detection of EAC and its precursor lesions of Barrett's esophagus (BE). However, the majority of EACs develop in patients without prior symptoms, and current approaches of endoscopic screening of individuals with persistent symptoms of gastro-esophageal reflux disease, combined with longitudinal screening of those found to have BE, have accordingly not had significant impact on reducing deaths from EACs. As demonstrated herein, vimentin methylation is a highly common and early biomarker of the BE pathway.

As further demonstrated herein, detection of vimentin methylation in 82% of signet ring and 40% of intestinal type gastric cancers makes vimentin methylation among the most common DNA alteration associated with gastric cancer. Although gastric cancers account for fewer annual deaths in the American population than do esophageal cancers, gastric cancers still remain as a significant cause of cancer mortality. Vimentin methylation provides a useful biomarker for early detection of this disease, and may particularly be of utility in combination with other methylated markers that have also been described as detecting subsets of gastric carcinomas.

Combined with the finding that vimentin methylation is present in up to 83% of colon cancers, vimentin methylation emerges as a highly common epigenetic accompaniment of neoplasias arising throughout the gastrointestinal tract.

Vimentin is one of the cytoskeletal proteins which form the cytoplasmic intermediate filament (IF). The cytoskeleton is composed of three different classes: microfilaments, microtubules, and intermediated filaments. Intermediate filaments are a major component of the cytoskeleton of higher eukaryotes. Vimentin is the IF protein characteristic of mesenchymal cells, such as fibroblasts and endothelial cells (see, e.g., Evans, 1998, *BioEssays*, 20:79-86). Expression of vimentin is developmentally regulated, suggesting important functions for this protein besides its roles as an intracellular scaffold. Vimentin shares structural sequence similarities with the DNA binding region of certain transcription factors such as c-fos, fra1, CREB, and c-jun, further suggesting a regulatory role for vimentin (see, e.g., Capetanaki, et al., 1990, *Oncogene*, 5:645-655). Recently, it has been demonstrated that vimentin acts as a functional perinuclear adapter for the cytosolic phospholipase A2, thus suggesting a role for the vimentin IF in the modulation of prostaglandin biosynthesis (see, e.g., Murakami et al., 2000, *Biochim Biophys Acta*, 1488:159-66). A number of proteins have been reported as having some interaction with vimentin, for example: 1) filament-associated proteins such as plectin and IAF-300 (Svitkina, et al., 1996, *J Cell Biol*, 135:991-1007; Yang, et al., 1985, *J Cell Biol*, 100:620-631); 2) chaperon proteins such as Hsc70 and alpha-crystallin (Lee, et al., 1995, *J Cell Biol*, 57:150-162; Nicholl, et al., 1994, *EMBO J*, 13:945-953); 3) kinases such as protein kinase C (PKC), cGMP kinase, and Yes kinase (Murti, et al., 1992, *Exp Cell Res*, 202:36-44; Owen, et al., 1996, *Exp Cell Res*, 225:366-373; Pryzwansky et al., 1995, *Blood*, 85:222-230; Ciesielski-Treska, et al., 1996, *Eur J Cell Biol*, 68:369-376). In addition, association of vimentin with 14-3-3 proteins can be induced by treatment with the phosphatase inhibitor calyculin A (Tzivion et al., 2000, *J Biol Chem*, 275:29772-8). 14-3-3 proteins bind to their target through a specific serine/threonine-phosphorylated motif present on the target protein. This binding is likely a crucial step in the phosphorylation-dependent regulation of various key proteins involved in signal transduction and cell cycle control. Further, it has been shown that Cdc42Hs and Rac1 GTPases (two Rho family members) can control vimentin IF organization involving tyrosine phosphorylation events. For example, expression of active Cdc42Hs and Rac1 led to the reorganization of the IF network, showing a perinuclear collapse (Meriane et al., 2000, *J Biol Chem*, 275:33046-52).

As noted above, early detection of gastrointestinal neoplasia (e.g., neoplasia of the upper and lower gastrointestinal tract) coupled with appropriate intervention, is important for increasing patient survival rates. Present systems for screening for colon neoplasia are deficient for a variety of reasons, including a lack of specificity and/or sensitivity (e.g., Fecal Occult Blood Test, flexible sigmoidoscopy) or a high cost and intensive use of medical resources (e.g., colonoscopy). Alternative systems for detection of colon neoplasia would be useful in a wide range of other clinical circumstances as well. For example, patients who receive surgical and/or pharmaceutical therapy for colon cancer may experience a relapse. It would be advantageous to have an alternative system for determining whether such patients have a recurrent or relapsed neoplasia of the upper and lower gastrointestinal tract. As a further example, an alternative diagnostic system would facilitate monitoring an increase, decrease or persistence of neoplasia of the upper and lower gastrointestinal tract in a patient known to have such a neoplasia. A patient undergoing chemotherapy may be monitored to assess the effectiveness of the therapy.

III. Vimentin Nucleic Acids, Polypeptides, and Antibodies

The present invention is based, at least in part, on the observation that vimentin nucleotide sequences are differentially methylated in certain vimentin-associated neoplasia, such as neoplasia of the upper or lower gastrointestinal tract, neoplasia of the pancreas, and neoplasia of the bladder. In one aspect, the application discloses vimentin nucleotide sequences having certain regions that are differentially methylated in vimentin-associated neoplasia, for example, SEQ ID NOs: 2 and 45 and fragments thereof. Accordingly, in one embodiment, the application provides isolated or recombinant nucleotide sequences that are at least 80%, 85%, 90%, 95%, 97%, 98%, 99% or 100% identical to the differentially methylated nucleic acid sequences, wherein detection of methylation in any one of said differentially methylated nucleic acid sequences would be indicative of a vimentin-associated neoplasia such as neoplasia. One of ordinary skill in the art will appreciate that vimentin nucleic acid sequences complementary to SEQ ID NOs: 2 and 45 and variants thereof are also within the scope of this invention. Such variant nucleotide sequences include sequences that differ by one or more nucleotide substitutions, additions or deletions, such as allelic variants.

In yet other embodiments, vimentin nucleotide sequences also include nucleotide sequences that will hybridize under highly stringent conditions to the nucleotide sequences designated in SEQ ID NO: 2 or 45 or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

In yet another aspect, the application provides the methylated forms of nucleotide sequence of SEQ ID NO: 2 or 45 or fragments thereof, wherein the cytosine bases of the CpG islands present in said sequences are methylated. In other words, the vimentin nucleotide sequences may be either in the methylated status (e.g., as seen in vimentin-associated neoplasias) or in the unmethylated status (e.g., as seen in normal cells). In further embodiments, the vimentin nucleotide sequences of the invention can be isolated, recombinant, and/or fused with a heterologous nucleotide sequence, or in a DNA library.

In addition to the differentially methylated vimentin nucleotide sequences, constitutively methylated nucleotide sequences are also present in the vimentin sequence (e.g., the Alu repeats and the non-Alu constitutively methylated region in the C region). Since constitutively methylated vimentin nucleotide sequences are methylated in both normal cells and cancer cells, a person skilled in the art would appreciate the significance of detecting the differentially methylated vimentin nucleotide sequences as provided herein.

In certain embodiments, the present invention provides bisulfite-converted vimentin template DNA sequences, for example, SEQ ID NOs: 3-4, 6-7, 46-47, and 49-50, and fragments thereof. Such bisulfite-converted vimentin template DNA can be used for detecting the methylation status, for example, by an MSP reaction or by direct sequencing. These bisulfite-converted vimentin sequences are also of use for designing primers for MS-PCR reactions that specifically detect methylated or unmethylated vimentin templates following bisulfite conversion. In yet other embodiments, the bisulfite-converted vimentin nucleotide sequences of the invention also include nucleotide sequences that will hybridize under highly stringent conditions to any nucleotide sequence selected from SEQ ID NOs: 3-4, 6-7, 46-47, and 49-50.

In further aspects, the application provides methods for producing such bisulfite-converted nucleotide sequences, for example, the application provides methods for treating a nucleotide sequence with a bisulfite agent such that the unmethylated cytosine bases are converted to a different nucleotide base such as a uracil.

In yet other aspects, the application provides oligonucleotide primers for amplifying a region within the vimentin nucleic acid sequence of any one of SEQ ID NOs: 8-39 or any one listed in FIG. 35. In certain aspects, a pair of the oligonucleotide primers (e.g., SEQ ID NOs: 8-13) can be used in a detection assay, such as the HpaII assay. In certain aspects, primers used in an MSP reaction can specifically distinguish between methylated and non-methylated vimentin DNA, for example, SEQ ID NOs: 14-39 or the primers listed in FIG. 35.

The primers of the invention have sufficient length and appropriate sequence so as to provide specific initiation of amplification of vimentin nucleic acids. Primers of the invention are designed to be "substantially" complementary to each strand of the vimentin nucleic acid sequence to be amplified. While exemplary primers are provided in SEQ ID NOs: 8-39 and in FIG. 35, it is understood that any primers that hybridizes with the bisulfite-converted vimentin sequence of SEQ ID NO: 2 or 45 are included within the scope of this invention and is useful in the method of the invention for detecting methylated nucleic acid, as described. Similarly, it is understood that any primers that would serve to amplify a methylation sensitive restriction site or sites within the differentially methylated region of SEQ ID NO: 2 or 45 are included within the scope of this invention and is useful in the method of the invention for detecting nucleic methylated nucleic acid, as described.

The oligonucleotide primers of the invention may be prepared by using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859-1862, 1981). One method for synthesizing oligonucleotides on a modified solid support is described in U.S. Pat. No. 4,458,066.

The various Sequence Identification Numbers that have been used in this application are summarized below in Table I.

TABLE I

Sequence Identification Numbers that have been used in this application.

| SEQ ID NO | Description/Name | Corre-sponding Figure |
|---|---|---|
| 1 | amino acid sequence of human vimentin protein. | FIG. 20 |
| 2 | 5' genomic sequence of human vimentin gene, corresponding to basepairs 56,822-58,822 of AL133415, sense strand. | FIG. 21 |
| 3 | 5' genomic sequence of human vimentin gene, corresponding to basepairs 56,822-58,822 of AL133415, sense strand (bisulfite-converted/methylated). | FIG. 22 |
| 4 | 5' genomic sequence of human vimentin gene, corresponding to basepairs 56,822-58,822 of AL133415, sense strand (bisulfite-converted/unmethylated). | FIG. 23 |
| 5 | 5' genomic sequence of human vimentin gene, corresponding to basepairs 56,822-58,822 of AL133415, antisense strand. | FIG. 24 |
| 6 | 5' genomic sequence of human vimentin gene, corresponding to basepairs 56,822-58,822 of AL133415, antisense strand (bisulfite-converted/methylated). | FIG. 25 |
| 7 | 5' genomic sequence of human vimentin gene, corresponding to basepairs 56,822-58,822 of AL133415, antisense strand (bisulfite-converted/unmethylated). | FIG. 26 |
| 8 | VM-HpaII-679U | FIG. 13 |
| 9 | VM-HpaII-1266D | FIG. 13 |
| 10 | VM-HpaII-1826U | FIG. 13 |
| 11 | VM-HpaII-2195D | FIG. 13 |
| 12 | VM-HpaII-2264U | FIG. 13 |
| 13 | VM-HpaII-2695D | FIG. 13 |
| 14 | VIM1374MF | FIGS. 14 and 35 |
| 15 | VIM1504MR | FIGS. 14 and 35 |
| 16 | VIM1368UF | FIG. 14 |
| 17 | VIM1506UR | FIG. 14 |
| 18 | VIM1506MR | FIGS. 14 and 35 |
| 19 | VIM1655MF(ASS) | FIGS. 14 and 35 |
| 20 | VIM1797MR(ASS) | FIGS. 14 and 35 |
| 21 | VIM1651UF(ASS) | FIG. 14 |
| 22 | VIM1799UR(ASS) | FIG. 14 |
| 23 | VIM1776MF | FIGS. 14 and 35 |
| 24 | VIM1982MR | FIGS. 14 and 35 |
| 25 | VIM1771UF | FIG. 14 |
| 26 | VIM1986UR | FIG. 14 |
| 27 | VIM1935MF(ASS) | FIGS. 14 and 35 |
| 28 | VIM2094MR(ASS) | FIGS. 14 and 35 |
| 29 | VIM1934UF(ASS) | FIG. 14 |
| 30 | VIM2089UR(ASS) | FIG. 14 |
| 31 | VIM1655MF | FIGS. 15 and 35 |
| 32 | VIM1792MR | FIGS. 15 and 35 |
| 33 | VIM1651UF | FIG. 15 |
| 34 | VIM1800UR | FIG. 15 |
| 35 | VIM1796MR | FIG. 15 |
| 36 | VIM1804MR | FIGS. 15 and 35 |
| 37 | VIM1843MF | FIGS. 15 and 35 |
| 38 | VIM1843UR | FIG. 15 |
| 39 | VIM1929MF | FIGS. 15 and 35 |
| 40 | A region of human vimentin gene | FIG. 27 |
| 41 | B region of human vimentin gene | FIG. 28 |
| 42 | C region of human vimentin gene | FIG. 29 |
| 43 | D region of human vimentin gene | FIG. 30 |
| 44 | B' region of human vimentin gene | FIG. 31 |
| 45 | 5' genomic sequence of human vimentin gene, corresponding to basepairs 57,427-58,326 of AL133415, sense strand. | FIG. 45 |
| 46 | 5' genomic sequence of human vimentin gene, corresponding to basepairs 57,427-58,326 of AL133415, sense strand (bisulfite-converted/methylated). | FIG. 46 |
| 47 | 5' genomic sequence of human vimentin gene, corresponding to basepairs 57,427-58,326 of AL133415, sense strand (bisulfite-converted/unmethylated). | FIG. 47 |

TABLE I-continued

Sequence Identification Numbers that have been used in this application.

| SEQ ID NO | Description/Name | Corre-sponding Figure |
|---|---|---|
| 48 | 5' genomic sequence of human vimentin gene, corresponding to basepairs 57,427-58,326 of AL133415, antisense strand. | FIG. 48 |
| 49 | 5' genomic sequence of human vimentin gene, corresponding to basepairs 57,427-58,326 of AL133415, antisense strand (bisulfite-converted/methylated). | FIG. 49 |
| 50 | 5' genomic sequence of human vimentin gene, corresponding to basepairs 57,427-58,326 of AL133415, antisense strand (bisulfite-converted/unmethylated). | FIG. 50 |
| 51 | 5' genomic sequence of the vimentin gene, corresponding to basepairs 56,123-62,340 of AL133415 sequence | FIG. 1B |
| 52-72 | All MS-PCR primer sets of vimentin | FIG. 35 |

In certain other aspects, the invention relates to vimentin nucleic acids that encode the vimentin polypeptide of SEQ ID NO: 1 and variants thereof. Variant include sequences that differ by one or more nucleotide substitutions, additions or deletions, such as allelic variants; and will, therefore, include coding sequences that differ from the nucleotide sequence of the coding sequence e.g., due to the degeneracy of the genetic code. In certain embodiments, variant nucleic acids will also include sequences that will hybridize under highly stringent conditions to a nucleotide sequence encoding SEQ ID NO: 1.

Isolated vimentin nucleic acids which differ from the nucleic acids encoding SEQ ID NO: 1 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant vimentin nucleic acid may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the invention relates to vimentin polypeptide (SEQ ID NO: 1) described herein, and variants polypeptides thereof. In certain embodiments, variant polypeptides have an amino acid sequence that is at least 75% identical to an amino acid sequence as set forth in SEQ ID NO: 1. In other embodiments, the variant polypeptide has an amino acid sequence at least 80%, 85%, 90%, 95%, 97%, 98%, 99% or 100% identical to an amino acid sequence as set forth in SEQ ID NO: 1.

In certain aspects, variant vimentin polypeptides are agonists or antagonists of the vimentin polypeptide as set forth in SEQ ID NO: 1. Variants of these polypeptides may have a hyperactive or constitutive activity, or, alternatively, act to prevent the tumor suppressor activity of vimentin. For example, a truncated form lacking one or more domain may have a dominant negative effect.

In certain aspects, isolated peptidyl portions of the vimentin polypeptide can be obtained by screening polypeptides recombinantly produced from the corresponding fragment of the nucleic acid encoding the polypeptide as set forth in SEQ ID NO: 1. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments which can function as either agonists or antagonists of the tumor suppressor function of vimentin.

In certain aspects, variant vimentin polypeptides comprise one or more fusion domains. Well known examples of such fusion domains include, for example, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion polypeptide by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. Another fusion domain well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion vimentin polypeptide. The GFP tag is also useful for isolating cells which express the fusion vimentin polypeptide by flow cytometric methods such as a fluorescence activated cell sorting (FACS). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allow the relevant protease to partially digest the fusion vimentin polypeptide and thereby liberate the recombinant polypeptide therefrom. The liberated polypeptide can then be isolated from the fusion partner by subsequent chromatographic separation.

Another aspect of the invention pertains to an isolated antibody specifically immunoreactive with an epitope of a vimentin polypeptide. For example, by using immunogens derived from a vimentin polypeptide (e.g., based on its cDNA sequences), anti-protein/anti-peptide antisera or monoclonal antibodies can be made by standard protocols (see, for example, *Antibodies*: A Laboratory Manual ed. by Harlow and Lane (Cold Spring Harbor Press: 1988)). A mammal, such as a mouse, a hamster or rabbit can be immunized with an immunogenic form of the vimentin peptide. Techniques for conferring immunogenicity on a protein or peptide include conjugation to carriers or other techniques well known in the art. An immunogenic portion of a polypeptide can be administered in the presence of adjuvant. The progress of immunization can be monitored by detection of antibody titers in plasma or serum. Standard ELISA or other immunoassays can be used with the immunogen as antigen to assess the levels of antibodies.

In certain embodiment, antibodies of the invention may be useful as diagnostic or therapeutic agents for detecting or treating vimentin-associated diseases.

The term "antibody" as used herein is intended to include fragments thereof which are also specifically reactive with one of the vimentin polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragments can be treated to reduce disulfide bridges to produce Fab fragments. The antibody of the invention is further intended to include bispecific, single-chain, and chimeric and humanized molecules having affinity for the vimentin protein. In preferred embodiments, the antibody further comprises a label attached thereto and able to be detected, (e.g., the label can be a radioisotope, fluorescent compound, enzyme or enzyme co-factor).

IV. Assays and Drug Screening Methodologies

In certain aspects, the application provides assays and methods using the vimentin nucleotide sequences as molecular markers that distinguish between healthy cells and vimentin-associated diseased cells. For example, in one embodiment, the application provides methods and assays using the vimentin nucleotide sequences as markers that distinguish between healthy cells and neoplasia cells. In other embodiments, the application provides methods and assays using the vimentin nucleotide sequences as markers that distinguish between healthy cells and cells derived from neoplasias of the upper and lower gastrointestinal tract. In one aspect, a molecular marker of the invention is a differentially methylated vimentin nucleotide sequence. In another aspect, another marker provided herein is the vimentin gene expression product.

In certain embodiments, the invention provides assays for detecting differentially methylated vimentin nucleotide sequences, such as the differential methylation patterns seen in the B and C regions (e.g., SEQ ID NO: 45). Thus, a differentially methylated vimentin nucleotide sequence, in its methylated state, can be a vimentin-associated neoplasia-specific modification that serves as a target for detection using various methods described herein and the methods that are well within the purview of the skilled artisan in view of the teachings of this application.

In certain aspects, such methods for detecting methylated vimentin nucleotide sequences are based on treatment of vimentin genomic DNA with a chemical compound which converts non-methylated C, but not methylated C (i.e., 5 mC), to a different nucleotide base. One such compound is sodium bisulfite, which converts C, but not 5 mC, to U. Methods for bisulfite treatment of DNA are known in the art (Herman, et al., 1996, Proc Natl Acad Sci USA, 93:9821-6; Herman and Baylin, 1998, Current Protocols in Human Genetics, N. E. A. Dracopoli, ed., John Wiley & Sons, 2:10.6.1-10.6.10; U.S. Pat. No. 5,786,146). To illustrate, when a DNA molecule that contains unmethylated C nucleotides is treated with sodium bisulfite to become a compound-converted DNA, the sequence of that DNA is changed (C→U). Detection of the U in the converted nucleotide sequence is indicative of an unmethylated C.

The different nucleotide base (e.g., U) present in compound-converted nucleotide sequences can subsequently be detected in a variety of ways. In a preferred embodiment, the present invention provides a method of detecting U in compound-converted vimentin DNA sequences by using "methylation sensitive PCR" (MSP) (see, e.g., Herman, et al., 1996, *Proc. Natl. Acad. Sci. USA,* 93:9821-9826; U.S. Pat. No. 6,265,171; U.S. Pat. No. 6,017,704; U.S. Pat. No. 6,200,756). In MSP, one set of primers (i.e., comprising a forward and a reverse primer) amplifies the compound-converted template sequence if C bases in CpG dinucleotides within the vimentin DNA are methylated. This set of primers is called "methylation-specific primers." Another set of primers amplifies the compound-converted template sequence if C bases in CpG dinucleotides within the vimentin 5' flanking sequence are not methylated. This set of primers is called "unmethylation-specific primers."

In MS-PCR, the reactions use the compound-converted DNA from a sample in a subject. In assays for vimentin methylated DNA, methylation-specific primers are used. In the case where C within CpG dinucleotides of the target sequence of the DNA are methylated, the methylation-specific primers will amplify the compound-converted template sequence in the presence of a polymerase and an MSP product will be produced. If C within CpG dinucleotides of the target sequence of the DNA is not methylated, the methylation-specific primers will not amplify the compound-converted template sequence in the presence of a polymerase and an MSP product will not be produced.

It is often also useful to run a control reaction for the detection of unmethylated vimentin DNA. The reactions uses the compound-converted DNA from a sample in a subject and unmethylation-specific primers are used. In the case where C within CpG dinucleotides of the target sequence of the DNA are unmethylated, the unmethylation specific primers will amplify the compound-converted template sequence in the presence of a polymerase and an MSP product will be produced. If C within CpG dinucleotides of the target sequence of the DNA is methylated, the unmethylation-specific primers will not amplify the compound-converted template sequence in the presence of a polymerase and an MSP product will not be produced. Note that a biologic sample will often contain a mixture of both neoplastic cells that give rise to a signal with methylation specific primers, and normal cellular elements that give rise to a signal with unmethylation-specific primers. The unmethyl specific signal is often of use as a control reaction, but does not in this instance imply the absence of neoplasia as indicated by the positive signal derived from reactions using the methylation specific primers.

Primers for an MSP reaction are derived from the compound-converted vimentin template sequence. Herein, "derived from" means that the sequences of the primers are chosen such that the primers amplify the compound-converted template sequence in an MSP reaction. Each primer comprises a single-stranded DNA fragment which is at least 8 nucleotides in length. Preferably, the primers are less than 50 nucleotides in length, more preferably from 15 to 35 nucleotides in length. Because the compound-converted vimentin template sequence can be either the Watson strand or the Crick strand of the double-stranded DNA that is treated with sodium bisulfite, the sequences of the primers is dependent upon whether the Watson or Crick compound-converted template sequence is chosen to be amplified in the MSP. Either the Watson or Crick strand can be chosen to be amplified.

The compound-converted vimentin template sequence, and therefore the product of the MSP reaction, can be between 20 to 3000 nucleotides in length, preferably between 50 to 500 nucleotides in length, more preferably between 80 to 150 nucleotides in length. Preferably, the methylation-specific primers result in an MSP product of a different length than the MSP product produced by the unmethylation-specific primers.

A variety of methods can be used to determine if an MSP product has been produced in a reaction assay. One way to determine if an MSP product has been produced in the reaction is to analyze a portion of the reaction by agarose gel electrophoresis. For example, a horizontal agarose gel of from 0.6 to 2.0% agarose is made and a portion of the MSP reaction mixture is electrophoresed through the agarose gel. After electrophoresis, the agarose gel is stained with ethidium bromide. MSP products are visible when the gel is viewed during illumination with ultraviolet light. By comparison to standardized size markers, it is determined if the MSP product is of the correct expected size.

Other methods can be used to determine whether a product is made in an MSP reaction. One such method is called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a product can be quantified and whose quantification is indicative of copy number of that sequence in the template. One such reagent is a fluorescent dye, called SYBR® Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR® Green I, resulting DNA products bind SYBR® Green I and fluorescence. The fluorescence is detected and quantified by the fluorimeter. Such technique is particularly useful for quantification of the amount of the product in the PCR reaction. Additionally, the product from the PCR reaction may be quantitated in "real-time PCR" by the use of a variety of probes that hybridize to the product including TAQMAN® probes and molecular beacons. Quantitation may be on an absolute basis, or may be relative to a constitutively methylated DNA standard, or may be relative to an unmethylated DNA standard. In one instance the ratio of methylated vimentin derived product to unmethylated derived vimentin product may be constructed.

Methods for detecting methylation of the vimentin DNA in this invention are not limited to MSP, and may cover any assay for detecting DNA methylation. Another example method for detecting methylation of the vimentin DNA is by using "methylation-sensitive" restriction endonucleases. Such methods comprise treating the genomic DNA isolated from a subject with a methylation-sensitive restriction endonuclease and then using the restriction endonuclease-treated DNA as a template in a PCR reaction. Herein, methylation-sensitive restriction endonucleases recognize and cleave a specific sequence within the DNA if C bases within the recognition sequence are not methylated. If C bases within the recognition sequence of the restriction endonuclease are methylated, the DNA will not be cleaved. Examples of such methylation-sensitive restriction endonucleases include, but are not limited to HpaII, SmaI, SacII, EagI, MspI, BstUI, and BssHII. In this technique, a recognition sequence for a methylation-sensitive restriction endonuclease is located within the template DNA, at a position between the forward and reverse primers used for the PCR reaction. In the case that a C base within the methylation-sensitive restriction endonuclease recognition sequence is not methylated, the endonuclease will cleave the DNA template and a PCR product will not be formed when the DNA is used as a template in the PCR reaction. In the case that a C base within the methylation-sensitive restriction endonuclease recognition sequence is methylated, the endonuclease will not cleave the DNA template and a PCR product will be formed when the DNA is used as a template in the PCR reaction. Therefore, methylation of C bases can be determined by the absence or presence of a PCR product (Kane, et al., 1997, Cancer Res, 57:808-11). No sodium bisulfite is used in this technique.

Yet another exemplary method for detecting methylation of the vimentin DNA is called the modified MSP, which method utilizes primers that are designed and chosen such that products of the MSP reaction are susceptible to digestion by restriction endonucleases, depending upon whether the compound-converted template sequence contains CpG dinucleotides or UpG dinucleotides.

Yet other methods for detecting methylation of the vimentin DNA include the MS-SnuPE methods. This method uses compound-converted vimentin DNA as a template in a primer extension reaction wherein the primers used produce a product, dependent upon whether the compound-converted template contains CpG dinucleotides or UpG dinucleotides (see e.g., Gonzalgo, et al., 1997, *Nucleic Acids Res.,* 25:2529-31).

Another exemplary method for detecting methylation of the vimentin DNA is called COBRA (i.e., combined bisulfite restriction analysis). This method has been routinely used for DNA methylation detection and is well known in the art (see, e.g., Xiong, et al., 1997, *Nucleic Acids Res,* 25:2532-4).

Another exemplary method for detecting methylation of vimentin DNA requires hybridization of a compound converted DNA to arrays that include probes that hybridize to sequences derived from a methylated vimentin template.

Another exemplary method for detecting methylation of vimentin DNA includes precipitation of methylated DNA with antibodies that bind methylated DNA or with other proteins that bind methylated DNA, and then detection of vimentin DNA sequences in the precipitate. The detection of vimentin DNA could be done by PCR based methods, by hybridization to arrays, or by other methods known to those skilled in the art.

In certain embodiments, the invention provides methods that involve directly sequencing the product resulting from an MSP reaction to determine if the compound-converted vimentin template sequence contains CpG dinucleotides or UpG dinucleotides. Molecular biology techniques such as directly sequencing a PCR product are well known in the art.

In some embodiments, methylation of DNA may be measured as a percentage of total DNA. High levels of vimentin methylation may be 10-100% methylation, for example, 10%, 20%, 30%, 40%, 50%, 60%, 70%, 80%, 90%, or 100% methylation. Low levels of vimentin methylation may be 0%-9.99% methylation, for example, 0%, 0.1%, 0.5%, 1%, 2%, 3%, 4%, 5%, 6%, 7%, 8%, 9%, or 9.99%. At least some normal tissues, for example, normal esophagus samples, may not have any detectable vimentin methylation.

In alternative embodiments, the skilled artisan will appreciate that the present invention is based in part, on the recognition that vimentin may function as a tumor suppressor gene. Accordingly, in certain aspects, the invention provides assays for detecting molecular markers that distinguish between healthy cells and vimentin-associated diseased cells, such as cells derived from a neoplasia of the upper or lower gastrointestinal tract. As described above, one of the molecular markers of the present application includes that methylated vimentin nucleotide sequences. Thus, in one embodiment, assaying for the methylation status of the vimentin nucleotide sequence can be monitored for detecting a vimentin-silencing associated disease.

This application further provides another molecular marker: the vimentin gene expression transcript or the gene product. Thus, in another embodiment, expression of the vimentin nucleic acid or protein can be monitored for detecting a vimentin-silencing associated disease such as a neoplasia of the upper or lower gastrointestinal tract.

In certain embodiments, the invention provides detection methods by assaying the above-mentioned vimentin molecular markers so as to determine whether a patient has or does not have a disease condition. Further, such a disease condition may be characterized by decreased expression of vimentin nucleic acid or protein described herein. In certain embodiments, the invention provides methods for determining whether a patient is or is not likely to have a vimentin-associated disease by detecting the expression of the vimentin nucleotide sequences. In further embodiments, the invention provides methods for determining whether the patient is having a relapse or determining whether a patient's cancer is responding to treatment.

In a preferred embodiment, the application provides method for detecting neoplasia of the upper or lower gastrointestinal tract, the pancreas, and/or the bladder. In certain embodiments, the present invention provides methods for detecting a neoplasia that is associated with silencing of vimentin gene. Such methods comprise assaying for the presence of a methylated vimentin nucleotide sequence in a sample obtained from a subject. In other aspects, the invention relates to methods for determining whether a patient is likely or unlikely to have e.g., a neoplasia of the upper or lower gastrointestinal tract. In further aspects, the invention relates to methods for monitoring, e.g., a neoplasia of the upper or lower gastrointestinal tract in a subject.

In certain embodiments, the invention provides assays for detecting vimentin protein or nucleic acid transcript described herein. In certain embodiments, a method of the invention comprises providing a biological sample and probing the biological sample for the vimentin expression which include protein or nucleic acid transcript of the vimentin. Information regarding the vimentin expression status, and optionally the quantitative level of the vimentin expression, may then be used to draw inferences about the nature of the biological sample and, if the biological sample was obtained from a subject, the health state of the subject.

In certain embodiments, a method of the invention comprises detecting the presence of vimentin protein in a sample. Optionally, the method involves obtaining a quantitative measure of the vimentin protein in the sample. In view of this specification, one of skill in the art will recognize a wide range of techniques that may be employed to detect and optionally quantitate the presence of a protein. In preferred embodiments, vimentin protein is detected with an antibody. In many embodiments, an antibody-based detection assay involves bringing the sample and the antibody into contact so that the antibody has an opportunity to bind to proteins having the corresponding epitope. In many embodiments, an antibody-based detection assay also typically involves a system for detecting the presence of antibody-epitope complexes, thereby achieving a detection of the presence of the proteins having the corresponding epitope. Antibodies may be used in a variety of detection techniques, including enzyme-linked immunosorbent assays (ELISAs), immunoprecipitations, Western blots. Antibody-independent techniques for identifying a protein may also be employed. For example, mass spectroscopy, particularly coupled with liquid chromatography, permits detection and quantification of large numbers of proteins in a sample. Two-dimensional gel electrophoresis may also be used to identify proteins, and may be coupled with mass spectroscopy or other detection techniques, such as N-terminal protein sequencing. RNA aptamers with specific binding for the protein of interest may also be generated and used as a detection reagent.

Samples should generally be prepared in a manner that is consistent with the detection system to be employed. For example, a sample to be used in a protein detection system should generally be prepared in the absence of proteases. Likewise, a sample to be used in a nucleic acid detection system should generally be prepared in the absence of nucleases. In many instances, a sample for use in an antibody-based detection system will not be subjected to substantial preparatory steps. For example, urine may be used directly, as may saliva and blood, although blood will, in certain preferred embodiments, be separated into fractions such as plasma and serum.

In certain embodiments, the invention provides nucleic acid probes that bind specifically to a vimentin nucleic acid. Such probes may be labeled with, for example, a fluorescent moiety, a radionuclide, an enzyme or an affinity tag such as a biotin moiety. For example, the TAQMAN® system employs nucleic acid probes that are labeled in such a way that the fluorescent signal is quenched when the probe is free in solution and bright when the probe is incorporated into a larger nucleic acid.

In certain embodiments, the invention provides nucleic acid probes that bind specifically to a vimentin nucleic acid. Such probes may be labeled with, for example, a fluorescent moiety, a radionuclide, an enzyme or an affinity tag such as a biotin moiety. For example, the TaqMan® system employs nucleic acid probes that are labeled in such a way that the fluorescent signal is quenched when the probe is free in solution and bright when the probe is incorporated into a larger nucleic acid.

Immunoscintigraphy using monoclonal antibodies directed at the vimentin marker may be used to detect and/or diagnose a cancer. For example, monoclonal antibodies against the vimentin marker labeled with $^{99}$Technetium, $^{111}$Indium, $^{125}$Iodine-may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

In certain embodiments, the present invention provides drug screening assays for identifying test compounds which potentiate the tumor suppressor function of the vimentin gene. In one aspect, the assays detect test compounds which potentiate the expression level of the vimentin. In another aspect, the assays detect test compounds which inhibit the methylation of the vimentin nucleotide sequences. In certain embodiments, drug screening assays can be generated which detect test compounds on the basis of their ability to interfere with stability or function of the vimentin polypeptide. Alternatively, simple binding assays can be used to detect compounds that inhibit or potentiate the interaction between the vimentin polypeptide and its interacting protein (e.g., plectin, IFAP-300, Hsc70, alpha-crystallin, PKC, cGMP kinase, or Yes kinase) or the binding of the vimentin polypeptide to a target DNA.

A variety of assay formats may be used and, in light of the present disclosure, those not expressly described herein will nevertheless be considered to be within the purview of ordinary skill in the art. Assay formats can approximate such conditions as vimentin expression level, methylation status of vimentin sequence, tumor suppressing activity, intermediate filament formation activity, and may be generated in many different forms. In many embodiments, the invention provides assays including both cell-free systems and cell-based assays which utilize intact cells.

Compounds to be tested can be produced, for example, by bacteria, yeast or other organisms (e.g., natural products), produced chemically (e.g., small molecules, including peptidomimetics), or produced recombinantly. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In certain embodiments, test compounds identified from these assays may be used in a therapeutic method for treating a vimentin-associated proliferative disease.

Still another aspect of the application provides transgenic non-human animals which express a heterologous vimentin gene, or which have had one or more genomic vimentin gene(s) disrupted in at least one of the tissue or cell-types of the animal. For instance, transgenic mice that are disrupted at their vimentin gene locus can be generated.

In another aspect, the application provides an animal model for a vimentin-associated proliferative disease, which has a mis-expressed vimentin allele. For example, a mouse can be bred which has a vimentin allele deleted, or in which all or part of one or more vimentin exons are deleted. Such a mouse model can then be used to study disorders arising from mis-expression of the vimentin gene.

Accordingly, the present application discloses transgenic animals which are comprised of cells (of that animal) containing a vimentin transgene and which preferably (though optionally) express an exogenous vimentin protein in one or more cells in the animal. The vimentin transgene can encode the wild-type form of the protein, or can encode homologs thereof, including both agonists and antagonists, as well as antisense constructs. The vimentin transgene can include a vimentin nucleotide sequence (e.g., SEQ ID NO: 2) or fragments thereof. In preferred embodiments, the expression of the transgene is restricted to specific subsets of cells, tissues or developmental stages utilizing, for example, cis-acting sequences that control expression in the desired pattern.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the vimentin polypeptides. For example, excision of a target sequence which interferes with the expression of a recombinant vimentin gene can be designed to activate expression of that gene. This interference with expression of the protein can result from a variety of mechanisms, such as spatial separation of the vimentin gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al., (1992) *Proc. Natl. Acad. Sci. USA* 89:6232-6236; Orban et al., (1992) *Proc. Natl. Acad. Sci. USA* 89:6861-6865) or the FLP recombinase system of *Saccharomyces cerevisiae* (O'Gorman et al., (1991) *Science* 251:1351-1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) *J. Biol. Chem.* 259:1509-1514); catalyzing the excision of the target sequence when the loxP sequences are oriented as direct repeats and catalyzes inversion of the target sequence when loxP sequences are oriented as inverted repeats.

V. Subjects and Samples

In certain aspects, the invention relates to a subject suspected of having or has a vimentin-associated disease such as a neoplasia of the upper or lower gastrointestinal tract. Alternatively, a subject may be undergoing routine screening and may not necessarily be suspected of having such a vimentin-associated disease or condition. In a preferred embodiment, the subject is a human subject, and the vimentin-associated disease is colon neoplasia. In other embodiments, the subject is a human, and the vimentin-associated disease is a neoplasia of the upper gastrointestinal tract.

Assaying for vimentin markers discussed above in a sample from subjects not known to have, e.g., a neoplasia of the upper or lower gastrointestinal tract can aid in diagnosis of such a neoplasia in the subject. To illustrate, detecting the methylation status of the vimentin nucleotide sequence by MSP can be used by itself, or in combination with other various assays, to improve the sensitivity and/or specificity for detecting, e.g., a neoplasia of the upper or lower gastrointestinal tract. Preferably, such detection is made at an early stage in the development of cancer, so that treatment is more likely to be effective.

In addition to diagnosis, assaying of a vimentin marker in a sample from a subject not known to have, e.g., a neoplasia of the upper or lower gastrointestinal tract, can be prognostic for the subject (i.e., indicating the probable course of the disease). To illustrate, subjects having a predisposition to develop a neoplasia of the upper or lower gastrointestinal tract may possess methylated vimentin nucleotide sequences. Assaying of vimentin markers in a sample from subjects can also be used to select a particular therapy or therapies which are particularly effective against, e.g., a neoplasia of the upper or lower gastrointestinal tract in the subject, or to exclude therapies that are not likely to be effective.

Assaying of vimentin markers in samples from subjects that are known to have, or to have had, a cancer associated with silencing of the vimentin gene is also useful. For example, the present methods can be used to identify whether therapy is effective or not for certain subjects. One or more samples are taken from the same subject prior to and following therapy, and assayed for the vimentin markers. A finding that the vimentin marker is present in the sample taken prior to therapy and absent (or at a lower level) after therapy would indicate that the therapy is effective and need not be altered. In those cases where the vimentin marker is present in the sample taken before therapy and in the sample taken after therapy, it may be desirable to alter the therapy to increase the likelihood that the cancer will be eradicated in the subject. Thus, the present method may obviate the need to perform more invasive procedures which are used to determine a patient's response to therapy.

Cancers frequently recur following therapy in patients with advanced cancers. In this and other instances, the assays of the invention are useful for monitoring over time the status of a cancer associated with silencing of the vimentin gene. For subjects in which a cancer is progressing, a vimentin marker may be absent from some or all samples when the first sample is taken and then appear in one or more samples when the second sample is taken. For subjects in which cancer is regressing, a vimentin marker may be present in one or a number of samples when the first sample is taken and then be absent in some or all of these samples when the second sample is taken.

Samples for use with the methods described herein may be essentially any biological material of interest. For example, a sample may be a bodily fluid sample from a subject, a tissue sample from a subject, a solid or semi-solid sample from a subject, a primary cell culture or tissue culture of materials derived from a subject, cells from a cell line, or medium or other extracellular material from a cell or tissue culture, or a xenograft (meaning a sample of a cancer from a first subject, e.g., a human, that has been cultured in a second subject, e.g., an immuno-compromised mouse). The term "sample" as used herein is intended to encompass both a biological material obtained directly from a subject (which may be described as the primary sample) as well as any manipulated forms or portions of a primary sample. A sample may also be obtained by contacting a biological material with an exogenous liquid, resulting in the production of a lavage liquid containing some portion of the contacted biological material. Furthermore, the term "sample" is intended to encompass the primary sample after it has been mixed with one or more additive, such as preservatives, chelators, anti-clotting factors, etc.

In certain embodiments, a bodily fluid sample is a blood sample. In this case, the term "sample" is intended to encompass not only the blood as obtained directly from the patient but also fractions of the blood, such as plasma, serum, cell fractions (e.g., platelets, erythrocytes, and lymphocytes), protein preparations, nucleic acid preparations, etc. In certain embodiments, a bodily fluid sample is a urine sample or a colonic effluent sample. In certain embodiments, a bodily fluid sample is a stool sample. In some embodiments, the bodily fluid may be derived from the stomach, for example, gastric secretions, acid reflux, or vomit. In other embodiments, the bodily fluid may be a fluid secreted by the pancreas or bladder. In other embodiments, the body fluid may be saliva or spit.

In certain embodiments, a tissue sample is a biopsy taken from the mucosa of the gastrointestinal tract. In other embodiments, a tissue sample is the brushings from, e.g., the esophagus of a subject.

A subject is preferably a human subject, but it is expected that the molecular markers disclosed herein, and particularly their homologs from other animals, are of similar utility in other animals. In certain embodiments, it may be possible to detect a vimentin marker directly in an organism without obtaining a separate portion of biological material. In such instances, the term "sample" is intended to encompass that portion of biological material that is contacted with a reagent or device involved in the detection process.

In certain embodiments, DNA which is used as the template in an MSP reaction is obtained from a bodily fluid sample. Examples of preferred bodily fluids are blood, serum, plasma, a blood-derived fraction, stool, colonic effluent or urine. Other body fluids can also be used. Because they can be easily obtained from a subject and can be used to screen for multiple diseases, blood or blood-derived fractions are especially useful. For example, it has been shown that DNA alterations in colorectal cancer patients can be detected in the blood of subjects (Hibi, et al., 1998, Cancer Res, 58:1405-7). Blood-derived fractions can comprise blood, serum, plasma, or other fractions. For example, a cellular fraction can be prepared as a "buffy coat" (i.e., leukocyte-enriched blood portion) by centrifuging 5 ml of whole blood for 10 min at 800 times gravity at room temperature. Red blood cells sediment most rapidly and are present as the bottom-most fraction in the centrifuge tube. The buffy coat is present as a thin creamy white colored layer on top of the red blood cells. The plasma portion of the blood forms a layer above the buffy coat. Fractions from blood can also be isolated in a variety of other ways. One method is by taking a fraction or fractions from a gradient used in centrifugation to enrich for a specific size or density of cells.

DNA is then isolated from samples from the bodily fluids. Procedures for isolation of DNA from such samples are well known to those skilled in the art. Commonly, such DNA isolation procedures comprise lysis of any cells present in the samples using detergents, for example. After cell lysis, proteins are commonly removed from the DNA using various proteases. RNA is removed using RNase. The DNA is then commonly extracted with phenol, precipitated in alcohol and dissolved in an aqueous solution.

VI. Therapeutic Methods for Vimentin-Associated Diseases

Yet another aspect of this application pertains to methods of treating a vimentin-associated proliferative disease which arises from reduced expression or over-expression of the vimentin gene in cells. Such vimentin-associated proliferative diseases (for example, a neoplasia of the upper or lower gastrointestinal tract) can result from a wide variety of pathological cell proliferative conditions. In certain embodiments, treatment of a vimentin-associated proliferative disorder includes modulation of the vimentin gene expression or vimentin activity. The term "modulate" envisions the suppression of expression of vimentin when it is over-expressed, or augmentation of vimentin expression when it is under-expressed.

In an embodiment, the present invention provides a therapeutic method by using a vimentin gene construct as a part of a gene therapy protocol, such as to reconstitute the function of a vimentin protein (e.g., SEQ ID NO: 1) in a cell in which the vimentin protein is mis-expressed or non-expressed. To illustrate, cell types which exhibit pathological or abnormal growth presumably depend at least in part on a function of a vimentin protein. For example, gene therapy constructs encoding the vimentin protein can be utilized in, e.g., a neoplasia of the upper or lower gastrointestinal tract that is associated with silencing of the vimentin gene.

In certain embodiments, the invention provides therapeutic methods using agents which induce re-expression of vimentin. Loss of vimentin gene expression in a vimentin-associated diseased cell may be due at least in part to methylation of the vimentin nucleotide sequence, methylation suppressive agents such as 5-deoxyazacytidine or 5-azacytidine can be introduced into the diseased cells. Other similar agents will be known to those of skill in the art. In a preferred embodiment, the vimentin-associated disease is, e.g., a neoplasia of the upper or lower gastrointestinal tract associated with increased methylation of vimentin nucleotide sequences.

In certain embodiments, the invention provides therapeutic methods using a nucleic acid approach, for example, antisense nucleic acid, ribozymes or triplex agents, to block transcription or translation of a specific vimentin mRNA, either by masking that mRNA with an antisense nucleic acid or triplex agent or by cleaving it with a ribozyme. Such disorders include neurodegenerative diseases, for example. Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into a target vimentin over-producing cell. Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6): 569, 1991). Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988).

The present invention also provides gene therapy for the treatment of proliferative or immunologic disorders which are mediated by vimentin protein. Such therapy would achieve its therapeutic effect by introduction of the vimentin antisense polynucleotide into cells having the proliferative disorder. Alternatively, it may be desirable to introduce polynucleotides encoding full-length vimentin into diseased cells.

Delivery of antisense vimentin polynucleotide or the vimentin gene can be achieved using a recombinant expression vector such as a chimeric virus or a colloidal dispersion system. Especially preferred for therapeutic delivery of antisense sequences is the use of targeted liposomes. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a vimentin sequence of interest into the viral vector, along with another gene which encodes the ligand for a receptor on a specific target cell, for example, the vector is target-specific. Retroviral vectors can be made target-specific by attaching, for example, a sugar, a glycolipid or a protein. Preferred targeting is accomplished by using an antibody to target the retroviral vector. Those skilled in the art will know of, or can readily ascertain without undue experimentation, specific polynucleotide sequences which can be inserted into the retroviral genome or attached to a viral envelope to allow target-specific delivery of the retroviral vector containing antisense vimentin polynucleotide or the vimentin gene.

The invention also relates to a medicament or pharmaceutical composition comprising a vimentin 5' flanking polynucleotide or a vimentin 5' flanking polynucleotide operably linked to the vimentin structural gene, respectively, in a pharmaceutically acceptable excipient or medium wherein the medicament is used for therapy of vimentin-associated cell proliferative disorders, such as, e.g., a neoplasia of the upper or lower gastrointestinal tract.

EXEMPLIFICATION

The invention now being generally described, it will be more readily understood by reference to the following examples, which are included merely for purposes of illustration of certain aspects and embodiments of the present invention, and are not intended to limit the invention.

Example 1

1. Cell Culture and 5-Azacytidine Treatment

The cultures were grown and treated as described previously (Veigl, et al., 1998, *Proc. Natl. Acad. Sci. USA*, 95:8698-8702). The optimal tolerated doses were determined for each treated line, and two doses were used for some lines, ranging from 1 μg/ml to 3 μg/ml.

2. Methylation-Sensitive Restriction Endonuclease Assays (e.g., HpaII Assays)

We examined the genomic sequence upstream of and within the vimentin gene (herein referred to as 5'-vimentin genomic sequence) which contained a CpG dense region that could potentially be methylated (FIGS. 1 and 6). To test for methylation of this CpG-rich region, we first utilized the HpaII assays. Sample DNAs were digested with the methylation-sensitive enzyme HpaII, and then amplified by a pair of PCR primers. When the DNA is methylated, it is resistant to the HpaII digestion and accordingly a PCR product is produced. On the other hand, when the DNA is unmethylated, it is susceptible to the HpaII digestion and accordingly a PCR product is not produced. The positions of the CpG dinucleotides are shown as balloons in the 5' genomic region of the vimentin gene and four subdomains A-D of this genomic region were tested for aberrant methylation in colon cancer (FIG. 1). The positions of the PCR primers used for the HpaII assays are also shown in FIG. 1. Sequences of the PCR primers used to amplify the A, C, and D regions in the HpaII assays are provided in FIG. 13.

3. Reduced Vimentin Expression in Colon Cancer Cells

Figure 2:
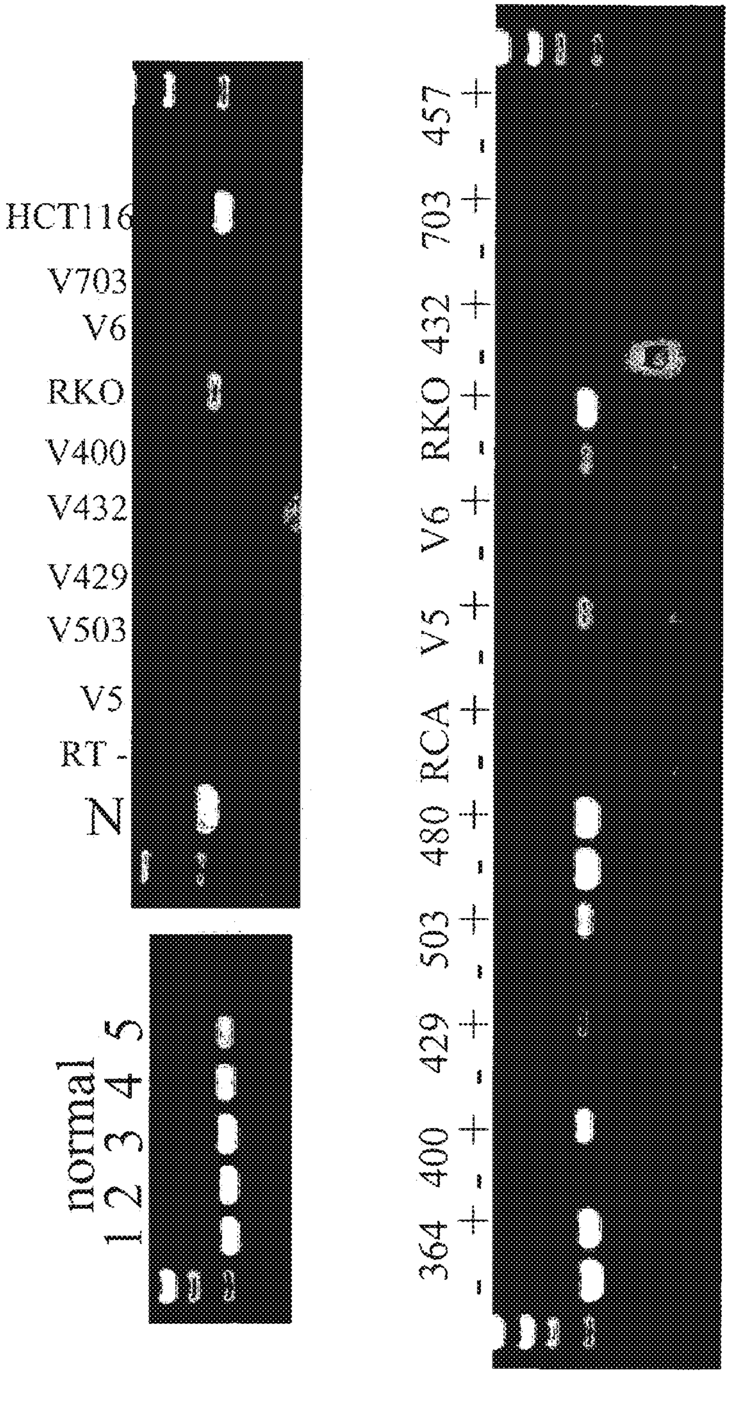
FIG. 2 shows the RT-PCR results that vimentin is well expressed in normal colon cell lines, but is poorly expressed in colon cancer cell lines. The vimentin expression is induced by the demethylating agent 5-AzaCytidine in 9 of 12 colon cancer cell lines.

RT-PCR results showed that the vimentin is well expressed in normal colon, but is scantily expressed in colon cancer cell lines (FIG. 2). To establish that methylation was responsible for silencing vimentin gene expression, cell lines with vimentin DNA methylation were treated with 5-azacytidine (5-azaC), a demethylating agent. As shown in FIG. 2, 5-azaC treatment reactivated vimentin expression in 9 of 12 colon cancer cell lines (V400, V429, V503, RCA, V5, RKO, V432, V703, and V457).

Figure 3:
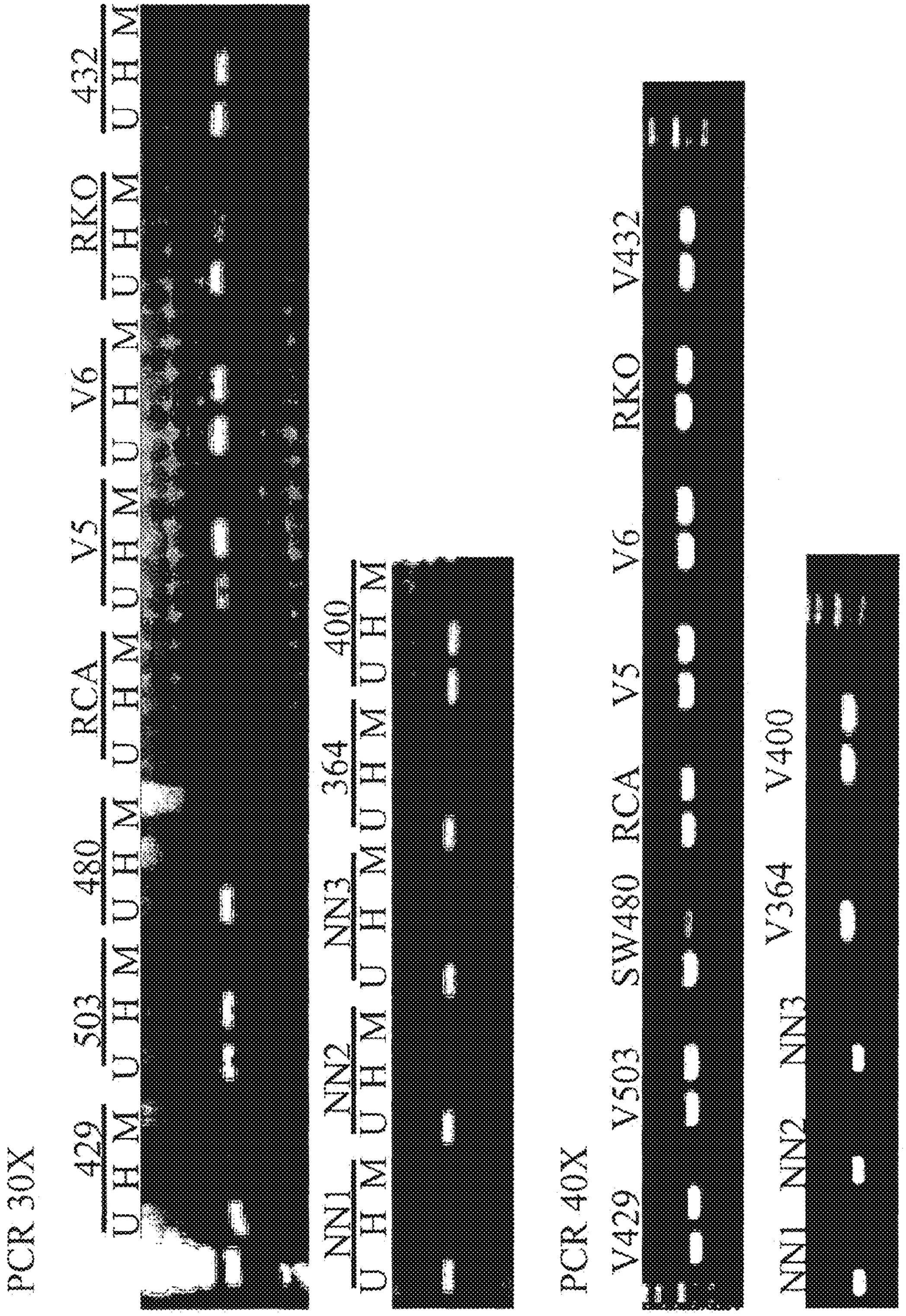
FIG. 3 illustrates the results from HpaII assays for vimentin methylation in the C region by PCR amplification at 30 cycles (upper panel) or 40 cycles (lower panel). The PCR reactions are performed after no digestion (U), digestion with the methylation sensitive restriction enzyme HpaII (H), or digestion with the methylation indifferent enzyme Msp1 (M). Three Non-Cancer Normal tissues (NN1, NN2, and NN3) are all unmethylated, whereas 9 of 10 colon cancer cell lines all show methylation.
Figure 4:
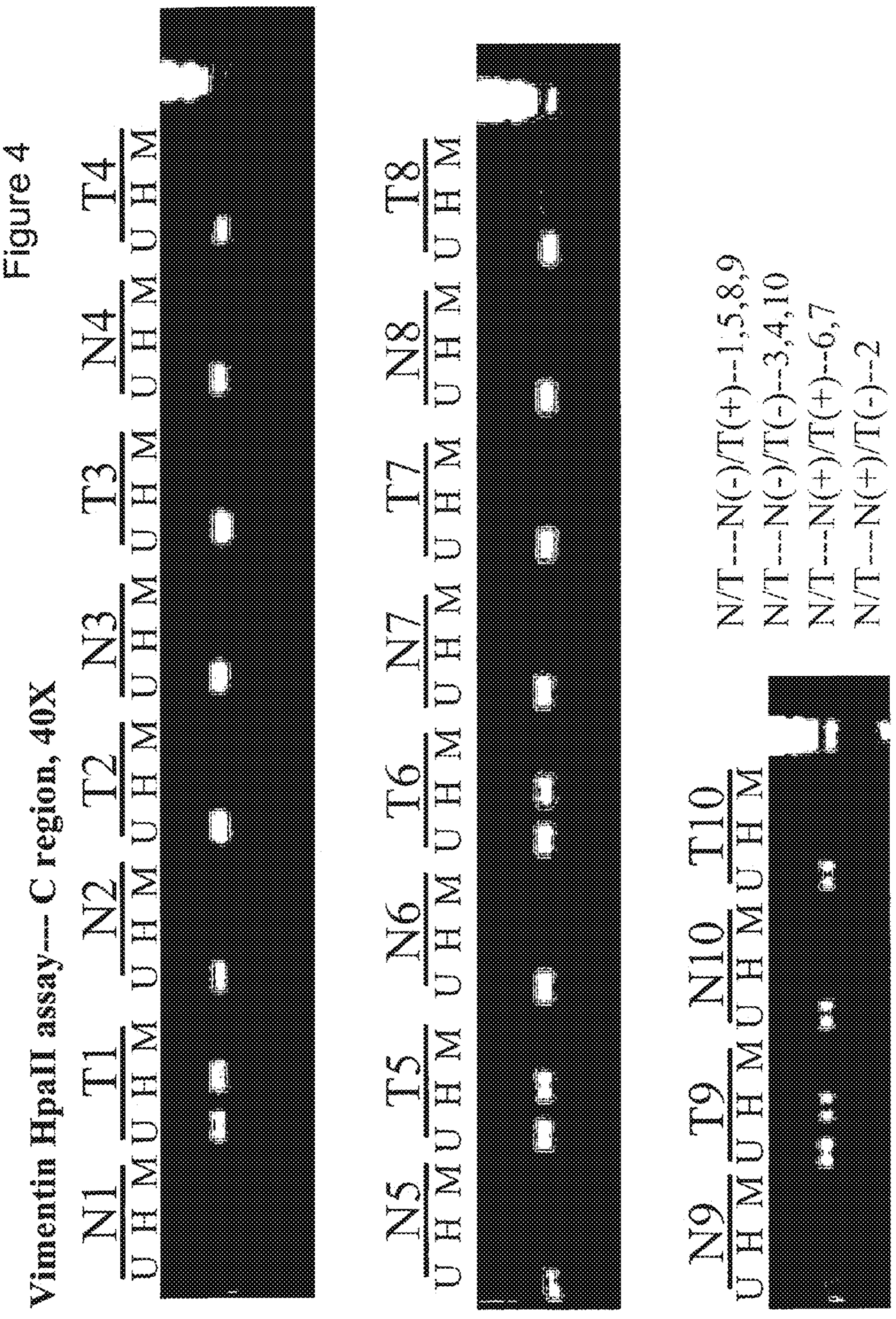
FIG. 4 illustrates the results from HpaII assays for vimentin methylation in the C region in 10 paired Normal/Tumor colon tissue samples (N1-10, and T1-10), by PCR amplification at 40 cycles after restriction enzyme digestion by HpaII.
Figure 5:
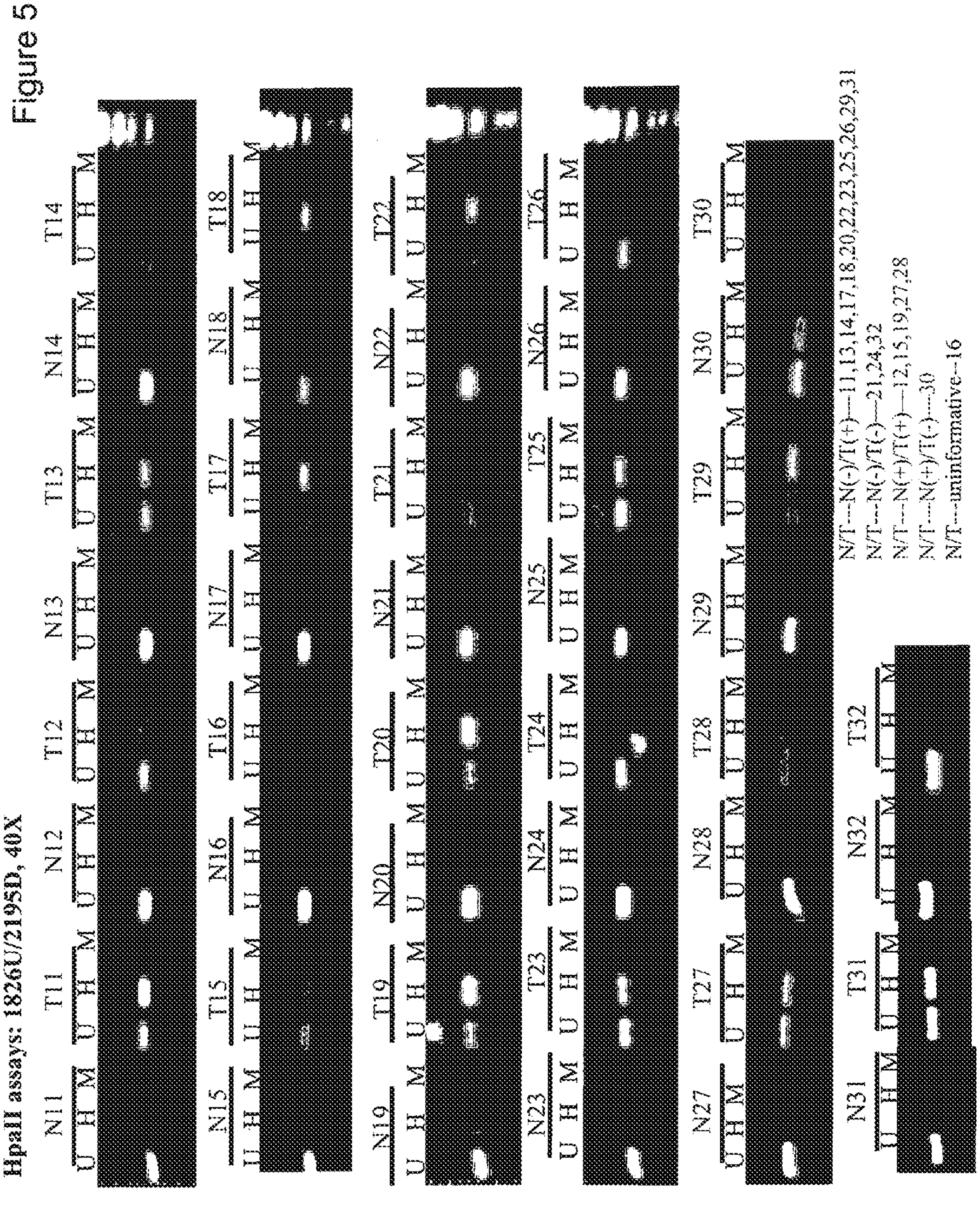
FIG. 5 illustrates the results from HpaII assays for vimentin methylation in the C region in 22 paired Normal/Tumor colon tissue samples (N11-32, and T11-32), by PCR amplification at 40 cycles after restriction enzyme digestion by HpaII.
Figure 6A:
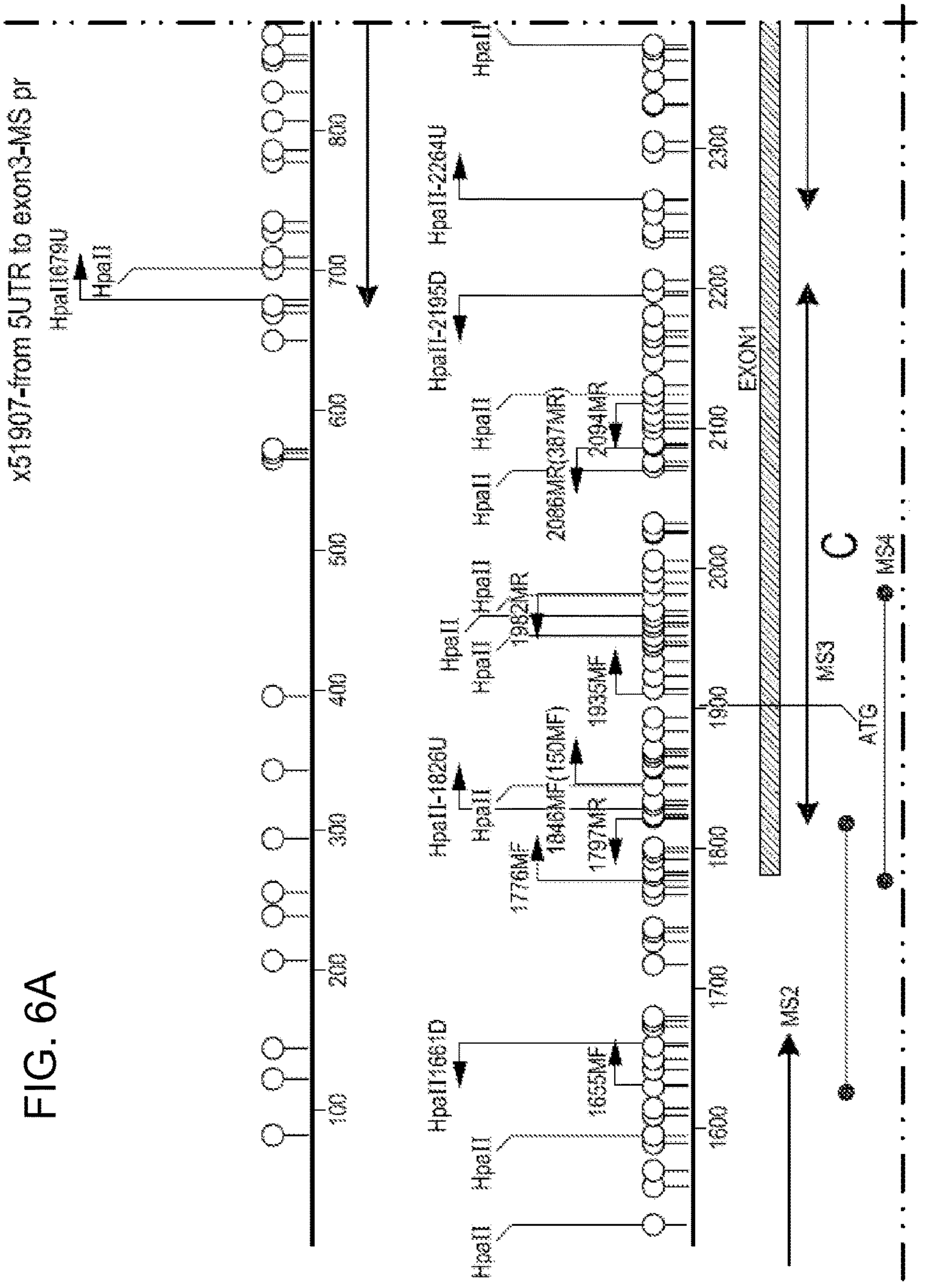
FIGS. 6A-6D show a further diagrammatic depiction of the vimentin gene. The positions of primers for MS-PCR inside the B and C regions are indicated as MS-PCR pairs 1-5.
Figure 6B:
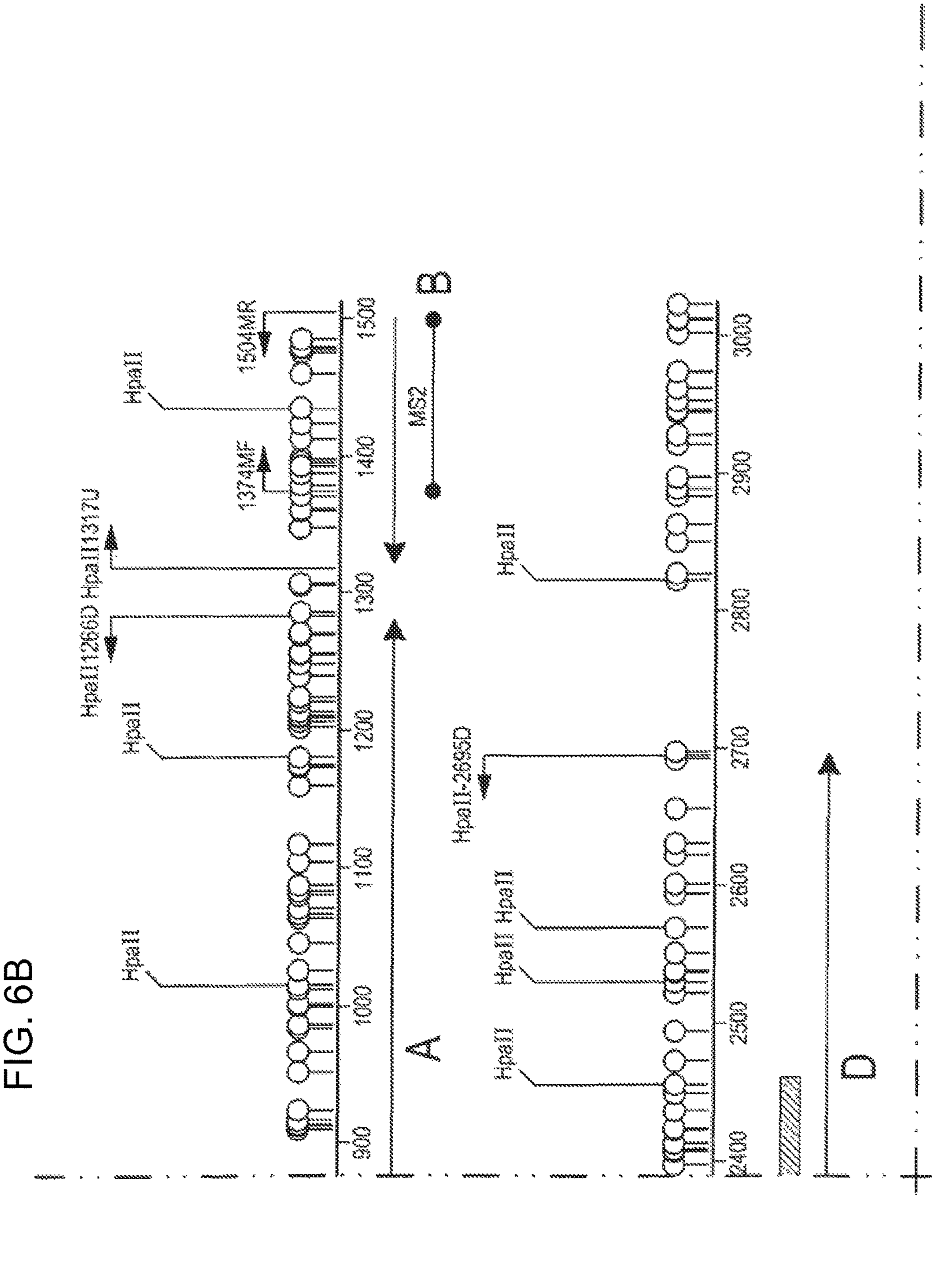
Figure 6C:
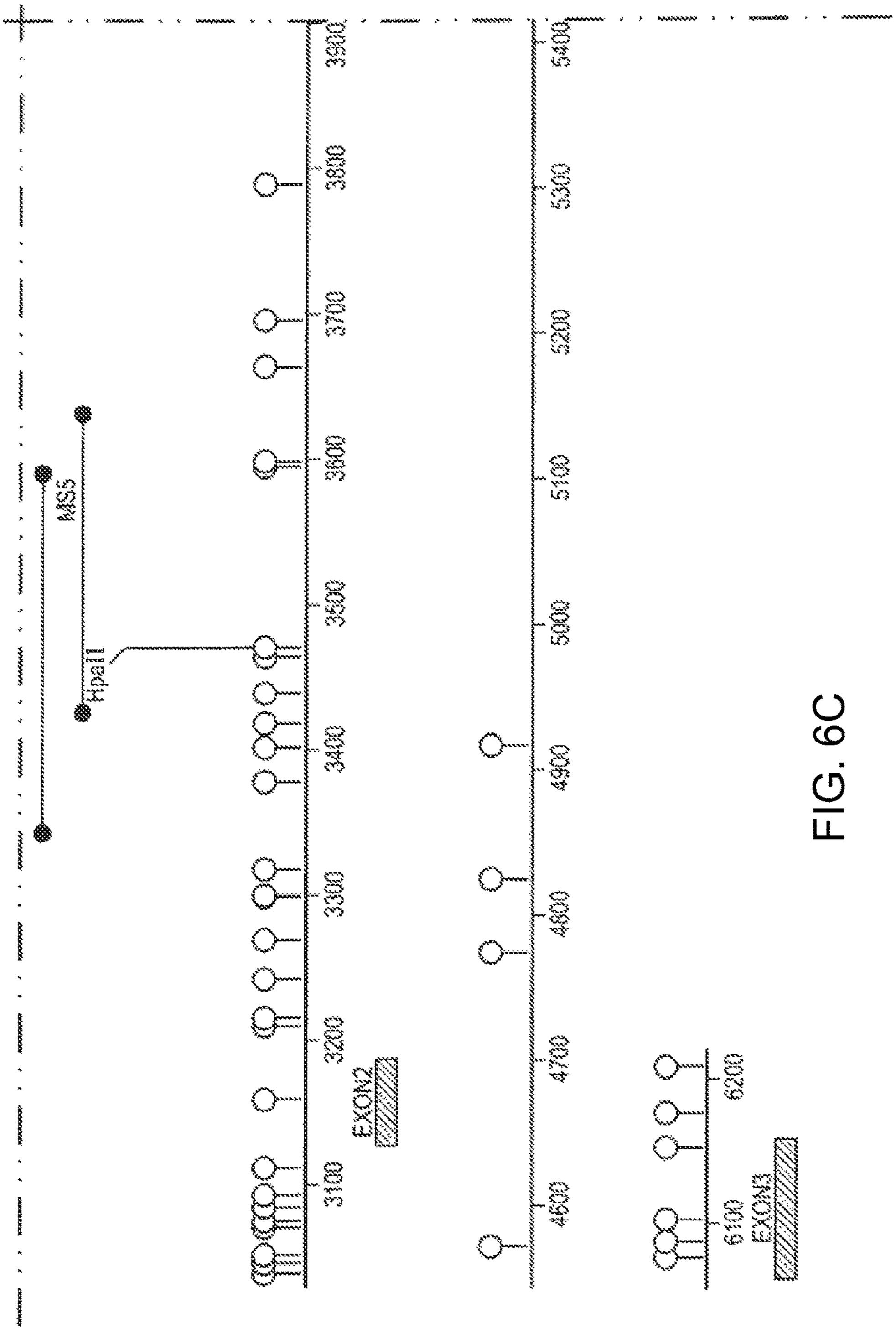
Figure 6D:
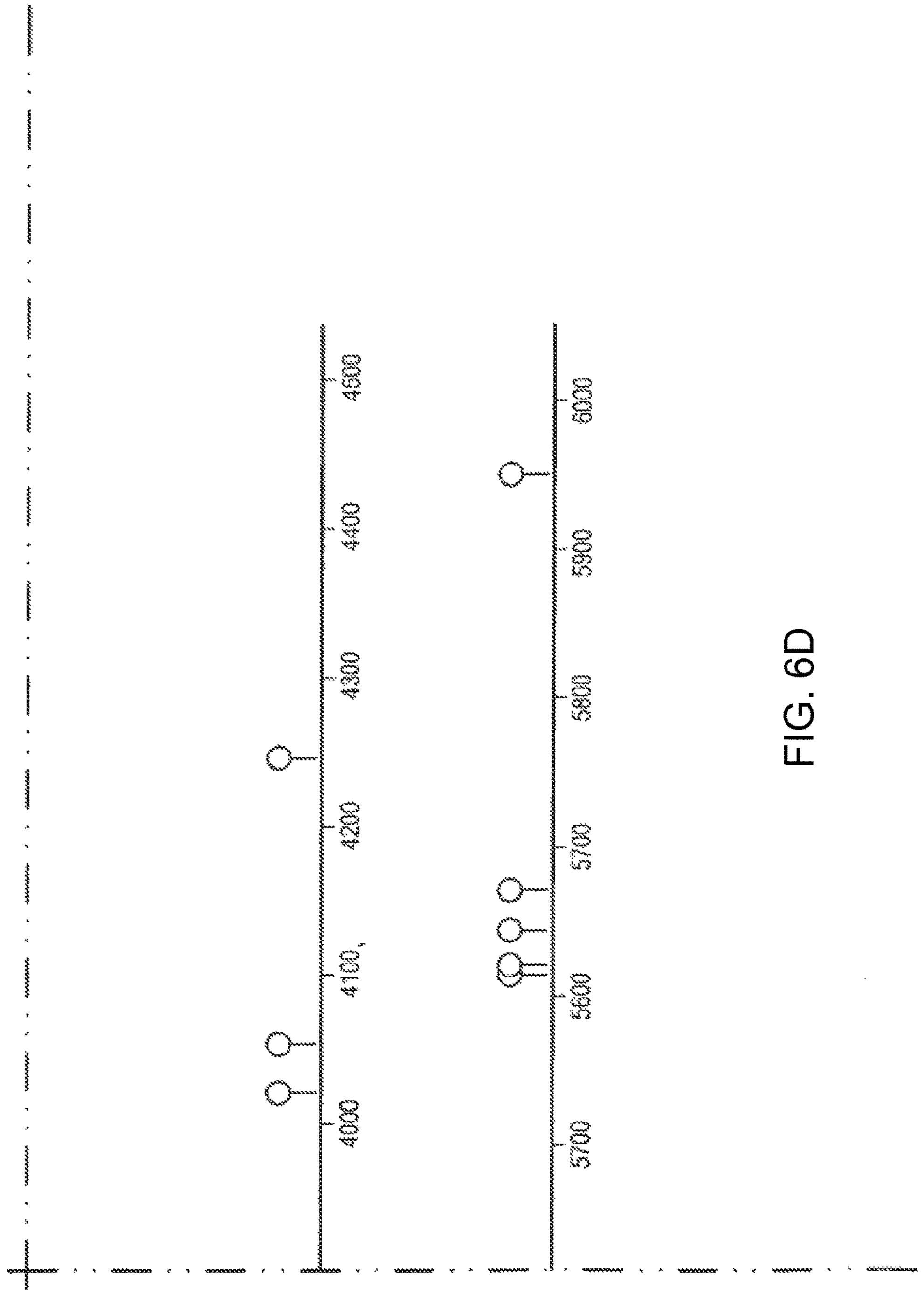

4. Vimentin is Frequently Methylated and Silenced in Colon Cancer Cell Lines Methylation of the vimentin genomic sequence in the C region was detected by HpaII assays in colon cancer cell lines (FIG. 3) or colon tumors (FIGS. 4-5). PCR amplification was performed at either 30 or 40 cycles after no digestion (U), digestion with the methylation sensitive restriction enzyme HpaII (H), or digestion with the methylation indifferent enzyme Msp1 (M). Three Non-Cancer Normal tissues (NN) are all unmethylated, whereas 9 of 10 colon cancer cell lines all show methylation (FIG. 3). Methylation of the vimentin genomic sequence in the C region was also detected in paired Normal/Tumor samples by HpaII assays. As shown in FIGS. 4 and 5, differential methylation of vimentin in the C region was detected in 16 of 31 colon tumors after PCR amplification of 40 cycles.

Overall, HpaII assays demonstrate methylation of vimentin in the C region, with a sensitivity for diagnosis of colon cancer of 74% and a specificity of 93% (2 false positive normal tissues in persons without colon cancer). These results establish vimentin as a gene that is differentially methylated in colon cancer.

In addition, similar HpaII assays results suggested that the incidence of aberrant methylation of the vimentin nucleotide sequence in colon cancers was lesser in the A and D regions taken as total blocks, than in the C region. However, the B region and the 3' portion of the A region, also remain good candidate regions, that in addition to the C region, could harbor cancer specific aberrant methylation of vimentin. Results of HpaII assays in the A, C, D regions in colon cancer cell lines is summarized in Table II immediately below.

TABLE II

Results of HpaII assays in the A, C, D regions in colon cancer cell lines.

| Colon cancer cell line | A region assay | C region assay | D region assay |
|---|---|---|---|
| V364 | U | U | U |
| V400 | faint M | M | faint M |
| V429 | U | M | NA |
| V503 | U | M | U |
| SW480 | U | U | U |
| RCA | U | M | U |
| V5 | M | M | U |
| V6 | M | M | U |
| RKO | M | M | M |
| V432 | M | M | NA |

5. Methylation-Specific PCR (MS-PCR)

500 ng DNA from each sample in a volume of 50 μl were denatured by NaOH (freshly made, final concentration, 0.2 M) at 37° C. for 15 min. Next, 30 μl 10 mM hydroquinone (fresh) and 520 μl 3.0 M $NaHSO_4$ (freshly prepared sodium bisulfite, pH 5.0) were added, and incubated at 55° C. for 16 hrs. Modified DNA was purified using Wizard DNA Clean-Up System (Promega). The reaction was desulphonated by NaOH at a final concentration of 0.3 M at room temperature for 15 min and neutralized by adding 10 M $NH_4OAc$, pH 7.0, to a final concentration of 3 M. DNA was precipitated with 3 volumes of absolute ethanol for 30 min at −80° C. The DNA pellet was then dissolved in distilled water to give approximately 10 ng/μl. Sodium bisulfite treated DNA was used as the template for subsequent methylation-specific PCR.

The positions of primers for MS-PCR inside the B and C regions of the vimentin genomic sequence are indicated as MS-PCR pairs 1-5 (FIG. 6). The positions of additional MS-PCR primer pair 1-2 and MSP pairs 6-10 are indicated in FIG. 16. All the primer sequences were designed based on the vimentin 5' genomic sequence and were specific for fully modified DNA. The sequences of the MSP-PCR primer sets 1, 1-2, and 3-10 are shown in FIGS. 14 and 15. Sequences of control primer sets used to amplify bisulfite-converted sequences (sense or antisense) of the duplex unmethylated vimentin DNA (designated as UF or UR), are also provided in FIGS. 14 and 15. PCR was carried out and the PCR products were run on 3.0% agarose gel.

Figure 7:
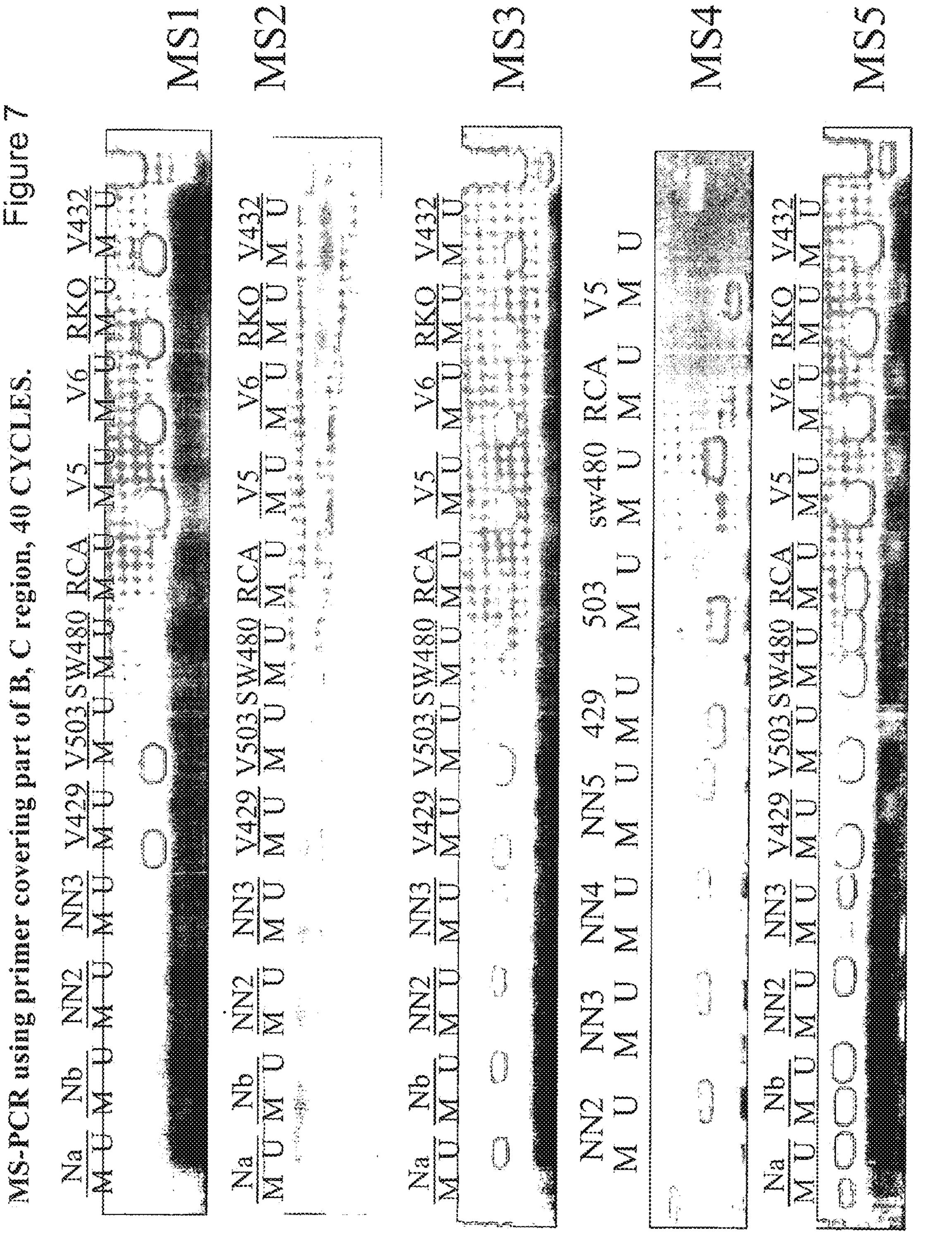
FIG. 7 shows the results from MS-PCR using primer pairs 1-5 which cover partially the B and C regions of the vimentin genomic sequence. Primer pairs 1, 4, and 5 all detect vimentin methylation in normal colon tissues (designated N) when assayed by MS-PCR at 40 cycles. In contrast, the primer pair 3 defines a differentially methylated region that is methylated in vimentin non-expressing colon cancer cell lines, but not in normal colon tissues or in vimentin expressing cell line SW480.
Figure 8:
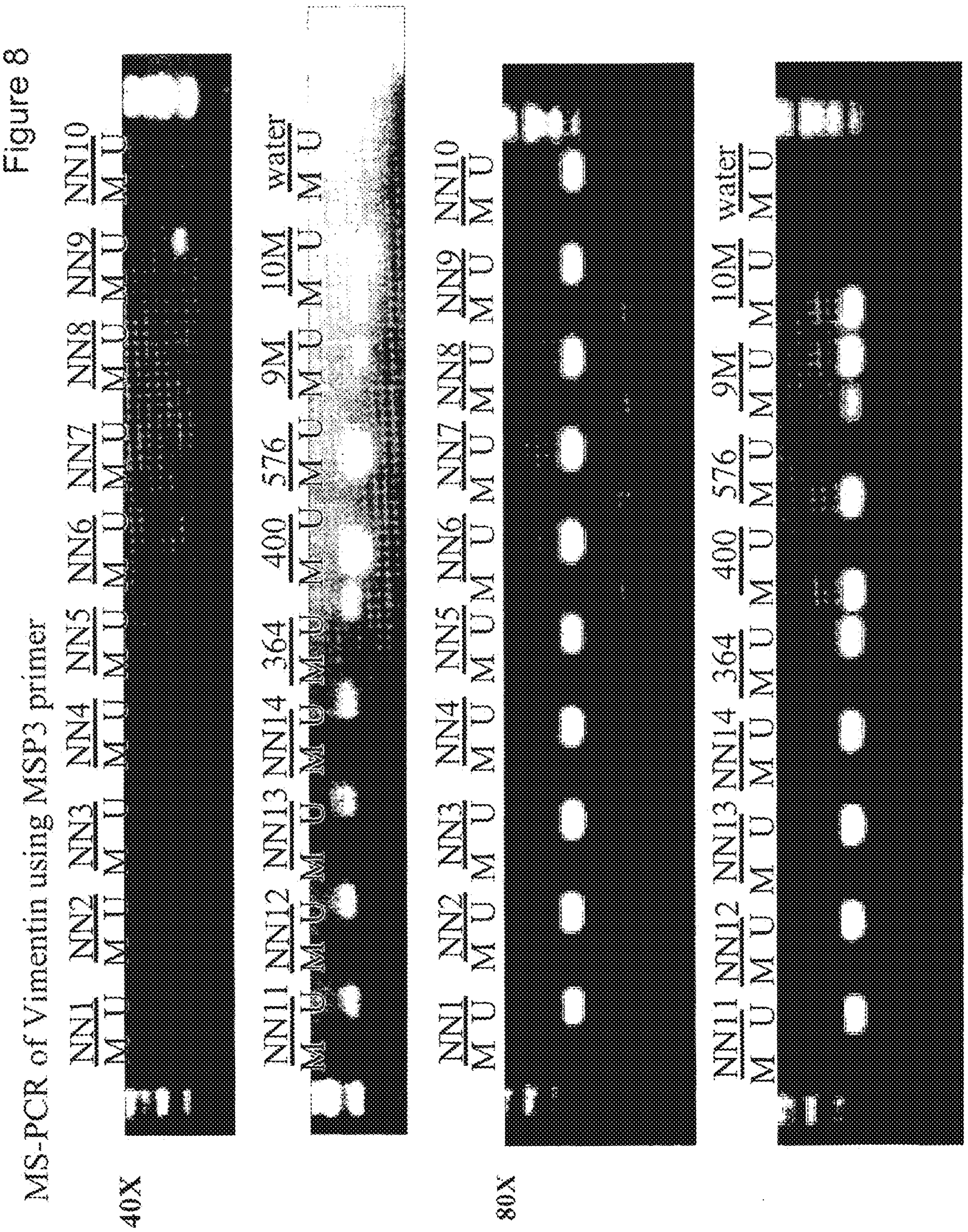
FIG. 8 shows the results from MS-PCR using the primer pair MSP3. No methylation of vimentin is detected in any of the 14 normal colon tissue samples from non-cancer resections (designated as NN) even when the MSP3 reaction is run to 80 cycles of PCR by performing 2 sequential 40 cycle reactions.

6. Improved Sensitivity and Specificity of MS-PCR for Detecting Vimentin Methylation We further used the methylation-specific PCR technique to test for methylation of the CpG-rich region of vimentin, employing PCR primers specific for amplification of either methylated or unmethylated DNA templates (FIGS. 7-12). As shown in FIG. 7, MS-PCR primer pairs 1, 4, and 5 all detected methylation in normal colon tissues when assayed by PCR at 40 cycles. In contrast, MS-PCR primer pair 3 defined a differentially methylated region that is methylated in vimentin non-expressing colon cancer cell lines, but not in normal colonic tissue or in vimentin expressing cell line SW480. Independent MS-PCR assays confirmed that that the MS-PCR primer pair MS3 detected no methylation of vimentin in any of 14 normal colon resections from non-cancer resections even when the PCR reaction was run to 80 cycles by performing 2 sequential 40-cycle reactions (FIG. 8).

Figure 9:
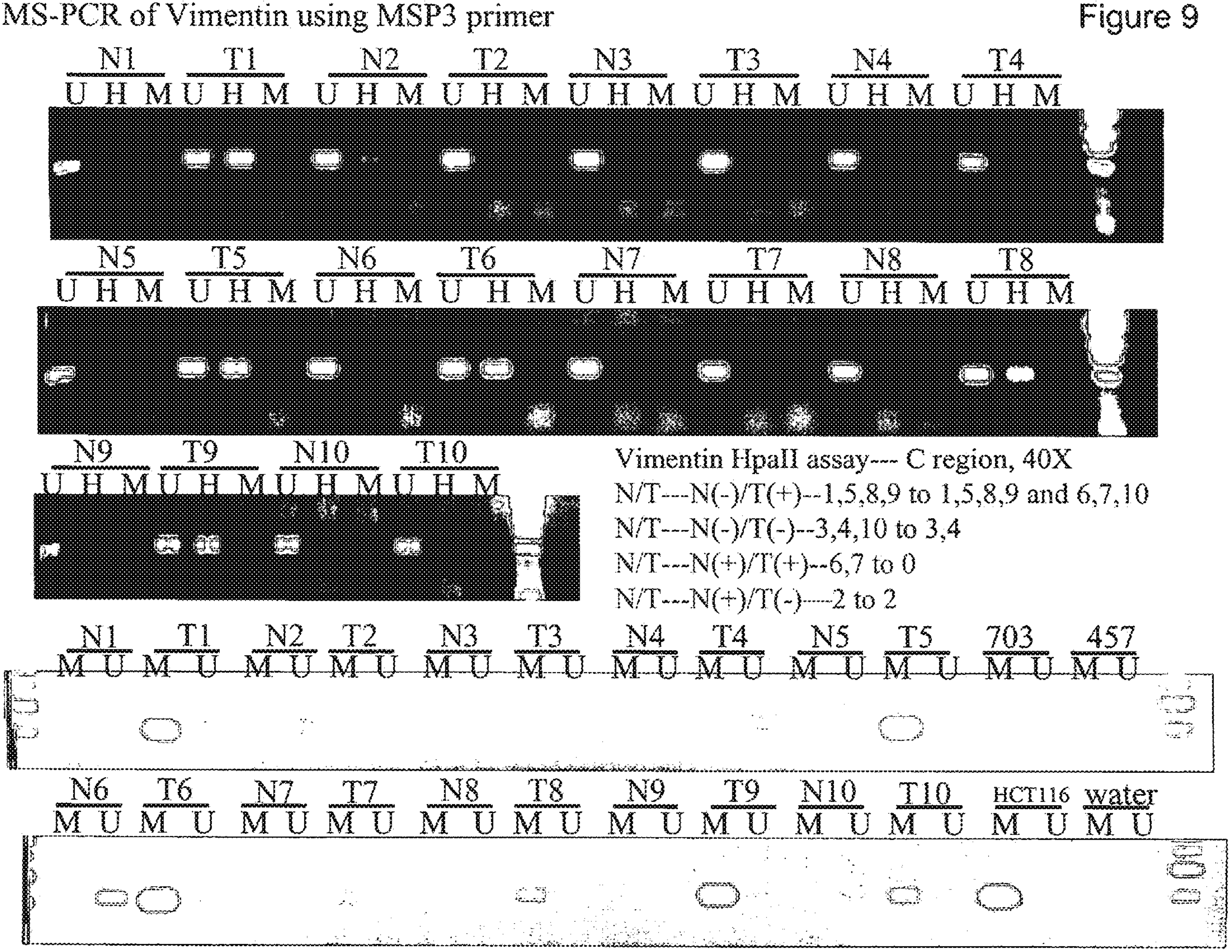
FIG. 9 shows the comparison between the HpaII assays (upper rows) to the MS-PCR using MSP3 at 40 cycles (lower rows) for detecting vimentin methylation in the C region in 10 paired Normal/Tumor colon tissue samples.

As shown in FIG. 9, the MS-PCR assays using the primer pair MSP3 was compared with the HpaII assays for the methylation of vimentin in the C Region in 10 paired Normal/Tumor samples. In these 10 cases, the MS-PCR assays using the primer pair MSP3 showed substantially improved sensitivity and specificity for detecting vimentin methylation as summarized below in Table III. Specifically, the MSP3 primer in the MS-PCR assays shows 70% sensitivity and 90% specificity (one false positive with an unmethylated tumor) for detecting colon cancer.

TABLE III

Comparison of sensitivity and specificity between MS-PCR assays (using the MSP3 primer pair) and HpaII assays.

| Normal | Tumor | MS-PCR Assays | HpaII Assays |
|---|---|---|---|
| unmethylated | methylated | 7 | 4 |
| unmethylated | unmethylated | 2 | 3 |
| methylated | methylated | 0 | 2 |
| methylated | unmethylated | 1 | 1 |

Figure 10:
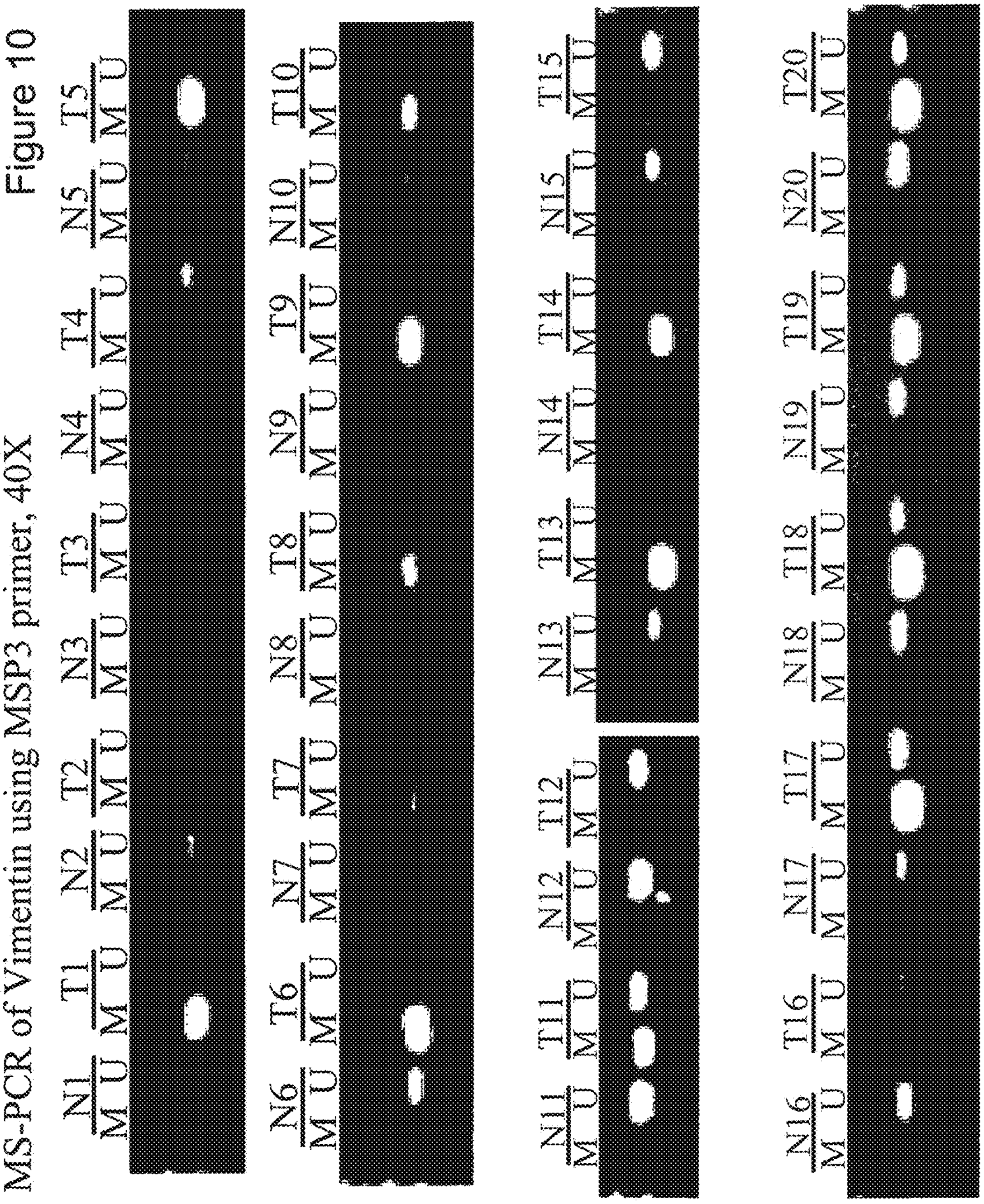
FIG. 10 shows the MS-PCR using the MSP3 primer at 40 cycles for detecting vimentin methylation in 20 paired Normal/Tumor colon tissue samples (N1-20 and T1-20).
Figure 11:
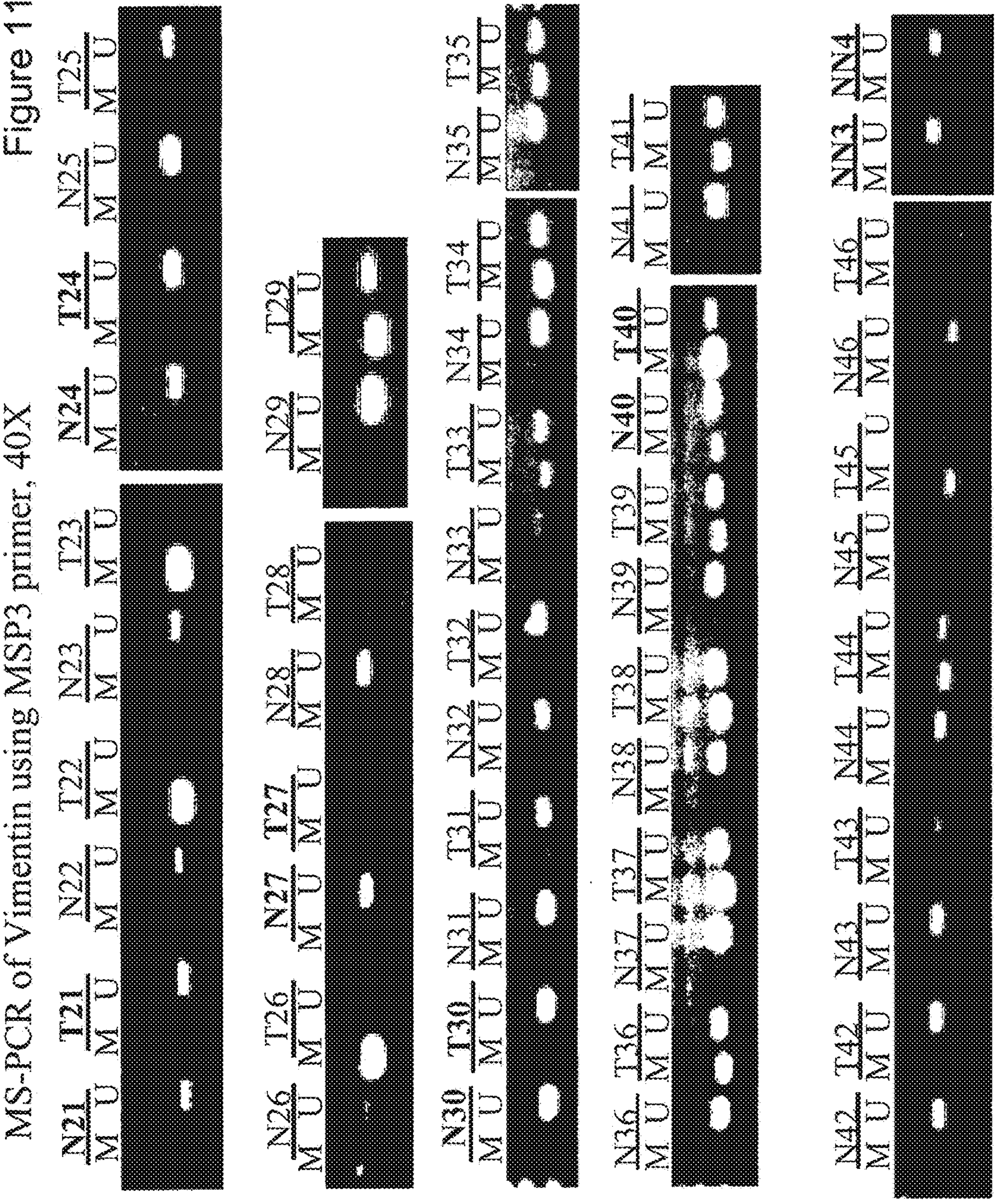
FIG. 11 shows the MS-PCR using the MSP3 primer at 40 cycles for detecting vimentin methylation in 26 paired Normal/Tumor colon tissue samples (N21-46 and T21-46).

MS-PCR assays using the MSP3 primer was further extended to the analysis of 46 paired Normal/Tumor samples as shown in FIG. 10 (samples N1-20 and T1-20) and FIG. 11 (samples N21-46 and T21-46). These 46 paired samples were assayed by MS-PCR of 40 cycles using the MSP3 primer for methylation (M) or unmethylation (U) of the vimentin nucleotide sequence. In these 46 cases, the MS-PCR assays using the primer pair MSP3 showed 84% sensitivity and 96% specificity for detecting colon cancer as summarized below in Table IV.

TABLE IV

Sensitivity and specificity of MS-PCR assays (using the MSP3 primer pair) in 46 paired Normal/Tumor samples.

| Normal | Tumor | MS-PCR Assays |
|---|---|---|
| unmethylated | methylated | 37 |
| unmethylated | unmethylated | 6 |

TABLE IV-continued

| Sensitivity and specificity of MS-PCR assays (using the MSP3 primer pair) in 46 paired Normal/Tumor samples. | | |
|---|---|---|
| Normal | Tumor | MS-PCR Assays |
| methylated | methylated | 1 |
| methylated | unmethylated | 2 |

Figure 12:
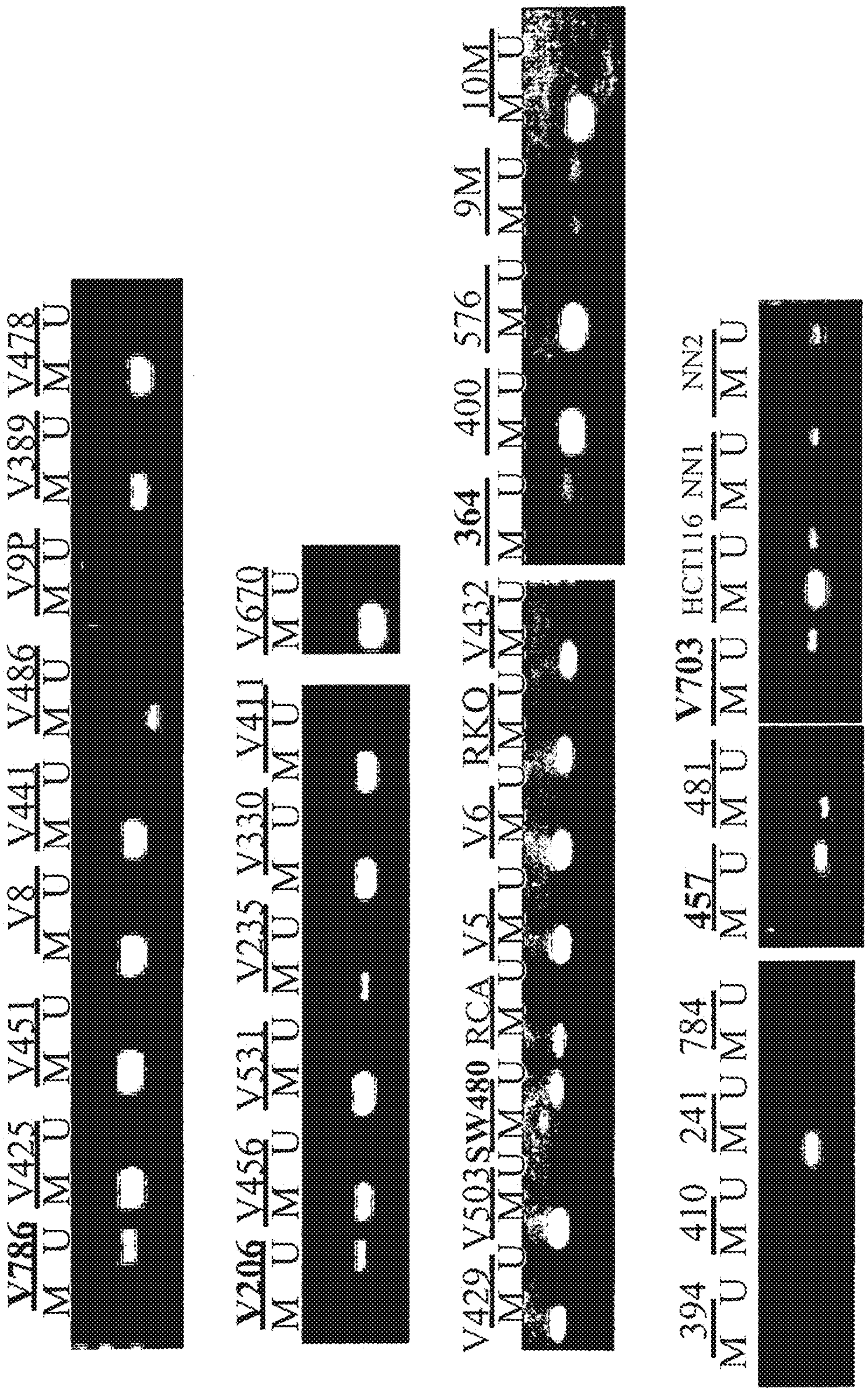
FIG. 12 shows the MS-PCR using the MSP3 primer at 40 cycles for detecting vimentin methylation in a set of colon cancer cell lines.
Figure 16A:
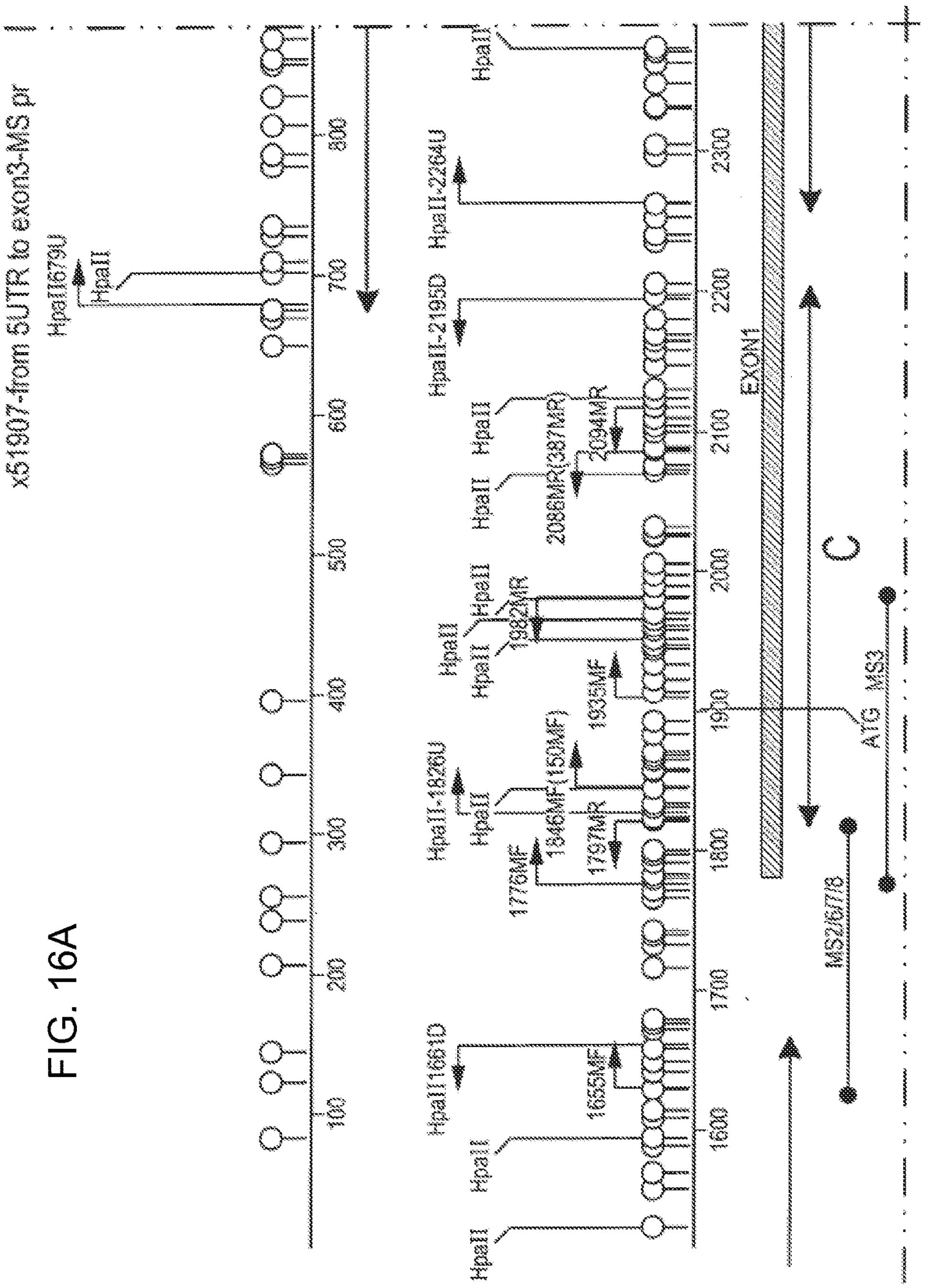
FIGS. 16A-16D show a diagrammatic depiction of the vimentin gene. A set of 10 pairs of MS-PCR primers were designed that interrogated parts of the vimentin B and C regions between by 1347 and 2094. The regions interrogated by these primer pairs are shown schematically.
Figure 16B:
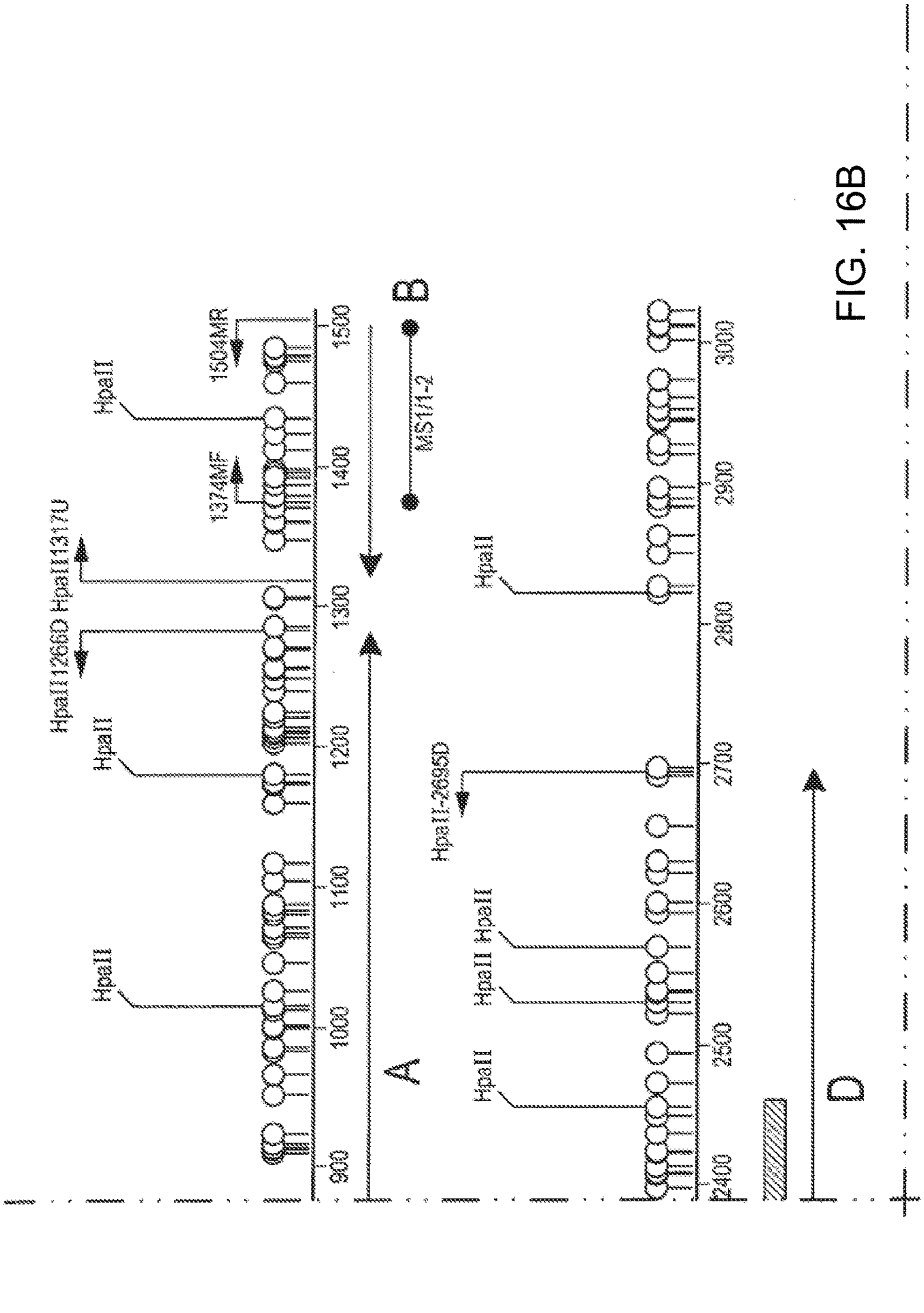
Figure 16C:
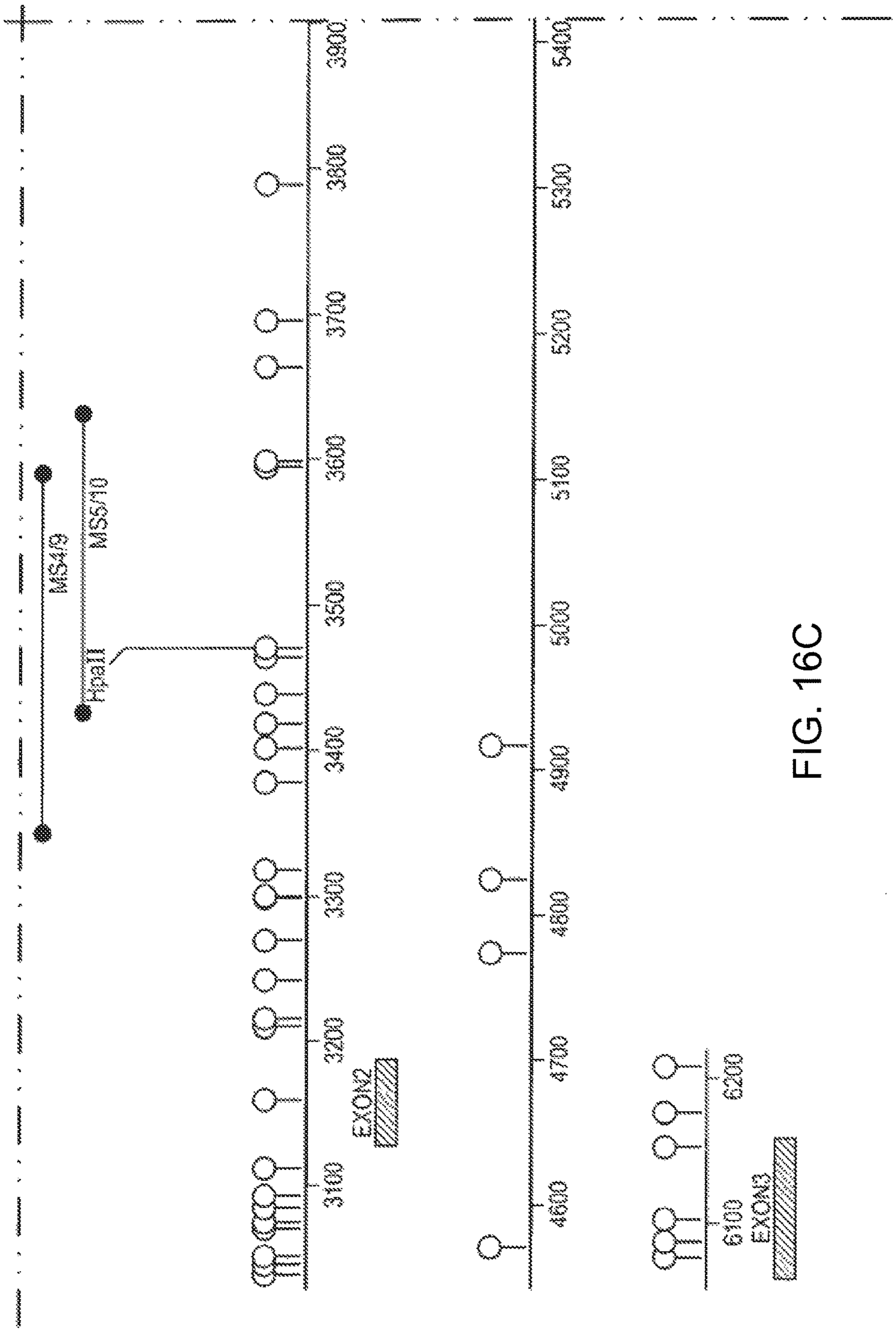
Figure 16D:
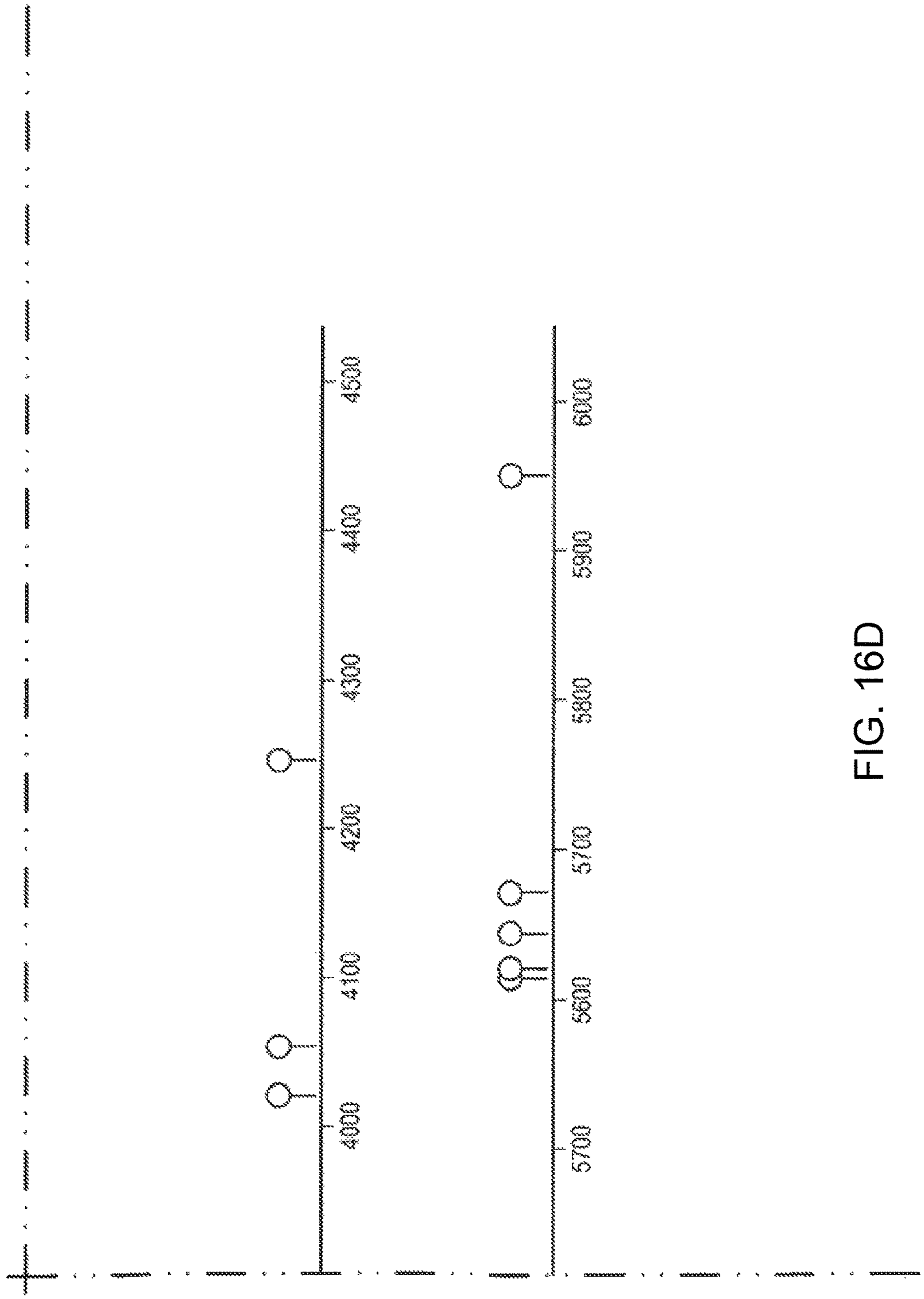

The MS-PCR reaction was further used to characterize a set of colon cancer cell lines as shown in FIG. 12. In the 39 cell line samples, the MSP3 primer used in MS-PCR assays for vimentin methylation is 82% sensitive for detecting colon cancer.

The above results indicate that the vimentin genomic sequence (nucleotides 1-6200, SEQ ID NO: 2) contains a differentially methylated region that is methylated in colon cancer and not in normal tissue. The HpaII assays and the MS-PCR assays using the MSP3 primer pair can be utilized for assaying differential methylation within the vimentin 5' flank and Exon 1-Intron 1 region. Detection of methylated vimentin DNA in body fluids and excreta such as blood and stool may provide a useful early diagnostic of colon cancer and premalignant colon adenomas.

7. Additional Results of MS-PCR Assays for Detecting Vimentin Methylation

To further investigate the extent of differential methylation in the vimentin genomic sequence, an additional set of 6 pairs of MS-PCR primers were designed inside the B and C regions. All the MS-PCR primer sequences are shown in FIGS. 14 and 15, and their positions are illustrated in FIG. 16.

Figure 17:
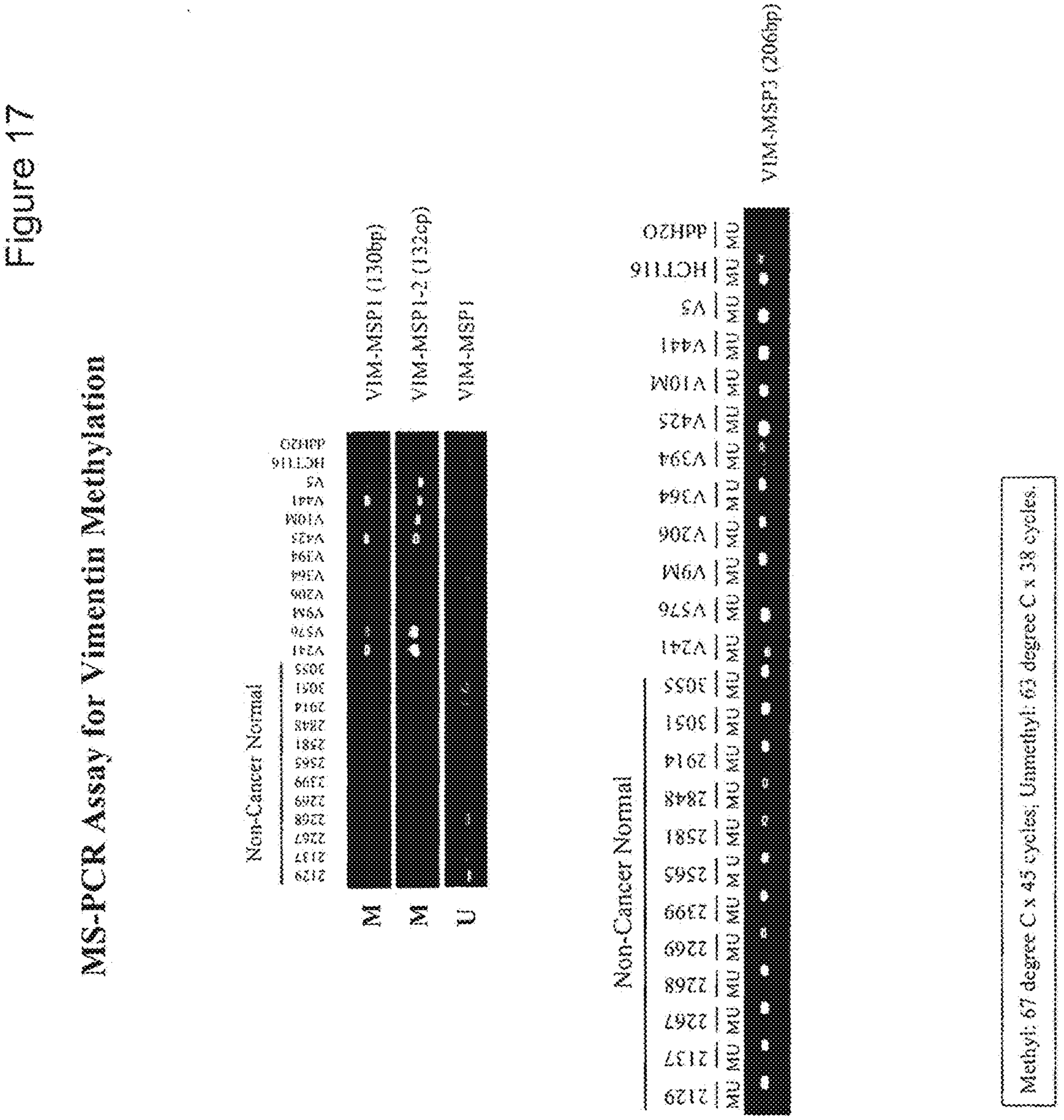
FIG. 17 shows the MS-PCR results using the 3 pairs of primer sets MSP1, MSP1-2, and MSP3 for detecting vimentin methylation in 12 non-cancer normal samples versus 12 colon cancer cell lines.
Figure 18:
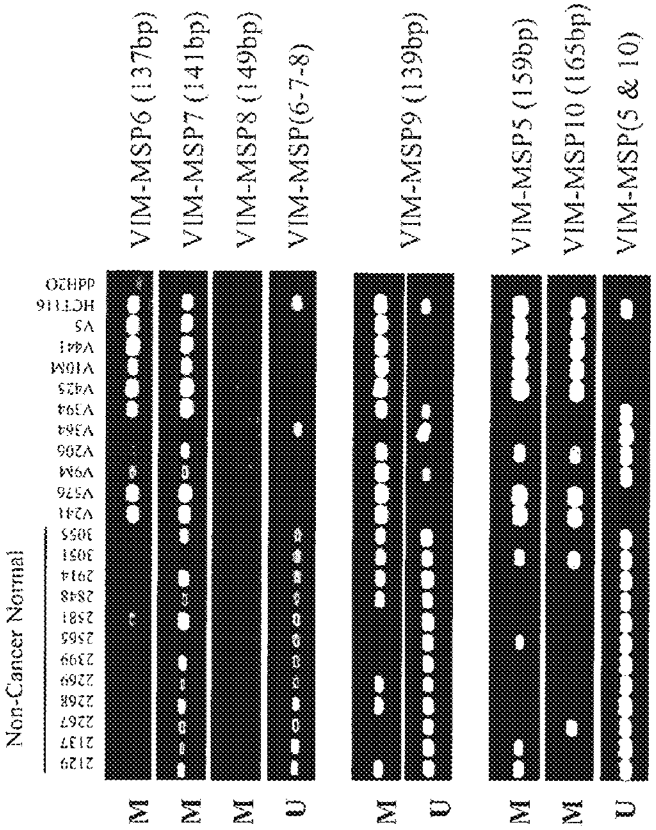
FIG. 18 shows the MS-PCR results using the 3 pairs of primer sets MSP5, MSP6, MSP7, MSP8, MSP9, and MSP10 for detecting vimentin methylation in 12 non-cancer normal samples versus 12 colon cancer cell lines.

These MS-PCR primers were evaluated in a set of 12 non-cancer normal samples versus 12 colon cancer cell lines (FIGS. 17 and 18). As indicated by the bold designations in FIG. 14, the best performing set of primers are the originally evaluated primers MSP3, and the new primer set MSP1-2. MSP-1-2 thus identifies a new differentially methylated region that is within the B region.

Further, aberrant methylation of vimentin nucleotide sequence appears to be an early event in colon neoplasia. 13 colon adenoma samples were assayed by MS-PCR reaction using the MSP3 primer for aberrant methylation of vimentin DNA, with results that such methylation was detected in 7 of 13 cases. The results are summarized below in Table V.

TABLE V

| MS-PCR assays (using the MSP1-2 and MSP3 primer pairs) in adenoma samples. | | |
|---|---|---|
| Adenoma | MSP1-2 | MSP3 |
| 14-16P | M | M |
| 14-25P | U | M |
| 23-6P | M | M |
| 24-23P | U | U |
| 28-3P | M | M |
| 453P | U | U |
| 461P | U | U |
| 431P | M | M |
| 493P | U | M |
| 418P | M | M |
| 400 4696P | U | U |
| 400 4828P | U | U |
| 400 5426P | U | U |
| | 5/13 | 7/13 |

Figure 19:
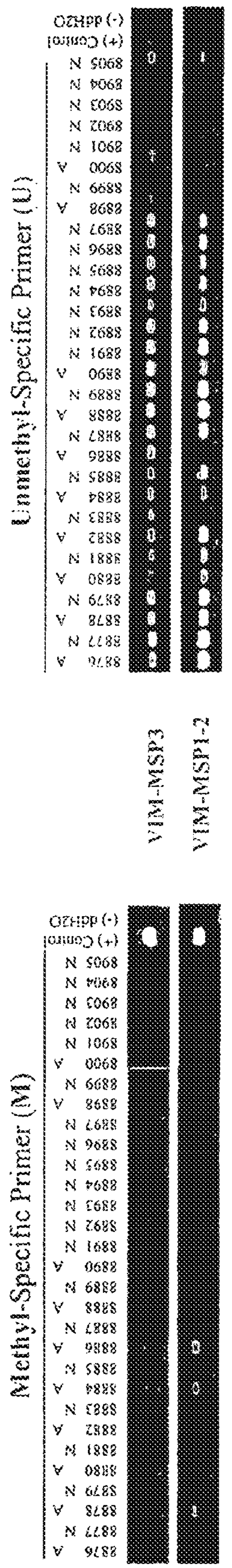
FIG. 19 shows the MS-PCR results using the 2 pairs of primer sets MSP3 and MSP1-2 for detecting vimentin methylation in microdissected aberrant crypt foci (ACF, shown as "A").

Additionally, FIG. 19 shows the results of detecting aberrant vimentin methylation in some microdissected aberrant crypt foci (i.e., ACF, abbreviated as "A" in FIG. 19) which are microscopic early colonic neoplasms. In contrast, the vimentin methylation was not detected in microdissected normal tissue (abbreviated as "N" in FIG. 19) from the same individuals.

In conclusion, the present invention discloses at least three assays of vimentin methylation: 1) MS-PCR assays using the MSP3 primer; 2) MS-PCR assays using the MSP1-2; and 3) HpaII assays. All the assays can be employed to identify differential methylation of the vimentin genomic sequence in cancer cells but not in normal cells. Similar assays likely can be fashioned to other CpG sequences present within the vimentin genomic sequence. Such assays, when applied to body fluids, can be used for early detection of cancers such as colon cancer, precancerous colon adenoma, and for detection of individuals at increased risk for development of colon cancer due to a high load of aberrant crypt foci.

Example 2

The following experiments and data further specify specific regions and their sequences of vimentin whose aberrant methylation is a high frequency marker of colon cancer. These data additionally specify assays for these sequences.

Figure 32:
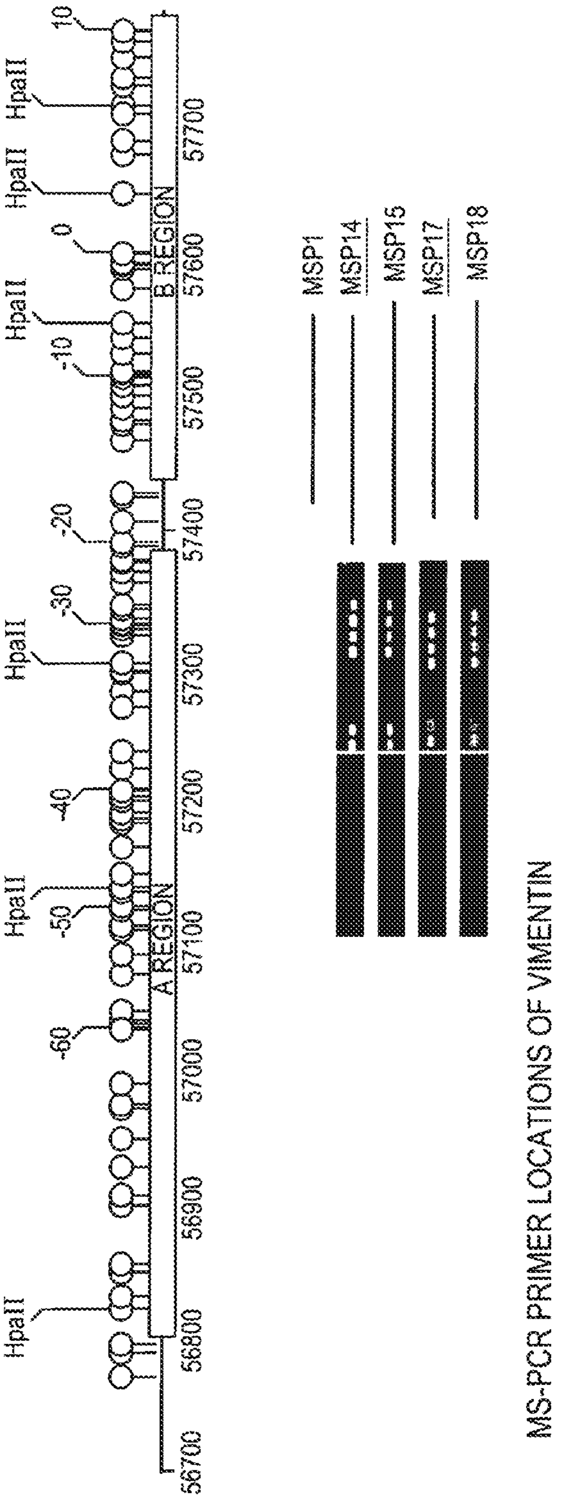
FIGS. 32-34 show a diagrammatic display of the vimentin 5' genomic region from basepairs 56700 to 58800 of NCBI human genomic sequence entry AL133415. Boxes show the vimentin regions A, B, C, and D. Balloons indicate CpG dinucleotides that are targets for potential methylation. Dark balloons designate CpGs that are population polymorphisms.
Figure 33:
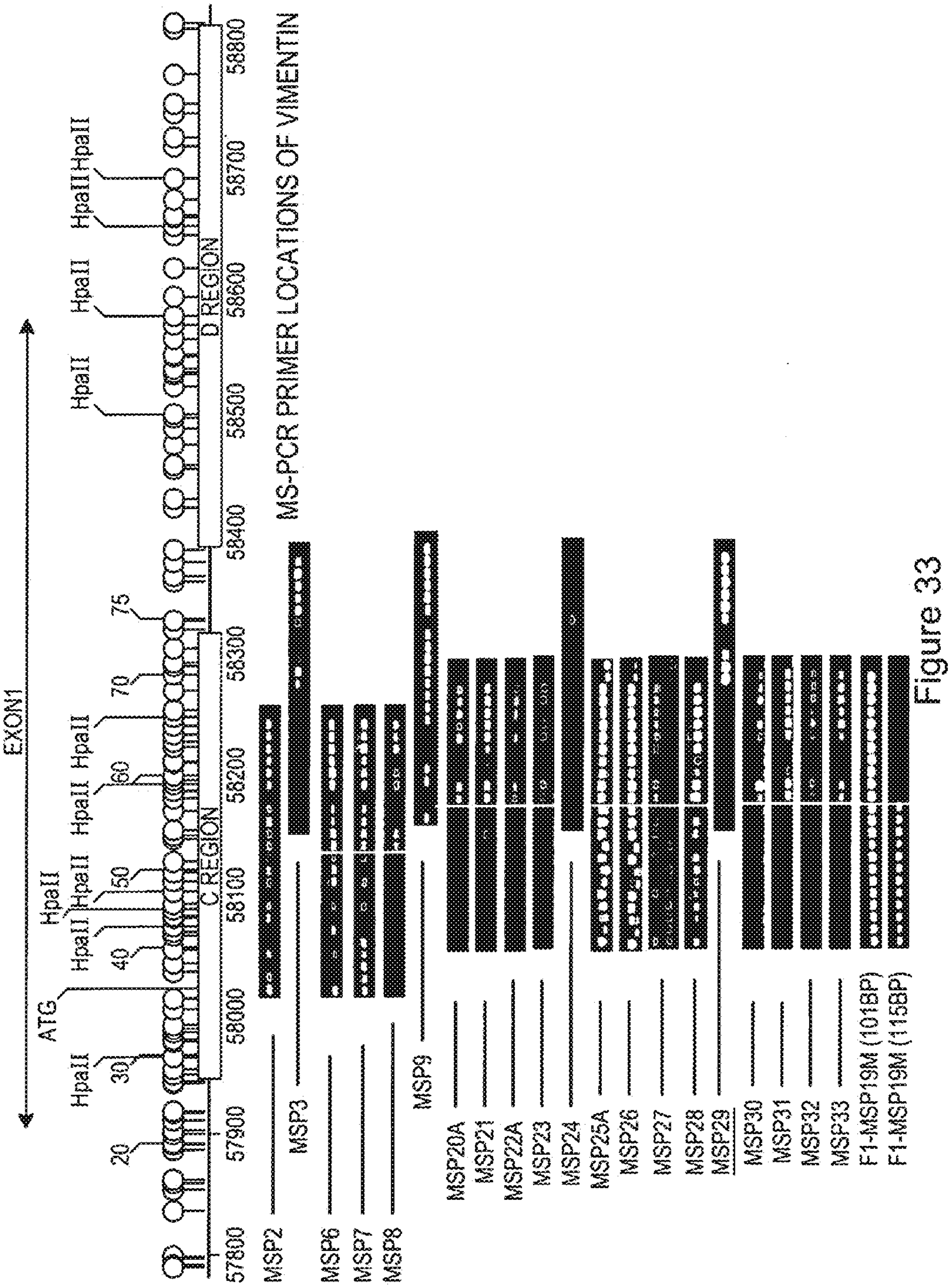
Figure 34:
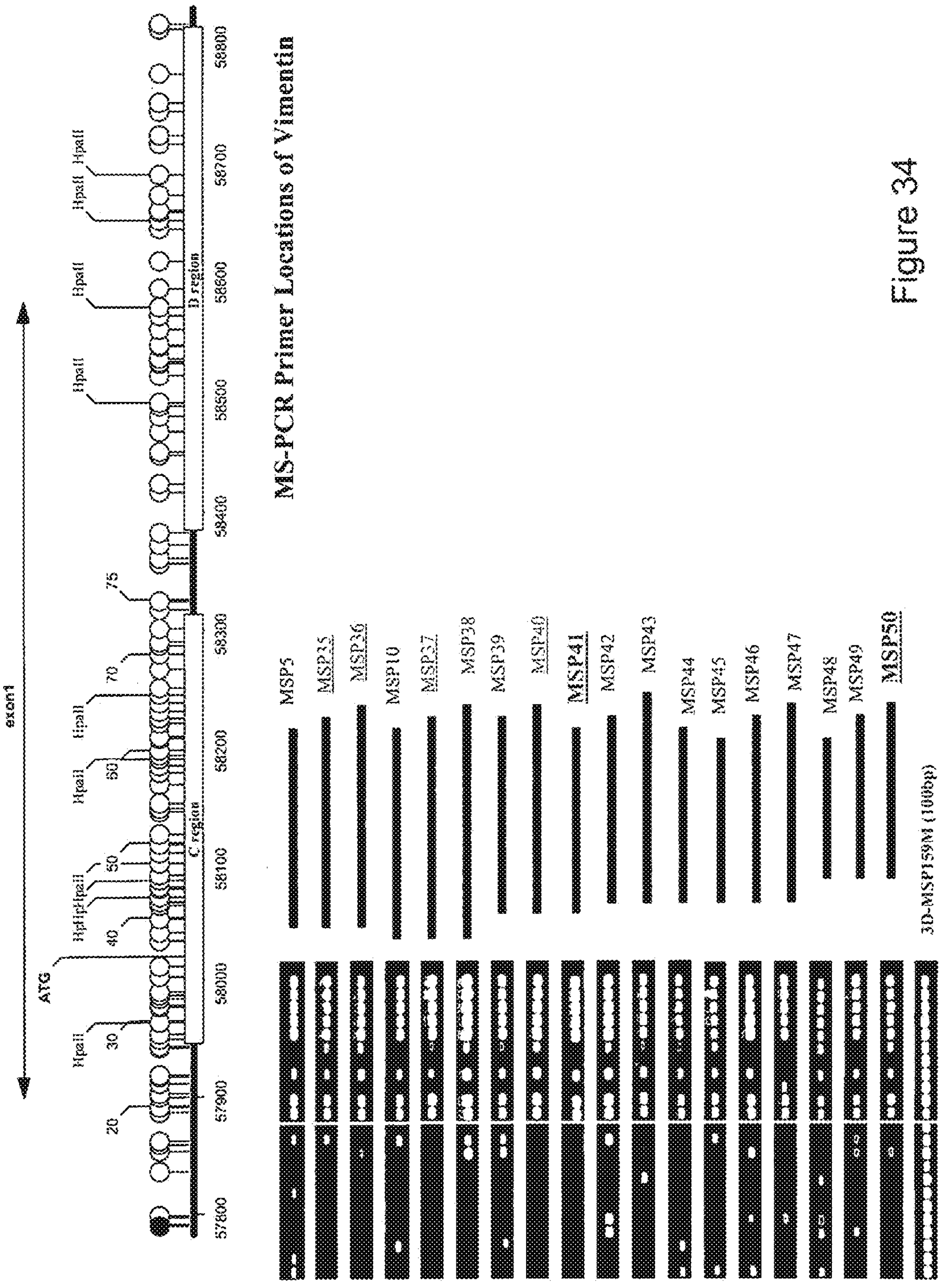

FIGS. 32-34 are a summary that show a diagrammatic display of the vimentin 5' genomic region from basepairs 56700 to 58800 of NCBI human genomic sequence entry AL133415. Boxes show the vimentin regions A, B, C and D. Previous HpaII digestion assays had demonstrated that regions A and D were not methylated in cancer. Accordingly, regions through C were exhaustively interrogated with methylation specific PCR assays. Balloons on the figure indicate CpG dinucleotides that are targets for potential methylation. Dark balloons designate CpGs that are population polymorphisms. FIG. 32 designates regions A through B, and FIGS. 33-34 designates regions C through D. Bars under the figure indicate regions interrogated by different methylation specific PCR reactions, as numbered by MSP1-MSP50. In these figures, the primary results of the MS-PCR reactions are shown next to the bar. The leftmost set of reactions are the results of MS-PCR in 12 non-cancer normal samples; wherein a negative result is the preferred outcome. The rightmost set of reactions are the results of assay of 11 colon cancer cell lines; wherein the preferred outcome is a positive reaction.

The MS-PCR assays in FIGS. 32-34 were categorized into five different groups as determined by assays of 11 colon cancer cell lines in comparison to 12 non-cancer normal-colon samples at 45 cycles of MS-PCR. The first group (including MSP1, MSP14, MSP17 on FIG. 32; MSP3, MSP20A, MSP29, MSP30, MSP31 on FIG. 33; and MSP50 on FIG. 34) shows assays that detected methylation in a high percentage of colon cancer cell lines, with a strong MS-PCR gel band, and detected 0% methylation in non-cancer normal samples. The best of these reactions are further designated by being numerically indicated in underlined numerals, and the very best of these are further designated by being numerically indicated in bold underlined numerals. The second group (including MSP8, MSP22A, MSP23, MSP24, MSP32 on FIG. 33) shows assays that detected methylation in a high percentage of colon cancer cell lines, with a weak MS-PCR gel band, and detected 0% methylation in non-cancer normal samples. The third group (including MSP33 on FIG. 33; and MSP35, MSP36, MSP37, MSP40, MSP41, MSP47 on FIG. 34) shows assays that detected methylation in a high percentage of colon cancer cell lines, with a strong MS-PCR gel band, and detected 10% of samples with methylation among non-cancer normal samples. The fourth group (including MSP21 on FIG. 33; and MSP10, MSP38, MSP39, MSP43, MSP44, MSP45 on FIG. 34) shows assays that detected methylation in a high percentage of colon cancer cell lines, with a strong MS-PCR gel band, and detected 20% of samples with methylation among non-cancer normal samples. The fifth group (including MSP2, MSP6, MSP7, MSP9, MSP25A, MSP26, MSP27, MSP28 on FIG. 33; and MSP5, MSP42, MSP46, MSP48, MSP49 on FIG. 34) shows assays that detected methylation in a high percentage of colon cancer cell lines, with a strong MS-PCR gel band, and detected 30% of samples with methylation among non-cancer normal samples.

FIG. 35 provides the primer sequences for the MS-PCR reactions summarized in FIGS. 32-34. MF indicates forward primers, while MR indicates reverse primers. Primers are presumed to amplify the bisulfite converted sequences of the sense genomic strand. Primers that amplify the bisulfite converted sequence of the antisense genomic strand are indicated by (ASS). The table also provides the genomic location corresponding to the amplified product, relative to the basepair numbering system of clone AL133415. The table also provides the length of the amplified fragments. Primers shaded in dark provide the best and preferred reaction.

Figure 36:
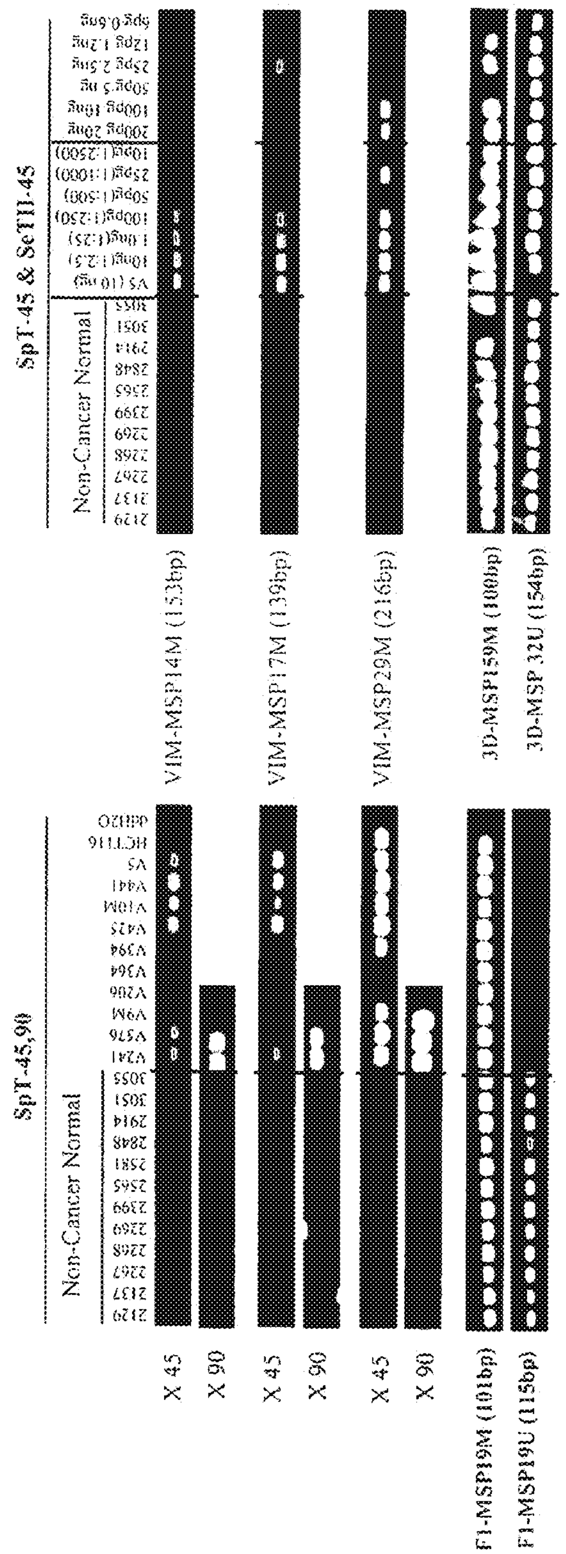
FIG. 36 demonstrates technical sensitivity and specificity of the different MS-PCR assays. At far left is shown results of MS-PCR reactions performed on non-cancer normal colon tissue for either 45 or 90 cycles of PCR. 90 cycle reactions were performed by taking an aliquot from a 45 cycle PCR reaction, diluting it into a fresh PCR reaction, and repeating for an additional 45 cycles. For the reactions shown, the MS-PCR reactions detect no false positives in up to 90 cycles of PCR on normal tissue. Positive control colon cancer cell lines are shown immediately juxtaposed at right. On the far right is shown assays of the technical sensitivity of different MS-PCR reaction. The middle and right most sets of reactions show a dilution series of MS-PCR done on DNA from Vaco5, a cell line with vimentin methylation. Positive reactions are obtained down to a level of 100 picogram of input methylated Vaco5 DNA FIG. 37 demonstrates technical sensitivity and specificity of the different MS-PCR assays for additional primer sets. Column at left shows results of assay against a panel of 11 colon cancer cell lines at 45 cycles of MS-PCR. Results at the right show a column that evaluates the MS-CPR reactions at 45 and 90 cycles against a group of non-cancer normal tissues. Next shows two columns demonstrating assay of a dilution series in which candidate reactions are assayed against increasing dilutions of Vaco5 DNA. The best reactions, for example VIM-MSP50M, show high technical sensitivity for detecting most colon cancer cell lines, show low positive rates for detecting normal colon, and show high sensitivity for detecting dilutions of Vaco5 DNA down to 50 picograms of input DNA. The two dilution series shown at right differ in whether they are done by admixing previously bisulfite treated normal and Vaco5 DNA (middle column) versus (rightmost column) first admixing Vaco5 and normal DNA; diluting the mixture; and then bisulfite treating the diluted mixture.
Figure 37:
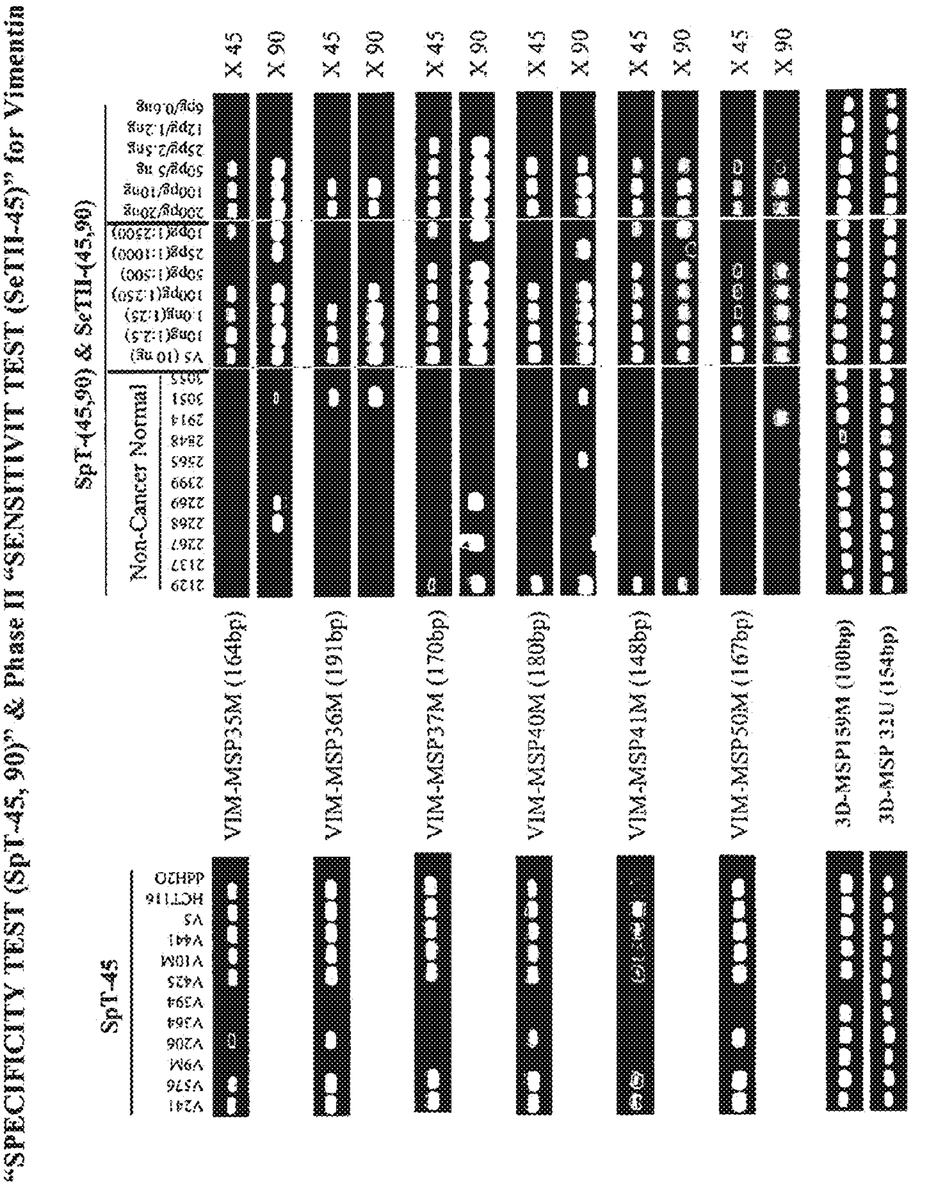
Figure 41:
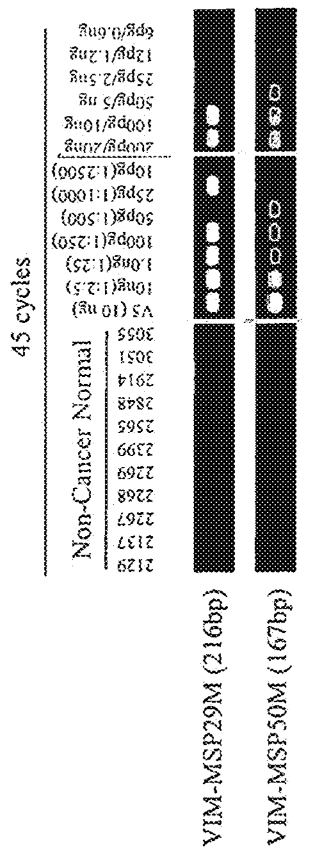
FIG. 41 supplements FIG. 37, further demonstrating technical sensitivity of the different MS-PCR assays for vimentin DNA methylation. Two primer sets (MSP29M and MSP50M) were tested.

FIGS. 36-37 demonstrate technical sensitivity and specificity of the different MS-PCR assays. FIG. 41 supplements FIGS. 36 and 37, with two primer sets (MSP29M and MSP50M) further tested.

FIG. 36 at left shows technical specificity for different MS-PCR reactions. At far left is shown results of MS-PCR reactions performed on non-cancer normal colon tissue for either 45 or 90 cycles of PCR. 90 cycle reactions were performed by taking an aliquot from a 45 cycle PCR reaction, diluting it into a fresh PCR reaction, and repeating for an additional 45 cycles. For the reactions shown, the MS-PCR reactions detect no false positives in up to 90 cycles of PCR on normal tissue. Positive control colon cancer cell lines are shown immediately juxtaposed at right. One the far rights is shown assay of the technical sensitivity of different MS-PCR reaction. The middle and right most sets of reactions show a dilution series of MS-PCR done on DNA from Vaco5, a cell line with vimentin methylation. Positive reactions are obtained down to a level of 100 picogram of input methylated Vaco5 DNA.

FIG. 37 shows similar data for additional primer sets. Column at left shows results of assay against a panel of 11 colon cancer cell lines at 45 cycles of MS-PCR. Results at the right show a column that evaluates the MS-CPR reactions at 45 and 90 cycles against a group of non-cancer normal tissues. Next shows two columns demonstrating assay of a dilution series in which candidate reactions are assayed against increasing dilutions of Vaco5 DNA. The best reactions, for example VIM-MSP50M, show high technical sensitivity for detecting most colon cancer cell lines, show low positive rates for detecting normal colon, and show high sensitivity for detecting dilutions of Vaco5 DNA down to 50 picograms of input DNA. The two dilution series shown at right differ in whether they are done by admixing previously bisulfite treated normal and Vaco5 DNA (middle column) versus (rightmost column) first admixing Vaco5 and normal DNA; diluting the mixture; and then bisulfite treating the diluted mixture.

The different vimentin MS-PCR primers were evaluated for detection of methylation in 47 colon cancer cell lines. In these assays, MSP-29 is maximally sensitive, detecting methylation in 80% of cell lines. Increased sensitivity would be achieved by combining MSP-29 with MSP-14 or MSP-17. In a separate experiment, the different vimentin MS-PCR primers were analogously evaluated in a panel of matched colon cancer tissue and paired normal colon tissue from an extensive group of colon cancer patients. Sensitivity for detection of colon cancer exceeds 85% in these assays. MSP-29 shows sensitivity of 85% with only one normal sample detected as methylated, and so is a preferred reaction. In another separate experiment, the different vimentin MS-PCR primers were analogously evaluated in a panel of 13 colon adenoma samples. Sensitivities of 62-69% are achieved for detection of aberrant methylation in adenoma samples.

FIGS. 21-26 provide the definitive sequences of the vimentin genomic region. Sequences are provided for the native sense and antisense vimentin genomic region, for the bisulfite converted sequences of templates derived from methylated and unmethylated forms of the vimentin sense strand, and for the bisulfite converted sequences of the templates derived from the methylated and unmethylated forms of the vimentin antisense strand. Each figure provides sequences corresponding to basepairs 56,822-58,822 of NCBI human genomic clone AL133415 that spans the 5' region of the vimentin gene encompassing regions A-D. Each figure designates in bold the region from basepairs 57,427-58,326 that we have shown is differentially methylated in colon cancer (that is methylated at high frequency in colon cancer and not methylated in normal colon tissue). This region encompasses all of the high quality MS-PCR reactions that we have defined. Moreover, each figure underlines specific sequences that are interrogated by MS-PCR primers corresponding to the best MS-PCR reactions.

Specifically, FIG. 21 shows the vimentin sense strand sequence, 5' to 3', corresponding to AL133415 sequences 56,822-58,822, with the differentially methylated region from 57,427-58,326 in bold. FIG. 22 shows the bisulfite converted sequence of a methylated template derived from the vimentin genetic sense strand corresponding to FIG. 21, with the sequence derived from the differentially methylated region 57,427-58,326 in bold. FIG. 23 shows the bisulfite converted sequence of an unmethylated template derived from the vimentin genetic sense strand corresponding to FIG. 21, with the sequence derived from the differentially methylated region 57,427-58,326 in bold. FIG. 24 shows the vimentin antisense strand sequence, corresponding to AL133415 sequences 56,822-58,822, with the differentially methylated region from 57,427-58,326 in bold. Note sequence is written out 3' to 5'. FIG. 25 shows the bisulfite converted sequence of a methylated template derived from the vimentin genetic antisense strand corresponding to FIG. 24, with the sequence derived from the differentially methylated region 57,427-58,326 in bold. Note sequence is written out 3' to 5'. FIG. 26 shows the bisulfite converted sequence of an unmethylated template derived from the vimentin genetic antisense strand corresponding to FIG. 24, with the sequence derived from the differentially methylated region 57,427-58,326 in bold. Note sequence is written out 3' to 5'.

The above data provides the core information for the final disclosure of the invention of finding a region of the vimentin gene whose differential methylation is a specific marker for human colon cancer and precancerous adenomas. This application also provides some additional supporting data as follows.

Figure 38:
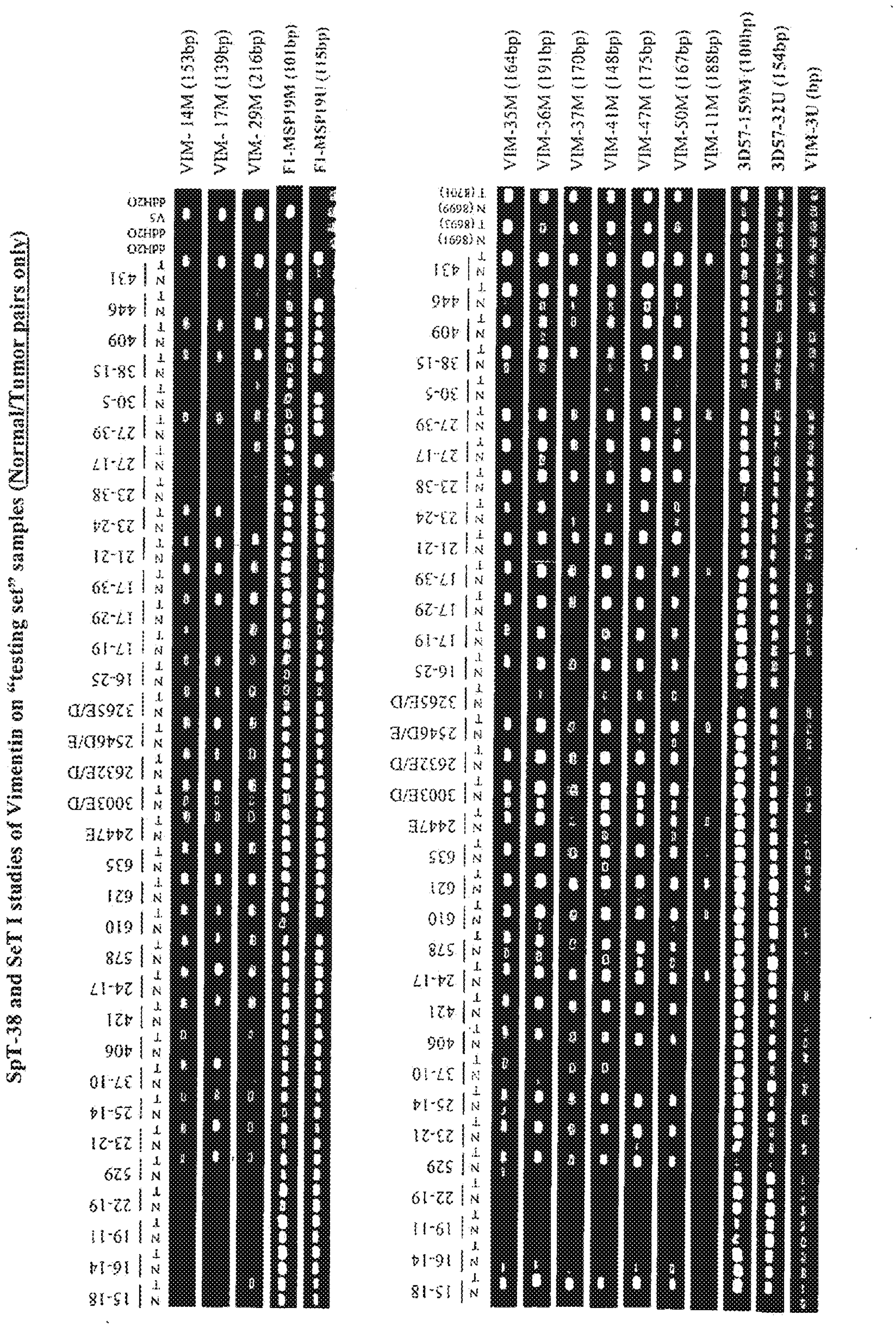
FIG. 38 shows primary data from assays of Normal and Tumor pairs by different vimentin MS-PCR reactions.
Figure 42:
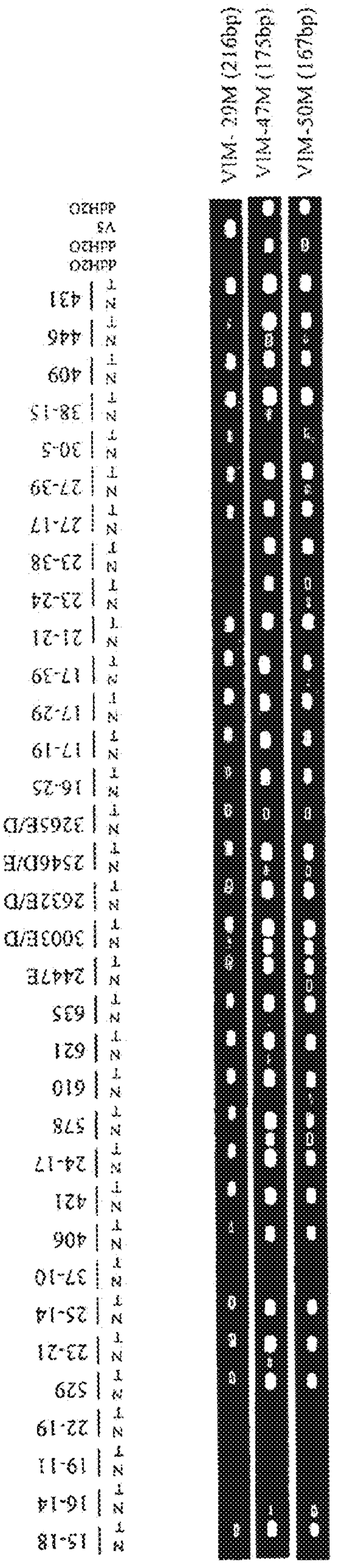
FIG. 42 supplements FIG. 38, further demonstrating clinical sensitivity of the different MS-PCR assays for vimentin DNA methylation. The primary data were obtained from assays of Normal and Tumor pairs. Three primer sets (MSP29M, MSP47M, and MSP50M) were used.

FIG. 38 shows primary data from assays of Normal and Tumor pairs by different vimentin MS-PCR reactions. FIG. 42 supplements FIG. 38, further demonstrating clinical sensitivity of the MS-PCR assays using three primer sets (MSP29M, MSP47M, and MSP50M).

Figure 39:
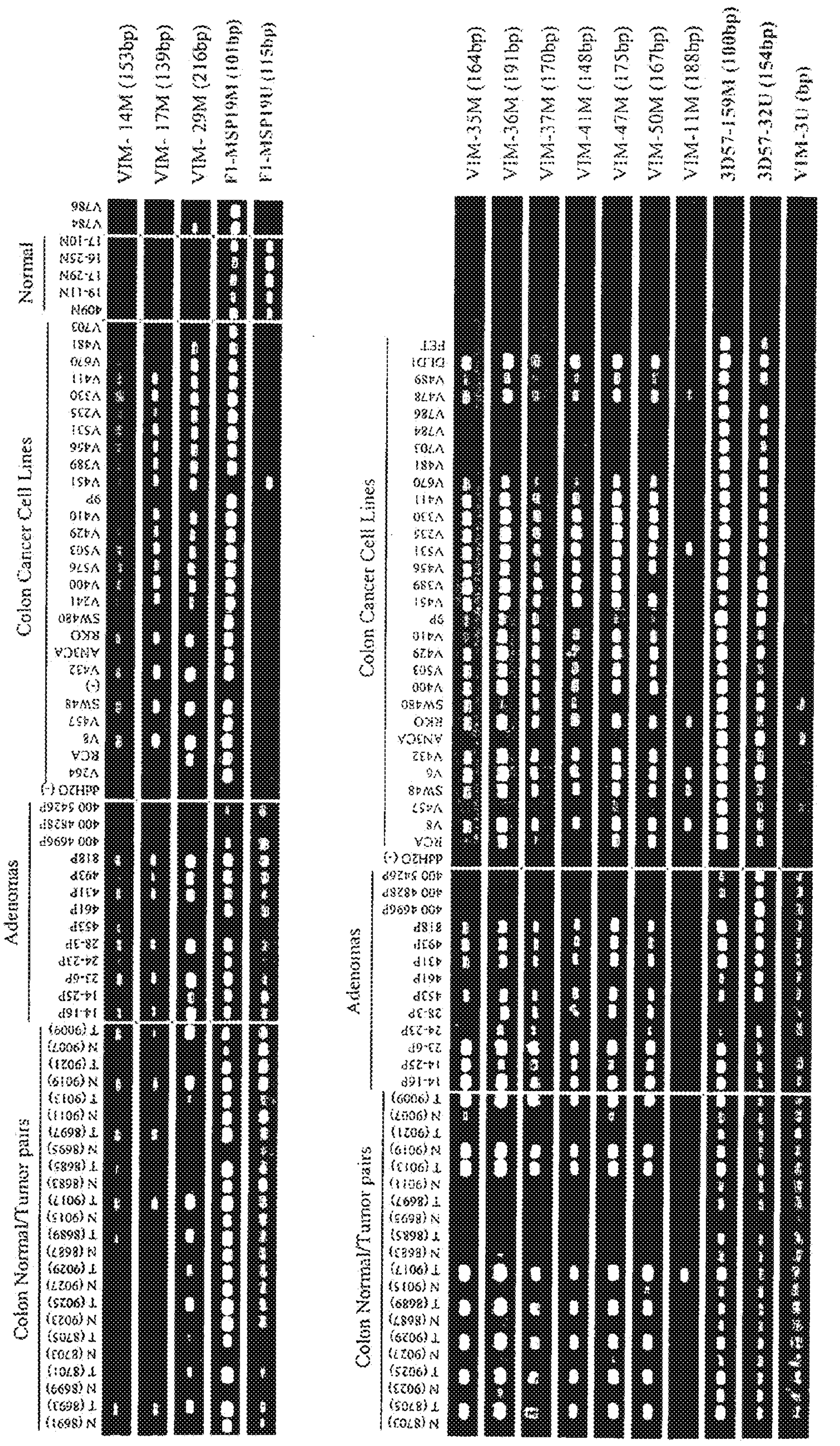
FIG. 39 shows primary data from assays of colon normal and cancer pairs, colon adenomas, and colon cancer cell lines, by different MS-PCR reactions.
Figure 40:
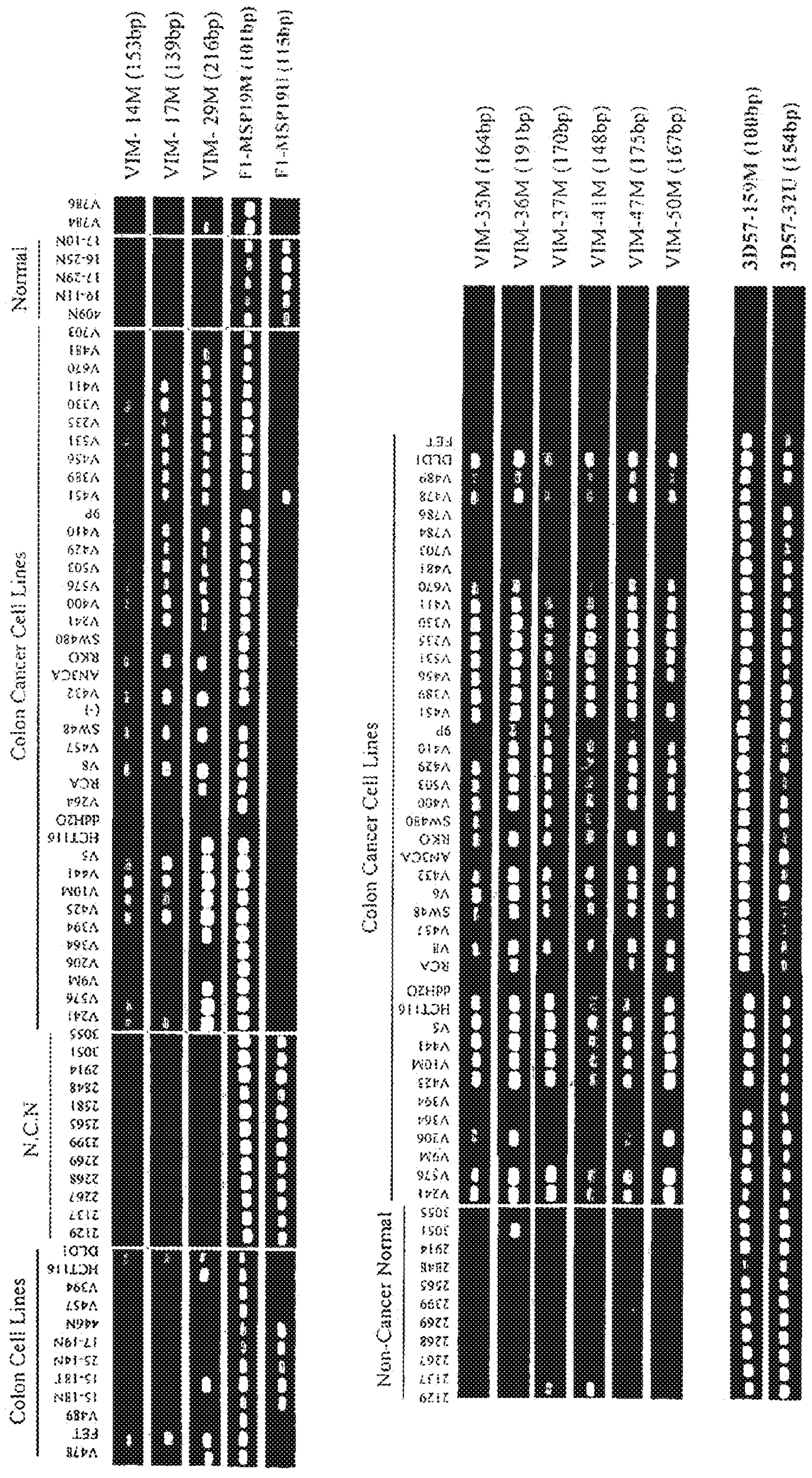
FIG. 40 shows primary data from assays of colon cancer cell lines and non-cancer normal colon samples by different MS-PCR reactions.
Figure 43:
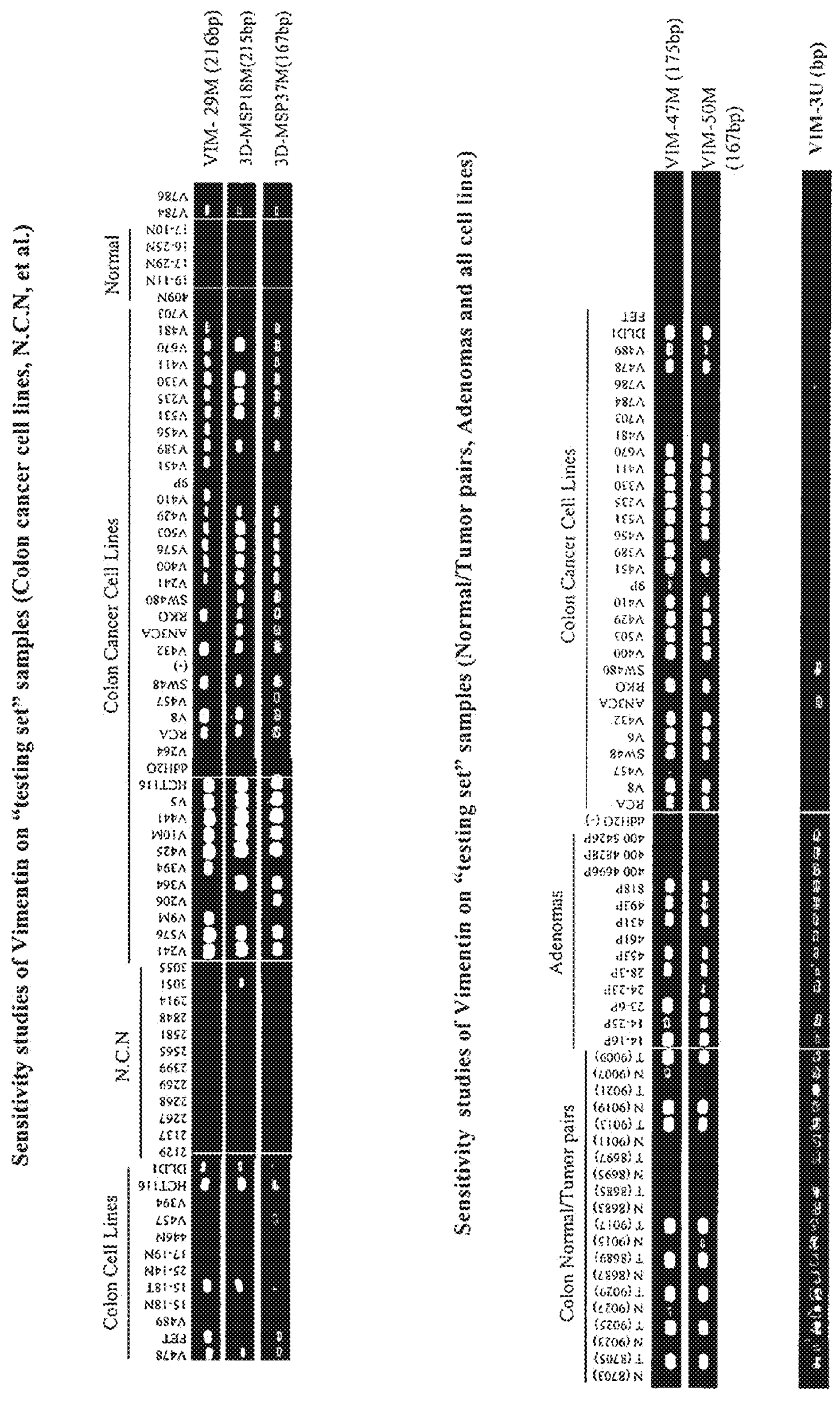
FIG. 43 supplements FIGS. 39 and 40, further demonstrating clinical sensitivity of the different MS-PCR assays for vimentin DNA methylation. The primary data were obtained from assays of colon cancer cell lines, non-cancer normal colon samples (N.C.N), colon Normal/Tumor pairs, and colon adenomas. Three primer sets (MSP29M, MSP47M, and MSP50M) were used.

FIGS. 39 and 40 show primary data from assays on colon Normal/Tumor pairs, colon adenomas, colon cancer cell lines, and non-cancer normal colon samples (N.C.N) by different MS-PCR reactions. FIG. 43 supplements FIGS. 39 and 40, further demonstrating clinical sensitivity of the different MS-PCR assays using three primer sets (MSP29M, MSP47M, and MSP50M).

FIG. 44 provides raw data from MS-PCR assays with three primer sets (MSP29, MSP47, and MSP50). The data are shown in three tables for cell lines, N/T pairs, and colon adenoma samples, respectively. Methylated samples are coded red and labeled M, while unmethylated samples are coded green and labeled U. V-MSP29, VMSP-47, and V-MSP50 are vimentin primers. H-MSP5 is a control primer (HLTF-MSP5) for comparison. A summary of the above sensitivity data is listed in Table VI below. For example, MSP29 shows 80% sensitivity for identifying cell lines (41 lines tested), and 85% sensitivity for identifying tumors (46 tumors tested). MSP50 shows 73% sensitivity for identifying colon cancer cell lines, and 87% sensitivity for identifying colon cancer tumors.

TABLE VI

Data summary on sensitivity tests of MS-PCR based biomarkers.

| MS-PCR primers | Cell lines (source: Markowitz lab) | Normal/Tumor pairs (source: Markowitz lab) |
|---|---|---|
| V-MSP29 | 33/41 (80%) | 39/46 (85%) |
| V-MSP47 | 30/41 (73%) | 40/46 (87%) |
| V-MSP50 | 30/41 (73%) | 40/46 (87%) |
| H-MSP5 | 13/36 (36%) | 18/46 (39%) |

In summary, the data provides a description of colon cancer and adenoma specific aberrant methylation of vimentin gene sequences basepairs 57,427-58,326 in NCBI clone AL133415, and provides MS-PCR reactions that can detect this aberrant methylation in a cancer specific reaction with sensitivities of about 85% as a single reaction and with sensitivities of about 90% in combination panels with other MS-PCR reactions.

Example 3

The following studies further examined the development of vimentin methylation in pathologies of the upper gastrointestinal tract using quantitative real-time-based MS-PCR for methylation detection. For these studies, vimentin methylation was detected in formalin fixed and paraffin embedded (FFPE) archived tissues. The assay was applied to samples of Barrett's esophagus, esophageal adenocarcinomas, and gastric cancers.

1. Tissues and FFPE DNA Preparation

Normal and neoplastic gastrointestinal tissue samples were retrieved as FFPE samples that were obtained under an IRB approved protocol. Samples were retrieved either as sections cut from tissue blocks or as cores prepared from tissue blocks. DNA was purified using QIAamp DNA micro kit according to the manufacturer's protocol with the following modifications: initial incubation in buffer ATL with Proteinase K was carried out at 60° C. instead of 56° C. and proceeded for 4 days instead of 16 hours. An additional 1.5 ml of Proteinase K was added after 3-24 hours of incubation. The DNA was eluted from columns in 50 ml of distilled water and used immediately for bisulfite conversion, or frozen at −80° C. until use.

2. Bisulfite Conversion of the Genomic DNA and Real-Time MS-PCR Assay

To create a template for methylation-specific PCR, DNA samples were subjected to bisulfite conversion and purified using an EPITECT® kit according to the manufacturer's protocol. 4 ml of bisulfite-converted DNA at a concentration of 0.2-25 ng/ml was used as a template for real-time MS-PCR assay. To normalize input DNA amounts, a companion real-time PCR assay was designed against bisulfite converted Actin gene sequences that lack CpG dinucleotides and so are not modified by methylation. The assay for Actin was designed to generate an amplification product of the same size as the assay for methylated vimentin. For both Actin and vimentin real-time PCR, a mixture of DNA from 4 colon cancer cell lines that are each fully methylated across the vimentin CpG island, was used to generate a dilution standard curve that was run with all real-time assays and used as part of data analysis in BioRad CFX manager software to convert the Ct values into ng DNA amounts. Vimentin methylation was calculated as percentage ratio of the amount of methylated DNA measured by vimentin PCR, divided by total bisulfite-converted DNA amount in the sample, as measured by Actin qPCR. The real-time MS-PCR reactions were performed in triplicates in 20 ul volume using a LIGHTCYCLER® PCR master mix (Roche) with 400 nM each primer and 200 nM probe (sequences below). BHQ1 is added to the probe as a quencher that is used in combination with 6FAM to create a fluorogenic hybridization probe for the real-time MS-PCR reaction. Amplifications were done in 96-well plates in a CFX96 Real-Time System (Biorad) under the following conditions: 95° C. for 10 minutes, followed by 50 cycles of 30 sec at 95° C. and 60 sec at primer-specific annealing/extension temperature (see Table VII).

TABLE VII

Primers used in this study. [+N] denotes Locked Nucleic Acid (LNA) bases.

| Gene | Primer/ probe | Primer/probe sequence | Annealing/ Extension | Size (bp) |
|---|---|---|---|---|
| VIM | Forward Primer | TCGTTTCGAGGTTTTCGCGTTA GAGAC (SEQ ID NO: 62) | 68° C. | 217 |
| | Reverse Primer | CGACTAAAACTCGACCGACTCG CGA (SEQ ID NO: 24) | | |

TABLE VII-continued

Primers used in this study. [+N] denotes Locked Nucleic Acid (LNA) bases.

| Gene | Primer/ probe | Primer/probe sequence | Annealing/ Extension | Size (bp) |
|---|---|---|---|---|
| | Probe | CGGGAGTTAGT[+T]CGCGTTAT CGTCGTCGTTT (SEQ ID NO: 73) | | |
| Actin | Forward Primer | GGATAGGATAGTTTTATTTTTA G (SEQ ID NO: 74) | 57° C. | 217 |
| | Reverse Primer | ATACAAAACTATACTCAACCAA (SEQ ID NO: 75) | | |
| | Probe | 5'-ACCACCACCCAACACACAATAA CAAACACA-3' (SEQ ID NO: 76) | | |

3. Vimentin Methylation in Esophageal Neoplasms and Precursor Lesions.

Figure 51:
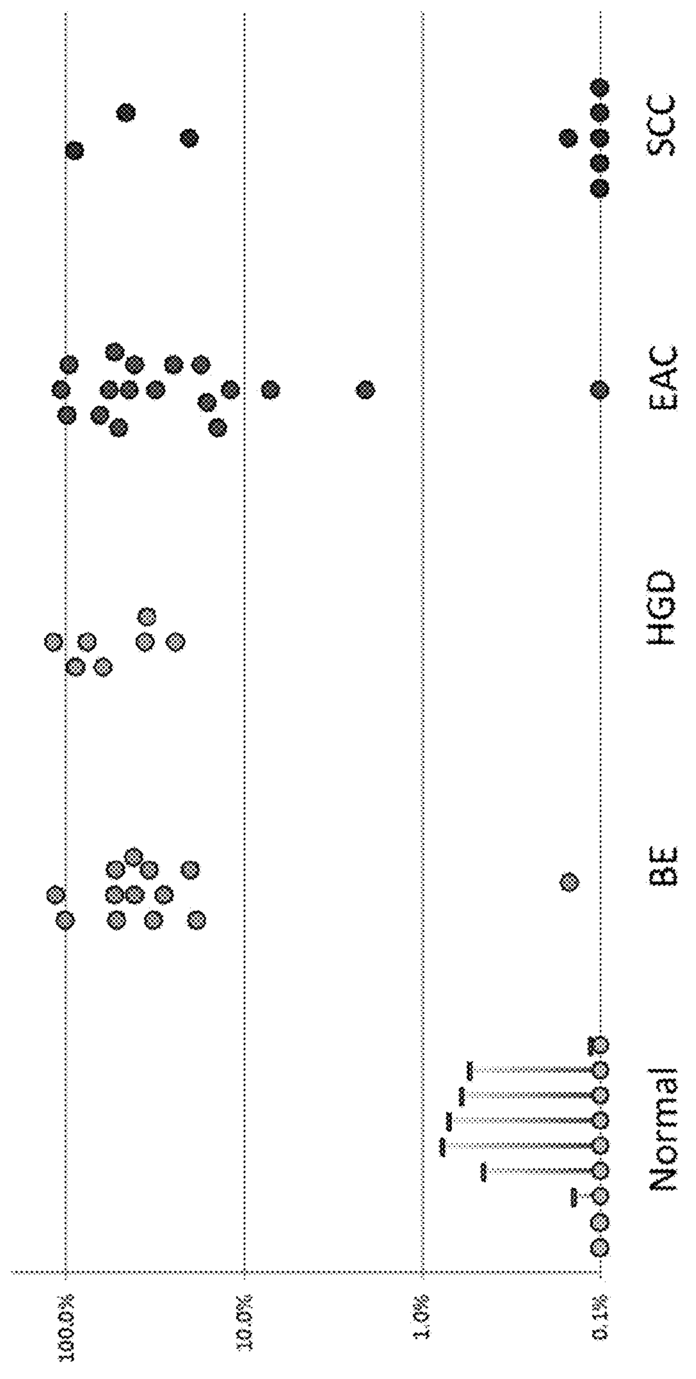
FIG. 51 shows vimentin methylation in Barrett's Esophagus and esophageal neoplasias. Shown is percent of vimentin methylation relative to total actin DNA in each sample. Circles denote individual samples. Samples in which no vimentin methylation was detected are depicted as having 0.1% methylated DNA, which in most cases represented the lower limit of detection of the assay. In a few samples in which a lesser amount of input DNA was available, bars raised above the 0.1% level designate the slightly higher threshold that applied as the lower limit for detection of positive vimentin methylation. Normal: Normal Squamous Mucosa; BE: Barrett's Esophagus; HGD: High-Grade Dysplasia; EAC: Esophageal Adenocarcinoma; SCC: Squamous Cell Cancer of the Esophagus.

Evidence of vimentin methylation in esophageal adenocarcinomas (EAC) was examined. EAC primarily arises in the distal esophagus. Out of 18 cases of EAC examined, 15 cases (83%) showed high level vimentin methylation, of from 10%-100% of total input tumor DNA (FIG. 51). As tumor tissues contained both cancer and normal stromal elements, we interpret these levels as suggesting vimentin methylation was likely present in all of the cancer cells. Two additional EAC cases showed lower levels of vimentin methylation of between 1%-10%. No vimentin methylation was detected in this assay in any of 9 normal esophagus samples tested. High level vimentin methylation was also detected in some squamous carcinomas of the esophagus, cancers that primarily arise in the upper esophagus, and for which 3 of 9 cases (33%) demonstrated vimentin methylation at levels between 10%-100% of total tumor DNA.

To further interrogate the timing of vimentin methylation in esophageal neoplasias, we next examined samples of Barrett's Esophagus (BE), a precursor lesion of neoplasias of the distal esophagus that can ultimately give rise to EAC. As shown in FIG. 51, for 7 of 7 cases of advanced BE that showed high grade dysplasia, all had high level vimentin methylation of from 10%-100%. High level vimentin methylation was also detected in 12 of 13 (92%) cases of BE without dysplasia. These findings suggest that vimentin methylation is an early and highly common epigenetic change in the pathway of glandular neoplasia of the esophagus.

Figure 52:
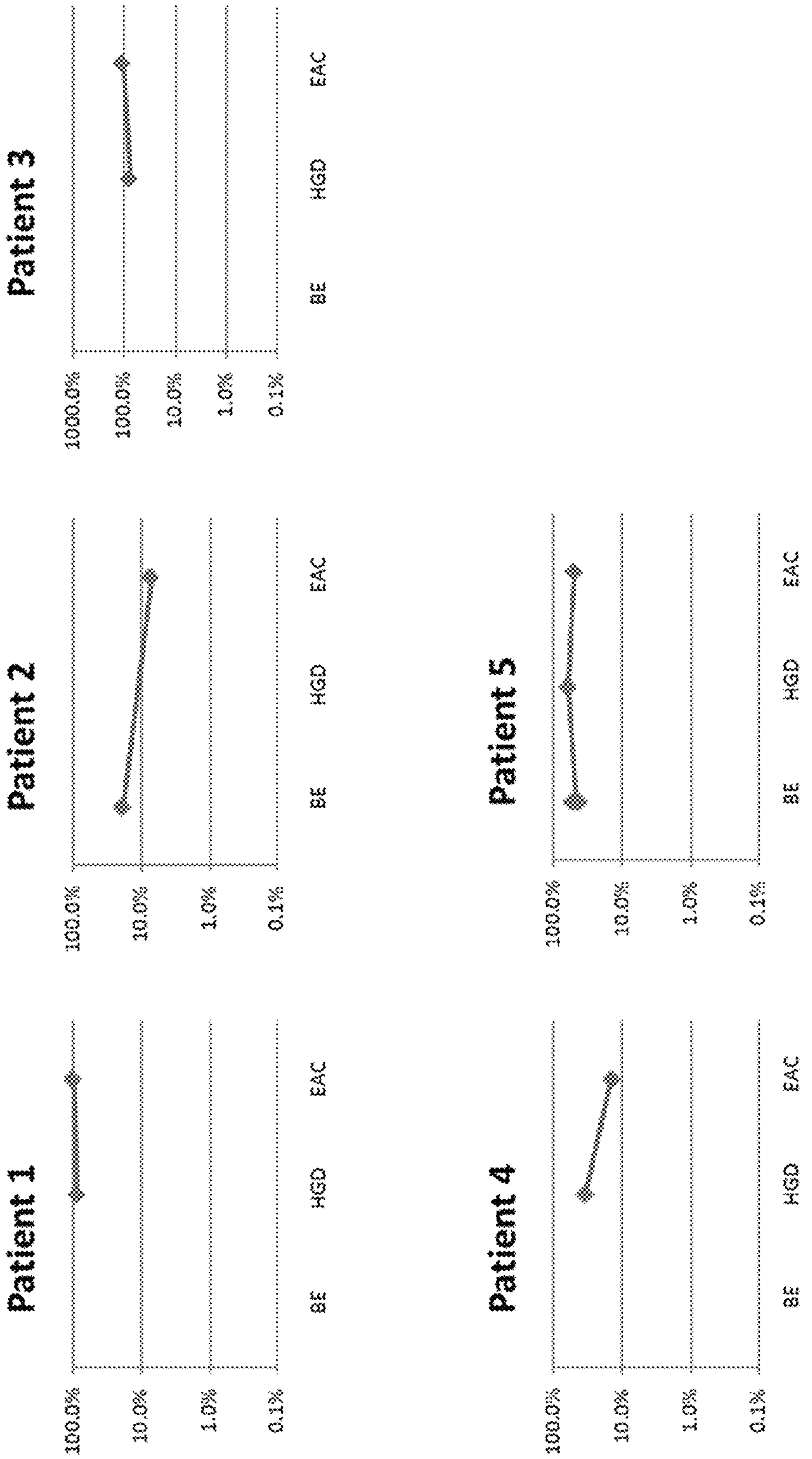
FIG. 52 shows percent vimentin methylation in esophageal adenocarcinomas and matched concurrent pre-cancerous Barrett's esophagus lesions in individual patients. BE: Barrett's Esophagus; HGD: High Grade Dysplasia; EAC: Adenocarcinoma of the Esophagus.

From 5 cases of EAC, additional concurrent biopsies were also available from regions of esophagus that showed either simple BE or BE with high grade dysplasia (FIG. 52). In each of these cases, the high level of vimentin methylation detected in the EAC was also detected in the concurrent BE and/or BE with high grade dysplasia tissue. This is consistent with a model of vimentin methylation being an early event present throughout the neoplastic clone, and of EAC arising from an initiated field of BE tissue.

Figure 53:
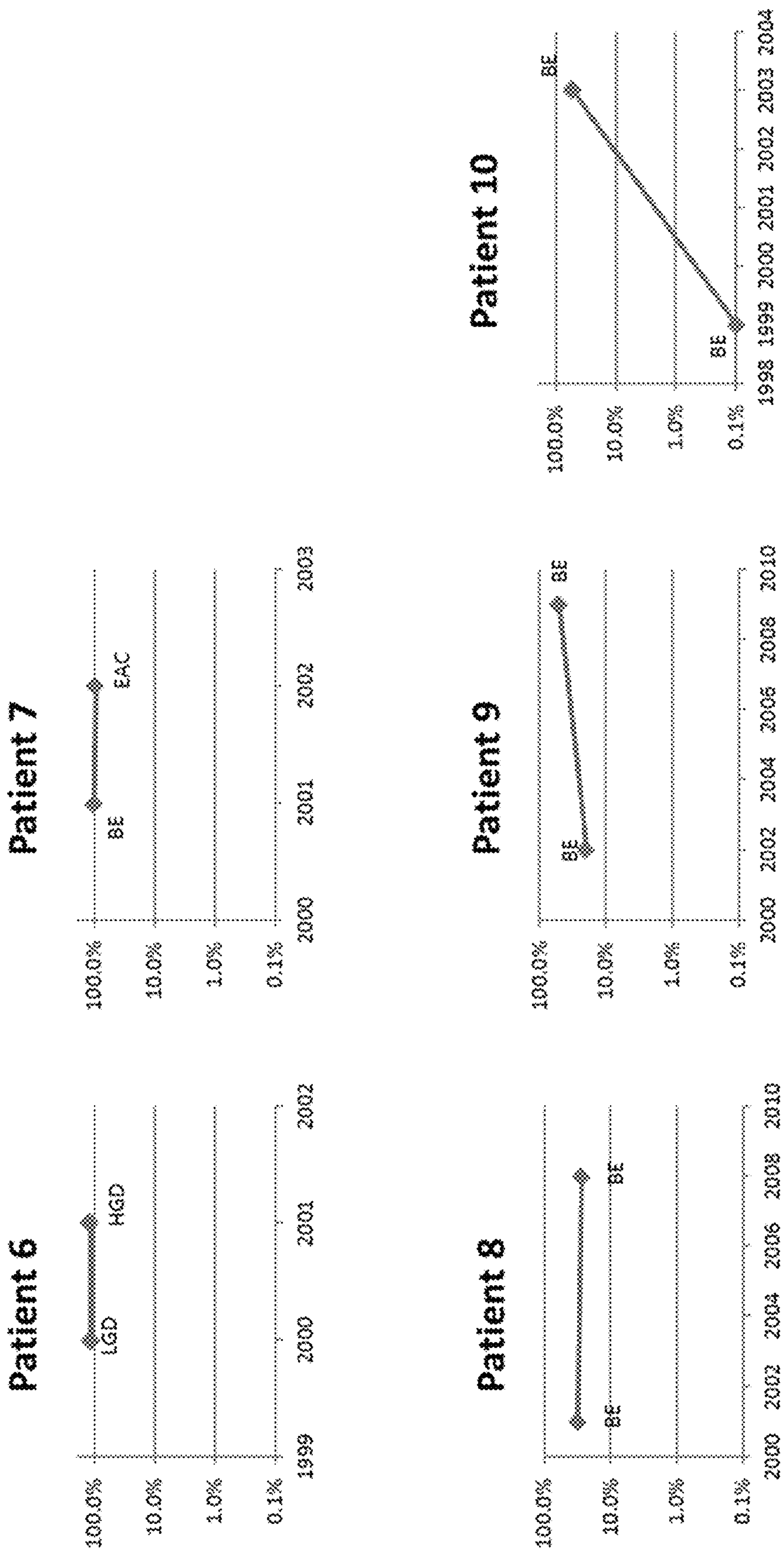
FIG. 53 shows percent vimentin methylation in matched longitudinal esophageal neoplasias sampled over time in individual patients.

Current clinical practice provides for longitudinal endoscopic surveillance of individuals with Barrett's esophagus. In 5 individuals with esophageal neoplasias that showed vimentin methylation, we were able to identify additional tissue samples from prior biopsies of Barrett's epithelium obtained from 1 to 7 years earlier in time. In 4 of these 5 cases, vimentin methylation was also detected as present in the earlier sample. (FIG. 53) In one individual, vimentin methylation was detected in each of 2 concurrent biopsies of BE, but was absent in the same individual's BE sampled 4 years previously (Patient 10: FIG. 53 and data not shown). These data further support a model which vimentin methylation principally occurs as an early epigenetic event in the pathway of esophageal carcinogenesis, and in which EACs arise from an initiated field of BE.

Figure 55:
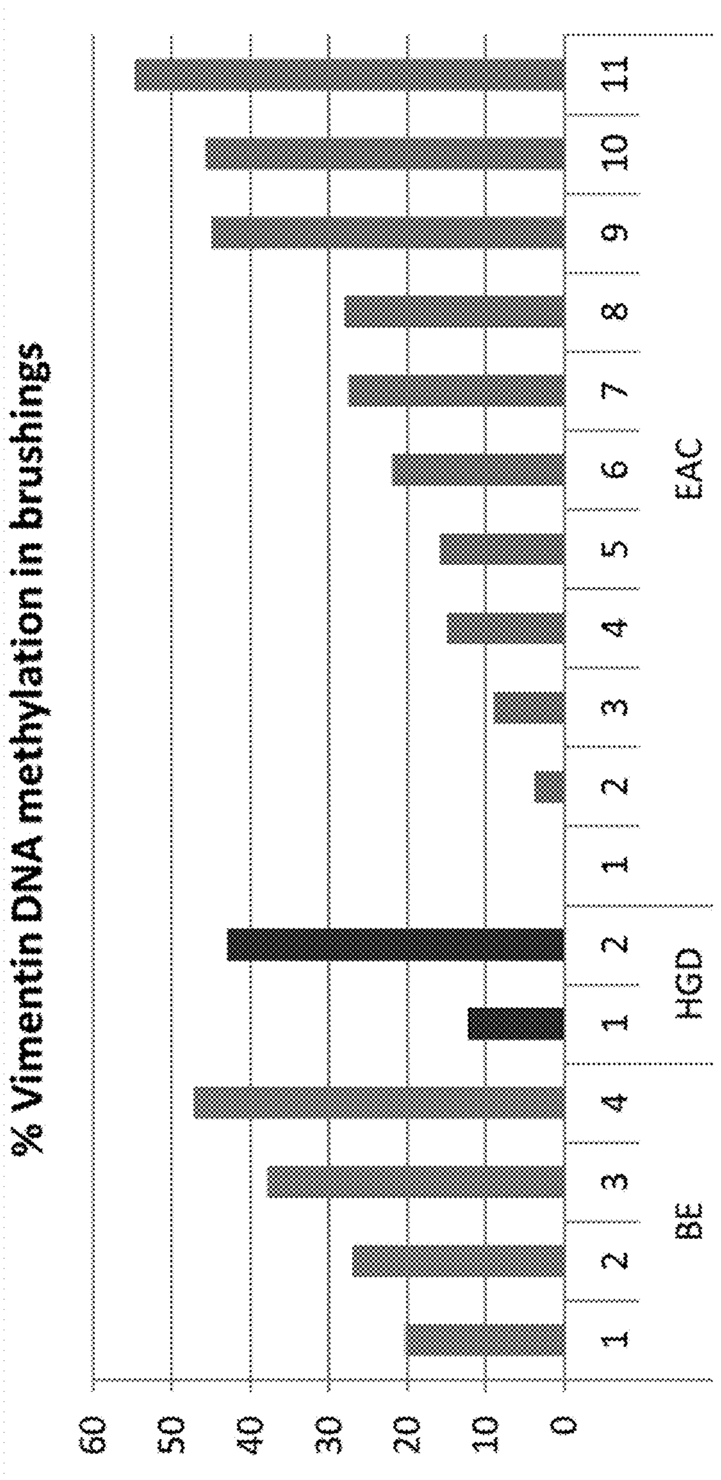
FIG. 55 shows the results of vimentin DNA methylation measured in esophageal brushings taken from patients with Barrett's Esophagus (BE), Barrett's Esophagus with High Grade Dysplasia (HGD), and Esophageal Adenocarcinomas (EAC).

FIG. 55 summarizes additional results obtained by measuring DNA methylation of vimentin in esophageal brushings of Barrett's Esophagus (BE), Barrett's Esophagus with High Grade Dysplasia (HGD), and Esophageal Adenocarcinoma (EAC).

4. Vimentin Methylation in Gastric Cancer

Figure 54:
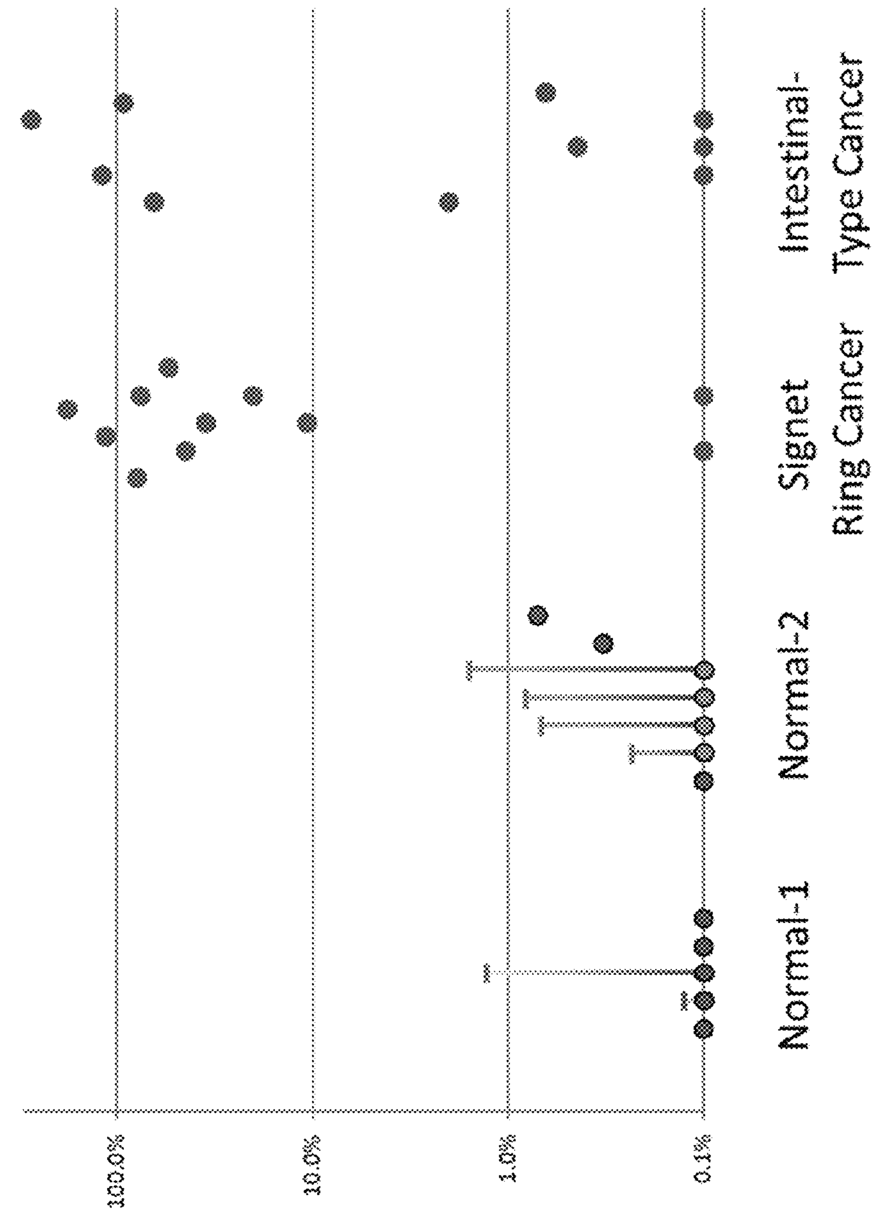
FIG. 54 shows vimentin methylation in gastric cancer. Shown is percent of vimentin methylation relative to total actin DNA in each sample. Circles denote individual samples. Samples in which no vimentin methylation was detected are depicted as having 0.1% methylated DNA, which in most cases represented the lower limit of detection of the assay. In a few samples in which a lesser amount of input DNA was available, bars raised above the 0.1% level designate the slightly higher threshold that applied as the lower limit for detection of positive vimentin methylation. Normal-1: Normal gastric mucosa from cancer free cases; Normal-2: Normal gastric mucosa from cases with concurrent gastric cancers; Signet Ring Cancer: Signet Ring Gastric Cancer samples; Intestinal Type Cancer: Intestinal Type Gastric Cancer samples.

Similar to our findings in esophageal neoplasias, vimentin methylation also proved commonly present in gastric cancers. High levels of vimentin methylation (10%-100%) were identified in nine of eleven (82%) signet ring gastric cancers and in four of 10 (40%) intestinal type gastric cancers (FIG. 54). The difference between these two gastric cancer types was not statistically significant (P=0.08). Low level vimentin methylation was further detected in an additional 3 intestinal type cancers. Vimentin methylation was not detected in any of 5 normal gastric mucosa samples from cancer free individuals, and was also not detected in 5 of 7 gastric mucosa samples from individuals whose stomachs did harbor gastric cancer. In the remaining 2 persons with gastric cancers, trace (<1%) vimentin methylation was detected in the accompanying normal gastric mucosa. In these two cases this suggests that either the trace cancer cells were present in the normal mucosa, or alternatively, that the cancers may have developed from a field of initiated cells already marked by acquisition of vimentin methylation. Supporting this latter possibility was the finding that in one individual who harbored both a gastric cancer and a gastric dysplasia, both lesions were positive for vimentin methylation (data not shown).

In summary, the data presented above demonstrate that acquisition of aberrant vimentin methylation is highly common in each of these neoplasms or pre-neoplastic conditions (e.g., Barrett's esophagus, esophageal adenocarcinomas, and gastric cancers), and is largely absent from the corresponding normal tissues. Vimentin methylation was detected in 92% of Barrett's esophagus, 100% of Barrett's esophagus with high grade dysplasia, and 83% of adenocarcinomas of the esophagus. Vimentin methylation similarly was detected in 82% of signet ring and 40% of intestinal type gastric cancers. These findings establish aberrant vimentin methylation as a highly common epigenetic alteration in neoplasias that arise throughout the gut and also demonstrate that Barrett's esophagus, even without dysplasia, already contains epigenetic alterations typical of adenocarcinomas of the esophagus. These findings further demonstrate that vimentin methylation is a useful biomarker of gastrointestinal neoplasia in both the upper and lower gastrointestinal tract.

4. Vimentin Methylation in Pancreatic Cancer

Figure 56:
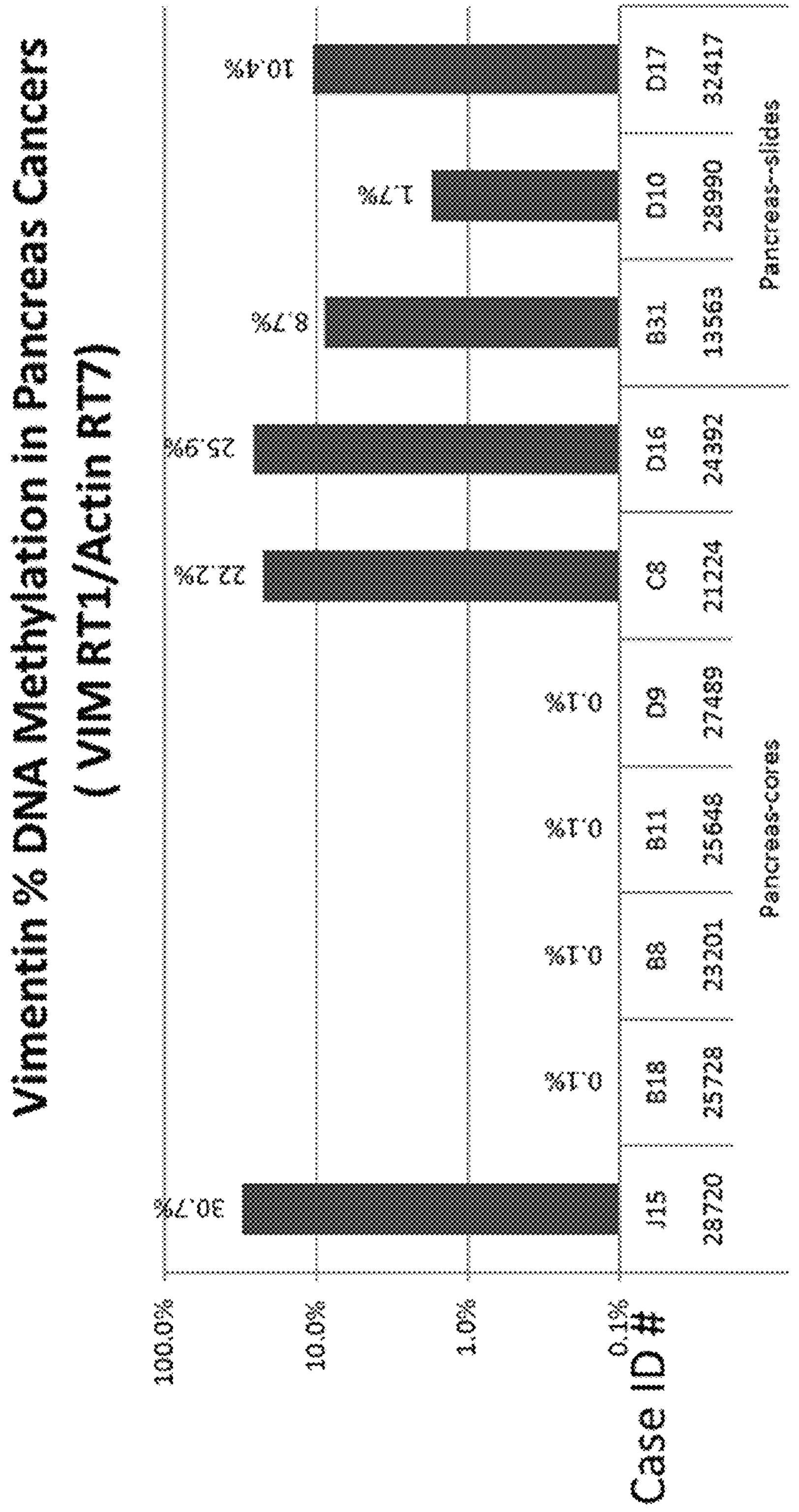
FIG. 56 shows the results of vimentin DNA methylation measured in pancreas cancers. The x-axis indicates case identification numbers and origin of the samples (either pancreas cores or pancreas slides that have been obtained from biopsied samples taken from cancer patients). The y-axis indicates the percentage of vimentin DNA methylation.

To determine the presence of aberrant vimentin methylation in pancreatic cancer, ten pancreatic cancer samples were obtained from formalin fixed paraffin embedded (FFPE) tissue samples. FFPE pancreatic cancer tissues were sampled either as core samples from the FFPE tissue block (7/10) or as slides cut from the FFPE tissue block (3/10). Aberrant vimentin methylation was detected in 3 of the core samples, and in all of the slides. The data is summarized in FIG. 56.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An isolated polynucleotide comprising a bisulfite-converted nucleic acid; wherein the polynucleotide is 20-3000 nucleotides in length; wherein the polynucleotide comprises a region having:

a) a nucleotide sequence comprising the bisulfite-converted methylated nucleotide sequence of SEQ ID NO: 41, SEQ ID NO: 42, or SEQ ID NO: 44, a complement thereof, or a fragment thereof; wherein said nucleotide sequence, said complement or said fragment is at least 20 nucleotides in length; or b) a nucleotide sequence that is at least 95% identical to the bisulfite-converted methylated nucleotide sequence of SEQ ID NO: 41, SEQ ID NO: 42, or SEQ ID NO: 44, a complement thereof, or a fragment thereof; wherein said nucleotide sequence, said complement or said fragment is at least 20 nucleotides in length;

and wherein said nucleic acid, prior to bisulfite conversion, comprises at least one methylated cytosine and at least one unmethylated cytosine.

2. The isolated polynucleotide of claim 1, wherein said polynucleotide consists of a nucleotide sequence that is at least 95% identical to the bisulfite-converted methylated nucleotide sequence of SEQ ID NO: 41, SEQ ID NO: 42, or SEQ ID NO: 44, or a complement thereof or a fragment thereof.

3. The isolated polynucleotide of claim 2, wherein said polynucleotide consists of a nucleotide sequence that is at least 95% identical to the bisulfite-converted methylated nucleotide sequence of SEQ ID NO: 41, or a fragment thereof or a complement thereof.

4. The isolated polynucleotide of claim 2, wherein said polynucleotide consists of a nucleotide sequence that is at least 95% identical to the bisulfite-converted methylated nucleotide sequence of SEQ ID NO: 42, or a fragment thereof or a complement thereof.

5. The isolated polynucleotide of claim 2, wherein said polynucleotide consists of a nucleotide sequence that is at least 95% identical to the bisulfite-converted methylated nucleotide sequence of SEQ ID NO: 44, or a fragment thereof or a complement thereof.

6. The isolated polynucleotide of claim 1, wherein said complement thereof consists of the bisulfite-converted methylated nucleotide sequence of SEQ ID NO: 48, or a fragment thereof.

7. The isolated polynucleotide of claim 1, wherein the polynucleotide is generated by amplifying at least a portion of the bisulfite-converted methylated nucleic acid derived from the vimentin gene locus of SEQ ID NO: 51, and wherein said polynucleotide may be amplified using polynucleotide primers having the nucleotide sequences of SEQ ID NOs: 62 and 63.

8. The isolated polynucleotide of claim 1, wherein the polynucleotide is generated by amplifying at least a portion of the bisulfite-converted methylated nucleic acid derived from the vimentin gene locus of SEQ ID NO: 51, and wherein said polynucleotide may be amplified using polynucleotide primers having the nucleotide sequences of SEQ ID NOs: 72 and 71.

9. The isolated polynucleotide of claim 1, wherein the polynucleotide is generated by amplifying at least a portion of the bisulfite-converted methylated nucleic acid derived from the vimentin gene locus of SEQ ID NO: 51, and wherein said polynucleotide may be amplified using polynucleotide primers having the nucleotide sequences of SEQ ID NOs: 68 and 71.

10. The isolated polynucleotide of claim 1, wherein the polynucleotide is between 50 to 500 nucleotides in length.

11. The isolated polynucleotide of claim 1, wherein the polynucleotide is between 80 to 150 nucleotides in length.

12. The isolated polynucleotide of claim 1, wherein the polynucleotide is a bisulfite-converted fragment of a nucleic acid obtained from a biological sample taken from a patient suspected of having a colon neoplasia.

* * * * *

UNITED STATES PATENT AND TRADEMARK OFFICE

CERTIFICATE OF CORRECTION

PATENT NO. : 9,580,754 B2
APPLICATION NO. : 13/670155
DATED : February 28, 2017
INVENTOR(S) : Markowitz et al.

It is certified that error appears in the above-identified patent and that said Letters Patent is hereby corrected as shown below:

On the Title Page

(72) Inventors: please replace "Sanford D. Markowitz, Pepper Pike; OH (US); Joseph Willis, Shaker Heights, OH (US); Amitabh Chak, University Heights, OH (US); Rom Leidner, Cleveland Heights, OH (US)" with: --Sanford D. Markowitz, Pepper Pike, OH (US); Wei-Dong Chen, South Euclid, OH (US)--

Signed and Sealed this
Tenth Day of July, 2018

Andrei Iancu
*Director of the United States Patent and Trademark Office*

UNITED STATES PATENT AND TRADEMARK OFFICE

CERTIFICATE OF CORRECTION

PATENT NO. : 9,580,754 B2
APPLICATION NO. : 13/670155
DATED : February 28, 2017
INVENTOR(S) : Markowitz et al.

It is certified that error appears in the above-identified patent and that said Letters Patent is hereby corrected as shown below:

In the Specification

Column 1, Line 23 under the heading "FUNDING" please replace:
"Work described herein was supported by National Institutes of Health Grant RO1CA 67409 and U01CA88130 and U01CA15275. The United States Government has certain rights in the invention."
With:
--This invention was made with government support under Grants R01CA67409; U01CA88130 and U01CA15275 awarded by the National Institutes of Health. The government has certain rights in the invention.--

Signed and Sealed this
Twenty-sixth Day of March, 2019

Andrei Iancu
*Director of the United States Patent and Trademark Office*

UNITED STATES PATENT AND TRADEMARK OFFICE

CERTIFICATE OF CORRECTION

PATENT NO. : 9,580,754 B2
APPLICATION NO. : 13/670155
DATED : February 28, 2017
INVENTOR(S) : Sanford D. Markowitz et al.

It is certified that error appears in the above-identified patent and that said Letters Patent is hereby corrected as shown below:

In the Specification

Column 1, Line 23 under the heading "FUNDING" please replace:
"This invention was made with government support under Grants R01CA67409; U01CA88130 and U01CA15275 awarded by the National Institutes of Health. The government has certain rights in the invention."

With:
--This invention was made with government support under CA088130, CA067409, and CA152756 awarded by the National Institutes of Health. The United States Government has certain rights in the invention.--

This certificate supersedes the Certificate of Correction issued July 10, 2018.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*

```
SEQUENCE LISTING


<160> NUMBER OF SEQ ID NOS: 77

<210> SEQ ID NO 1
<211> LENGTH: 466
<212> TYPE: PRT
<213> ORGANISM: Homo sapiens

<400> SEQUENCE: 1

Met Ser Thr Arg Ser Val Ser Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
```

-continued

```
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Phe Leu Ile Lys Thr Val Glu
        435                 440                 445

Thr Arg Asp Gly Gln Val Ile Asn Glu Thr Ser Gln His His Asp Asp
    450                 455                 460

Leu Glu
465


<210> SEQ ID NO 2
<211> LENGTH: 2001
<212> TYPE: DNA
<213> ORGANISM: Homo sapiens

<400> SEQUENCE: 2

ggtgcaatcg tgatctggga ggcccacgta tggcgcctct ccaaaggctg cagaagtttc      60

ttgctaacaa aaagtccgca cattcgagca aagacaggct ttagcgagtt attaaaaact     120

taggggcgct cttgtccccc acagggcccg accgcacaca gcaaggcgat ggcccagctg     180

taagttggta gcactgagaa ctagcagcgc gcgcggagcc cgctgagact tgaatcaatc     240

tggtctaacg gtttccccta aaccgctagg agccctcaat cggcgggaca gcagggcgcg     300

gtgagtcacc gccggtgact aagcgacccc accccctctcc ctcgggcttt cctctgccac     360

cgccgtctcg caactcccgc cgtccgaagc tggactgagc ccgttaggtc cctcgacaga     420

acctcccctc cccccaacat ctctccgcca aggcaagtcg atggacagag gcgcgggccg     480

gagcagcccc cctttccaag cgggcggcgc gcgaggctgc ggcgaggcct gagccctgcg     540

ttcctgcgct gtgcgcgccc ccacccccgcg ttccaatctc aggcgctctt tgtttctttc     600

tccgcgactt cagatctgag ggattcctta ctctttcctc ttcccgctcc tttgcccgcg     660

ggtctccccg cctgaccgca gccccgagac cgccgcgcac ctcctcccac gcccctttgg     720

cgtggtgcca ccggacccct ctggttcagt cccaggcgga ccccccccctc accgcgcgac     780

cccgcctttt tcagcacccc agggtgagcc cagctcagac tatcatccgg aaagccccca     840
```

-continued

```
aaagtcccag cccagcgctg aagtaacggg accatgccca gtcccaggcc ccggagcagg    900
aaggctcgag ggcgccccca ccccacccgc ccaccctccc cgcttctcgc taggtcccta    960
ttggctggcg cgctccgcgg ctgggatggc agtgggaggg gaccctcttt cctaacgggg   1020
ttataaaaac agcgccctcg gcggggtcca gtcctctgcc actctcgctc cgaggtcccc   1080
gcgccagaga cgcagccgcg ctcccaccac ccacacccac cgcgccctcg ttcgcctctt   1140
ctccgggagc cagtccgcgc caccgccgcc gcccaggcca tcgccaccct ccgcagccat   1200
gtccaccagg tccgtgtcct cgtcctccta ccgcaggatg ttcggcggcc cgggcaccgc   1260
gagccggccg agctccagcc ggagctacgt gactacgtcc acccgcacct acagcctggg   1320
cagcgcgctg cgccccagca ccagccgcag cctctacgcc tcgtccccgg gcggcgtgta   1380
tgccacgcgc tcctctgccg tgcgcctgcg gagcagcgtg cccggggtgc ggctcctgca   1440
ggactcggtg gacttctcgc tggccgacgc catcaacacc gagttcaaga acacccgcac   1500
caacgagaag gtggagctgc aggagctgaa tgaccgcttc gccaactaca tcgacaaggt   1560
gcgcttcctg gagcagcaga ataagatcct gctggccgag ctcgagcagc tcaagggcca   1620
aggcaagtcg cgcctggggg acctctacga ggaggagatg cgggagctgc gccggcaggt   1680
ggaccagcta accaacgaca aagcccgcgt cgaggtggag cgcgacaacc tggccgagga   1740
catcatgcgc ctccgggaga agtaaggctg cgcccatgca agtagctggg cctcgggagg   1800
gggctggagg gagaggggaa cgcccccccg gcccccgcga gagctgccac gcccttgggg   1860
atgtggccgg ggggaggcct gccagggaga cagcggagag cggggctgtg gctgtggtgg   1920
cgcagccccg cccagaaccc agaccttgca gttcgcattt cctcctctgt ccccacacat   1980
tgcccaagga cgctccgttt c                                             2001
```

<210> SEQ ID NO 3
<211> LENGTH: 2001
<212> TYPE: DNA
<213> ORGANISM: Homo sapiens

<400> SEQUENCE: 3

```
ggtgtaatcg tgatttggga ggtttacgta tggcgttttt ttaaaggttg tagaagtttt     60
ttgttaataa aaagttcgta tattcgagta aagataggtt ttagcgagtt attaaaaatt    120
taggggcgtt tttgtttttt atagggttcg atcgtatata gtaaggcgat ggtttagttg    180
taagttggta gtattgagaa ttagtagcgc gcgcggagtt cgttgagatt tgaattaatt    240
tggtttaacg gtttttttta aatcgttagg agtttttaat cggcgggata gtagggcgcg    300
gtgagttatc gtcggtgatt aagcgatttt attttttttt ttcgggtttt tttttgttat    360
cgtcgtttcg taattttcgt cgttcgaagt tggattgagt tcgttaggtt tttcgataga    420
attttttttt tttttaatat tttttcgtta aggtaagtcg atggatagag gcgcgggtcg    480
gagtagtttt ttttttaag cgggcggcgc gcgaggttgc ggcgaggttt gagttttgcg    540
tttttgcgtt gtgcgcgttt ttatttcgcg ttttaatttt aggcgttttt tgtttttttt    600
ttcgcgattt tagatttgag ggatttttta tttttttttt ttttcgtttt tttgttcgcg    660
ggtttttttcg tttgatcgta gtttcgagat cgtcgcgtat ttttttttac gttttttttgg    720
cgtggtgtta tcggattttt ttggtttagt tttaggcgga tttttttttt atcgcgcgat    780
ttcgtttttt ttagtatttt agggtgagtt tagtttagat tattattcgg aaagttttta    840
aaagttttag tttagcgttg aagtaacggg attatgttta gttttaggtt tcggagtagg    900
```

aaggttcgag ggcgttttta ttttattcgt ttattttttt cgtttttcgt taggttttta 960
ttggttggcg cgtttcgcgg ttgggatggt agtgggaggg gattttttttt tttaacgggg 1020 ttataaaaat agcgttttcg gcggggttta gtttttttgtt attttcgttt cgaggttttc 1080
gcgttagaga cgtagtcgcg tttttattat ttatatttat cgcgttttcg ttcgtttttt 1140
tttcgggagt tagttcgcgt tatcgtcgtc gtttaggtta tcgttatttt tcgtagttat 1200
gtttattagg ttcgtgtttt cgttttttta tcgtaggatg ttcggcggtt cgggtatcgc 1260
gagtcggtcg agttttagtc ggagttacgt gattacgttt attcgtattt atagtttggg 1320
tagcgcgttg cgttttagta ttagtcgtag tttttacgtt tcgttttcgg gcggcgtgta 1380
tgttacgcgt tttttgtcg tgcgtttgcg gagtagcgtg ttcggggtgc ggtttttgta 1440
ggattcggtg gatttttcgt tggtcgacgt tattaatatc gagtttaaga atattcgtat 1500
taacgagaag gtggagttgt aggagttgaa tgatcgtttc gttaattata tcgataaggt 1560 gcgtttttttg gagtagtaga ataagatttt gttggtcgag ttcgagtagt ttaagggtta 1620
aggtaagtcg cgtttggggg atttttacga ggaggagatg cgggagttgc gtcggtaggt 1680
ggattagtta attaacgata aagttcgcgt cgaggtggag cgcgataatt tggtcgagga 1740
tattatgcgt tttcgggaga agtaaggttg cgtttatgta agtagttggg tttcgggagg 1800
gggttggagg gagaggggaa cgtttttttcg gttttcgcga gagttgttac gtttttgggg 1860
atgtggtcgg ggggaggttt gttagggaga tagcggagag cggggttgtg gttgtggtgg 1920
cgtagtttcg tttagaattt agattttgta gttcgtattt tttttttgt ttttatatat 1980 tgtttaagga cgtttcgttt t 2001

<210> SEQ ID NO 4
<211> LENGTH: 2001
<212> TYPE: DNA
<213> ORGANISM: Homo sapiens

<400> SEQUENCE: 4
ggtgtaattg tgatttggga ggtttatgta tggtgttttt ttaaaggttg tagaagtttt 60
ttgttaataa aaagtttgta tatttgagta aagataggtt ttagtgagtt attaaaaatt 120
taggggtgtt tttgtttttt atagggtttg attgtatata gtaaggtgat ggtttagttg 180
taagttggta gtattgagaa ttagtagtgt gtgtggagtt tgttgagatt tgaattaatt 240
tggtttaatg gtttttttta aattgttagg agtttttaat tggtgggata gtagggtgtg 300
gtgagttatt gttggtgatt aagtgatttt attttttttt tttgggtttt tttttgttat 360
tgttgttttg taatttttgt tgtttgaagt tggattgagt ttgttaggtt ttttgataga 420
attttttttt tttttaatat ttttttgtta aggtaagttg atggatagag gtgtgggttg 480
gagtagtttt ttttttttaag tgggtggtgt gtgaggttgt ggtgaggttt gagttttgtg 540
tttttgtgtt gtgtgtgttt ttattttgtg ttttaatttt aggtgttttt tgtttttttt 600
tttgtgattt tagatttgag ggatttttta tttttttttt tttttgtttt tttgtttgtg 660
ggtttttttg tttgattgta gttttgagat tgttgtgtat tttttttttat gtttttttgg 720 tgtggtgtta ttggattttt ttggtttagt tttaggtgga tttttttttt attgtgtgat 780
tttgtttttt ttagtatttt agggtgagtt tagtttagat tattatttgg aaagttttta 840
aaagttttag tttagtgttg aagtaatggg attatgttta gttttaggtt ttggagtagg 900
aaggtttgag ggtgttttta ttttatttgt ttattttttt tgttttttgt taggttttta 960
ttggttggtg tgttttgtgg ttgggatggt agtgggaggg gattttttttt tttaatgggg 1020 ttataaaaat agtgtttttg gtggggttta gtttttgtt attttgttt tgaggttttt 1080 gtgttagaga tgtagttgtg tttttattat ttatatttat tgtgtttttg tttgtttttt 1140
ttttgggagt tagtttgtgt tattgttgtt gtttaggtta ttgttatttt ttgtagttat 1200
gtttattagg tttgtgtttt tgttttttta ttgtaggatg tttggtggtt tgggtattgt 1260
gagttggttg agttttagtt ggagttatgt gattatgttt atttgtattt atagtttggg 1320
tagtgtgttg tgttttagta ttagttgtag tttttatgtt ttgtttttgg gtggtgtgta 1380
tgttatgtgt ttttttgttg tgtgtttgtg gagtagtgtg tttggggtgt ggtttttgta 1440
ggatttggtg gattttttgt tggttgatgt tattaatatt gagtttaaga atatttgtat 1500
taatgagaag gtggagttgt aggagttgaa tgattgtttt gttaattata ttgataaggt 1560 gtgtttttttg gagtagtaga ataagatttt gttggttgag tttgagtagt ttaagggtta 1620
aggtaagttg tgtttggggg atttttatga ggaggagatg tgggagttgt gttggtaggt 1680
ggattagtta attaatgata aagtttgtgt tgaggtggag tgtgataatt tggttgagga 1740
tattatgtgt ttttgggaga agtaaggttg tgtttatgta agtagttggg ttttgggagg 1800
gggttggagg gagaggggaa tgtttttttg gtttttgtga gagttgttat gtttttgggg 1860
atgtggttgg ggggaggttt gttagggaga tagtggagag tggggttgtg gttgtggtgg 1920
tgtagttttg tttagaattt agattttgta gtttgtattt tttttttgt ttttatatat 1980 tgtttaagga tgttttgttt t 2001

<210> SEQ ID NO 5
<211> LENGTH: 2001
<212> TYPE: DNA
<213> ORGANISM: Homo sapiens

<400> SEQUENCE: 5
gaaacggagc gtccttgggc aatgtgtggg gacagaggag gaaatgcgaa ctgcaaggtc 60
tgggttctgg gcggggctgc gccaccacag ccacagcccc gctctccgct gtctccctgg 120
caggcctccc cccggccaca tccccaaggg cgtggcagct ctcgcggggg ccggggggggc 180 gttcccctct ccctccagcc ccctcccgag gcccagctac ttgcatgggc gcagccttac 240
ttctcccgga ggcgcatgat gtcctcggcc aggttgtcgc gctccacctc gacgcgggct 300
ttgtcgttgg ttagctggtc cacctgccgg cgcagctccc gcatctcctc ctcgtagagg 360
tcccccaggc gcgacttgcc ttggcccttg agctgctcga gctcggccag caggatctta 420
ttctgctgct ccaggaagcg caccttgtcg atgtagttgg cgaagcggtc attcagctcc 480
tgcagctcca ccttctcgtt ggtgcgggtg ttcttgaact cggtgttgat ggcgtcggcc 540
agcgagaagt ccaccgagtc ctgcaggagc cgcaccccgg gcacgctgct ccgcaggcgc 600
acggcagagg agcgcgtggc atacacgccg cccggggacg aggcgtagag gctgcggctg 660
gtgctggggc gcagcgcgct gcccaggctg taggtgcggg tggacgtagt cacgtagctc 720
cggctggagc tcggccggct cgcggtgccc gggccgccga acatcctgcg gtaggaggac 780
gaggacacgg acctggtgga catggctgcg gagggtggcg atggcctggg cggcggcggt 840
ggcgcggact ggctcccgga gaagaggcga acgagggcgc ggtgggtgtg ggtggtggga 900
gcgcggctgc gtctctggcg cggggacctc ggagcgagag tggcagagga ctggaccccg 960
ccgagggcgc tgtttttata accccgttag gaaagagggt cccctcccac tgccatccca 1020
gccgcggagc gcgccagcca atagggacct agcgagaagc ggggagggtg ggcgggtggg 1080

-continued

```
gtgggggcgc cctcgagcct tcctgctccg gggcctggga ctgggcatgg tcccgttact   1140

tcagcgctgg gctgggactt ttgggggctt tccggatgat agtctgagct gggctcaccc   1200

tggggtgctg aaaaaggcgg ggtcgcgcgg tgaggggggg gtccgcctgg gactgaacca   1260

gaggggtccg gtggcaccac gccaaagggg cgtgggagga ggtgcgcggc ggtctcgggg   1320

ctgcggtcag gcggggagac ccgcgggcaa aggagcggga agaggaaaga gtaaggaatc   1380

cctcagatct gaagtcgcgg agaaagaaac aaagagcgcc tgagattgga acgcggggtg   1440

ggggcgcgca cagcgcagga acgcagggct caggcctcgc cgcagcctcg cgcgccgccc   1500

gcttggaaag gggggctgct ccggcccgcg cctctgtcca tcgacttgcc ttggcggaga   1560

gatgttgggg ggaggggagg ttctgtcgag ggacctaacg ggctcagtcc agcttcggac   1620

ggcgggagtt gcgagacggc ggtggcagag gaaagcccga gggagagggg tggggtcgct   1680

tagtcaccgg cggtgactca ccgcgccctg ctgtcccgcc gattgagggc tcctagcggt   1740

ttaggggaaa ccgttagacc agattgattc aagtctcagc gggctccgcg cgcgctgcta   1800

gttctcagtg ctaccaactt acagctgggc catcgccttg ctgtgtgcgg tcgggccctg   1860

tgggggacaa gagcgcccct aagtttttaa taactcgcta aagcctgtct ttgctcgaat   1920

gtgcggactt tttgttagca agaaacttct gcagcctttg gagaggcgcc atacgtgggc   1980

ctcccagatc acgattgcac c                                             2001
```

<210> SEQ ID NO 6
<211> LENGTH: 2001
<212> TYPE: DNA
<213> ORGANISM: Homo sapiens

<400> SEQUENCE: 6

```
gaaacggagc gtttttgggt aatgtgtggg gatagaggag gaaatgcgaa ttgtaaggtt     60

tgggttttgg gcggggttgc gttattatag ttatagtttc gtttttcgtt gttttttgg     120

taggtttttt ttcggttata tttttaaggg cgtggtagtt ttcgcggggg tcgggggggc    180

gttttttttt ttttttagtt ttttttcgag gtttagttat ttgtatgggc gtagttttat    240

ttttttcgga ggcgtatgat gttttcggtt aggttgtcgc gttttatttc gacgcgggtt    300

ttgtcgttgg ttagttggtt tatttgtcgg cgtagttttc gtattttttt ttcgtagagg    360

ttttttaggc gcgatttgtt ttggtttttg agttgttcga gttcggttag taggatttta    420

ttttgttgtt ttaggaagcg tattttgtcg atgtagttgg cgaagcggtt atttagtttt    480

tgtagtttta ttttttcgtt ggtgcgggtg tttttgaatt cggtgttgat ggcgtcggtt    540

agcgagaagt ttatcgagtt ttgtaggagt cgtatttcgg gtacgttgtt tcgtaggcgt    600

acggtagagg agcgcgtggt atatacgtcg ttcggggacg aggcgtagag gttgcggttg    660

gtgttggggc gtagcgcgtt gtttaggttg taggtgcggg tggacgtagt tacgtagttt    720

cggttggagt tcggtcggtt cgcggtgttc gggtcgtcga atattttgcg gtaggaggac    780

gaggatacgg atttggtgga tatggttgcg gagggtggcg atggtttggg cggcggcggt    840

ggcgcggatt ggttttcgga gaagaggcga acgagggcgc ggtgggtgtg ggtggtggga    900

gcgcggttgc gtttttggcg cggggatttc ggagcgagag tggtagagga ttggatttcg    960

tcgagggcgt tgtttttata atttcgttag gaaagagggt ttttttttat tgttatttta   1020

gtcgcggagc gcgttagtta atagggattt agcgagaagc ggggagggtg ggcgggtggg   1080

gtgggggcgt tttcgagttt ttttgtttcg gggtttggga ttgggtatgg tttcgttatt   1140

ttagcgttgg gttgggattt ttgggggttt ttcggatgat agtttgagtt gggtttattt   1200
```

tggggtgttg aaaaaggcgg ggtcgcgcgg tgaggggggg gttcgtttgg gattgaatta 1260
gaggggttcg gtggtattac gttaaagggg cgtgggagga ggtgcgcggc ggtttcgggg 1320
ttgcggttag gcggggagat tcgcgggtaa aggagcggga agaggaaaga gtaaggaatt 1380
ttttagattt gaagtcgcgg agaaagaaat aaagagcgtt tgagattgga acgcggggtg 1440
ggggcgcgta tagcgtagga acgtagggtt taggtttcgt cgtagtttcg cgcgtcgttc 1500
gtttggaaag gggggttgtt tcggttcgcg tttttgttta tcgatttgtt ttggcggaga 1560
gatgttgggg ggaggggagg ttttgtcgag ggatttaacg ggtttagttt agtttcggac 1620
ggcgggagtt gcgagacggc ggtggtagag gaaagttcga gggagagggg tggggtcgtt 1680
tagttatcgg cggtgattta tcgcgttttg ttgtttcgtc gattgagggt ttttagcggt 1740
ttaggggaaa tcgttagatt agattgattt aagttttagc gggtttcgcg cgcgttgtta 1800
gtttttagtg ttattaattt atagttgggt tatcgttttg ttgtgtgcgg tcgggttttg 1860
tgggggataa gagcgttttt aagtttttaa taattcgtta aagtttgttt ttgttcgaat 1920
gtgcggattt tttgttagta agaaattttt gtagtttttg gagaggcgtt atacgtgggt 1980
tttttagatt acgattgtat t 2001

<210> SEQ ID NO 7
<211> LENGTH: 2001
<212> TYPE: DNA
<213> ORGANISM: Homo sapiens

<400> SEQUENCE: 7
gaaatggagt gtttttgggt aatgtgtggg gatagaggag gaaatgtgaa ttgtaaggtt 60
tgggttttgg gtggggttgt gttattatag ttatagtttt gtttttttgtt gtttttttgg 120 taggtttttt tttggttata tttttaaggg tgtggtagtt tttgtggggg ttgggggggt 180
gttttttttt ttttttagtt tttttttgag gtttagttat ttgtatgggt gtagttttat 240
tttttttgga ggtgtatgat gtttttggtt aggttgttgt gttttatttt gatgtgggtt 300
ttgttgttgg ttagttggtt tatttgttgg tgtagttttt gtattttttt tttgtagagg 360 tttttttaggt gtgatttgtt ttggtttttg agttgtttga gtttggttag taggatttta 420
ttttgttgtt ttaggaagtg tattttgttg atgtagttgg tgaagtggtt atttagtttt 480
tgtagtttta ttttttttgtt ggtgtgggtg tttttgaatt tggtgttgat ggtgttggtt 540
agtgagaagt ttattgagtt ttgtaggagt tgtattttgg gtatgttgtt ttgtaggtgt 600
atggtagagg agtgtgtggt atatatgttg tttggggatg aggtgtagag gttgtggttg 660
gtgttggggt gtagtgtgtt gtttaggttg taggtgtggg tggatgtagt tatgtagttt 720
tggttggagt ttggttggtt tgtggtgttt gggttgttga atattttgtg gtaggaggat 780
gaggatatgg atttggtgga tatggttgtg gagggtggtg atggtttggg tggtggtggt 840
ggtgtggatt ggtttttgga gaagaggtga atgagggtgt ggtgggtgtg ggtggtggga 900
gtgtggttgt gtttttggtg tggggatttt ggagtgagag tggtagagga ttggattttg 960
ttgagggtgt tgtttttata attttgttag gaaagagggt ttttttttat tgttatttta 1020
gttgtggagt gtgttagtta atagggattt agtgagaagt ggggagggtg ggtgggtggg 1080
gtgggggtgt ttttgagttt ttttgttttg gggtttggga ttgggtatgg ttttgttatt 1140
ttagtgttgg gttgggattt ttgggggttt tttggatgat agtttgagtt gggtttattt 1200
tggggtgttg aaaaaggtgg ggttgtgtgg tgaggggggg gtttgtttgg gattgaatta 1260

-continued gaggggtttg gtggtattat gttaaagggg tgtgggagga ggtgtgtggt ggttttgggg 1320
ttgtggttag gtggggagat ttgtgggtaa aggagtggga agaggaaaga gtaaggaatt 1380
ttttagattt gaagttgtgg agaaagaaat aaagagtgtt tgagattgga atgtggggtg 1440
ggggtgtgta tagtgtagga atgtagggtt taggttttgt tgtagttttg tgtgttgttt 1500
gtttggaaag gggggttgtt ttggtttgtg tttttgttta ttgatttgtt ttggtggaga 1560
gatgttgggg ggaggggagg ttttgttgag ggatttaatg ggtttagttt agttttggat 1620
ggtgggagtt gtgagatggt ggtggtagag gaaagtttga gggagagggg tggggttgtt 1680
tagttattgg tggtgattta ttgtgttttg ttgttttgtt gattgagggt ttttagtggt 1740
ttaggggaaa ttgttagatt agattgattt aagttttagt gggttttgtg tgtgttgtta 1800
gtttttagtg ttattaattt atagttgggt tattgttttg ttgtgtgtgg ttgggttttg 1860
tgggggataa gagtgttttt aagtttttaa taatttgtta aagtttgttt ttgtttgaat 1920
gtgtggattt tttgttagta agaaattttt gtagtttttg gagaggtgtt atatgtgggt 1980
tttttagatt atgattgtat t 2001

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gactctgcaa gaaaaacctt cc 22

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
tgagattgga acgcgggg 18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ccctcgttcg cctcttctcc 20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gtgttcttga actcggtgtt gatg 24

-continued

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcttcctgga gcagcagaat aa 22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
agcgtccttg ggcaatgtgt 20

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ttgatcgtag tttcgaggtc gtcgc 25

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ctaaaatact aaaaaaaacg aaatcgcgcg 30

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ttttgtttga ttgtagtttt gaggttgttg t 31

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ccctaaaata ctaaaaaaaa caaaatcaca ca 32

<210> SEQ ID NO 18

-continued

<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
ccctaaaata ctaaaaaaaa cgaaatcgcg 30

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
atcccgatta actaaaacgc tccgcg 26

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gttgcgtttt tggcgcgggg atttc 25

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ctaaatccca attaactaaa acactccaca 30

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
tggttgtgtt tttggtgtgg ggatttt 27

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gttttcgcgt tagagacgta gtcgc 25

<210> SEQ ID NO 24
<211> LENGTH: 25

<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
cgactaaaac tcgaccgact cgcga 25

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
ttgaggtttt tgtgttagag atgtagttgt 30

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
actccaacta aaactcaacc aactcaca 28

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
caaaatattc gacgacccga acaccg 26

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
ggagcgcgtg gtatatacgt cgttc 25

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
acaaaatatt caacaaccca aacaccaca 29

<210> SEQ ID NO 30
<211> LENGTH: 29
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 30

tagaggagtg tgtggtatat atgttgttt                                        29


<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

gtttcgattg gttggggcgt ttcgc                                            25


<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

gtctctaacg cgaaaacctc gaaacg                                           26


<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

ttaggtttcg attggttggg gtgttttgt                                        29


<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

acaactacat ctctaacaca aaaacctca                                        29


<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

ctacgtctct aacgcgaaaa cctcga                                           26


<210> SEQ ID NO 36
<211> LENGTH: 25
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 36
aaacgcgact acgtctctaa cgcga 25

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ttcgggagtt agttcgcgtt atcgtc 26

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
tttgggagtt agtttgtgtt attgttgttg t 31

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ctaccgcaaa atattcgacg acccga 26

<210> SEQ ID NO 40
<211> LENGTH: 588
<212> TYPE: DNA
<213> ORGANISM: Homo sapiens

<400> SEQUENCE: 40
gactctgcaa gaaaaacctt cccggtgcaa tcgtgatctg ggaggcccac gtatggcgcc 60
tctccaaagg ctgcagaagt ttcttgctaa caaaaagtcc gcacattcga gcaaagacag 120
gctttagcga gttattaaaa acttaggggc gctcttgtcc cccacagggc ccgaccgcac 180
acagcaaggc gatgggccca gctgtaagtt ggtagcactg agaactagca gcgcgcgcgg 240
agcccgctga gacttgaatc aatctggtct aacggtttcc cctaaaccgc taggagccct 300
caatcggcgg gacagcaggg cgcggtgagt caccgccggt gactaagcga ccccacccct 360
ctccctcggg ctttcctctg ccaccgccgt ctcgcaactc ccgccgtccg aagctggact 420
gagcccgtta ggtccctcga cagaacctcc cctcccccca acatctcccc ccaaggcaag 480
tcgatggaca gaggcgcggg ccggagcagc ccccctttcc aagcgggcgg cgcgcgaggc 540
tgcggcgagg cctgagccct gcgttcctgc gctgtgcgcg ccccccac 588

<210> SEQ ID NO 41
<211> LENGTH: 345
<212> TYPE: DNA

<213> ORGANISM: Homo sapiens

<400> SEQUENCE: 41
tctgagggat tccttactct ttcctcttcc cgctcctttg cccgcgggtc tccccgcctg 60
accgcagccc cgaggccgcc gcgcacctcc tcccacgccc ctttggcgtg gtgccaccgg 120
acccctctgg ttcagtccca ggcggacccc cccctcaccg cgcgaccccg cctttttcag 180
caccccaggg tgagcccagc tcagactatc atccggaaag cccccaaaag tcccagccca 240
gcgctgaagt aacgggacca tgcccagtcc cacgccccgg agcaggaagg ctcgaggcgc 300
ccccacccca cccgcccacc ctccccgctt ctcgctaggt cccga 345

<210> SEQ ID NO 42
<211> LENGTH: 370
<212> TYPE: DNA
<213> ORGANISM: Homo sapiens

<400> SEQUENCE: 42
ccctcgttcg cctcttctcc gggagccagt ccgcgccacc gccgccgccc aggccatcgc 60
caccctccgc agccatgtcc accaggtccg tgtcctcgtc ctcctaccgc aggatgttcg 120
gcggcccggg caccgcgagc cggccgagct ccagccggag ctacgtgact acgtccaccc 180
gcacctacag cctgggcagc gcgctgcgcc ccagcaccag ccgcagcctc tacgcctcgt 240
ccccgggcgg cgtgtatgcc acgcgctcct ctgccgtgcg cctgcggagc agcgtgcccg 300
gggtgcggct cctgcaggac tcggtggact tctcgctggc cgacgccatc aacaccgagt 360
tcaagaacac 370

<210> SEQ ID NO 43
<211> LENGTH: 432
<212> TYPE: DNA
<213> ORGANISM: Homo sapiens

<400> SEQUENCE: 43
gcttcctgga gcagcagaat aagatcctgc tggccgagct cgagcagctc aagggccaag 60
gcaagtcgcg cctaggggac ctctacgagg aggagatgcg ggagctgcgc cggcaggtgg 120
accagctaac caacgacaaa gcccgcgtcg aggtggagcg cgacaacctg gccgaggaca 180
tcatgcgcct ccgggagaag taaggctgcg cccatgcaag tagctgggcc tcgggagggg 240
gctggaggga gaggggaacg cccccccggc ccccgcgaga gctgccacgc ccttggggat 300
gtggccgggg ggaggcctgc cagggagaca gcggagagcg gggctgtggc tgtggtggcg 360
cagccccgcc cagaacccag accttgcagt tcgcatttcc tcctctgtcc ccacacattg 420
cccaaggacg ct 432

<210> SEQ ID NO 44
<211> LENGTH: 509
<212> TYPE: DNA
<213> ORGANISM: Homo sapiens

<400> SEQUENCE: 44
tctgagggat tccttactct ttcctcttcc cgctcctttg cccgcgggtc tccccgcctg 60
accgcagccc cgaggccgcc gcgcacctcc tcccacgccc ctttggcgtg gtgccaccgg 120
acccctctgg ttcagtccca ggcggacccc cccctcaccg cgcgaccccg cctttttcag 180
caccccaggg tgagcccagc tcagactatc atccggaaag cccccaaaag tcccagccca 240
gcgctgaagt aacgggacca tgcccagtcc cacgccccgg agcaggaagg ctcgaggcgc 300

```
ccccacccca cccgcccacc ctccccgctt ctcgctaggt cccgattggc tggggcgctc    360

cgcggctggg atggcagtgg gaggggaccc tctttcctaa cggggttata aaaacagcgc    420

cctcggcggg gtccagtcct ctgccactct cgctccgagg tccccgcgcc agagacgcag    480

ccgcgctccc accacccaca cccaccgcg                                      509
```

<210> SEQ ID NO 45
<211> LENGTH: 900
<212> TYPE: DNA
<213> ORGANISM: Homo sapiens

<400> SEQUENCE: 45

```
gacttcagat ctgagggatt ccttactctt tcctcttccc gctcctttgc ccgcgggtct     60

ccccgcctga ccgcagcccc gagaccgccg cgcacctcct cccacgcccc tttggcgtgg    120

tgccaccgga cccctctggt tcagtcccag gcggaccccc ccctcaccgc gcgaccccgc    180

ctttttcagc accccagggt gagcccagct cagactatca tccggaaagc ccccaaaagt    240

cccagcccag cgctgaagta acgggaccat gcccagtccc aggccccgga gcaggaaggc    300

tcgagggcgc ccccacccca cccgcccacc ctccccgctt ctcgctaggt ccctattggc    360

tggcgcgctc cgcggctggg atggcagtgg gaggggaccc tctttcctaa cggggttata    420

aaaacagcgc cctcggcggg gtccagtcct ctgccactct cgctccgagg tccccgcgcc    480

agagacgcag ccgcgctccc accacccaca cccaccgcgc cctcgttcgc ctcttctccg    540

ggagccagtc cgcgccaccg ccgccgccca ggccatcgcc accctccgca gccatgtcca    600

ccaggtccgt gtcctcgtcc tcctaccgca ggatgttcgg cggcccgggc accgcgagcc    660

ggccgagctc cagccggagc tacgtgacta cgtccacccg cacctacagc ctgggcagcg    720

cgctgcgccc cagcaccagc cgcagcctct acgcctcgtc cccgggcggc gtgtatgcca    780

cgcgctcctc tgccgtgcgc ctgcggagca gcgtgcccgg ggtgcggctc ctgcaggact    840

cggtggactt ctcgctggcc gacgccatca acaccgagtt caagaacacc cgcaccaacg    900
```

<210> SEQ ID NO 46
<211> LENGTH: 899
<212> TYPE: DNA
<213> ORGANISM: Homo sapiens

<400> SEQUENCE: 46

```
attttagatt tgagggattt tttatttttt tttttttcg ttttttttgtt cgcgggtttt     60

ttcgtttgat cgtagtttcg agatcgtcgc gtattttttt ttacgttttt ttggcgtggt    120

gttatcggat ttttttggtt tagttttagg cggatttttt ttttatcgcg cgatttcgtt    180

ttttttagta ttttagggtg agtttagttt agattattat tcggaaagtt tttaaaagtt    240

ttagtttagc gttgaagtaa cgggattatg tttagtttta ggtttcggag taggaaggtt    300

cgagggcgtt tttattttat tcgtttattt ttttcgtttt tcgttaggtt tttattggtt    360

ggcgcgtttc gcggttggga tggtagtggg aggggatttt ttttttaac ggggttataa    420

aaatagcgtt ttcggcgggg tttagttttt tgttattttc gtttcgaggt tttcgcgtta    480

gagacgtagt cgcgttttta ttatttatat ttatcgcgtt ttcgttcgtt tttttttcgg    540

gagttagttc gcgttatcgt cgtcgtttag gttatcgtta tttttcgtag ttatgtttat    600

taggttcgtg ttttcgtttt tttatcgtag gatgttcggc ggttcgggta tcgcgagtcg    660

gtcgagtttt agtcggagtt acgtgattac gtttattcgt atttatagtt tgggtagcgc    720
```

gttgcgtttt agtattagtc gtagttttta cgtttcgttt tcgggcggcg tgtatgttac 780
gcgttttttt gtcgtgcgtt tgcggagtag cgtgttcggg gtgcggtttt tgtaggattc 840
ggtggatttt tcgttggtcg acgttattaa tatcgagttt aagaatattc gtattaacg 899

<210> SEQ ID NO 47
<211> LENGTH: 899
<212> TYPE: DNA
<213> ORGANISM: Homo sapiens

<400> SEQUENCE: 47
attttagatt tgagggattt tttatttttt tttttttttg ttttttttgtt tgtgggtttt 60 tttgtttgat tgtagttttg agattgttgt gtattttttt ttatgttttt ttggtgtggt 120
gttattggat ttttttggtt tagttttagg tggatttttt ttttattgtg tgattttgtt 180
ttttttagta ttttagggtg agtttagttt agattattat ttggaaagtt tttaaaagtt 240
ttagtttagt gttgaagtaa tgggattatg tttagtttta ggttttggag taggaaggtt 300
tgagggtgtt tttattttat ttgtttattt tttttgtttt ttgttaggtt tttattggtt 360
ggtgtgtttt gtggttggga tggtagtggg aggggatttt tttttttaat ggggttataa 420
aaatagtgtt tttggtgggg tttagttttt tgttattttt gttttgaggt ttttgtgtta 480
gagatgtagt tgtgttttta ttatttatat ttattgtgtt tttgtttgtt ttttttttgg 540
gagttagttt gtgttattgt tgttgtttag gttattgtta tttttttgtag ttatgtttat 600 taggtttgtg tttttgtttt tttattgtag gatgtttggt ggtttgggta ttgtgagttg 660
gttgagtttt agttggagtt atgtgattat gtttatttgt atttatagtt tgggtagtgt 720
gttgtgtttt agtattagtt gtagttttta tgttttgttt ttgggtggtg tgtatgttat 780
gtgttttttt gttgtgtgtt tgtggagtag tgtgtttggg gtgtggtttt tgtaggattt 840
ggtggatttt ttgttggttg atgttattaa tattgagttt aagaatattt gtattaatg 899

<210> SEQ ID NO 48
<211> LENGTH: 900
<212> TYPE: DNA
<213> ORGANISM: Homo sapiens

<400> SEQUENCE: 48
cgttggtgcg ggtgttcttg aactcggtgt tgatggcgtc ggccagcgag aagtccaccg 60
agtcctgcag gagccgcacc ccgggcacgc tgctccgcag gcgcacggca gaggagcgcg 120
tggcatacac gccgcccggg gacgaggcgt agaggctgcg gctggtgctg gggcgcagcg 180
cgctgcccag gctgtaggtg cgggtggacg tagtcacgta gctccggctg gagctcggcc 240
ggctcgcggt gcccgggccg ccgaacatcc tgcggtagga ggacgaggac acggacctgg 300
tggacatggc tgcggagggt ggcgatggcc tgggcggcgg cggtggcgcg gactggctcc 360
cggagaagag gcgaacgagg gcgcggtggg tgtgggtggt gggagcgcgg ctgcgtctct 420
ggcgcgggga cctcggagcg agagtggcag aggactggac cccgccgagg gcgctgtttt 480
tataaccccg ttaggaaaga gggtcccctc ccactgccat cccagccgcg gagcgcgcca 540
gccaataggg acctagcgag aagcggggag ggtgggcggg tggggtgggg gcgccctcga 600
gccttcctgc tccggggcct gggactgggc atggtcccgt tacttcagcg ctgggctggg 660
acttttgggg gctttccgga tgatagtctg agctgggctc accctggggt gctgaaaaag 720
gcggggtcgc gcggtgaggg gggggtccgc ctgggactga accagagggg tccggtggca 780
ccacgccaaa ggggcgtggg aggaggtgcg cggcggtctc ggggctgcgg tcaggcgggg 840
agacccgcgg gcaaaggagc gggaagagga aagagtaagg aatccctcag atctgaagtc 900

<210> SEQ ID NO 49
<211> LENGTH: 899
<212> TYPE: DNA
<213> ORGANISM: Homo sapiens

<400> SEQUENCE: 49
cgttggtgcg ggtgtttttg aattcggtgt tgatggcgtc ggttagcgag aagtttatcg 60
agttttgtag gagtcgtatt tcgggtacgt tgtttcgtag gcgtacggta gaggagcgcg 120
tggtatatac gtcgttcggg gacgaggcgt agaggttgcg gttggtgttg gggcgtagcg 180
cgttgtttag gttgtaggtg cgggtggacg tagttacgta gtttcggttg gagttcggtc 240
ggttcgcggt gttcgggtcg tcgaatattt tgcggtagga ggacgaggat acggatttgg 300
tggatatggt tgcggagggt ggcgatggtt tgggcggcgg cggtggcgcg gattggtttt 360
cggagaagag gcgaacgagg gcgcggtggg tgtgggtggt gggagcgcgg ttgcgttttt 420
ggcgcgggga tttcggagcg agagtggtag aggattggat ttcgtcgagg gcgttgtttt 480
tataatttcg ttaggaaaga gggttttttt ttattgttat tttagtcgcg gagcgcgtta 540
gttaataggg atttagcgag aagcggggag ggtgggcggg tggggtgggg gcgttttcga 600
gtttttttgt ttcggggttt gggattgggt atggtttcgt tattttagcg ttgggttggg 660
atttttgggg gtttttcgga tgatagtttg agttgggttt attttggggt gttgaaaaag 720
gcggggtcgc gcggtgaggg gggggttcgt ttgggattga attagagggg ttcggtggta 780
ttacgttaaa ggggcgtggg aggaggtgcg cggcggtttc ggggttgcgg ttaggcgggg 840
agattcgcgg gtaaaggagc gggaagagga aagagtaagg aatttttttag atttgaagt 899

<210> SEQ ID NO 50
<211> LENGTH: 899
<212> TYPE: DNA
<213> ORGANISM: Homo sapiens

<400> SEQUENCE: 50
tgttggtgtg ggtgtttttg aatttggtgt tgatggtgtt ggttagtgag aagtttattg 60
agttttgtag gagttgtatt ttgggtatgt tgttttgtag gtgtatggta gaggagtgtg 120
tggtatatat gttgtttggg gatgaggtgt agaggttgtg gttggtgttg gggtgtagtg 180
tgttgtttag gttgtaggtg tgggtggatg tagttatgta gttttggttg gagtttggtt 240
ggtttgtggt gtttgggttg ttgaatattt tgtggtagga ggatgaggat atggatttgg 300
tggatatggt tgtggagggt ggtgatggtt tgggtggtgg tggtggtgtg gattggtttt 360
tggagaagag gtgaatgagg gtgtggtggg tgtgggtggt gggagtgtgg ttgtgttttt 420
ggtgtgggga ttttggagtg agagtggtag aggattggat tttgttgagg gtgttgtttt 480
tataattttg ttaggaaaga gggttttttt ttattgttat tttagttgtg gagtgtgtta 540
gttaataggg atttagtgag aagtggggag ggtgggtggg tggggtgggg gtgtttttga 600
gtttttttgt tttggggttt gggattgggt atggttttgt tattttagtg ttgggttggg 660
atttttgggg gtttttttgga tgatagtttg agttgggttt attttggggt gttgaaaaag 720
gtggggttgt gtggtgaggg gggggtttgt ttgggattga attagagggg tttggtggta 780
ttatgttaaa ggggtgtggg aggaggtgtg tggtggtttt ggggttgtgg ttaggtgggg 840
agatttgtgg gtaaaggagt gggaagagga aagagtaagg aatttttttag atttgaagt 899

<210> SEQ ID NO 51
<211> LENGTH: 6220
<212> TYPE: DNA
<213> ORGANISM: Homo sapiens

<400> SEQUENCE: 51
ctgcagttaa tccttttcag tacaccataa atctaaatac tctcaaaaaa acctgtgcct 60
tttcaattgc tactaaatca cgagaagact gatttacata gtctcctttt atctcccttg 120
gcgggtaagt actcagctct gctcgttact aatattgaaa caacagccct tgaattgagt 180
gatttcccta gaaaggttaa ggtgaccgaa tctgaacact ccctccatgt cttggacacg 240
aagttttttt tctgcgtaga cagttttatc ccctcatccc aaggtcaatt gcacgaattc 300
ttttggaaaa cagaacctat ggcatttccc agacaaatca ccgtgaaccc tgtactgtgc 360
attgctgtcc taaaattaac acataaatct attgccgcca aagattctgt catttgtgtt 420
acataattgc ctttcatttg aactcattaa tcaaattggg gtttttaagc aacacctaat 480
taattcttta actggctcat attaaccttt aatgacttcc accagggtaa aaaccactga 540
tcactgagtt ctattttgaa actacggacg tcgagtttcc tctttcaccc agaattttca 600
gatcttgttt aaaaagttgg gtgtggtttc atggggggag gggaagagc gagaggagac 660 cagagggacg ggggcgggga ctctgcaaga aaaaccttcc cggtgcaatc gtgatctggg 720
aggcccacgt atggcgcctc tccaaaggct gcagaagttt cttgctaaca aaaagtccgc 780
acattcgagc aaagacaggc tttagcgagt tattaaaaac ttaggggcgc tcttgtcccc 840
cacagggccc gaccgcacac agcaaggcga tgggcccagc tgtaagttgg tagcactgag 900
aactagcagc gcgcgcggag cccgctgaga cttgaatcaa tctggtctaa cggtttcccc 960
taaaccgcta ggagccctca atcggcggga cagcagggcg cggtgagtca ccgccggtga 1020
ctaagcgacc ccacccctct ccctcgggct ttcctctgcc accgccgtct cgcaactccc 1080
gccgtccgaa gctggactga gcccgttagg tccctcgaca gaacctcccc tccccccaac 1140
atctcccccc aaggcaagtc gatggacaga ggcgcgggcc ggagcagccc ccctttccaa 1200
gcgggcggcg cgcgaggctg cggcgaggcc tgagccctgc gttcctgcgc tgtgcgcgcc 1260
ccccaccccg cgttccaatc tcaggcgctc tttgtttctt tctccgcgac ttcagatctg 1320
agggattcct tactctttcc tcttcccgct cctttgcccg cgggtctccc cgcctgaccg 1380
cagccccgag gccgccgcgc acctcctccc acgcccccttt ggcgtggtgc caccggaccc 1440
ctctggttca gtcccaggcg gacccccccc tcaccgcgcg accccgcctt tttcagcacc 1500
ccagggtgag cccagctcag actatcatcc ggaaagcccc caaaagtccc agcccagcgc 1560
tgaagtaacg ggaccatgcc cagtcccacg ccccggagca ggaaggctcg aggcgccccc 1620
accccacccg cccaccctcc ccgcttctcg ctaggtcccg attggctggg gcgctccgcg 1680
gctgggatgg cagtgggagg ggaccctctt tcctaacggg gttataaaaa cagcgccctc 1740
ggcggggtcc agtcctctgc cactctcgct ccgaggtccc cgcgccagag acgcagccgc 1800
gctcccacca cccacaccca ccgcgccctc gttcgcctct tctccgggag ccagtccgcg 1860
ccaccgccgc cgcccaggcc atcgccaccc tccgcagcca tgtccaccag gtccgtgtcc 1920
tcgtcctcct accgcaggat gttcggcggc ccgggcaccg cgagccggcc gagctccagc 1980
cggagctacg tgactacgtc cacccgcacc tacagcctgg gcagcgcgct gcgccccagc 2040
accagccgca gcctctacgc ctcgtccccg ggcggcgtgt atgccacgcg ctcctctgcc 2100
gtgcgcctgc ggagcagcgt gcccggggtg cggctcctgc aggactcggt ggacttctcg 2160
ctggccgacg ccatcaacac cgagttcaag aacacccgca ccaacgagaa ggtggagctg 2220
caggagctga atgaccgctt cgccaactac atcgacaagg tgcgcttcct ggagcagcag 2280
aataagatcc tgctggccga gctcgagcag ctcaagggcc aaggcaagtc gcgcctaggg 2340
gacctctacg aggaggagat gcgggagctg cgccggcagg tggaccagct aaccaacgac 2400
aaagcccgcg tcgaggtgga gcgcgacaac ctggccgagg acatcatgcg cctccgggag 2460
aagtaaggct gcgcccatgc aagtagctgg gcctcgggag ggggctggag ggagagggga 2520
acgccccccc ggcccccgcg agagctgcca cgcccttggg gatgtggccg gggggaggcc 2580
tgccagggag acagcggaga gcggggctgt ggctgtggtg gcgcagcccc gcccagaacc 2640
cagaccttgc agttcgcatt tcctcctctg tccccacaca ttgcccaagg acgctccgtt 2700
tcaagttaca gatttcttaa aactaccact ttgtgtgcag ttgaaggccc ttgggcacaa 2760
tgagagccag tcctccaaac tttcagaaag tttcctgccc cttctggcag gctgccaatc 2820
accgggcggg agaaggaagg aggggaaggc ggtggaggga gcgagacaaa gggatggtcc 2880
ctcgggggcg gggatggcgg ggctgtcctg taggtctgtg cggccaccgt gattgcccct 2940
ctgcgcggtg cccgaagtcc cgctgaaacc tgccgagggc agcaggtctg aaagctgcag 3000
gcgctagttg cgcggaggtg gcgcagctgc tctggaggcg cagagcgaat acgtggtgtt 3060
tgggtgtggc cgccccgccc ctggcggttt cctcgttccc ctttggttaa tgcgcaactg 3120
tttcagattg caggaggaga tgcttcagag agaggaagcc gaaaacaccc tgcaatcttt 3180
cagacaggtt tgtagactct cttcccactc gcagccgcct gaccccaccc aacacaaccc 3240
acgagcaatt ctaaaagttg cttaactcac gtctaaaaag tgcaaaactt cagggctgcg 3300
cgtaaagccc tctagtggcg ggaagaccac aggttggagc ttctcatgat tagaaaaata 3360
ttaataaaac cccttgagcg attttttttt tttttttgag acggagtctt actctgtcgc 3420
ccaggctgga gtgcagtggc gagatcttgg ctcactgcat cctccgcctc ccgggttcaa 3480
gcgatccttg aatgatttct aagcagttcc ttgggacata aagaaaaatc ttttaacttt 3540
ttactttgtt tcccaaatgt tgcacagttt tgcaacacat tgaccttctg gtttcgaacg 3600
gttacaattt tagattgtgg tttgccaaag tcaagttgct taatttttac aaggccacaa 3660
aaagcgcaat tatgccctgc agtttaaaat ggaaaacgtg ttggaagata agaaaactta 3720
gtttccaact ggaatggagc cagcaagttt cttttcttct ttgcaaattc tattgtgtca 3780
ttaaagttcg atggaagtat cactatgcac aactattttg tgatctaata agggtgaaaa 3840
ggagccatct gtccccttgg ctaaggggta ttaatggttt ctatgggctt cactatggaa 3900
tgtagataca gacattctgg caaatgtggt ggctctggac agaaataata ggagtctttg 3960
tattcccagg gaagctttgc aacaggctac attcttactg aatatgtaat gatgtaagca 4020
cggttctaat tggacacaag tatttgctaa catccgttat ctaatatctg gcccagactt 4080
gagaagtagg taatgtgaaa agtttttaaa gctacaagca tacctcacat tttaaaagtc 4140
ctttcttgat tgggttcttg tgttctttag cactcttgcc ataaaaaata ataacagtaa 4200
taaacccaag gctgaaaaac tgaattttaa ctaaagggtt tttgtgcgtg tttttttttt 4260
ttttcaccaa aattagatgg acttacagaa tttttaactt aaaattggaa tccaaaagcc 4320
agaagatccc cattatagtt tatagttgta ttccctggaa tatttactgg gattaactgc 4380
aaagcactct cagatgaata gtgtagtata acattttgaa actgaaatac atttaccaaa 4440
ttaatttaac cacagcaatg tgtgtggttc attttagtcc ttgagcattt ttgattatca 4500

-continued tacctgtcat gttttctgca gtgtagtgag ttaacataaa acaacatcaa tacaaaagat 4560
cctctgtttc gagattaagc aaaattcctc attctcttca atgtgataga ataccacatt 4620
gatctttctt tggaggttag taaaatatct tttatgtatt tttcagggct taacaagtaa 4680
aaatcaatgt tttcatcaag tctgatcttt ttgtcaccca ctcttcattc atttttccac 4740
taaggtgata gaaaagtctc aacagtttaa gaccgtaagg ctatgaactc caaatataat 4800
tgctgacaag ataagcaatc ctcacgcatc cttttgagag gaaataaaat cttagttgca 4860
agattacata ttctgatttg gaatgctgag ctttttaaat ggaaatatag aaggacggct 4920
gaatcagcaa aaatccttta tgtagtttca ttctttgcaa gcttgaccag tcattctgaa 4980
acaggctaac tgaactgata cagtggcaag tgaaaaagac atgcctttac aggatgagtc 5040
aaaggagttt tagaagaaaa atccaccaga gaaagccaag caaatacagt tcagagttac 5100
atttcttttc catttttttcc tgaactgaat ctttggcatg catatcctga attgggttat 5160
tgaatataaa tctagccttg tacaatggat gccagatgac tacatatttg ctttggagcc 5220
taaggataag tttcaaaaga tttgagtgga gaagaaaagc taaaactctt gaagcacaag 5280
tttctgttct ccatgtactc aagtgtacat gaagttgtga aaatttgtcc acctctatca 5340
tcatgttatt ccatgaaatt acaaaacaaa tcttaaaaat gttgtggcat agattttcta 5400
gatttaaaaa gtaattaaat taaatgaatt actttatttt ttgagacaga gtgtcactct 5460
gttgcccagg ctggagtgca gtggcactat gttggctcac tgcaacctct gcctcctggg 5520
ttgaagaaat tctcctgcct caacctccca agtagctggg actacaggca tgtgccacca 5580
cacccagcta atttttgtat ttttggtaga gacggggttt cgccatgttg gctaggctgg 5640
tctcgaactc ctgacctcaa gtgatccacc cgtctcagcc tcccaaagtg ctgggattac 5700
aggcataagc caccatgacc agccttaaaa agtaatttta aaatatcact ggtaaaatgt 5760
ggattcagtc atgattgagt gcagtttacc atgtgtgtgg acatttattt attttaaaat 5820
tgtctgatca ccaccttgag taaaacacaa gcagtcacaa ttaaaatata ttagtgagca 5880
ggagaaagca cagcatatta tagcactgaa tgatttataa acctattcca gggtcataaa 5940
atgtgtcaac ggcttttcta tagtaaggag actaggttca gatggttaat ctaagacaaa 6000
taaatgagat aagccataca cttttacatc ctccatgtcc tgtcttttct ctgttcaaaa 6060
taggatgttg acaatgcgtc tctggcacgt cttgaccttg aacgcaaagt ggaatctttg 6120
caagaagaga ttgccttttt gaagaaactc cacgaagagg ttagtggagt gactttcggg 6180
gaatgaatga gggtaaggca gcccccacgg ttggcagagc 6220

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ggtttttatt ggttggcgcg tttcgc 26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
ctacgtctct aacgcgaaaa cctcga 26

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tttttgttcg cgggtttttt cgtttgatcg 30

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ctaaaatact aaaaaaaacg aaatcgcgcg a 31

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ttttttcgtt tgatcgtagt ttcgagatc 29

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
tttttgttat tttcgtttcg aggttttcgc 30

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tcccgaaaaa aaaacgaacg aaaacgcga 29

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tcccgaaaaa aaaacgaacg aaaacgcg 28

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ataacctaaa cgacgacgat aacgcga 27

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ataacctaaa cgacgacgat aacgcg 26

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
tcgtttcgag gttttcgcgt tagagac 27

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
cgactaaaac tcgaccgact cgcga 25

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gtagaggagc gcgtggtata tacgtc 26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 65

-continued tcgggtacgt tgtttcgtag gcgtac 26

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
acgacccgaa caccgcgaac cga 23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
acccgaacac cgcgaaccga ccg 23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ggttcgggta tcgcgagtcg gtc 23

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
atacacgccg cccgaaaacg aaacg 25

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ccgcaaacgc acgacaaaaa aacgcg 26

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 71

```
aacacgctac tccgcaaacg cacga                                          25


<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

tatcgcgagt cggtcgagtt ttagtc                                         26


<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73

cgggagttag ttcgcgttat cgtcgtcgtt t                                   31


<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

ggataggata gttttatttt tag                                            23


<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

atacaaaact atactcaacc aa                                             22


<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76

accaccaccc aacacacaat aacaaacaca                                     30


<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

-continued

<400> SEQUENCE: 77

```
His His His His His His
1               5
```